US010898530B2

(12) United States Patent
Pouillot et al.

(10) Patent No.: US 10,898,530 B2
(45) Date of Patent: Jan. 26, 2021

(54) PHAGE THERAPY

(71) Applicant: PHERECYDES PHARMA, Romainville (FR)

(72) Inventors: Flavie Pouillot, Paris (FR); Helene Blois, Paris (FR)

(73) Assignee: PHERECYDES PHARMA, Romainville (FR)

( * ) Notice: Subject to any disclaimer, the term of this patent is extended or adjusted under 35 U.S.C. 154(b) by 82 days.

(21) Appl. No.: 15/524,271

(22) PCT Filed: Nov. 6, 2015

(86) PCT No.: PCT/EP2015/075949

§ 371 (c)(1),
(2) Date: May 4, 2017

(87) PCT Pub. No.: WO2016/071503

PCT Pub. Date: May 12, 2016

(65) Prior Publication Data

US 2017/0319637 A1 Nov. 9, 2017

(30) Foreign Application Priority Data

Nov. 7, 2014 (EP) .................................... 14306788

(51) Int. Cl.
*C12N 7/00* (2006.01)
*A61K 35/76* (2015.01)

(52) U.S. Cl.
CPC ................ *A61K 35/76* (2013.01); *C12N 7/00* (2013.01); *C12N 2795/00021* (2013.01); *C12N 2795/00032* (2013.01); *C12N 2795/10121* (2013.01); *C12N 2795/10132* (2013.01); *C12N 2795/10221* (2013.01); *C12N 2795/10232* (2013.01)

(58) Field of Classification Search
None
See application file for complete search history.

(56) References Cited

U.S. PATENT DOCUMENTS

| | | | |
|---|---|---|---|
| 10,077,431 | B2 | 9/2018 | Pouillot et al. |
| 2017/0000831 | A1 | 1/2017 | Pouillot et al. |
| 2019/0002840 | A1 | 1/2019 | Pouillot et al. |

FOREIGN PATENT DOCUMENTS

| | | |
|---|---|---|
| EP | 2465926 | 6/2012 |
| WO | WO 02/07742 | 1/2002 |
| WO | WO 2009/075884 | 6/2009 |

OTHER PUBLICATIONS

Baker et al., Protein Structure Predication and Structural Genomics, Science (2001) vol. 294, No. 5540, pp. 93-96 (Year: 2001).*
Attwood, T. The Babel of Bioinformatics, Science (2000) vol. 290, No. 5491, pp. 471-473 (Year: 2000).*

(Continued)

*Primary Examiner* — Michelle S Horning
(74) *Attorney, Agent, or Firm* — Saliwanchik, Lloyd & Eisenschenk

(57) ABSTRACT

The present invention relates to bacteriophage therapy. More particularly, the present invention relates to novel bacteriophages having a high specificity against *Pseudomonas aeruginosa* strains, their manufacture, components thereof, compositions comprising the same and the uses thereof in phage therapy.

17 Claims, 5 Drawing Sheets

Specification includes a Sequence Listing.

Efficacy of bacteriophage 1384 on PAO1 strain

(56) References Cited

OTHER PUBLICATIONS

GenBank: JQ067092.2 Pseudomonas phage, 2012 (Year: 2012).*
Drulis-Kawa et al. Learning from Bacteriophages—Advantages and Limitations of Phage and Phage-Encoded Protein Applications. Current Protein & Peptide Science, vol. 13 , Issue 8 , 2012, p. 699-722 (Year: 2012).*
Alemayehu, D. et al. "Bacteriophages ØMR299-2 and ØNH-4 Can Eliminate *Pseudomonas aeruginosa* in the Murine Lung and on Cystic Fibrosis Lung Airway Cells" *MBio*, Mar./Apr. 2012, pp. 1-9, vol. 3, No. 2.
Fu, W. et al. "Bacteriophage Cocktail for the Prevention of Biofilm Formation by *Pseudomonas aeruginosa* on Catheters in an in Vitro Model System" *Antimicrobial Agents and Chemotherapy*, Jan. 2010, pp. 397-404, vol. 54, No. 1.
Reardon, S. "Phage therapy gets revitalized" *Nature*, Jun. 5, 2014, pp. 15-16, vol. 510.
Wright, A. et al. "A controlled clinical trial of a therapeutic bacteriophage preparation in chronic otitis due to antibiotic-resistant *Pseudomonas aeruginosa*; a preliminary report of efficacy" *Clinical Otolaryngology*, 2009, pp. 349-357, vol. 34.
Database EMBL [Online] Accession No. JN254800, "Pseudomonas phage NH-4, complete genome" Jul. 14, 2011, pp. 1-41, XP-002718982.
Database EMBL [Online] Accession No. AM910650, "Pseudomonas phage LUZ24, complete genome" Nov. 16, 2007, pp. 1-26, XP-002718980.
Database EMBL [Online] Accession No. FM887021, "Pseudomonas phage SN, complete genome" Dec. 9, 2008, pp. 1-36, XP-002718979.
Database EBI [Online] Accession No. FM897211, "Pseudomonas phage 14-1, complete genome" Dec. 14, 2008, pp. 1-2, XP-002738707.
NCBI [online], "Pseudomonas phage JG024, complete genome" retrieved from the internet on Jan. 14, 2015, URL: http://www.ncbi.nlm.nih.gov/nuccore/GU815091, Dec. 16, 2010, pp. 1-64.
Database EBI [Online] Accession No. KF856712, "Pseudomonas phage philBB-PAA2, complete genome" Dec. 4, 2013, p. 1, XP-002738709.
Database EMBL [Online] Accession No. AB560486, "Pseudomonas phage KPP12 DNA, complete genome" Aug. 23, 2012, pp. 1-35, XP-002718984.
Database EBI [Online] Accession No. FM201281, "Pseudomonas phage LBL3 complete genome" Aug. 22, 2008, pp. 1-2, XP-002738708.
Database EMBL [Online] Accession No. FM201282, "Pseudomonas phage LMA2 complete genome" Jul. 22, 2008, pp. 1-37, XP-002718985.
Written Opinion in International Application No. PCT/EP2015/075949, dated Jan. 14, 2016, pp. 1-8.
Ceyssens, P.-J. et al. "Comparative analysis of the widespread and conserved PB1-like viruses infecting *Pseudomonas aeruginosa*" *Environmental Microbiology*, 2009, pp. 2874-2883, vol. 11, No. 11.
Fukuda, K. et al. "*Pseudomonas aeruginosa* Keratitis in Mice: Effects of Topical Bacteriophage KPP12 Administration" *PLOS One*, Oct. 2012, pp. 1-8, vol. 7, No. 10, Article No. e47742.
Garbe, J. et al. "Characterization of JG024, a pseudomonas aeruginosa PB1-like broad host range phage under simulated infection conditions" *BMC Microbiology*, Nov. 26, 2010, pp. 1-10, vol. 10, No. 1.
Krylov, V. et al. "A Genetic Approach to the Development of New Therapeutic Phages to Fight *Pseudomonas Aeruginosa* in Wound Infections" *Viruses*, Dec. 21, 2012, pp. 15-53, vol. 5.
McVay, C.S. et al. "Phage Therapy of *Pseudomonas aeruginosa* Infection in a Mouse Burn Wound Model" *Antimicrobial Agents and Chemotherapy*, Jun. 2007, pp. 1934-1938, vol. 51, No. 6.
Oikonomou, O. et al. "Investigation of carbapenem heteroresistance among different sequence types of *Pseudomonas aeruginosa* clinical isolates reveals further diversity" *J. Med. Microbiology*, May 19, 2011, pp. 1556-1558, vol. 60, No. 10.
Database EMBL [Online] Accession No. FM887021, "Comparative analysis of the widespread and conserved PB1-like viruses infecting Pseudomonas aeruginosa" Dec. 16, 2008, pp. 1-36, XP-002718979.
Database EMBL [Online] Accession No. JN254801, "Bacteriophages PhiMR299-2 and PhiNH-4 Can Eliminate Pseudomonas aeruginosa in the Murine Lung and on Cystic Fibrosis Lung Airway Cells" Apr. 27, 2012, pp. 1-32, XP-055161973.
Database EMBL [Online] Accession No. EU716414, "Comparative analysis of the widespread and conserved PB1-like viruses infecting Pseudomonas aeruginosa" Jan. 6, 2009, pp. 1-39, XP-002718981.
Database EMBL [Online] Accession No. KC294142, "Pseudomonas aeruginosa phage PaP4" Jan. 16, 2013, pp. 1-29, XP-002718983.
Written Opinion in International Application No. PCT/EP2014/072905, dated Jan. 27, 2015, pp. 1-11.
Wang, I.-N., et al. "HOLINS: The Protein Clocks of Bacteriophage Infections" *Annu. Rev. Microbiol*. 2000, pp. 1-34, vol. 54.
Carter, C.D. et al. "Bacteriophage cocktail significantly reduces *Escherichia coil* O157:H7 contamination of lettuce and beef, but does not protect against recontamination" *Bacteriophage*, Jul. 2012, pp. 178-185, vol. 2, No. 3.
Pouillot, F. et al. "Genetically Engineered Virulent Phage Banks in the Detection and Control of Emergent Pathogenic Bacteria" *Biosecurity and Bioterrorism: Biodefense Strategy, Practice, and Science*, Jun. 1, 2010, pp. 155-169, vol. 8, No. 2.
Stone, R. "Bacteriophage Therapy: Stalin's Forgotten Cure" *Science*, Oct. 25, 2002, pp. 728-731, vol. 298, No. 5594.
Database EMBL [Online] Accession No. M38308, "Bacteriophage T7 RNA polymerase gene, complete cds" Nov. 7, 1990, p. 1, XP-002725532.
Database EMBL [Online] Accession No. AY303349, "Enterobacteria phage RB69, complete genome" Jul. 1, 2003, pp. 1-58, XP-002725574.
Database EMBL [Online] Accession No. AY370674, "Enterobacteria phage K1-5, complete genome" Feb. 3, 2004, pp. 1-12, XP-002725533.
Database EMBL [Online] Accession No. AM084414, "Enterobacteria phage K1F, complete genome" Dec. 5, 2005, pp. 1-13, XP-002725538.
Database EMBL [Online] Accession No. EF056009, "Enterobacteria phage N4, complete genome" Nov. 15, 2006, pp. 1-18, XP-002725539.
Database EMBL [Online] Accession No. EU330206, "Enterobacteria phage phiEco32, complete genome" Jan. 5, 2008, pp. 1-25, XP-002725530.
Database EMBL [Online] Accession No. DQ832317, "*Escherichia coli* bacteriophage rv5, complete sequence" Jun. 30, 2008, pp. 1-42, XP-002725541.
Database EMBL [Online] Accession No. EU734171, "Enterobacteria phage BA14, complete genome" Jul. 2, 2008, pp. 1-13, XP-002725534.
Database EMBL [Online] Accession No. EU734174, "Enterobacteria phage 13a, complete genome" Jul. 2, 2008, pp. 1-14, XP-002725540.
Database EMBL [Online] Accession No. AZU35935, "Bacteriophage F488/08 genomic DNA, SEQ ID 3" May 10, 2012, pp. 1-30, XP-002725537.
Database EMBL [Online] Accession No. JX128259, "Escherichia phage ECML-134, complete genome" Jul. 29, 2012, pp. 1-53, XP-002725536.
Database EMBL [Online] Accession No. JN986844, "Enterobacteria phage vB_EcoP_ACG-091, complete genome" Nov. 1, 2012, pp. 1-13, XP-002725531.
Written Opinion in International Application No. PCT/EP2015/050355, dated May 6, 2015, pp. 1-12.
Baker et al. "Protein Structure Prediction and Structural Genomics" *Science*, Oct. 5, 2001, pp. 93-96, vol. 294, No. 5540.
Attwood, T. K. "The Babel of Bioinformatics" *Science*, 2000, pp. 471-473, vol. 290, No. 5491.
Cuevas, J. M. et al. "Point Mutation Rate of Bacteriophage ϕX174" *Genetics*, Oct. 2009, pp. 747-749, vol. 183.
Ofir, G. et al. "Contemporary Phage Biology: From Classic Models to New Insights" *Cell*, Mar. 8, 2018, pp. 1260-1270, vol. 172.

* cited by examiner

SEQUENCE LISTING

```
<160> NUMBER OF SEQ ID NOS: 7

<210> SEQ ID NO 1
<211> LENGTH: 63902
<212> TYPE: DNA
<213> ORGANISM: Bacteriophage P1384
<220> FEATURE:
<221> NAME/KEY: misc_feature
<222> LOCATION: (63895)..(63902)
<223> OTHER INFORMATION: n is a, c, g, or t

<400> SEQUENCE: 1

tcgcgtttcg atgaggagat tatgccgata gtcagaatgg aagtaaagtg tctgagtgag     60

aaaaattctg cacaccgacg aacggttgtg ctcgaccgtc tgttgcggcg tcgatatact    120

cggcctattg ctaacaccgg actgattgga atgtacaaac tcaatcctgc gctgcgagcg    180

gtctggcgaa ctcgtgcccg ttacaaagtc atctatggcg gccgggcgtc ttcgaagtcg    240

cacgacgctg gcggtatagc cgttttcctc gcggccaact acaagctaaa gttcctctgt    300

gctcgccagt ttcagaaccg catcagcgaa tcggtctaca cgttgatcaa ggacaagatc    360

gaaaactcag agtataatgg cgaattcatc ttcaccaaga actctatcaa gcacaagagt    420
```

```
accgggtcag agttcctatt ctatgggatc gcccgtaacc tgtcggaaat caagtccacc    480
gaaggcatcg acattctctg gcttgaggaa gctcactatc tgacccagga gcaatgggaa    540
gtcatcgagc cgaccatccg gaaagagaac tcagaaatct ggatcatctt caacccgaac    600
gaagtgaccg acttcgtgta tcagaacttc gtggtcaagc cccgaaaga ttcctgcgtc    660
aagatgatca actggaatga aaatccgttc ctcagtgaga cgatgcttaa agtcattcac    720
gaagcatatg agcgcgaccg ggagcaggcc gagcacattt atggcgggat tccgaagact    780
ggaggcgaca aatccgtcat caacctcaag ttcatcctcg cggccatcga cgcccacaag    840
aaactcggct gggagccagc cggatcgaag cgcatcggct tcgacgttgc ggacgacggc    900
gatgatgcga acgccaccac gctcatgcac ggaaacgtca taatggaagt ggacgaatgg    960
gacggcctgg aagatgaact gctcaagtcg tccagccgcg tttacaatct ggcgaagctg   1020
aaaggcgcct cggtcactta tgactccatc ggcgtcggcg ctcatgtcgg ttcgaagttc   1080
gccgagttga acgatgccag ccccgacttc aaacttatct atgatccatt caacgcgggc   1140
ggcgctgtcg ataagcctga tgatgtctac atgaagctgc cgcacacgac gatcaagaac   1200
aaagaccact tcagcaacat caaggcgcag aagtgggaag aagtcgcgac ccgattcagg   1260
aagacttatg aagcggttga gcatggaaag gtttatccat tcgacgaatt gatttcgatc   1320
aactctgaaa cgattcaccc ggacaaacta aatcaattgt gtattgaact ttcgtcgccg   1380
cgcaaagacc tggacatgaa cggccggttc aaagtcgagt ccaagaagga tatgcgcgag   1440
aaacgcaaga tcaagtcacc gaacatcgct gactcggtga ttatgtcggc cattctgccg   1500
atccggaagc ccaaaggctt cttcgacttc taaacataga aaagcccgga tcgctccggg   1560
cttcgggtct tactcggtgt ggttcctggc gctgagtgtc gacgcaacgg cctcgccgac   1620
tcccagggct tcctggccgg ccgcgagcgc ttcggcttcc gactcgacga tgaaatcatc   1680
accttggcca tcgcctggcg gaacctcgac cagcacggct tcttcgcctt cgaaccgcag   1740
gtcataggtc ttttcgacgg acagaccgta acgagcgttg agcgcgtccc agagctgggc   1800
ctcataggtc cgcaggtctt gcagagcttt ctggtggctg agcatggcca tgtcaacagc   1860
ccgttgcagg gtttcgtcca ggacgttgaa tcgcatgcga agagaacgaa tccgctcgac   1920
cacttccgca tccactacat gcctttcgat catcgctttt cacctttgct gaatgttacg   1980
ttgtagccgt tgtcggccag ataggtcaag gcgccttcga aagaagttcc gacaaggtgc   2040
ttgagctgca tttcgcgttg cgcggcgatc cagaatgccg ttccggagaa ctctgcgcgg   2100
ccttccgaca aaacctttcc atcaggcccg tcgatccgta catggacgga agatagcttc   2160
agcgccatca gtgaaccgtc cctgtgaagg cgcgcgccgc cgcgcattga tcgcaagggc   2220
actccctctg gatgcgcgcc aggtcgtttg catccagggc gtagagtttt ccatctacgg   2280
tatcgtgagc cattgcgatg tccggatatt cgttttcgtc caggccggat gccgcacgga   2340
tgttgttcca gatgccggca tgttccgcgc gatggcgcgc ggtcaactca tcttgctctt   2400
tgttcgccct ttcaacgaat ttctccagga gttcggtgaa tttctcatcg atgactcgtg   2460
cagacttgac agagctgagt cgaatcgggt ctttcttcat ggtgattctc ttttgctggt   2520
ggttgttcgc tgcccagacc tattcaaagt ctgggcagca tgatgaaaat gaacacgaag   2580
gctgcaaacg ccaatagcgt tcctgtaagc attttggctt gactctgcac ctcagcgtac   2640
tgcttagtgg acattccgtg ctgcgccgcc tcggccgcga agcgagcttt cgcctcgata   2700
acttccgggc gcagcgacag gacatattct aaggcctctt cccgcgcttt tcggcctcga   2760
```

-continued

```
ccaacctagg gtcgcgggcc gagacttcgc tgtgccctgg cctcgcggga tgggcctgca   2820
gcgatggcgg aagttcggcg gccacgactc catagtcggc gcaggcccaa gcgatcccga   2880
tgaggatcgc gaggatggat tgaacgattc gtagcatcac tttgtcgcta gggaagctca   2940
tgatcaatcc tccacagacc gaacgatttc catgttgcgg ccggcattgg tcccggcatt   3000
gaaggcgcgc cgaccgtcgc tatcgtccag acgcatgagc ttagcaacat tgtacttctt   3060
gtagccagga tcgccgaaat gttcgtgaac cgcagcttcc ttcaccacaa ccagagacgt   3120
tccggcagaa gataccagct ccatgcgctt cctggttatg gcctgaaggc gatagctgat   3180
ttcctgggtc gcggccagct tgaattgcgc ggcaaccttg acgttgaatc gtccgtatcc   3240
ttgagccttc tgatactccc ggcacagacg atcaaccgct tcgacaaggg agttgaacat   3300
gttcaccgcc agctcaacgt ccgatttgta gcctttaaag cggacggcat gaccccagcg   3360
cttcgtagtc ccgccgtttg cggcgtgcca agaagccttg gcggtcgctc ggtgatcgtt   3420
gatgccaccg gcgaaatcca tgatgaagtc gttgtacgtc gccacggcca ccgagaagaa   3480
cttcatccag ttcgggattg cggaatagta acgagtcgcg atctgctcat cgaactcttc   3540
gcaaatctcg ccggtcactt cgaagtcgtg aaggtcatat ttgtccttca gcttcttcac   3600
acgctcggct gcaatggcag cttcgtgcgg gctggaggag tcggccgcca tggcagtcag   3660
tttgcggatg cggtctttcg ccttctcgat ggcttccggg gtgaattcgt tctggtaggt   3720
catggtcggt tccttttgtc tgaagggttt cgcgtttcaa tggagctatt ttgccttcat   3780
tcagaatgga agtaaagcat tttcttccac tatttcggca ttgactggaa gaaattccag   3840
atccaatcgc ctgctaccag caggaggatg agagcggcga agaacaagac ggcggccgcg   3900
agctgtgcgc ccggcttcag cttgggatgg ctgagcttgg gctctacggg aacggccgga   3960
gcgctggcgc tgcaaacggc atctcctgga ccgtagccga tgccgcgttc acgcgcctgg   4020
agcgacacca gggatttcag atgctcggtc tgcttttgcg actcttcgta gatgccggcg   4080
acggcgaacc agagggcgaa cacgacggac gtacacacaa cccaggcgcc ggtcagcagg   4140
agggccagcg ggccgatgac gaagacggta gcagccagga cgattgcgcc gccccagatg   4200
atgaagccgg ccagaccatt ggcgatgtcg atacagaact tttcatttg cggattcctt   4260
cggctacagg atggagggga tttggaactc tgcgccgccg agcacatcgg tgacgacttc   4320
ccagagcgtc ggcaccgacc actggtagcg gtcgaagtcg gtttcgggat cgaagcccaa   4380
cgtcacatag gaagtggcag gccatttatg aacgctacct ttccgcatga gagtcgccac   4440
gcgtccgtca acgagcgggt tcgtcttgtg cggaacgtac gcagacatcg aatattgctg   4500
cccggcgtca acaacaaatc tttgcctctg gcgcagacat acagagccca caggattcca   4560
gccgcgaccg ccgcaagcct ggcgagccga agagtgttca taaccttcgt gagtcatttc   4620
gccgaggcaa gccgagcgat cctcgtaata gttgatgttc tccatcgatc caaccagtac   4680
cagagactcg aaatcgaatc tatgatcgtg gatggccgag tgattgaagc aaagccggcg   4740
cggcaactcc gggtgccaaa catggaggcg ccctgccggg agctggactt gaatgaaccc   4800
caggccgtgc agcgtgatct tgtccttcat cgggtcatgg acggtgctca tggataatcc   4860
tcagtagcag aaatgtatgg tgagagttac gatggccaag ccggtcgccc ataggagggc   4920
gaaccaggcc atggctttga tggttatgta gatcatccga agaactttcc ggcacagatc   4980
ggtccaatgc ccatttcgat ggatgcgtgg ttggtcaact cgcgaccgca gcaggagcat   5040
tgaccagtct tccggccgta ggcgactgcc gattccatcg gcttttcaaa catcttcaga   5100
acgtcgtcat gctcagtgtc ggtgcagtcg cgactcttga tgaatttgcc attggtgatc   5160
```

```
cggccgaggt agatgtcgcc caagacgtac aagctaccgg cgttccggct gtgagcgcta   5220
gcctctttca caataacgat gagcggctcc tcgccttcgc cagccaggcg gattttcggg   5280
cgcttgatgc cagattcttt cgccttctca aacgccttct cgattccgga aatgtccaga   5340
gtcggcgcag cagcttcctg cgcggccact ttctcgcgat atttggcgag gttttcgatg   5400
gcgcgcttcg cagcagcgat ctgattttct gtcaaggagc cgtatttata caacgactcc   5460
tgaaggctct gagcgaagct gaaggaattt ccagtccacc actcgacgat gtccgggtgc   5520
gcatcttcga aggctttaat tttgaggtcg cgctcttgcg ccgcgctaca gattttctcg   5580
atgcgctttt ctgccgcctt agcacggctc ttggcgcgct gctccgggct ggttttgtac   5640
tctttgtatc caacaccgcc gcaggcgaag caggcgcgac cataagacga agggccacgg   5700
tacaggccgg tgcctgcgca tttggtgcac ttgtcgcgat acagcttcac ttccttccgg   5760
gaattcgggc gagcgcccat ggacgcgtct tccagggtct tcggcgcttc gttgttgatc   5820
gctacggtag cgaagtcgtc acccaggtct tcgaagcctg tgaacagatt ctctgctgcg   5880
ttcatatcga ttctcctgtt tggaaagttc gtttcgatga gttgactata cgccagaaat   5940
gggaaaacgg tagcactttc gcactaccgt tcgtcgggtc gcagagggtc aggctacacg   6000
gatcaactgc gacatgactg ccaggttacg ctcggcgacg cctatgatga ggttggttcc   6060
gatgtcgaac ttccaagggt cttccctgtt cttgtcgtag aacggatttc tgaacagggt   6120
ccgccatgtc tcttcagtga agaacgtttt atggtccagg tcttggtggg cgatgttgga   6180
gttgtagaat ggaacaacga cattgagcgt cgcgccgact gccatggccc gctgcaggtc   6240
tttcaccaaa tcgatgacct gggctccggt gagatgttcg aagaagtgaa atgcgtagac   6300
cgccgtcaat tcgccgtctt catacggcac tcggccgctg gcgccgtccc agttcggcca   6360
gtcgagcgat tcgacgccgg gaatcggcga attgcctgcg cccaggttta ctgcgcggcg   6420
gtgatccggc tcgatcaact gagcgatgtc gcgcttcatg ccgagtttga acaggttttg   6480
aatatccatt tttctctcca ggttgctgct agtaaatgtc gctgttgatc ttgaatccat   6540
gctcagcgcc gtcgttgtag tcatactcgg catagctgtc gcagtaatcg ttcaaatgtt   6600
gaatgatacc aagaacgtcg ttcgcggcct tgtgccgttt cgcggcgatg gtcttggcga   6660
tgctgtcgcc gacttccagg gtttcggccg tccggcggtg gatcagaaga cgactccaaa   6720
gatagagccg gacgcgacga atgatgtcgc gatggcgctc caatcgaact tccaactctt   6780
caagttcttg ctcgcgagat ttgatgactc gtcgaagctg atgaactttc agttccaaat   6840
cgtccttagt agccatattt acctcagaaa gggaaatcgt ctggaactcc aggaagctcg   6900
acgattgttg ttgagcctga tcggtctaga atgcatccga ccgagccagc cctgtgggga   6960
tagggcctac acgaactata acaggtaact tccatgacta ttcgccaggt cgatcctcca   7020
caccatctac aaattggcgg tcgcttcgac tttagttttc gttcgtccag gacggcgcgt   7080
ctgtcgcagg aaaggcagcg cgccttaacc gacgtaacca tgggtatagt cgatcattcg   7140
gatgagttca tcatcctctg attctctcga cttcagaccg cccaaagagt ccgactggcc   7200
gtagcatttc gcatcgatat ccatcgaaga caggaatcct gccgatactg cggagatatc   7260
aactttgtcg ccggccttct tgaaaccttc gcactcagca tcaagggcca caatcgcact   7320
cgcggccatg ttcgcatgac ttatgaggtc ggggaagatc acaggaactt cacgcgacat   7380
gccacggacc gtcatcttca ggactacata cttcatactc actatccctt ttgtatgtga   7440
ggaaagaatt tgctgttttc aggatggtgg aagcgctcgg ccgcaggcgg tctttcttcc   7500
```

-continued

```
ggacattgaa tcgtcgaagg cgggaaaacc gcgccggcga taatcgccgc gaggagtgca   7560
gcggatgtcg acatccagag ggcggtttcc aggctcaccc gaacttccgg acggcgcggc   7620
ttcattcgct ccaccctctt cccggttcat aggatggtag actgccgccg cgaacccagt   7680
tgtcccacat atggttcaga ccagtcggtg gctggggcgg cgaactgtag aatccgggag   7740
tctcagtgct gctcaggaaa taaggagtgc aaacggcctg gacggccagt tggtgccgct   7800
cccacatctt atcaatcgct cttagcatga cgtcttcgca ctgagcctta ctgtcgaacc   7860
gtctgctagt atggtccggt atctggacac atccgtctcc agtgcaaagg aaagcagtag   7920
caatccatac ggtgatactc gccatttcgt caccctcttt agttgatgag cagagtctat   7980
tccatctgct cgccaggagt aaagcgcttt tcgtcgggat aaatgccgat gatgtctgcg   8040
tcgagcatcc aaatgtccac ggacggatcg tcgctgctga tttgatatag gttgtacagc   8100
tcccgtccgc cgacagcacg ctcgcctcgc ggctcaaccg ccagaacctt gccatgtcct   8160
tctccgtgct cgtccaggta tatgacgtga tcaccgactt catagctttc ttttgtaacg   8220
aggcgtgaac gcgagctgtt ctgcgattcc actacccagg aatccagcac gccgcctttc   8280
atgtcgcgaa acaatcttgc cgatttgtcg caatcgaata cgcccagaac ttcgccgtct   8340
ttcaacacga tatgtacgat tggcaaaaga gtattcatgt ttaatctcca ttggttgata   8400
attagagtct aatctgccga aaagttcccg taaagaatta ttttctcata actgattagt   8460
tgcaactgtt aacctgatgt atatgtttga atctcttttg aacgtttgat gtttccccta   8520
taataagcgc acacagccaa caaccacgtg gaactacaat gtttaaactt tcctggatat   8580
tcgggcgcaa aaaggataat gctgcctgtt ctgaatcggc gccggagaaa gtcgcacaaa   8640
tccctcagca cgatccgctc gaccccatga tcaagctggg aaggattcgc ggctggaacg   8700
tcgagccgga gaaagccccg gtaattcgta gcgtgaaaga tttcctggag ccgggcctat   8760
ctgtagcaat ggatagtgcg tatggtgatg gaccaactcc ggcagcgaag gctgctgcgg   8820
gcggccagaa tccctatgta gtcccgacta tgttgcagga ctggtacaac tcccaagggt   8880
tcatcggata ccaagcttgc gcaatcattt cccaacactg gttggtggac aaagcttgtt   8940
ccatgtctgg ggaagacgca gcacggaacg gatgggaact caaatcggac ggcaggaagc   9000
tatccgatga acaaagcgcg ctgatcgccc ggcgcgacat ggagtttcgc gtcaaagaca   9060
accttgtcga actcaacaga ttcaagaacg ttttcggcgt tcgcatcgcg ctgttcgttg   9120
tggagtctga cgatccggac tattacgaga aaccgttcaa cccggatgga atcacacccg   9180
gctcctacaa gggaatctcc cagatcgatc catattgggc gatgccgcag ctcactgccg   9240
actcgacggc cgatccgtct tccgaacatt tctatgagcc ggacttctgg atcatcagcg   9300
gtaagaaata tcaccgaagt cacctagtag tcgttcgcgg accgcagccg ccagatatcc   9360
tgaagcctac atacatcttc ggcggcatcc cgctcaccca gagaatctat gagcgcgtgt   9420
atgcagcgga acggacggcg aacgaagccc cgctgcttgc catgtcgaag cgaaccagca   9480
ccattcacgt tgacgtggaa aaggccatcg cgaatgagga cgctttcaat gctcgcctgg   9540
cgttctggat cgccaaccgt gataaccacg gcgtgaaagt tctgggaatt gacgaaggca   9600
tggagcagtt cgacacgaac ctggccgact tcgacagcat cattatgaac caatatcagc   9660
tggtcgcggc catcgccaag actccagcca cgaagctcct cggcacttct ccaaaaggat   9720
tcaacgccac tggtgagcac gaaacgattt cttatcatga agaactggag tccattcaag   9780
agcacatatt cgacccactt ctcgaacgtc actatttgct tctggcgaag tcggaagaaa   9840
tcgatgtgca gctggaaatc gtctggaatc ctgtagactc cacgtccagc cagcaacaag   9900
```

```
ccgaattgaa caacaagaaa gccgctaccg acgaaatcta catcaactct ggcgttgtgt   9960
ctccggatga agttcgcgag cgtctgcgcg acgatccgcg ttccggctac aaccgactca  10020
ccgacgatca ggcagaaacc gaaccgggca tgtctccgga aaacctggcc gaattcgaga  10080
aggccggtgc acagtcggtc aaggcgaaag gcgaagccga gcgagccgaa gcccaggcgg  10140
gagccgtaga gggcgcaggc ggcccggttc ccgccgctcc acgcgcgact aagcctctcg  10200
cgaaggcggc cgaggaaggg gccagcgagg ccgctgaacc gccgtcgcgg ccggacccca  10260
aggccgagct gcggaacttg ttggtcgatc ttttgtcgaa gctccaagac ctggacgaca  10320
ttaaggcgcc ggacggcgta gacatagagc acaatgatgc gcctggctta aagcgcacgt  10380
ccaaacctgg cgtgtctggc atggagcctt cagtgttttc gtccaaccgc atcgtcgggc  10440
ctcgtgatca ttcggaactc cagagaatca aggtgaatgg aataaccacc ttgatcgaaa  10500
atccgcgcgg aagcattcgg caaggaaagg atgggagttg gcgagttcag atgaaacacc  10560
actatgggtt catcaaggga acgaaaggcg ctgatgggga tgaagtcgat tgcttcgtcg  10620
gtccgaatct gggatccaaa cgggtcttcg tcgtcaacca ggtgaacaag gaaggtcagt  10680
ttgacgagca caagtgcatg ctcggcttca acaacatcaa cgatgcgaag tctggatatc  10740
tgtcatgctt ccgcccaggt tgggatggtc tcggctccat ccatgaagtt gacctacccg  10800
ctttccgtcg ctggctggcg aacggcgaca caaccaaacc gtttggaggc gagtgatggc  10860
attcaaggcc tccaaaaagc gcgaacgccg ggcacctctt ccggtcggaa gagggaagcc  10920
cataattcca tcggcaggaa tcgaggcctg gtatcgaaag cagatgaagg atatttccaa  10980
gctcatgatc gccgactatc gaagcgagat tgagaaggca ctgtcccagc ctgcggccga  11040
acggttcttc gccagcgacg aatccgttaa cgtcctgttc aagatgaccc ttcgaagcct  11100
acagcagcga tggagccgca tttttgaagg tttcgcggcc aagatcgccc cggagttcgt  11160
caaccggacc gaagaagccg ccactgccgc gacccttcac agcttgtcgg tggccggcgt  11220
cgatcagcca cgagctgcgt ataatgagag cgtcaggaac accctggagg ccgcaaccaa  11280
ttacaatcat actctcatca ccaagatcca agaggaagtc cacgagaaga tttacacatc  11340
agtaatgctg tctctgactt ccccgaatcc ggaagagcaa ggaacttccg gcataactaa  11400
cgcacttcgc aaagtcggga agttttctga agatcgaatc gaactcatcg caagagatca  11460
aacaagcaag ctttacagtt ctctgagcga tgagagaatg gcggaaaatg gagtcgagga  11520
gttcgagtgg ctacactctt ctgccggcaa gactcctcgc cacacccacc tggagaaaga  11580
tgggaagaga ttcaagctga atgaccccag actttgggag ggtccgaaag cagaccaggg  11640
gccgccagga tgggcgatta actgtagatg cagaaagata ccagtcattt gacatcgata  11700
ggagcgctat atgccgttag ttcatggcac ttccaatgag gctcgttctg aaaacatcaa  11760
gcgggaaatc gaagccggta aggacccaaa gcaggctgcg gccatcgctt actccatcca  11820
gcgcagtgag aaagggaaga cggcgaaaga ttgttcgcct gagctcgtcg ccgatcttcg  11880
cgccctggtg gactctctgt cgaggctcgt gaaatgaacc gcaagacgtg ccggcgccga  11940
ctcgtggtcg atgtaatcag ggccaatatt cacggcggat tcttcagcct gaagtttgcc  12000
gccatcgatt tggcaatcat cggcgtcgcc atcttgatgg cttttggccg ataatgctga  12060
gaaaatctgg attctgacta aaaattctag tccggatagc cgcaagttac cgtttacgga  12120
aaatagcagt aatttggaaa gcctactgcc gcgaggcttt aacagagcca gttcctaatt  12180
tccgatttag ccgcatgctt caaaagtata tagcctgtga aattagaagt aacgttacaa  12240
```

```
tagaattcat ctataagtaa cgttataata taacgtcaat ctatatgctc tagacgtatt  12300
gaaattcaat ttttaatcgg taaattggta atttgaatta gtttagaagt tgaaagtctc  12360
gcggcagtag gcttagacaa atcccgtcaa gtttccgaga ccaaattacc ggattttcgc  12420
ggctgaggaa actggtaatt agatcataat acaaattata atgtaagtta acagtcgcgg  12480
ctacatctaa ttattgttcc gcttatttac ccttggatgt actgcgtata taatacagcc  12540
atagtccacg actcttcgaa ttaacgatgg caaagtcgaa aagaaaaatt gacgaaaatg  12600
gatatatgac catcgagggc tgcccgatca gctcttatgg cgttttccag tattctgctg  12660
gtcaactcgg tcttccgggc gatccgacgc ggattgtcaa cgtatatcgc ccggagtctg  12720
ccgtcagcga tccggagtac atcgaatctc tgaagaatct cccgttgatc gacgagcatg  12780
agatgctgtc gggattcgac gacgatgacg acagtgtggc ccccgaagac aaaggggtgg  12840
agggcatcat cacatccaac gcttactacg aagccccatg ggcacgcggc gatatccgca  12900
tctattcccg caacatgcag aatcagctgg aaaggggcaa agaagacctg tccctaggct  12960
atagttgccg ctacactgag caacccggca tctggaacgg aacgccttat gaagtcgtcc  13020
aggacaagat gcgcggcaac cacattgccc tggtaaaaga gggtcgtgtg ccgggggcca  13080
gagtattgga tggtctgtgt tttgaccatc tcagttttga tttcagacca tccgatgagg  13140
gtaatgaaat gagtctcaag aaagccaagc ggaagccccc tgtccagcgc gtagggcaag  13200
ctgctgactc ggcggtcgaa gagttgcgcg ccctgtggcc gaagctatct gcgtctgtcc  13260
agaagttcct gggcgaagaa gagcaggagc cggagcatca ggaaggcgca gctccggccg  13320
aaccgaccga cagcgagcac ctgaccgagc atccgactct ggaaggtgcc cagaaggatg  13380
acgaagagca ggaagaggag ccttccgttg tcgatccggc cgtggccgcc gtcgagccgg  13440
agcatcaaga aagcgccgca tccgaaatgt ccggtgaagg cgaagtcgcc gaactgatct  13500
ctcaggtcaa agccattctg gctcgactgg agggcacggt agccgaaggg gcagacgaag  13560
agcatggcga aggtcaagat gtcgtcgagg gcttggagga gcagagcagc ctcagcggct  13620
cgcaaaccgc cagcgacgat ggtggtgaga gcaaggataa cagcgaggaa cttcctgaaa  13680
tggcacagaa gaacgcgcaa gatgctgcaa ttcgcggtct ctatcgcgac attgctgcta  13740
aagatcgcct ctacaagcgt cttagctccg tggttggtgc gttcgatcac cgagctatgg  13800
actcggctga agtcgctgtt tacggcgtga aaaagctgaa catcagctgt gcgaagggcc  13860
aggaagctct ggcgctcgac atgtacctga aaggcgtcga agcctcgcgc ggcgcggcca  13920
gccgtcaatc gaaagcccag gattcggccg gttctgctcc gcagtgcgcc gagctggaca  13980
gctacctgaa gggggagtaa ctcatgttcc agaaacaagt ttaccgccag tacactcctg  14040
gttttccggg cgatctgatc gaggacggcc cgaagcgggc gcggccgggt cgaatcatgc  14100
ctctgtctgc cgtaaatccg gctgccaccg ccaccggccc caaccgcatc agtcgcgctt  14160
tcggttacgc cggtgacgtc agcgccctcg gcgaaggtca gccgaagacc atcgcggctc  14220
gcgcttctga agtcgtgatc ggcggcgcca acttctttgg tgtcctcggt catccgaagc  14280
actatgcgct gttcggttcg gccggagact ccctggctcc cagctatgat ctgcccgatg  14340
gcgccgaagg cgagttcttc gacatggcca ccggcctggt cgtcgaaatt ttcaacggcg  14400
ccgcaaccgc cctggacctg gactatggtg acctggtcgc ctatgtacca aacaacctgc  14460
ctaccgccga caacgcgctt ggcctgccgg ccggcgccct ggttggcttc aaggctggct  14520
ccatgccgac cggcttggtc cagattccca acgcacgcat cgttaacgcc atcagtctgc  14580
cggcccagtc ggcggggaat ctggttgctg gcgttaccat cgtccagctc acgcagtaag  14640
```

```
gaggcgtcat gagccagatc agcaagaccc attcgcgcct cgcaggccgc aatgcgaaac  14700
ctttcgacct gaaaaacatc accaatgacg ccgtggcgtc tctgcgccgc atcggcctgg  14760
tattcgatca cgccgtcgtc caggaccaga tcaaggcctt ggcgaaggcc ggcgcgttcc  14820
gctccggctc ggccatggac agcaacttca ccgccccggt gaccacgccg tccatcccga  14880
ctcccatcca gttcctgcag acctggctgc cgggcttcgt gaaggtcatg accgctgcac  14940
ggaagatcga cgaaatcatc ggcatcgata ccgttggctc ctgggaagat caagaaatcg  15000
tccagggcat cgtggagccg gccggcactg cggtggaata cggcgatcac accaacatcc  15060
cgctgaccag ctggaacgcc aacttcgaac gtcgcaccat cgttcgtggc gagctgggta  15120
tgatggtggg caccctggaa gagggtcgtg cctcggccat ccggctgaac agcgccgaaa  15180
ccaaacgcca acaggcggcc atcggtctgg aaatcttccg caacgccatc ggcttttatg  15240
gctggcagag cggcctgggc aaccgcacct atggttttct gaacgatccc aacctgccgc  15300
cgttccagac cccgccgagc cagggctggt ccactgccga ctgggcaggc atcatcggcg  15360
atatccgcga ggccgttcgc cagctgcgta ttcagagtca agatcagatc gatccgaagg  15420
cggaaaagat caccctggcc ctggccacca gcaaggtgga ctacctgtcg gtcaccacgc  15480
catacggcat ttcggtttct gactggatcg aacagaccta tccgaaaatg cggatcgtgt  15540
ctgctccgga actgtcaggc gtccagatga aagcccaaga gccggaagat gctctggtgc  15600
tcttcgtcga agacgtgaac gcggccgtcg atggaagcac cgatggcggc agcgtgttca  15660
gccagctggt acagagcaag ttcatcaccc tgggtgtcga aaagcgggcg aagtcgtatg  15720
tggaagactt ctccaacggc accgccggtg cgctgtgtaa gcgtccgtgg gccgtggtgc  15780
gctacctcgg catctaaccg atgcctattc accaaaggcc gggtttccgg cctttgttca  15840
ctctgactct gactcggttg taggggccgg ttagggcata attactagga ctacgccaat  15900
gactgtttac atcgtttccg ccatgactca atccgtgtct tacaatgcgt atgacacctc  15960
tgatccgtcc aatcctcgcc tccagcgaaa gattctgatt cgtggccgcg ccggcatcgc  16020
atccgaaact tccggcttcg gcgacatgat ttccgacgcg gccgggcgtc cgatctggac  16080
cccgcagggc gattgcactg ccgtgagcga ttcggatttc gagctgcttc aggccaataa  16140
gattttcatg cgtcacatgg ataagggcta tctgcgagtc gtgaagacag acatcaccag  16200
tgaccaccag cggattgcca aagagactcg caccatggag cgcgatggat tccagcctct  16260
ggacgctgct cgtttgcagc agaaaatcaa ggttaccacc gccagcgctt cccaggaaca  16320
agagttccgg atttaaccga gggtttcggt atggtgattt tcgacgaaaa taagtttcgc  16380
acgctgtttc cggagtttgc tgatccagcc gcttatccgg acgtgcgcct gcagatgtat  16440
ttcgacattg cgtgcgaatt catttctgat cgcgattcgc cataccggat tctcaacggc  16500
aaagccctgg aagcatgcct gtatcttctg actgcccacc tcctgtcgct gtccacgatg  16560
caagttcagg gcgcggctgg aggtggcgtc acagcaggtg ggactcaagg cggtttcatc  16620
accagcgcta ctgtcggcga ggttagcgtg gctaagctcg cgcccccggc caagaatggt  16680
tggcagtggt ggctgtccgg gacgccttat ggccaagagc tgtgggcgct cctcagcgtc  16740
aaagcggtgg gcggattcta catcggaggt cttccagagc gccgaggctt ccggaaggtt  16800
ggaggaacgt tctggtgatc cctggtgcga atcttctgcg aatggccttc ggggtcatcg  16860
gtactcaaat tgtgaaatat cgcaagtttg agcagcgagt gaagaatgat caagctcagt  16920
acgtttccat gttcgaggag cctttcgacc tggcagcgtc tgtccagcga gtccgacgcg  16980
```

```
atcagtatgt ccagtttaat ctggagttcc aacggaatta tgttatgatc ttcgccaact  17040
ttgagatggt tgacttggat cgcgatgtgg ccggtgacca gttcctctgg accggaagag  17100
tttttcagct ggagtctcaa ggctcctggt tttatcaaga cggctgggga gtttgcctgg  17160
ccgtggatat cggtgcggcc aagctcactg atgacgggaa accgactttc taggtgatgt  17220
atgtttgacg gcgaactgat agcgaaaatg gttgtcgagc tgaatgcggc gatgacatct  17280
gctcaagagg ctttgcagtt cccggatttt gaagtcgtcc agaaagctca gccgacccaa  17340
cagggaacgt caaccaggcc gaccatcttt ttccagaaac tgtttgacat tcctcgcggc  17400
tggcctgcca ccgattggca cctggacaac aaggctcgca aatatgtaga aataactcga  17460
cagcatgtag agacgacttt ccagattagt tcccttcatt ggcagaatcc tgaaataact  17520
cacgtggtta cggcttccga tatcgccaac tatgtgaggg cttatttcca agctcgatcc  17580
acgattgagc gcgtaaagga actggacttc ctcattcttc gcgtgtctca aatttccaac  17640
gaagcattcg agaacgataa tcaccagttc gaattccacc caagttttga catggttgta  17700
acttacaacc aatatattcg cctgtacgaa aacgcagcat attcggccga tggggtatta  17760
ataggcatat gagtctgagg cgcgattcag aactaatcgc cgcgcacctc cagatgttaa  17820
gagccatgcg cggcaggtcc gtttcggccg gatggtattc cacggctcga tatcctgaca  17880
aggcaggcgg atcggtcgga atacaagtcg cgagaatcgc acgtctcaat gagtacggcg  17940
gaactatcga ccatccgggc gggacaaggt atattaggga cgccattgtt cggggccggt  18000
ttgttggcgt tcggttcgtc agaaacgact ttccgggaga aaccgaggta actaagcctc  18060
acagaattac catcccggct agaccgttta tgcgatatgc ttggaacttg ttttccgcag  18120
atcgcgccgc aatccagaac cggatagcca tgaggctggc cagaggacag atcactccag  18180
atcaagctct tgcccagatc ggcctggcgt tggaaggata catagccaga agcatcagga  18240
ccgggccatg ggtggctaac tcagcatcta cggtcaggag aaagggattc aacagaccgc  18300
tggtcgatac ggcgcacatg cttcaatcga ttagcagcag agtaacataa ccaggagatc  18360
atccagtgat cagtcagagc cgttatatcc ggatcatttc gggcgtaggc gcaggcgctc  18420
cggtcgcagg ccgaaagctg attctgcgcg tcatgactac caacaacgtc atcccgcccg  18480
gaatcgtcat cgagttcgac aacgccaacg cagtcctgtc atacttcggc gcgcagtcgg  18540
aagagtatca gcgggctgcg gcttatttca agttcatcag taaaagcgtg aattcgccgt  18600
ccagcatcag cttcgctcgc tgggtaaaca ccggcatcgc gccgatggtt gttggtgaca  18660
atctgccgaa gaccatcgcc gatttcgccg gcttctcagc aggggttctg accatcatgg  18720
tcggcgcggc cgaacagaac atcaccgcca tcgatacgtc cgctgcgact tctatggaca  18780
acgtggcgtc gatcatccag accgaaatcc gcaagaacgc cgacccgcag ctggcccagg  18840
ctaccgttac ctggaatcag aacaccaacc agttcacctt ggtcggcgcc accatcggca  18900
ccggcgtcct ggctgtggcg aaatctgccg atccccagga catgtccact gccctcggct  18960
ggtccacctc caacgtcgtc aacgtcgccg gccaggctgc cgatcttccc gacgcggccg  19020
ttgccaagag caccaatgtc agcaacaact tcggttcgtt cctgttcgcc ggtgcgccgc  19080
tcgacaatga ccagatcaag gccgtgtcgg cctggaacgc ggctcagaac aaccagttca  19140
tctacacggt cgcaacttcc ctggcgaacc tcggcactct tttcaccttg gtgaatggca  19200
acgccgggac cgccctgaac gtgctgtcgg cgactgctgc caacgacttc gtggagcagt  19260
gccccagcga gattctggcc gccaccaact acgatgagcc gggcgcttcg caaaactaca  19320
tgtactacca attccctggc cgcaacatca ccgtttccga cgataccgtt gcgaacaccg  19380
```

```
tcgacaagag ccggggcaac tacatcggcg tcacccaggc caatggccag caactcgcgt  19440
tctaccagcg cggcattctg tgcggcggtc cgaccgatgc ggtggacatg aacgtctatg  19500
ccaacgaaat ctggctgaag tcggctatcg ctcaagcgct cctggacctg ttcctgaacg  19560
tcaatgcggt tccggcgagc agcactggcg aggcgatgac cctggcggtg ctgcagccgg  19620
ttctggacaa ggcgacagcc aacggcacgt tcacctacgg caaggaaatc agcgccgtcc  19680
agcagcagta catcacccaa gtcaccggtg atcgccgcgc ctggcgtcaa gtccaaaccc  19740
tgggttactg gatcaacatc accttctcca gctataccaa cagcaacaca ggcttgaccg  19800
agtggaaggc caattacacg ctgatctatt cgaagggcga tgccatccgc ttcgtcgaag  19860
gatcggatgt gatgatctaa tggtttgcgg cggactcgat ccgccgcgac cttccataaa  19920
tggagtgagg aataaacaat gatcaacatt tctgcgttcg gctcgatctg ccagttcacg  19980
gcaagtagaa ctttcccgaa cggattcacc gtcaccgagt ttgccgacga tgcggacccc  20040
atcgacagcc cgccgttcac tgcggccgat accggcgtcg gcctcaacgg tgacatggta  20100
gtctggaacc gggcgaacat cctggaagtc gtcgtcaacg ttatcccgaa caccgagggc  20160
gagcgcaacc tggcagtcct tctggatgcc aaccgcaccg gaaaggacaa gtcgggcgct  20220
cgtgatgtcg tcggtttggt cgtggcgatg ccggacggca gcaaaatcac ctgcaccaac  20280
ggcaccccaa tcgacggcgt tctgatcaac gcggtggcaa gcgtcggccg tctgaagacc  20340
aagccgtatc ggttccgatt tgaaaaagtg atcaaagccg gtactagctg atgaagaaaa  20400
ttccgctgac agcagtcccc aatcaagcga tctcatttaa cgccggtagc agctattgga  20460
agattcgcct gtaccagaac atggacatga tgaatgccga tatcagccgc gacggcgtga  20520
tcgtttgcca tggggtccgc tgcttcggcg ggattcctct tctccagtac agccatcagt  20580
accgacctga ctatggcaat ttcgtcttcg accgcgacgc cgattggaca ttgttcggcg  20640
acggcatcaa cctgttctat ctggacggcg ccgaattcgc cgagtatcag gcgcttgcca  20700
cgaggaaaga atgagcacat caacgatcag aaccgggacg aacaacgata tccttttgga  20760
cgacaatgga aacatggtta tcctcaggga tgtcgaagcg tgcgcccagg acgttcgggc  20820
ggcgatgctc atgcgcaccg gcgaaaacat tttcgatgtg aactccggcg tgggatattt  20880
cgaatacatc ttctcgccgc agaaaagcta tgatgacgct cgcaaatcca tcgcggacgc  20940
aattttatcc tcaccggatg tgaccggcat cgagcagctt gacatcgaca taaccgggga  21000
agtcttcggc gtcgatgcga aagtcatcac catccacggg cctgttacca caggagtttg  21060
aaatgagtac catccgcatc caatacgcca acggcaccca actgttcctg gacggcaaaa  21120
atccgccgcc cctggacccg ctaccctcgt ttaacccgtc tgtcgaagat ctggaaggcc  21180
tggaccgcga aaagaacacc gacaagggcg actcctctcc ggccggtctt cccgttcccc  21240
cggtaaacgt cgattcagat gtcgacaacg gcggaaccat cccggctccg gtatcgaccg  21300
acgctgctgc ggccgaatcg gccccggaag gcgcccagga agctcctgca gcaggccaag  21360
gcgacgagaa aggcgccgag gaagccccga ctacagcccc ggtagaaaag gccgaggaaa  21420
cggcctcgcc ggccgctgaa gaggaaaccc cggctcccgc caatgccacc tctcgcaaaa  21480
ccaccagcaa gtaaggactc gacatgatca acgtcagcgg cttcggcacc ggaattgtaa  21540
tagtttccgc ctcatcgttc ccgatggggt tttccttgtc gaagttcgct gatgatgaga  21600
gtccgatatc ctccaaagag ctggagccgt tcggatatga gatgctttat gacggtggcc  21660
tattcgcctt tgacaaggct gctcctctgg aagtatctgt atccgtcatc gcagggagcg  21720
```

```
aggatgatat taaccttcgc atccttctca attccaaaaa gggatcattc agatttcttc  21780
cgggaatcat cccggacatg acgactctcg tggccactct tcctgatggc ggccgcaccg  21840
ttctgtccaa tgggactatc atcaagggtc cggccatcga caccatacag aacaccggac  21900
gacgcaaagg caacacgtac acttttgttt tcggtagcta tcttggcgcc cagactgctc  21960
gtcaagccat ttctaacgtt atccaatcgg tactggaggt ggtctgatgt tagggatttt  22020
caccagcctc ctaagttcgc gatctttttc gattgtggac caaaacacaa accagctagt  22080
tgctgcggat ttgaggataa gccgggtcaa cacccggttt tcttctgtag ggcaacgcca  22140
catgctggaa gatggtacga ccaagatgga ttccagaacg atccacccta tggaaatcat  22200
cgtcgaagta ttttgccctt caattgatgt cgtcgatcag atcaatcaat tgctcctgga  22260
tcgcgacaca ctgtacaaag tcatcactcg cggcatggta ttcgaacgga tgatgtgtac  22320
cagcgaagcg ctcaatcaga ctccggatat gatatcggcg actcctgcgc ggctgacatt  22380
ctcccaagtt ctcgtccaga atcccaagcc tataatgttc agaaatgcag ggactcttc   22440
tatgatcgac cgagggctgg ccctagctga agacgtggtt ggctcggccg gcgatctgtt  22500
cgactacgca gtgaacggcg tccagaacgc cgcagacttg ttctgaggtg ccaattgaac  22560
tctttcctca agtctattct caacacgcct actctcacca tacgcgatga tgtcaccaaa  22620
cttcctgtct ggaagagtct tcaagtcaag aaagtggaaa tttactcgcc ggcttccgta  22680
gtgtcgaaac ctctggcgac gaaagaccag acggaagctc aagtgtacac cgaagctctg  22740
gacattgatg tgaagaatgg aaagatcatc caaccggtgc gactccgcat caatgctatc  22800
tgtccggacc tgtccaccgt tgaaagtatc atgaacgctt tcaatgataa cacctcgact  22860
ttcgctatca cttctaagtc gatattggcc gataaaatgg ccatcatgac gctcgatgta  22920
gatcagtcgc cagacatgtt gaacgcggct gagatcaata tggaattcga gcaggttgag  22980
cctccagtat tgaatgaatt cgatcctgcg ttccctcaag atagtccgac ttatggggta  23040
cagattcaat ctctttctga tgctaatttg ctggatttgg gcgccatcgg cgattcgata  23100
tcttcggccg caaaatcgct atataatcgc gtgaccagct acttctgagg atgtatcatg  23160
cttgaaatca atcttcccga tggccgtcaa actcgcgtac aaatcgaggc gtggtcggca  23220
ttggatggct gggaactcca gcgccgtttc gtcgaattcg ctgtcagcca agattccgac  23280
ttccgccgct ctttcaccat ggaaatcctg ggctatgcga aagtgctgct tggcgacgac  23340
gacaccggta ttccgctgac cactgcggcg gtcatcaaca accacctcgg ccactggaag  23400
aacgtggaac tggttttcaa ctctgttctc aagcacaatg gcatcgaccc ggccacgcac  23460
gccgaccggc cggactattg ggaacaagtc ggatcgcaga tggccatcgc atttctggcc  23520
gaggcgtcca agctcattgg tccagcaatg aagatcgccg aaggactcgc caacaagccg  23580
gagtgattca tgtctagtga tttggatgaa ttcatacttc ggtatgaggc cgatactgcc  23640
agagccgagc gcaatctgga gcgcctccag aaccagatca ggcgcgtgaa cagcgcatcg  23700
acgagtggcc ttcaggattt gcgccacttc gcagacggcg cggccactga actcggccga  23760
gtcgttccgc agatcgattc tgtgacgagc gcgattcgcg ggatgaacgc gcaactggcg  23820
ataggcgcca ctggcgtggc cctggtcgcg gccggcgtca aggcgttcat gaacaccagg  23880
gaccagtaca accagcaacg catccaggcg atggatatcg gcatcgcccc ggcgcgactg  23940
gaagagtacc agcggaagtt tgctcgccag tctggaggca cgatcagccg cgagcagggc  24000
gcggaaatga caaaaaatct ggccgacact ttccggcgag cttatcgcga tatcggacgg  24060
gtcggcccgg aagcgcgaat tctgcgtatg gccggcgttg atgtcgggag cttccaaaag  24120
```

```
ggcatgcggc cgctcaacga catcattact gatctggcca cgaaaatggc caagctgaag  24180
ccggacgaaa tttctgccta cgctgatgcc cttggcgtct cgcgagacta cctgagcacc  24240
ctggctaaga tcggcccagc catgggaaaa gtcaccgaga tgacgactgc ggaactccag  24300
tccagggtcc agggcgagtc caacattcag aaattcaacg atgctctggc gaatctcaac  24360
cagacgttca ccaccctgga aaaccgagtc ggcgaaaagc tcgcgcctgc gttcaccaag  24420
ctgatcgaaa tcatcgacaa gatagtccag gctattccca atgaagtgga agaattcgcc  24480
aaggacacca aagcccgctg ggatgacggc atcaccggaa aggctacggt tggtggtgat  24540
atcctttccc ttctcagccc tggcgccctg ctaggccgcc tggcctcctg ggaactcgg  24600
cgtgggatgg aagaggcagg cctgatcgac aagtcgaagg ttcccggcgc tcaaaccagc  24660
gaagacctgg ccaagaaaca agaagaccag gacaaggcta ctaagtccat gaaagagcta  24720
gagaagctgg ctgaccagac cacgaagtct accaatgatt ttgcggtggc gatcaacatg  24780
ttcagtggcg cggtatcgtc gttcgcgaat gccgttgacg agcgccaagc ttgggcagcc  24840
tgggcggggg aaattggtcg ggcggtcggt atgggaagca ccgcgccgac ttcgcgggcc  24900
accggcgtct atccgcacgc gatctatgat cagtcgaaga gtggcgcggc cggacaggtc  24960
ttcggcgagc caatcggcgc ccagtctctt cgcaatcgca tgttctcgcc gcagcgcaag  25020
gccgaaccgg tcaccgttcc atcgtacatc aacgatatca tcaaagatgc ttcgaagatg  25080
tacaacattc ctgagctgga catcaagaaa ctcatataca ccgaaagccg attcaacgcc  25140
agggccacca gcgaagccgg agctaaaggc ctcatgcagc tgatgccgga aatcgccaag  25200
gcgtatggta tcactgacgt atatgaccct cgccagaaca tcctcggcgg aacgcgccta  25260
ctgcgggaaa acctagatcg agcaaatggc gacatgcggt tggccttgac ctactatcat  25320
ggcggactcg atccgaagaa ctggggccca aggactcgcg catatccggg tttggtaatg  25380
agcgctccaa tcgagctgat ggaagaggct cagcgcaagc agaaggctgc ggccatgacc  25440
gtcgccaacg agacgttcgc cccggaaggc ggcgacatgg acattcgtcc ctatgatggc  25500
gggcgactgg aaaccccaga ccagggcaag aaggaagatg agcgccgcga agcccgtcga  25560
tatgacgaca gggttgtgcg accggaaatt cgcatcatcg accgcatgcc agaccgcagc  25620
gacggcgaaa tcctcaagat gtctagacgt caagaggccg accgggcaga ttctggattc  25680
cggaagttcc cgaatcaagt tcgcggcgag accaagcaga acatccaggc tcaactcact  25740
gcaggagcca tcgcgcaagt gatcggcgtt aaccccaacc agatcatgcg ccgcgaaatc  25800
agccgttctg acttgctgtt cggatacaac caagccatcc tggcaagca acaggagatc  25860
aaggccgccg cgaccgaagc caacaacgta ttcctgtctc cagccaagct tgccgaagcc  25920
acggccaagg tgaacgccgc atcgcgagaa atggatattc tcaggacgta cggcgagcaa  25980
cttctgaaga gcgctccaga gcgcggccag gagctgacca tcggtcggat cgacatgttg  26040
gtcaacgtca ccggcgcgaa ttctccggaa gaggctcgtg agatattcag caagcagact  26100
gcagaccagc tgactacggc aatccaggac gctcaaaacg attccgcaac taagatactc  26160
tactgatgaa aaagagaatt ctgcgagtaa cattcaacat gccttatgga cccgaagtca  26220
tccgcgaaga tctggatgtt cgggtccgga ttatgaaggc tgcgttgcgg attcagaacc  26280
gggcgacgat ggaaattttc ggcctcacca ctcagctgcg cgagtctctt ctgtcgcagt  26340
tcaccgcgtg gaagcaccgg caacgtcaag tgggcaggga agatgaattg atgatcaagg  26400
tgtcggtgga agccggctac tctgaccagg ggcgcgagca agtttccaga gtctttgtcg  26460
```

```
gcgaagttgc cattgtcgat atcatttctc cgccacctga cattggaatc cgcatccagt  26520
gctataccag gcaaatcgac aggacgaaga ccattcggaa tatgccgccc gccaacacga  26580
cgtttgtcaa gttcgtcgag tggggcgcga acgaaatggg attgaacttc atctgcgata  26640
ccagttacaa cgatcaagtt ctgaagaatc cgggccggtc tatcactgtc gcgtcggcaa  26700
tcctggcgtc gattcaggat atgtacatgc cggacgtggc cgcgttcgtc gatgatgaca  26760
tattgatcgt gaaggaccgc gataaagtca ttcgtccgga tgaggtgacc aacgtcaact  26820
cgtttgttgg aattccatct tggtctgaat ggggcgtgga attccagtgt ctgtttgagc  26880
catcgattcg tgtggctgga ggcgtagcgg tcgaatctct catgaatcca agtgttaatg  26940
gtaactatgt aataactgct ctggaatacg agttggccag tcgggatcgg ccgttctata  27000
tcaaagtcat ggggagtcca gcagcataat ggccagggaa atcaaatcat tcaacatgtt  27060
cggagttcac tatacttcgc ggcaattctc tgctgtcgat gggctcagca tgatgtcgga  27120
aattcagaac gtgccgccag aagaattgct caagggtact gatgtattgg cgcatccgga  27180
agaccatccg gaaggcatct ggcttccatt gactgctgcg aacatcaatc tttatgtcgt  27240
tgatcgagcg aaagtaatag ctcccgtaca agttcttgca cttctgtccg aagtggtaat  27300
cgactggaac tttggttttc tcaaagactg gaccggagtc aagattccat ccagatttgt  27360
cgaagatatc aaaagcgtga agacggcaca ttcaccttct gtagttgcga gcttggtcgc  27420
gaacggctca gcctctatgc gcgagttgga agagtattat tcgactcaag atgcgtttaa  27480
gatgatagac atcatgacgg cgaagagcgt gaacgaggcc ttggcgtccg aagcatcgca  27540
caacagaatc aaaaagggat aattcctaac cgggcctggg aaggctatac tagacctgcc  27600
aaatcagagg ctttcccatg tccaatattt ctctaacatc cgcaaaagct cccgacagga  27660
cgcgactgat cgccgctctt gacgctcggt cgcggcggga tgctctagat ttcgaagtaa  27720
tgataccggc tcaggttgtt caatatgaca gggccgagaa tatcgcgacg attcaacctc  27780
tcatcacctg ggttgacacg gaacacaacg ccgtccaaag gcatcagctg gttgatattc  27840
ctgtaatttc catgggggct ggcggcttcc acataagttt cccgattcag caaggtgaca  27900
taggctggat ttatgcggcc gaccgcgaca cgtctcagtt cctggagtcg ttgtcaatgt  27960
cgaagccgaa caccggccgc atccataagt tcgagcatgg cctgttcatc ccggacgtat  28020
tccgtcgata caccatcaat tccgaagatt cggccgctat ggtcatacaa tcgacttccg  28080
gagcgaccag aatttcgatt cgcggcgaca acatcaagat cactgcgccg tcgaatgtca  28140
ccgtggatac tccgcaggcg aatttcactg gtgatgtgac tatcgctaac actctggttg  28200
taaacggtat caacgtgaac aaccacggcc acctcgaaaa caacccgcct gatgcccgga  28260
cgaagggcgg catgattgct taaggagaat ttcatggcaa gttttgattt ttctgattta  28320
acagcggggg ggtgtaatgg ctaactacaa ctacatcgtc gatactggtg tgatagtcgc  28380
agataccgcc gacgttctga gtgacgttga agccgagttc cgcgccgccc tcggtgccaa  28440
tatcaacttg gccgcgagca ctccgcaggg atcgcttgtc gcggccgagg ccatcgcccg  28500
ttccagtgtc atgcggaatg aagcgcgaat tgccaatacc ataaacccga acgtttcatt  28560
cggaacgttc ctggacgcga tctgtgcctt gatggggatc gagcgcggtt ctgacctgtc  28620
aaccttcggc tatggagttc aagtcaccgg ccgcagccaa acccgcattt ccaacgggtc  28680
tagggtccag actccggccg gcgcgatctt cacagtgatg agtgatgtca cgattcctgc  28740
tggtggtgtc gcgaccatcg atatcaaatc gcaggagtat ggcaacattc ctctgccggt  28800
cgggaatctc atcatcatcg acggaacaat tggctggtcc ggagcgaaag tcatcgcctc  28860
```

```
cactcgcgtc gatccgggca gccgccaaat gagcgatgca gagttgaaga atgcccgcgt  28920
taatcgattg gccatccaag gccgcaactc gactatggcc atcaaggcgt atgtgagcgc  28980
cgttccaaac gtcacgtcgg tgaacgtaat cgagaacaac accggcgccg ttcaagtggt  29040
gaatggagtc tcgtttaccc ttccgtatgc tgtttgggtc tgcgtcgccg gaaacccgga  29100
taaacaagca gtcgccgatg cgttgtgggc cgcccataac ggcggaactc catgggacta  29160
tggtgcgacg aacaacggcg tcccggtgga cggtccgaat ggcgttcctg tgcgcgatcc  29220
ggcgtccggt cgaaagtatg tcgtgaagtg gaccactcca attatgtacg atggatatgt  29280
taacgtaaca gtccagcaag gttcctcctc tgtagctccg gaagccattc agaacgcagt  29340
ggtcaattac gcccagggga aagtggaagg ggaagagggg ctggtggtgg gcgcgagcct  29400
gtcggcattc gaagtcgccg gcgccatcgc tcgcgaaatt cccggcatct acatcaaact  29460
ctgccaggtc gcgtgcgtcg cggctggctc gccggctccg gctccgggcg atttcacttc  29520
ggaatacgtc atgagcgcat tcggccaggc taccatttcc gttggtaacg ttcgggtgac  29580
tttcgtatga ctctgcctgc gtacaattcg gacatccaac aagctctgaa atggctccat  29640
aaccaggcgc ctggaatcac cggcctgatc cagagaaagg cgcaatggta tgacagattc  29700
agccgccaat tctgggccaa ctgggagcgc gacgttttcc acttgaaaac tgccaacccg  29760
ttcggcctca tggtgtggtg catcatcctc ggcacgccgt cgaaaggatt cggcctatat  29820
ccaaaaaaca gttcttgggc attcggtcgg ctacgccaga acttcatcta tagcggtaca  29880
caagttccgc caccggcaga cgcatcgccg ggcggcaact tctacggtgg cggcaatgcc  29940
gaaattctca acttggacga aatcaggaaa gtgcttcagc taagatatgt agcgctgatt  30000
tcgaacggct cgattgcata tatcaatcgc atgcttcgct acatattcaa tgatgatgag  30060
ccgtgggacg aggcgaccgg tctgtacttc tatctcatgg actcaaccgg cgaggatggc  30120
cctgtggaga acttggccat atatcggaaa gattgggaag gtatggtgct gttgtacagt  30180
tcgcccagaa cgaaccatgt gctgacatcg acccctgcca gcgacgccga ttggccggga  30240
gtcgatccgg ccgcgagcgg ccgtccggta acggtcgaaa cggcgtccgc tacggccccg  30300
gacggctccg ctacggtgtg caagcttact aagccggccg ggagtaccgc ttacgtctcc  30360
gcgccgatag atgggccgct ggggtccggt agcactgtaa cgttctcgtt cttcgcgaaa  30420
gccggctcca cccgtttcat tgcaattcag tcggctgccg atttccccag tcgagccgat  30480
gccgttttcg acctggattc cggcgcacgtg atcagcgatc agatgttgga cagcagcgtg  30540
gtaagcgccc gaatgattcg tctggagaat ggctggtggc gttgcgttct cacgaccaag  30600
accgtcagct cttcgttccg cgctgcttac gtcgcgccgg cagaaaccaa cttcagctgg  30660
attgattcta attcaagtat ggcgattgac gtgcttatct ggggcgctca gatcgaactg  30720
ggtgatactc caaccggata cttggagact accggggcgc ccgtaaccat caccgattat  30780
gtcttgcaga atgcccagac cggaacggtc gagttcaccc agccccttcc gattggagta  30840
gaagcgtatt ggactggcga ctggaaaggc gggtctgcga ccgagccggc cagattcgcg  30900
gtaggggatg ggactcaaga tacattcaat ctgtccagtc ctgcatacat aggcctaccc  30960
actagtgggg cattcaagtt agaatacaga gttggtccgg cgcttaattt gtcgccgcaa  31020
ttgatcaacc tcatgaatga ccgggcggtc ggtatcatgc cgacttgcgc cggttgcgat  31080
gtaaaagtca ttcaggagta atgacgtgat cacacccgaa ctgataccca gtccgtttgc  31140
tgcgcagggc gacaaagacc cgatcccgca gacctcttcc actggctttg ccaaccttcg  31200
```

```
cgatggctac acgccggact acgaaatcag tctggagtcg aacaacccgc aggccaaagc  31260
ggtcgagcgg aaaattcaaa accaactctt cttcatcgcg acccagaacg cacaggcgtg  31320
gcagcggcaa atggcgccgc cgtggtttca gggcatgccg ggcggctacg aacagaatgc  31380
agaagtcgtg cgcgtcggaa atgacggcat aatgcgtcgc tatcgttcca tggtgaatgc  31440
caatgcgagc gaccctctta gcagcacgac ttgggaagaa caacccgcct ggtcggtgat  31500
gcgctccagc atcccgatgc cggctggagg cccaggccta tcttctggcg gagaagtcat  31560
cacgactggc cgcaacttca acgatttgtt gaatgggacg tgggagttct tctctgattc  31620
agtggttatc gcttctcaga atgccccgt atatccggcg tccgctggtg ccgctgctgg  31680
catgttggag gcgaaatctt ggatatccgg gtccaatacg ttctgcgttc aacgctacac  31740
tgaccgcgtc gggaacgtcg ctgtgcgcgg gcttaatgcc ggggcatgga ccaactggat  31800
gtatgctgta aacgtcatgg ccctccaaca aggtcgagtg acctatggag tcgcggccgg  31860
cccggcgaac gcttacacgt tgacgctcgt tccgcagctc caaggcggcc tggtggacgg  31920
catgatcctt cgggtcaagt tcaacaccgt gaacaccggc gcctctacca tcaacgtctc  31980
cggactcggc gccaaagcca tcgtcggcgc ggccaacttc cctctcactg gcggcgaact  32040
tggccaagga ctcatcgctg agcttgtctt cgacgcagca ggcgaccgct ggaggattct  32100
ggcaggcgcg ccgcgcatcc aagtgggcaa cgcagatcag gactaccagg cccccagctg  32160
gaaacaggtg aaggactatg tagcgtccca aaagctcacc gaagtggatt gggccgatgt  32220
cgtcaacaag ccgaacgtcg ccatccaaga caccacgccg tggttcgcca atctggagct  32280
gtctgacgct cggcctttca tcgattttca tttcaacaac aaccgcgcca aagacttcga  32340
ctatcgcttt atctctgagg ctgatgggtc gatggcattc tattctcgcc aggggtctgc  32400
cggtcctacc caggacatcc tgttcagcag gtcgaatgta acattcctcc agccgcgact  32460
ggatgttgcg aaaaacctcg catacatcgc gaactctggt cctctttggc agaacaccac  32520
tgccgatcag cctggttgga aattcacctt cgcacaaggc gtggacgcca acaacaacgc  32580
ggtgatagca gtcaatacca ccaatcctga cggctcttat cgctcgcaaa tcatgcgatg  32640
ggactgggcg tccacgaacg tcatattcaa caatcgccct ctgtttgctg gacaatacgt  32700
tccttgggac tccggaaact ttgatccagc caccaagctc actgtcggga ctaccaacaa  32760
catttcggga ccgaccggaa ttcgcaatac caccagcaat accggaaata tgaacacctg  32820
gggctccagc tccacaactg catcgtatgg aaacgcagct cttcaaatct tcggcagagg  32880
gggtggcgag cctgcggcca tctacttcga caactcccaa accggctggt atttgggtat  32940
ggacaaggac ggccagctga agcgagcagg ctggtcgctc ggcaataact cctatgtggt  33000
caccgacgag tcgaatattc gtttccacgt gaattccatg gctggcactc cggtatgggg  33060
cggaaatgaa ttctgggggc cgtggaactt caacccgaac accaagctga ccattaaagc  33120
cggcacgcag gaaactagca gcactgcgat attcagcgga acgatgccgt tcgccccaat  33180
cgcgtctctg tcagactatt cccaggcgcc gttgacggtt tacaactcgc cgactggtcc  33240
atctgctaag cctgccgtca tcgcgttcat tcgccctggc aactggggag cgttcttcgg  33300
catcgatacc gacaacaagc tgaaatgggg cggcggatcg ctcggcaaca gctccaggga  33360
gatcgccgat tccagcaaca tcatgaatct tgggcggcc aacccgaccg cgccgtcctg  33420
gaacggccaa accgtttggc gatccgggaa ctttgatccg gcaacgaagg tggatttgaa  33480
cgccgcgaac gccaccaacg gcaacatgat cttcaaccgc atcgccggaa ctggcagcgg  33540
gatcgcctct tcaggccgcg tcggcgcaat cagcctccag aacggcgcaa cggcaggcgc  33600
```

```
ggccgcagcc gtaacattcg agcggggcgg tggtttcttc gtcaacttcg gtttggacac  33660
cgacaacgtt ctcaaagtgg gcggcggaaa cctgggggcg aacgcctatc ccatcatcca  33720
ctccggcaac tacaacaact acatcaacca ggcgctggtt caggtgggtc ttggcggagt  33780
cggttcctat ggcatctttg cggttctgga cattgccgct ccaaccgcga ccgttcaacc  33840
gggagtggtt gtggacggtt ccattctcat ctactcgtct tgcgccgcaa actacaatag  33900
cggtcaaagg cctgccggaa cttggcgctg catgggatat gtagtcaacc gggatgccaa  33960
cactcctgac tccgcgaccc ttttccagcg agtgacgtaa aatgaaatgg acgcggatca  34020
gaaaccctcg ttggctggat gaaacaaaca tccacgccat ggtgactttc gaggggatcg  34080
gggaagttcc tttcaccgcc aatccgcacg acgtggaggc ccacggaagg gccatccacg  34140
ctgcgatcct atccggggcg cacggaccta tcgccccggt cgatgcgaag cgggagcagg  34200
ccttgcaggg cgctatacgg gccagggaaa agcgggctat ccttcgtgat acccgctggc  34260
ccatagatcg tcacgacgag cagaggcggc tgggtatcga acccacggat ggacctgggc  34320
tgatcgcagc ccttgtttac tggaggcagc agattcgcga ttggaatagc ggggatcggc  34380
cgcgacttcc catggctttg aaaacaatgt tcaaaaatca ggagtactga tgaaaataac  34440
gaaggatatt ttgatcacag gaaccggatg caccacggat cgggcgatca agtggctgga  34500
tgacgtccag gcggccatgg acaagttcca catcgagtca ccgcgagcca tcgcggccta  34560
cctcgccaac atcggcgtcg agtccggcgg actggtaagt ctggtggaga atctcaacta  34620
cagcgctcaa ggattggcca acacctggcc tcgccggtac gcagtagacc cgcgagtccg  34680
cccgtatgtc ccgaacgctc tggcgaaccg cctggcccgt aacccggtcg ccatcgccaa  34740
caacgtgtac gcggatcgca tgggtaatgg atgcgagcag gatggcgatg gttggaagta  34800
tcgcgggcgc ggcttgatcc agctgaccgg gaagtcgaac tattccctgt tcgccgaaga  34860
ctccggcatg gacgttctgg agaaaccgga gcttctggaa actccggccg gcgcgtcgat  34920
gtcttctgcc tggttcttct ggcgcaatcg ctgtatcccc atggcggagt ccaacaactt  34980
ctccctggtc gtgaaaacca tcaacggcgc cgcgcctaac gatgcgaacc acggccagct  35040
ccggatcaac cgctatatga agaccatcgc cgcgatcaat caaggctcct gacattccac  35100
ccaaagaaaa ggccgcttat tcagcggcct tttgctttc tggctttgcc tcttcagcca  35160
tcttgacctc gaccggcgcg gcggactcct cctgagttac cgaatccaca tagttcccta  35220
gtgaactcag aacgccgatt aacagcgctc ttactacctt gtccttgact gtctcgccta  35280
tgatcttggt cagaacggat atcaactctt cccggagtct tgggctgatt cttggccgaa  35340
agcgcttgcg atgctctttg cgtttcatgt ttagtcctct gtctgcggtc ttctcctcac  35400
cccgataatg gcttggggat gcgctgtgtt agtcggaagg gtcgggcgct attataaccc  35460
gtcgaaaatg ctcgcgctta actgtttaac gatacgcacc gcgatactaa atcgccttct  35520
ttctggccaa ggaactctgg cggcctggtc cggtctaagg cctaatttgt cgacattaaa  35580
acgagaaaac ccggatcgcc tgtaggacaa ggcgtccggg tttatttcga tctagtgtac  35640
gctagaatca gtggcttccg ccccaaccgt ccagccagca atcgaagacg gcgtgtctcg  35700
gcttgtcctt ggcgccatgg gagaagtgct tgaaccggat gacctggccc ttgagatact  35760
ccctgtcatt ccagcggcgc tgtttctcgt cgtgggtcag gctggaggcc gacacgttga  35820
aggtgactcc aggccacaga cgttcgttgc ggcagacgaa cgcaccgacc attccggacg  35880
gcgacaggtt ttctgcgtgg ctggagcggg ccgtgtggcc aagttcattg atgaaagctt  35940
```

```
cattgttgtt gtgcatcaac tcttccacgt cgatgatctc agcttcatcg tagtcgtatc  36000
gcttgacttt cacacagtgc ccttccttgg cagtcgagcg accgaacttg tacagtccat  36060
cagcgcgctt gcccatggac ccttcgaatc ccagcatcgt gtggcggcgc tcgacttcgc  36120
tgaactgttc gatggaagtc accagttcct gctcgaccag gtgaatcctc tcatagccga  36180
ggcagttacg caggaagttc acgcgctcgg tcgccctggc taggcgctct tcggtcggtg  36240
cacgatgatc ggtgaaatca tcgaacacat ggaaagacca gtccggctca ccgctgtggc  36300
ggcgaagatc gccggacgac ttctggaaaa ctttcgggtc gctgatgtcg ccgcagacca  36360
gctcgccgtc caggccgttg aacagtttat cgctgaggta ttcgtagatc gattgattgt  36420
tctgccgctt gagttgacga gtcagcgcct cgccttcgaa tacgaagcag cgaaatccat  36480
cgatcttcgg cgagaaatac atcggcagtt ggccttccag cagcttcggg tcaaaattcg  36540
atgcgagcat gggtttcata cagttctcca gaaaagaagc ccggcgaacc gggctaaatg  36600
gcggtaagcc ggctcagatg gtttcgttgg cgtggttcag ttcggccatg atcgacgcat  36660
agagctcatc cgactccttg atgaacacgc cgtcgtacat gacgcctttg cgatccttga  36720
tggtgtcgta ggcagcagcg tagcaggcga gcatggtggt gtcatgctct tccgtcacgt  36780
cgaacagagt catggcggcc gataccaggc tcttgatggc caacccatga tttccacgtg  36840
ccagagcgcc tgccagatcg ccgaggcgct gcaaatcgtc gccgtaggtg ggatgtactt  36900
cgccgctctc gatgaaggcc gacagatgat cgaacagatt ttcgccgagt tgcgcggcca  36960
tgatcgtggc aaccaccatt acgtcgccga tgccatcttt cacatcgacc gggttgttct  37020
gaacccaggc ttcgcatact tctgcgaact cttcgaccaa cttcaggaat tgatctttcg  37080
cagacgagcc tttgatcagg ttacggtcgg aagcccattt aaccaccagg tcgtgaagtt  37140
cgcggctcat gatttgttcg atgttcattc tttcgattcc ttctgtattt gggatttgac  37200
tgcgttgatg atggacgccg tgctctggcg cgatccgtcc ttggttgtgc caaaatagaa  37260
ggccataaca gacttcagtt cggcgaacca atagccgatg atggtgccga tggcgacaga  37320
ggaagtcggg tccatcagcg cctcgcggcc gaaggtgaag attgcgatga tgatgagaat  37380
ggagcctgtc agaagagcga atgtaatcgc cgggcgaacg aaatcgttct gctgcgcggc  37440
aagcctcctc gccgaatccc tgtctgccgc ctctgcggcg aactggctaa gctcggcctg  37500
gagctgattc tgctcagact gaaggcgatt ttgttcggct tgaatcgcaa gctcctggag  37560
acgaacgcgc tcggcgctct ggagttcggc gaggcgcgct agagcttccg gattcgcgtc  37620
tagagcgctc gcgactgagg ctgggtcggc cttcgacccc agcgccgtcg cgacgatagc  37680
gccaacggcg gcgcctgcag gcccacccag gagcgacccc agagccgggg cagccgcgcc  37740
gatcttacta cctatgtctt tccagtccat ttcgactcct caaaagaaag gcgccattac  37800
agcgcctttc tccggccggt gatttagaac tcttcggctt cggtcgcatc gccgacgcca  37860
ccggcgtcac tgcgaggctg ttcctgcttg ctgtagtcca ccttcacctc gccgccgacg  37920
aacgacttgt acaggtcggc cgcagccttg aagtgatccg ggttcttcac caggccttcc  37980
agctcgaact ggacgccgga ccagctaccc ttgtcgttcg acatgcctac ggtggtcata  38040
cggaccaggt tggcgaaagt cggcggggtg cgcaggccct gcggggtctg aacctttttc  38100
tgggacagcg cggtcatgag cttcttcgag gccttgatct gcgaagacga cagggagatc  38160
agagcctggc cgaaatcgcc ggtgtccgga tcgatgacga tgacgtaatg accacgggtg  38220
tcggcgaagt agtcagactt cttgtcgctg accgaaccgt cttcgttcgg cgcgtacagg  38280
cgtccttcga cttccttcac cttggtcggg tctttcatca tttccttgaa gtcttcgacg  38340
```

```
ctgatggcgc ccttgaaacc gccctcggcc tcgcgaccgg cccagcggat gaactcgcgg  38400
cggtacgcgg ccggaatgat cagcaggccg gtcttgccgt cgtaaacctt gccggtgacg  38460
gtattcagga acatgccggc cttcgcgccc tcgatgtact tcggatcgtc ttcatcgacc  38520
tgcggagaca tcttctgcag aacctggatg aaggggatgg cataggactc ggcatcggcg  38580
ccttcgaagc ctgcgccgtc atacgatccc aaatccatga agtcgggaac ttcggtagtt  38640
gcgacggcgc cgccaccggt ggcaacttct acggccttgg tttcttcggt tgcttcggaa  38700
gtttcggttt tcttaccagc catgttaggc tccttgtttg tcgaatttca gttatcgcta  38760
actgtgggtt tataataacg gaagttgcaa ctaagtaaag caaattacat atcaagattt  38820
gctctttttc accttcggtt tcgtgatctt ggcctctttg tattcgtgta cgccgatgaa  38880
atctggcagc tcttcgccct tctccaggta ctcgcgaccg aacgcctgga gggtctggta  38940
atggacatcg cggttgatgg tggcgtcata gccggcttcg atgatggcct cggccgcctt  39000
cttcgcatct tccatttcgc cgcgaccgaa ttcggccaga accttggtct tgatgatgcc  39060
gtcgttgtcg gtttcttcca gccacttcca gaacttcgat ttgttctctt ctttgacgga  39120
aatgatggcc ttcggctcga ctttgaccgt gcgaccgtca gccagagtag tggtcttttg  39180
accaagctcc tccagcagct ccggaatggt gttgcgcttg agggttttca gctcctcttc  39240
cttttcggcc agcgcctttt gaagatcgag gatttcgacg tccagctgcg aagccttgtc  39300
caccaggttc agcagtcgat ggccgatgtc ggtggcttca accgccattt catccatgac  39360
gccaaaatag tcgatttcgc ccggcgcgtt ctctttcaag tattccggga tttcaagctc  39420
ttgctctttc atgtccgcct ccaacttagt gatgttccct tacttgaacc aagtattgag  39480
tagatattat gccgcatctt ccttgatacg gctactgatt tacatattaa atttcgtcgc  39540
gagtgctaac gtcagcctca aacacgccat caacgacata acttgccagg ttgcgtttcc  39600
actccaagct gacctggatt ttctcgtcga tggaatccag acagatcagg tcgaagtaca  39660
gaaccgagtt gacggtgccg attcgatgat ttcggtcttc ggactgcatc cgcagctcgt  39720
tgtcttcgtc ggtcgtgtag tagatggcca cgtctgcggc tgtgagcgtg atcccgatcc  39780
ctgctgcggc cgggttgccc aggaacacct ggacgcgctt ggcctggaaa tcgtcgatca  39840
atttttcccg ctcggcctct ttggtctcgc cgtagtaggt gccaaacgaa atcccttggg  39900
cctccaaata cgccttgatc tggtcgattt cctgaatgcg catggcccag acgatgatgg  39960
aacgctccgg gtcttcctcc agcagaccct ccagaagatc agtaaacacg gcgaatcgcg  40020
ggttgtcttc gggcggcagg atcaccggct caccatagac gttgatatag ccggacgcca  40080
cttgcttgag tttcgagcgc gctgccgcgg catcgaaaga tacatcaagc atgaaatctt  40140
cgttctggag aacaaagtgg tagtcttctt ccacgcgctg gtaaaccttt cgttgctcag  40200
gcgacatttc gaagtatatg cgcttgtaca ctttgtccgg caggaatggg agtgcttctt  40260
tcttcgttac acggaaactg tgcggctcga tcagggaccg cagcttgtcc aggttccgga  40320
ataccgggcg cccacactcg tctttttcga ccagttgcgg cggcatggtt tgcttccctt  40380
ccagcttgcg catgatagcg atcattcgag gatcgtcact gggcaccaag acggaaaatt  40440
cggccacaaa cgcccgatag gatttagtcc ccagaattcc attccgcaag aattggaact  40500
gcatgaacaa atcggtcggt gcccgcgtca gaggagttcc ggaaaggatg cgacgggcca  40560
cggccttctc gcccagcttt acgatctttt tcgcacgctt ggcttgtggg tttttgatcc  40620
tcgttgactc gtccacaatt gcgcaaactt tgaatgtatc aaggaatcgc tcgacctcat  40680
```

```
catagccagc ctggtggttg attgcatcaa cgttgatggc gaagacgcga agaacttttt  40740
catctgcgaa cgtctcggaa tacagacggt ccaagcgcgc cctggccttt ttggaagtcg  40800
gtcggccgcg ccaatccacg ctcaaagtct tgatcgcgac gtgggtggga atctcgcgca  40860
gaatccagtt ggtgtggacg cctttggggg cgacgatgag cagcgcgtcc acgcgcccct  40920
gtaggaagag gcgaacggca tcagccaaag tcgtccaagt cttcccggtg ccctgctcca  40980
tcaggtatgc gaagttccgt ttgttcaggg acgctgccag ggcattgaat tggtgctgca  41040
tggcctcggt cttcatgccc ttgacgggat atgttttggc tttcatttgt tctccaaatc  41100
ggcgaggaac tgaacaatgt tatccagtcc ttctgcatag ctcgcaactt ccaccaagtc  41160
gcggctgtta agctcgaaca aatcgaacat aggattcagc agcagccaat cggttccgat  41220
cttggccagg acgaagcccc ggccacccca gccgatccgc tcccgaagaa aagggatttg  41280
cccaggttcg aaacatctgg ccattgggca ggtggaagcg cgtttcggcc actcctccaa  41340
agccttgaac tcgacccaga actggacacc tcgacgattc aggcagatcg aatcggacat  41400
gccagaccgc cgcgtctcca gaaagtcgat caggattcgg ccgagcgagc gctgcttaaa  41460
cgcattcgcc gctttcgttt cgcgatcatt catcaccttc gccctctttg gaaactttct  41520
ctgcttgcgc tgccaacttt gacttctcgc gctcggtcaa tatccgcttg acggccttca  41580
cgatgaacat gtcgatgccg ctgagcctcc atcctttgat caggaaccaa gcgccggtcg  41640
gcgtcccttc agcaatctgc tttccgtatt gcagatattt ttcaggccga attctgaaac  41700
gtatcggctg atcaaccgag tcatcaacgc acatgatgtc gagaaactgc gactggccct  41760
tgtacaccgg gtttttccct tgatcagccc tcttcttctg gcgaatcggt tcgttctcat  41820
cagacagaac tttttttcacc atcttgacaa tgaccagacc atcatctcca tcgcggatat  41880
cccgaatgtt ctgaatgggg tttccggaag ttactccaac cagctccgga ttgtcataag  41940
catgacccca gagcgtgtga gcttcgttca aatctgcgaa ttgaacttca gaattcgaca  42000
gactcgcggc gactttctcc caatcctgaa gcgtcttcag gtgggtgcct gccagctctt  42060
tatattgagc cttcagctcc ttaagatcgg ccttcaactc cttcagatcg gccttcaaca  42120
gtttctccag ttctttgtct tggctgattt tcgccgaaag aatctgggct tccagagctg  42180
ctacatcagc agccttgtcc tcaacatcct gtgccgatat cgggcaattg gccagggcga  42240
tcctcgcggc cttgacttcc tcgcgaagac gcaggaaccg ctcggccttc gccgggccga  42300
agcctttggc gttcatgatg ccgccgatca agcgtccatc cgccactacc cagttaagtt  42360
cggaatgctc cgggtccagg gccgtatatt ctacgccttc cttggccaat tcgcgaagta  42420
tggacacagt ttgctggtcg tctttcgccg cccgaagaca cgcggccgcg tattccaggc  42480
gatgatatcg cttcatgtag caggtccagt acgtcaccac agcgtagctg accgagtggg  42540
agcggttgaa tccccaggcg ccgaacgtta ccatttcctg ccaaacacgg tgagcatcgt  42600
ccggggcgac gcctatggtc ttggcgccct cgatgaacaa ttcccggcgc ttgttgaaaa  42660
attcttcgcc ctttcgcgca gacatggctt tccgaatcgc cgacgtttgt tcccagtcga  42720
actgcccaat gtccttcaca atggacatga tctgttcttg gtacaggaaa actccatatg  42780
ttccagacag atactgctcg acctgcggga tggtataggt cacaggctcg cgaccggcca  42840
cgcgctcgat gtatttggtg gccatgcccg aagacaacgg gcctggacgg gcgagcgccg  42900
ttatgtggtc gatgttttcg aacgcggtga tattgatcgc attggcgacc gagcggacgg  42960
cctggccttc gaactggaag atgccggaca tcttgtcttc gttgagaatg tccagaaccg  43020
ccttgtcgtt caacggcaag tcgtacagct cttgcgccgt cacgcaatta gcatcttgga  43080
```

```
tgacgcccag agttcgaagc ccgagcgcat cgatcttgag aagattcaga tattctgaat  43140
cgggcttgtc gagctgcgcg acaccttcag aagttaccgt gcagaagtcg atgacttcat  43200
cgttgcagac caggatgcct gccgcgtgga ctccagagtg ggatgggtga atttcgaggt  43260
cgcccatgca ggcggacgca atctcatact tttcacggaa gtcgcggccg ggttgagttt  43320
tttcgaaagt gtcctccaat ccttttccat atcgttcgtc cgccgatgta tattcgatga  43380
tcgagttttt gatgttgtcg gtatcgtgga aggggatgcc gaagcgtttt ccgacgtgag  43440
cgataaccga cgcggccttg agtgtgttga tgttacccaa cttcacaacg ttccaagtgc  43500
catacttctg ctggagatat tcgaacacta gatagcgatg ggtatcggcg aagtcgatat  43560
ctatatcggg aagatcggac cgggaaatgt cgataaagcg ctggaagaga aggcgatgag  43620
ggagcgggtc aacctcggta atgccaagga gatagcagac caaagagccg gccgaagagc  43680
cgcgagctgg accgaccagc atgtgcttct tggcaaacgc gaccagatct gccacgacca  43740
ggaagtagct gtcgaaatct ttcagctgaa tctgcttgat ctcttcttgg aatcgatcct  43800
catactcctg ggtccattcc ttgatgtggc cgcgactgag gcggtaggct tgcccctcgc  43860
gagccagagc gacgatatca ccatccaagt ggatcatcgg cgccttcgcc agtttcacat  43920
ccgccaaccg ctcgactacc gcacgagtat tggctgcggc agtatcgaac tcttcgcgag  43980
tcatgatgtg gcgtaaacgg ctccacagct cctcttcggt ggcgatgtgg cgaaggccga  44040
ccgattcccg caccttccag gccgacgcga aatcagcatg gtcgatggac ggcatgtcgt  44100
tgtaagaggt aattaccacc ggctttccga atgccctggc cgtctccata gcgccgtgcg  44160
cggcgaccat cgacgcggga ttgatgtcaa tgtagtcgat tccggccaga tccagatggg  44220
cataggcctc gccagcgaat ttgatgacgc cgtcagcttc ctggaattct tgcggagtca  44280
atccttgatt ctggaccgac ttggaagtca agcggtagaa cttcttggtg tccttggcga  44340
gcacccaggc tttgagcttc agctctttct cgccatcgtc ggcgcatttg atcgggattt  44400
ccatgccgaa tccgcgaggc agttctgcct tggtagcggc ttgttcccaa cggacgtggc  44460
cccatgttcc atcatcgacg atggcgacga atggggattc gatctctttg gcgcgctcga  44520
tgatctccgg gaatcgacca tatgcggcgc cgtaggagta accagagcga acgcggagct  44580
gagggaaaga catcatgcgg cctccattgc ttgatacgcc cgatacactc ccatgcgctt  44640
gcagacttcg tggagcagcc gcacgtcgtc gagcgcccgg tgtttctgta catatggtcc  44700
gcagtagtgc tcataaagat gttgcagccg catgcggtgg ccgaacaacg gcgccgactc  44760
ttccacagta cagatatcga gcgatgggaa attgacttcg tccaggccga acttgccgcg  44820
agccagatcg caggtcagca tgaacttatc gaatggcagg ttgtgggcaa tattcgcgtc  44880
ggctctggaa aagaagtcgc gaactttctg gcgctgatcg aggaaagatg ggtgcttgac  44940
caggtcttcg ttcttcaacc cggtgatctt ggtgatgatt tcctcgataa cgattccagg  45000
attgcagatg aactctactt catccaaaat cttttcgcca tcagttatca cgccggcgaa  45060
ttcgatgatt ctcggctgct ttctcagact caccctttgg tggaacggga gtcctgtggt  45120
ctcagtatcc catacagcga atatcatgtt tgttccctct tatgtcgaaa ggccggctgc  45180
tttcgcgacc ggcctgagga gtataccgcg acggctgaag atttacgcct tctgtccgtc  45240
tttcggcgtg atgcggccgg agcgcatggt ggcgtgaaca aacgccgaat agttgatcga  45300
gtccaaggcc gaatcggcat ccttgaaccc gctattcgcc aggcgagtga gtttacccac  45360
catgtgcatc acgaacaggg cgagtcgatg atcatcggcg gtcttcgcca ccaggccgtt  45420
```

```
cgggaagagg atttccatga tctttccgta catcagatca ttgcgaccat aggtgctctg  45480
gcgggcgcgg aagacttctg ctgcggcgta cagattgttg agaacatctt ccgcgaaatc  45540
atctggatgg gaatcatctt cgcccggcca gacggattcc atggcgaacg gcgcggcgtc  45600
ttcggtcggg tcttcggact gagccgtttc agcgagcgga gacggggctt tcgcaaacgc  45660
ctcgtcgagg gtaggggcgg agttcggggc ggccaggaac ggctcgcctg ccatgtcgtt  45720
gggcgcgcta tcggggtcgc tatcggccgc gacggcgaag aacggcgcat cgcaaccttc  45780
caggttcagg atgtaggagt cgatccccag gctattgtag gcatcgatga tgtcctggcg  45840
atcatcgaac gccgcgacga tcttggtgac gccttcgatt ttcttcagga tgtcgagcgc  45900
gactgcccgc ttgaactgag gcgccggctc ggtgttacca tacggccgca tgatgagttc  45960
atactcgcga tgttcggcga tgccgagttc gcggtggagc ttggccctgg tctggaaaaa  46020
gtggttgtcg gttcggccgg tgacgaagaa aatcatgagg tcggcgtcga tggcattcct  46080
gatgcgacct acagcgtgcg ggttgagagt gtccttgtcg agacgagaat gatactcgtc  46140
ccattgccgt tccaaggcga agctcttgcg gtggctatcg tcgaatacgc agccgtccag  46200
gtcgaagatg atgatgccat tctttggttt gcgttccata ttcagatttc cttactggtt  46260
gctttctggg tgacggtttt atcgatgaac gtcccatcag aagtgaggcg gaaaacttcg  46320
ccattctgga tgaaatcgaa cgattgcacg ttcatcgtga tgcgaatgga ttcgctgccg  46380
ttggtcactt cgacttgtgc gatgtcgcca actttctcga caatgatctt catgttacat  46440
ggacttccca ttgacggcca cagggttggc ctcttgtttt tccgatcccc agaaatcgcg  46500
gcgcagttct tcctgctcgg ccgagcgatc catccagggg cgatagaact tgcactggta  46560
gataggttcc aacggaacat caatcacagg aatctgacct ggctttgtct ccagagcggc  46620
catgaaccgg tcataggatt tctgctggat ttcctcttca ttcatcacct tcgacccata  46680
gcgcgggaag gcgcaggagc cggtggcgac gcagtgcggc tggagcaggc tgtcgaacat  46740
aggatagact tccagaacca gccggcgcat ttcgcggaat acttcctgat attcaccctg  46800
ggtccgaacg cacaggcgaa ccttcgccat gtcgctgaga gtccgcagat tgaacttggc  46860
cgcgatcttc gtttccatgt tggaagggat gatggcacga gcgtcctgga gcgacgcgcc  46920
ggcctccaga agcttctggt agctggtttg cgcgtcggca atggcgtcat gccacagacg  46980
gttcagctct tcgcggacat ggtaggtcgg gtcaggctcg ccatttaccg tagccggttc  47040
gtcgaattcc cagcggaagg cttccggctg aacgacggcg ctgatttcca gagcgcgact  47100
ggtttcctgc tgataagccc cggtacgagt ccgaacgagt tgatgggtga agttcttgct  47160
gacaccctcg atctggaaaa tgaagtccac gaactcgaac ggcgagcgga tggtgtccag  47220
catgtacttc cagtggtcaa gcttttcggc ctcggtcatg gtcgccgggt cttggccgcg  47280
catgcgagtg gatttcgtcc ccaggagaag ttcccaggcg ttctgggtgt aactgatcag  47340
agaaattttc atcagaaatc ttccggaatt ggcgtgaagt ggaatttttt ggttagagcc  47400
agggccaggc cttgggcttg ctctttacga aggccatact gctctatctc ttccttgagc  47460
agttcgcagg cctccagacg cgactcatac tcttcagcct cctgaacgga tgagaaaacg  47520
gttccaccag aggttcggta cacaagttca atcgacatga tgacctcagt agcagcggat  47580
gatttcggcg cggatatctc gacggtcgag gtagtgctca cgaatcttat cgcgggcgcg  47640
ctcggcctct tctcgactgc cgaacgacag gttgaacgaa gtgaaaggct tatcgtccag  47700
ttcagcgccg gtttgataca ggatgcctac cagaacgaaa gacggcgcgg tcttcggctg  47760
ctggtcggct tgcatttcga gttcgaggaa ggacatagga acctcttcag gatgatctgg  47820
```

```
tgcgtaaatt aatagcgctc ctgctgagca gctacggttt ccggctcgta gatgagcatg  47880
tcaacgattt ccgggcactg gcctttcacc cagtcgatgg ccgcgaccag tgtggtggaa  47940
gcggagaaag agaaagtgcg gtaagactca tggatgtacg gcgaccccat cgaatcgcgc  48000
tcggtcgtgc gagaaatgac tgctttgata ttaacgatcc ggcccatctt cggcctccac  48060
tttagcgatt atatctgaca ggctcagctt ctcgccattc aggaaataac tggcgcgaaa  48120
cttcctgtca ccctctggcc cgacgatccg ggccgttatg gtgagactcc cgccgccaag  48180
ggcatcggtg tccctgaaga aagccagcag cgcccgcttg agcgctgcct cgcgaggatc  48240
gacggccatt aacctaccac gttccagccg tgctgagcgc accaaaccgc accggcccct  48300
gcaggaaggc tattcagaag gaacacagga gtcaggcggc cgtcctcggt catatggatg  48360
aagtagcggg cgccttcacc gagccactcg gccttggcga tagcgcgttc gagattggcc  48420
ttggtggcgt aggttttggt gtggttcttg tcggtggaga aggttacttc gcgggccatt  48480
tgtcgattcc ttttggttga agggtttcgc gtttcgatga gggaatatta cgcccacctg  48540
atccagaagt aaagcacttt tgtaaattac ttcacgaaca tccgcttggc cttctgataa  48600
gacgaagaag tcatcaggcg ctcgatgacg tccatgtccg aaaccagatc gtccagaagg  48660
acgttgcgcc aggtagcgaa ccggccgagc gagaagatgc cggcttcatg ggtgagattc  48720
cagatcatgg attcgcgctc gtcgcggccg agcggaacga ttttgccttt ggtctggatg  48780
gtcggctcgc cgtcctcgat tagctgtttc cttctgatcc cgaaggccgc gcagacttca  48840
tccaggtccc atgccggatt ccattcgatg gtttcgatct caccatcagc gttctccaaa  48900
acgccattcg cgacggattc cacgatcaga gtatcgccgg tgatggacgc gcgaaatgtc  48960
ccgaagtcgg gactggggaa ataaacggtc tggaagacgt cacaagggat ggaaagcttg  49020
tatcgactca cgatgatgga tgttcctttg ccgaatgacg ggtcgatacc caggtccatc  49080
cccgcagcag ccaggttggc gcggaacggc gcggtgctta tgacattcac atggtcatct  49140
tgccggcgaa ggtactggaa gaaagaggcg tcgaaaggac ggctccaagt gatacgattc  49200
gcaagcttag ccaccagctt ctcatagtag tcagccggtg cgatccaacg cttttcagtc  49260
gccagattcc agatggaccg gtccgacagg ccgcccgtta ctttcctgga gtacatgttg  49320
cagtggtcga tgcgcggctg ggaaatgaac tcgccgtcga tgtagatagc tttgtgtaca  49380
gtgacttcgc ggaacgggat accggtgagt tggccaatta ctggcgagcg gaatcgcaag  49440
agggcgttgt gacgctcctt gttctccggc gtcgccgcgt cgatgatttg ggcttgagga  49500
aagcgatgcg cggcgatcag tccggcgagt ccagcaccta cgatgatgac tttctgatca  49560
ggaatcatga tttgttcctt ctgaatgtac aaaacttgag aggataaaaa agggacccat  49620
tttcatgagt cccttgaaga gctagacgat tcagtctcag aagagcggcg gcttactctt  49680
cttcaccatc ggaaccgtcg gcgccctgat cttcaccgtc gtgctcctgg ccttcatcac  49740
cggccttctc gtcatcgccc tggccagctt cgtcttcctt cgaagcgatg gcaaccagat  49800
cgacccagcc catgacttcc agcttgctca gatagctgcg aaccgaggct ccatacagca  49860
ggtgtgccac tttctcgccg aaagcttcga tttctaccgg ctcaccgacg gcgcagttct  49920
cgttgatgta ggcaaacacc ttgccgcgaa tcgaaatggc ctgcggggtg ccatggccgt  49980
cgccggtcgg gatgaagtgg gtggcgcggg ggcgacgcga gccgttggac ttcagttctt  50040
cacgacgggc ttcggccttc gcacggcgct cttcctgctc ttccttgcgg cgctgcttct  50100
cggcttcgcg ctcggccttc ttctgctcgg ccaggcgctt gcgctcttct tcacgagcga  50160
```

-continued

```
ctttctgagc ttcctgggcg gccttcttct cttcggcctt tttggctcgc tcggcttcct  50220
tctcggcctt cttctgctcg cgctcggctt ccttggcctt cgccttctcg gcctgctcgg  50280
cttccttcgc cttggccttt tcagcacgct cggcctcctt ggcggcggcc ttttccttcg  50340
ccttctcggc gcgctctgct tccttcttct cacgctcggc cttgcgcttc tcttcgcgct  50400
cggctttctt ctgttcggct tccttggcct tggcctcggc cttctcggcg cgctcgcgct  50460
ctttacgttg acgctcggcg gccttctcgg ccttgcgcag ggcggctgct tgttccttgg  50520
tcagctcttc gccttgggtc tgttcgttct ggtccatgtt cttactccgg gaatgtttga  50580
aatgatggct tattggcctg tgagaggatt atctctaaac taattgaaga agggaatacc  50640
tttcgcctga acttctctaa atatttttct ttcgggaaag tccagactcc agggaactta  50700
tttatgttag cgaagttttt aactcttacg caaaaacaac aagtattcaa ttgcgcgagt  50760
tatcccagta tacatcaact gactataagg gatggacggc aagttttctt ccaacatggc  50820
gacccgtttc cattccgatc cctgcgactt atggaacgtc atcgcccagc cgaagtcgaa  50880
tccgccaatg gccttctgtg cctccagccg cacatcttcc tcaaccgaaa agctaagagg  50940
attgaacttc acccagcgct catagttcgt gccgataatg cgaactttgg caaacagcat  51000
ttcatccggc tcgtcatcat cttcttggcc ttcggggacc ggcttgaagt ccagcagaat  51060
tgcttgctcg ccgttcatga tgccatattc gtgctggttc ccggtgcaca ccagcttctc  51120
gccgatttcc ggttgtacac ccttgtagcc gaggatgcgg cgcgccctgg cgttcaaacg  51180
gcggcgagta ttgttgtagg cgcaaaggat cacgccatca tcgtccaaga acgtccgcat  51240
ttcgtcgtcc gacatgtcga atccggcccg taccaggatg tcgtcatact cgcggcaggg  51300
taggcgcttg ccctggcgga cgaacatcga cgcccgaacg atattgccgg cgttgcgctc  51360
gatttcggtc atgatggtgt cacagctgtt ctcatggaaa atctggacgc cgcgcacagg  51420
aggaacttgg ccaaagtcac caatctccag aaccggaatc cggtgcgaca gcaagcgctc  51480
ttcatcccac tcgccgatca tggacgactc gtcgagcacg accaacttcg gcttctcgtc  51540
gagcgagtct ttgttggcaa acatgatttc gccgtcttca tcttcaccaa tcggccgata  51600
gatgaagctg tggagggtcc gggcattggt gcagcccttc tcgcgaagcc gcgctgctgc  51660
tttcccggtt ggcgcgacga agactgtcca gtccatcgag cagcaaagtt cggcgattat  51720
cttcgcgatg gaagtcttac cagttccggc gaaaccagcg agtctataga cctggcggcg  51780
gtgcgctcga tcacaccaac cgcgatacca gtccacaacg gaattgatcg cgtcgatctg  51840
ctgactgttt ggtcgaaagc cgaatcgctc ttcgatctga tcgacggtga agttagatgc  51900
tgacatattt gcgttctcca acgctaggtt taattgaatt gaggctcagt ttaagcaagc  51960
cgtccacaga ccatccagta tcacgacgat acttgcggcc gtgcggatcg acatagaagt  52020
ttttcgtgcg gcgcagcaga acataatgcc aagcggcgcc gagcgcgtgg actcttcctt  52080
tatatgggaa ggccttcgcc tgctctgcgg cctccttggc cccagggagc cagcggacgg  52140
tcgaaaggac caggaccgcc cccttaatag cctgggaagc ggcgcggccg tcctttgggc  52200
tatagcgatg tctatcgaag tctacccagt ggtggttgcc gcgccggagc ttgaccgttc  52260
gggatcgccc ctcgaacacc acagtgcctt cgtgagttaa aatatgttcc gccatcgaat  52320
gttcctttat aacgtacagt tatgctttac ctctgcgcag gaagagtata ctatcagctg  52380
actcgccaaa gcgagcgaat ttaatccaac tttacttcgg caggaaagtg gccgatacta  52440
gcgccgccgc ctgtactgcc ctccaaaaca gaggatacat taaatgcaag aatgcaagat  52500
ttaccgcgac caactcccgg tcggtaaccc gaatcccaat gtcgacaaga cccgcgaccc  52560
```

```
gaaccttaag cccggtttcc tgcgtcgcag tcgcgagctg gacccggcgc tggccgttcg  52620
catccgtcgc gagctgatcc acgccgaagc atccgacttg gccaaggccg gatgggtcaa  52680
ttcacagtcc agcctttatg gatcgaaagc cttcccgcgc cattccgtcg ttcgcgtgac  52740
cggagttccg gaagatggag ctttcatcgg catgctgatc ggcttcatcg agcatcgcga  52800
gcatggcgaa tgggcggtca tggaagccgg aacgaaagaa ggcggcgccg tcattattcc  52860
agtcgatcac atcatgcgag cgtcattcgc cgaagccgaa gagttctctg aaaagtggga  52920
gcggaacctg ggatggcgtc tgctgcgcca gctccgcgag tgcggcgccc ttgccgggac  52980
tgaagacgag tttctgcggc ggatcatcaa tcgatacgtt cgtgatcgca cgatcctcga  53040
tcaccacaaa gtcggcgcgg acaaaatcta cactgatgca gtgctcaaaa gcatcggcga  53100
aacatggccg aagattcctt cggggaaatt cgtcggacac cgagtcgcgc agctcctgat  53160
cggccacaag ctaggtcgag cggggaccat cctgaatgac ctggtggact tcttggagaa  53220
gttcgcggcc gggcgcgata aagttctcaa catcgccatc tgtaattgag gtgaatggca  53280
tgtataataa accgactttg aatcaccacc atcaaaccgc attgttatat ctgtataaca  53340
atcccgatca gccggccttc acagacccca acaatcaggc gctaaatgaa cttcggcaga  53400
tggggtatgt aaaggcgaaa aaattcgaaa actgggcagg caccggccat cttaggatgg  53460
aatggacgct caccaaggcc gggattgagc gcgtcgaagt cgggtttctg gggaagtgcg  53520
ccgcttgcaa gggaatcggt cagacgttgc ttcgggggaa gtgtactgtt tgcaatggcc  53580
gcggccaggg gtggatcagc gaatggtcgc agaagccaat cgaagataat cctcaaatcg  53640
tcccaaagtt cgaaaagaca gatgcgaatc ggctagcaga cgccattgaa gaaatcgccc  53700
ggctggaaaa ggcactggcc gaatccgaaa agcgcgggag cgaactggcc gcgagctatt  53760
gcgatggcgt gatcggcgat gaatacggcc atcctcattg tcgttataaa gtggagcgcg  53820
acgccgccct ggccgaagtc gagcgcctgc gagaatcaaa aggcgatccc tctggcagct  53880
tcgacagatg tatgaagatg atgtacgagc gagacgagaa agcaaaaacag ctggaagtcg  53940
ccctggccag ggtcgcggag ctggaaacgg ctctggcacc attcgcagcg gttgcccaac  54000
cacagccgtg cacgcaacca caggcccatc ctgctcgctg tggttgcgag cggtaagtgc  54060
caagtaagga gttcatgtaa tggaacataa gaaaccttca ccagtagatg gagtcatcat  54120
gaccagcctc gacgttctcc ggaaagcgaa gcccgaagca caggacgagt atgccgtgtc  54180
catgttcgca acggcgattc gccagaaact gcaacgctcc cgcgataaag gccgaggcgg  54240
ctggatcgac tgcgacgaag atattctgat caacggattc gccgaacatg cgctgaaggg  54300
aaatgagaac aacctcttgg acctggcgac gttcctgatg ttcatgtggg tgcgcggcat  54360
cgatgatgcg aagattcccc cggcgctcga aaaggcgcga cagcacaaga tcatggaagc  54420
ctggagtcga atccatgaag atggcctaaa ctccgccaga aaggcgagtg ctgcgcgaca  54480
gttcgtggaa gtgcctcgac gcaaggggcg cccggagcga cttgcatgaa gcctcacgaa  54540
ataagactgg cacaggccga agagttcctg cgcgaactcg gccgagggat tccggacgac  54600
gaacgggtaa tggtcggcta cgctgaagag gccacagtcc aaaccgacga gaacggccgc  54660
aagctcaacg ccggctggtg gcccgtgccc tggaaggaag gcaagtacat caattccaga  54720
tccaacgcat atgcctgtat ctcgtcgtcc atcaagacgc caaacccgaa gaccggccag  54780
atgcgatact ggcgcggcga ggcctctttc ggccacggcc tggcgttaat ggtcgatgac  54840
atcggctccg gcaaagggtc caagggcgac ttcgaccgcg acgagttccg cgagcgccta  54900
```

```
gagccgaccg cgattgtgga gacttcgccg aacaactacc agttctggta tttcttcaaa  54960
gagccgatgt cccacatgct ccagttcaag gcgctgctct attcgttcgt ggaccaggtg  55020
ctaaagaaag gcggcgacaa caccgtcaag gacgtcagcc gttacggccg gatgccattc  55080
ggcttcaaca acaagcgcgg gaaagacggc aagttcaaat atgccgacga aaacggcaag  55140
cccgaactcg tgcgactgtt cagtgccgac tattccaagc gctactcgcc agaagagatc  55200
gcccaggcat tcggcgtccg catcatcatg ccacagatga agaaggtgga gataaaccgc  55260
gacgattggt tgtatgacca agtatggttg aagtatgccg agcacatctg cacgaaatac  55320
aagatgggag aagcggcagg cggccaggtc cagcagaata tgtccggcaa ataccgcatc  55380
cgctgtccct ggggcgacga gcacaccaac ggcgatcctt tcggcgcata ctttcgcgga  55440
ccgatacctg gcgccgagca cgaatatgtg ttcggatgcg ggcacgatac ttgccgcaaa  55500
gagcatcgac ggacatgggc ggccttcacc gatgaagtcg tgctacccta tatcgtcgaa  55560
caattggaaa gaatcaacca ccgtcacatc ggtgaggagt agacaatatg caaaacgatc  55620
ctggaatcct gatcacggcc attggcttgc tgttcctcgg ccttatcatc ttcttcgaag  55680
gcctaaaggg atggaaaata caagtcgcaa acttcctcgc gtcgcttctg tgctttttct  55740
tcggcctttc tgctttgacg ttctggttcg tcgttgcgtt tgacgtattt taatcgacga  55800
acggtacaga aattttcgga tggggacgga acttattagc tatgccggtt taggtaggag  55860
ataatagccg tccctttcgc ctcaatatgt agaggcaatg ttgaatccga tcatgtaaag  55920
cagaaggcgg caaacctaac atgattatcg acgaagataa tatttttgat gatggcgaat  55980
cagggtccag tgagtttgat ctcacacaga tagaagatgc tggaatggac cctttgatga  56040
ccgccgcaag taaagcggcc gacgatgcga ttgcgaggaa tgagacgtac cgagcacaaa  56100
aggcagcaaa gtatgccgag gcgtatgcgg aaccagattt gaagaagcga gcgcgattgc  56160
tgatgctcga tcaggccttt gatcttccgg tcagccggct ggtgaaagga ccgttcgatg  56220
acttcatcac caagtacagc tcgacttcag acagcaacta cctcgcggtc tatgacacgt  56280
tgttctgtaa gggcgacgga accgtcccac acccgcactt cgacgagttt cgcggccggc  56340
tggtggacca tcgcggcgtg gcgttcaaca acaagaccct cgatccgatt gacctgatgg  56400
gcgccctcgc ggctgcggcc ttggacgatc cctcgattaa gaagacgatt gagacttgct  56460
gcgtttgggc gcgtcgatat cgccgcaact cgctgatcga gacgtttgag aagaagatac  56520
cggattggga cggcgaagag cggatcgaaa cgctgctgat cgacttgttc aaaccgttcg  56580
acaccgagct taaccggatg gtgagcaagt atttctggct gagcttgtac tgccgcatca  56640
actaccctgg aatctcggcg ccgatctcgt tggcgttgat tggtgggcag gatgcgggga  56700
aatcctattt cggcctgctg atctgcaaag aactgtctgg cggtcgcgat ctggctccag  56760
tccagctcga tctgagccga cacgaccaga cgccattcct gcgcaatatc accggcaact  56820
cggtcattgc gaacgtcggg gaaatgtccg gcttcaaaaa gggcgacatg gagcgcatca  56880
aggagttctt ggttcgttct tcggatacat tcgaccagaa gtttgagccg ggagaaacga  56940
tcaagcggca atggatcacc atcatggacg gcaacggata cgatggactc cagcgggacg  57000
actccggcaa ccgtcgattc tatccgatgt tcgtggcaca acttcccgac gaagatggaa  57060
agccgaactg ggttaagccg ggcgatggta atgaaccgtt caaggtggac ttcaccgact  57120
tcggccgcaa attctggcaa gcgatggctg aatgccgcgc atggatcgaa gagcatggtg  57180
tcgatggata cctggatatg gtgtcggaag cgaaccgcga agtgcagaag ttctctattt  57240
cggaaatgga gaatgcgcgt ggcgtggttc gtgatgacac gattgatatg tatctgatca  57300
```

```
acgtgctgat cagttgcgag ttcgaagaga tcaagcctgg caggaattca aagaatcctg  57360
gatggagagt tgacactgta gccattctga aatggttcga catcctcgcc aggaagaagc  57420
cgatttctcg tcaccttact ccgcacttga aggcgctggg atttgtcccg aataagaacg  57480
gcctgaatgg atggtgctta cctgtcgata aggttgcacc tggatggacg aagggtatgc  57540
atatgacact gccgccgttc aatgatgcgc ttgtgtactt gctgagaaag ggcgacccgg  57600
acatcactga tgaggctgca atgacaaaga ttcgggcggt acgggccgag cgagctaaga  57660
ttttgggcga ggatttctga tgtagtggtg gagtgtactt ggactaggcc gccttcgggc  57720
ggtcttttct ttggtgcggc gtacattcga tttcggtggc ggccgagtga gattcggaag  57780
ctatccggta attaggatgg gatggtggtg gcgtattgtg gaaagttcgt ggatggtgga  57840
tcgagaattt tgtgtggtga gggggtggat tatggaaaat cgacgattct gactggattt  57900
ttggggtcgg ccgcgtcgag cttaccggta atttacgaaa ccaggaatta gggtcgagcc  57960
ttagtgccgc gtgggcttga agcgctttcc cggatacttt ccggattcgg aagcagccgc  58020
aaaactatac tacagcgaaa atcgattgca caatcctaat agaaaaaatc tatcacggac  58080
gttacctatc tttaaaatta ataaaattaa tagtaatttg gtaatttggt atactttagt  58140
atttgaaagc cttgcggcac taagcctgta cacttcccgt caagtttccg attccgctca  58200
actcgcggca gggtcgccgg aaacttccgg acttacaatc catgggtcgc ggcaacacca  58260
cggcggacta agcggcaagt gccaaaactc gacgaacgga accggaaatt tgggagcgcg  58320
acagaatagc tcagctggac atatttctaa cattcgattt aacactcaat ccaaacactc  58380
accaccatcg tctcccacca acagccgact cgaccctcac ccaccagcag accgcccata  58440
taacatccta taacaccacc taacactcat tcaccatcaa acccacccag acctacagcc  58500
cacccacaag cagcccatag acgcgatccc tggccccata gtacaatcgc gccatactca  58560
gtgtcgcggc agagcaccag gggccatccg ccaaccaagc caccacgacg actccagaat  58620
cgaactccag ggacgcagca acaaatgacc gccaaattct acagccccga cgatttagtc  58680
acgccacagg aattcgcaga cccgcatttc gcggcgatca accaaaagcg attcgacctg  58740
tacatcgacc tgcgcgtcca aggctacagc tcctggcggg tcttccgagc catctggggc  58800
gaggagcata tggacggtcc cgctcaggcc cgcatcttcg cgatggagtc caatccgtac  58860
tatcgcaagc agttcaaggc caagttgaac gcgaccaaaa cgtccgactt gtggaatcca  58920
aagacggcgc tccatgaact cctccagatg gttcgcgacc caaccgtcaa ggattccagc  58980
cgtctgtcgg ccatcaagga gttgaacgtt ctggctgaaa tcacgttcgt ggacgagtcg  59040
ggcaagacca ggatcggtcg cggcctggcc gacttctacg catcggaagc cgaggctcag  59100
accgcgaccg tcgctgctgc ggccgaagcc aatggatatg tgccggaagg tgaagaggga  59160
gatttcccgt ctccgtctcc ggaaccgacc gaggaagacc gcgccaaccc catttagaca  59220
taaaataaca tcattctagg cccgaatcgg accgaactaa ggcgaaggta gcgggaaggg  59280
acgaaaaacg attctagggc ggttctagga agttgacgcc taaccctcag aaactacaaa  59340
ccccggactc tagttcagaa tccggggttt tcttttgggg ttcttattcg ccagtttcga  59400
tgatttcgaa gttgtatttg acgccttcgt gctcgaaggt caacttgcct gccgctttca  59460
gttgcatgcg gaatcggatg cacttagagg aaggcaaacc gaactcgatg aaggctgcgt  59520
tgcaggattt gaactctccg cgcttgcctt tcacggtgac cgctacgcca tgacgctcgg  59580
tgcgcttgcg ggcaacttct gggtctttcc aggagttggc tatggctgct gacaggtctt  59640
```

```
tggtctcttt ggttttctcc ggcgcgttct tcgcctcttc gcgcattttc cggatttctt  59700
ccagcgcttc ctcttcggtg atttcttctt ccggcttcag attctcttcg gccttctctt  59760
ctgccttctt cttggaagtg cgggttttgt aaacctttgc cggggcttcc tcttcctgga  59820
aggcttcttc ctcggccggc agagcattca ggatggcgag gcagcgacgc tcagcagtct  59880
tgcggtcaga gaaacgcttg acggtcgcat cggcgttgtg ggcgttgtag aaggcgacca  59940
gttctttcat ttctgcgtcc tggatgtcgc cgaaggtttt gatggagttg gtcattttgc  60000
gatcctctgt tttggaagat ttcgtttggg cttcagtttg tcgccccgtt gaaagagatt  60060
atgcctaggt cgatgctgcg tgtctacatt tatttagcag aatgatggtg aacccgacga  60120
acggtcgtcg gatgtgaaaa caccgcagag caggctgcgg tgtttgttgg cgttggggtg  60180
atgtcagaaa gtcgggacgg tgataggctc gatgggcgga tcgccgggcc tgtcgttgtc  60240
cgatgcgggc gccgggctgg aagggatcgc acccgaccga agcgccagcg attccgactg  60300
cctgcttacc tgtggagctg gaggagccgc tggtgccttt ggagggattg gaggcaggtc  60360
atttcgaccc ttgaccattt gcagaggttc tggaagatcg ggaagcgcgc cagcgatttc  60420
gccatacgtc cgcgccggat cgtcgccgaa catttcggcg gatcggttat ctttgacgat  60480
ctggctgatg gccgtcacat cgccgcccgg ttctgcagga tcgatgccca cgaatggagt  60540
ggtcacgcag cgcatgttcg gatgggtagg cagatttttc agaacgatgg agtctgccca  60600
gacatacgga ttcttgtggt tgccgggtcc gtggctgatg atctcggcag gaatatggcc  60660
gttcatggtg agccattccg ccatcccttg ccgagtcagc gggcttacca cgatctggcc  60720
agtggactct ttggcgatgg cgaacagatc accgaattcg aatccaatga ttgtgtagtt  60780
ggacctggac tcgccgacga aagccagagt ttcgatgttg tggtggatat cttgttcttc  60840
ccagatgtaa agcatgatgc gctcctcaat aaggctgctt gttgtattcg accagagaca  60900
taccggccgg aactttgaag cggacgtatt cgatcatcat cgccgtgcga cgccgattcg  60960
tgccagactc gtcattgacg aagagttcgc actgatgcgg aatgactcgc gtcaccaggc  61020
cttcgccttt cgagccgtag aacttgatgt aggctgcgac gcctcgcgtc atgttcagac  61080
ggatcgtttc gcagagtcgc tgcgcggccg acgcgctgga cagatcggtc ggactgaccg  61140
tcacccagta atggccactt tgttctttat cggacataag ctgccctcca atgagaaagc  61200
ctctgccgag tcgcataggc tggttgttgt tagtcgcgct tcaacagaac gactttgtca  61260
tatgcgcgat atttaccgcg ccagtcttcc cagtagtcgc cggccgggca ggtaagctcc  61320
agggtgattt cgtcgcgcca gcattcgaca gaaaggacaa ttgccttgtt cctggctgcg  61380
gaatccgccc tgagcttaat cagaatttcg tcgccagttt tcaactcatc aactctcaca  61440
actttggcca tgacacactc ctgtttgaag aggcgcggcc ggaaccaacc cagccgcgcc  61500
gatggattaa cgtttgtgaa ggatggacac tgcgtccacg tcgaggatgc tgatggtacg  61560
gcgacggcgc ggattgctgc gttcatggat gcgaatcagg ttcgcaactg gagcttcgtc  61620
caccacccat acatcttccg gcttctgcgt ccggagcagg accgtcactt ctgcgttctg  61680
ggcgaggccg ttgcagatga acgtgaactt ggacgaggga gttctgtaca tgtcgagatt  61740
cctttttgga cttcgggtcc ggcttttcag tcggtgaaga gattatgcct gatcatcacc  61800
gtcgagtaaa gcacttatgg accaattctc cagttaaatg gaaccaaagc gcggtatcgc  61860
tgatcgctac gcttccacgc catggccctt cttgctcaca gacttcgaac cacaagctaa  61920
tttccatcct ggccaggact cggccgaagg attcgagccg acgccggctg gccaggatgt  61980
cgacattcac ccgtcgatta atttcgtacc ggcgaccgtt gatgacgaag accaggcgca  62040
```

```
gggtgcgtcc gtccagacat tcccagtatt tggtttcata ccgaagccag tagcgcttgc  62100

cagccgggcc taccatggtc atttaatcga tgctcctggc cgcgccacgc ggtccggtcg  62160

gcgggacggg atcgaaccga cccaggatgt agtcgggccg gcgcgcttcc tgaggacaca  62220

cggcgagaag gcgccatcct gcgtccaggg cagactggag ttcgtccgtg cagcagtctt  62280

ccttgagcag cagacggttg acgttctgga gattcggacc aggtatggcc gatcctgtga  62340

gtgagttcca accttcgacg ccgtgcacca tctgcggttg gttgatgtag ccttcggacc  62400

tgccagccaa ccggcttgcg gccagctcca ggcgctccag catgggtcgc agagcggctt  62460

ccgggtcaac gtcgtcccag agaaggacca ggttgatgat ggtgtacgga tagtccttgt  62520

ccagatccca ggccgaagcg gtcaggcggc ccaggccgat ttcattacac ataacgggaa  62580

cgtcgttgct ccaggtggac ggctcccagt tccgctcacc aggattcccg attgttacgc  62640

cttccaggtt ccccaggaga acgtggagct tgctgacata ttccgcctcc aaggctttcc  62700

gctcttcgtc ggtctggttg tggcgataga aggatggagg gctgactttg gcatggtaga  62760

gtttcatgat tgttccttta tgtagggttc aacttcaaag aatttcgtcg cagaacttct  62820

cgaaaggact ccgccttttc ttctcgcagg cggcacaggt gatttccagg gccggaatct  62880

cgttataggt cttgccgaag tacagccagc gtttacatag gcttcgaccg tccgccatga  62940

agaagtgagc ttttcgagca gcgccgggtt gcgcccagcc gctcggcatc ttactggact  63000

tgttcatgcg gtctccctct tcggctcagg aatccatggt gtgatttcgt ccgcccattc  63060

cccatcgatg aacatcaagg acagaagacc atagcgcccg aagctgaagc ctacatagaa  63120

cgatccgggt tccacttcca tgctggcggt attgcgttct tcgatcatct ggaaatcgaa  63180

cattgcatag ctcataccat caccatgtcg atttcattga tgaagaaatg gacatcgaca  63240

ccatcggcgc ggccggtgta acgcagccga gtcgtcccat caatgtgggc ttcctcgacg  63300

ccgatgactt ccaggatggt gtcgttgcaa tacagcttga cgaacatctt gatgccggag  63360

ccaatcgcct cgaaggcaat ctgcttgtac aggtcttgct tgatcatgct ttacgctcct  63420

gtttgcggat gtattctgcc ctgacttcgg cttcgaattt cgcccaaagc gcgttgtcga  63480

ctggacccca gggaccggtc tgagttccgt ccaccggtgc gaacttgcca ccggcgcggc  63540

gatatttgga cagagttttc aggctgatga tcttctcatc ttgggaatcg aattggacta  63600

tcatttgacg tacttcccga agtagcaggt gtggaggatt tccaggcctt tggagatagc  63660

cttcagcttg atgccgaaat tcttgatcgc ccagtccaga tcgtggtgat agaactcgat  63720

gatgttgacg atttgaccgg cgctgtagtg gatgacgcga accttgccgt tccagcggaa  63780

atcttcgcgg ctgtttacgg cctcgacttc gatggtgtcg tttctgccga tggtccattt  63840

ggagctagtc atgtcgcaat cctctttttg gagtgtttcg cgtttcgatg aggannnnnn  63900

nn                                                                 63902
```

<210> SEQ ID NO 2
<211> LENGTH: 66024
<212> TYPE: DNA
<213> ORGANISM: Bacteriophage P1777

<400> SEQUENCE: 2

```
cgttcgacga cttcatcacc aagtacagct cgacttcaga cagcaactac ctcgcggtct     60

atgatacgtt gttctgtaag ggcgacggaa ctgtcccaca cccgcacttc gacgagtttc    120

gcggccggct ggtggaccac cgaggcgtgg cgttcaacaa caagaccctc gaccccattg    180
```

```
acctgatggg cgccctcgct gctgcggcct tggacgatcc atcgatcaag aagacgattg    240
aaacttgctg cgtttgggcg cgtcgatatc gccgcaactc gctgatcgag acgtttgaga    300
agaagatacc ggattgggac ggcgaagagc ggatcgaaac gctgctgatc gacttgttca    360
aaccgttcga caccgagctt aaccggatgg tgagcaagta tttctggctg agcttgtact    420
gccgcatcaa ctaccctgga atctcggcac cgatttcgtt ggcgttgatt ggtgggcagg    480
atgcggggaa gacttacttt tcaatcttga tctgtaaaga gttgtcgagc gaccgaaagt    540
tatcgccggt ccagcttgac ctgagccgtc atgaccagac gccatttttg cgcaatatca    600
ctggcaactc ggtgatcgcg aacgtcggcg aaatgtccgg cttcaaaaag ggcgacatgg    660
aacgaattaa agagttcctg gtgcgatccg atgatacttt cgatcagaag tttgaaccag    720
gcgaaactat cagccgacaa tggatcacca tcatggacgg caacggctat gatggtcttc    780
aacgggatga gtcaggaaac cgtcgatttt atccaatgtt cgtggcgcaa cttcccgacg    840
aggatggcaa gccgaattgg gttaaaccgg gcgatggaaa tgaaactttc cgcgttgact    900
tcaccgactt cggccgcaaa ttctggcaag ccatggctga gtgccgcgcc tggattaagg    960
cgaatggcgt ggagggatat ctcgatctag ttcgggcgac caacaacgaa gtccagaaat   1020
tctctatttc ggaaatggag aatgcgcgtg gcgtagttcg tgacgatacg attgacatgt   1080
atctgatcaa tgttctgatc agttgcgagt tcgaagagat caagcctggc aggaatgcca   1140
agaatcctgg atggagggct gataccgtcg ccattctgaa atggttcgat attctcgcca   1200
ggaagaagcc gatttctcgt caccttactc cgcacctgaa ggcgctggga ttcatcccga   1260
ataagaacgg cctggctggt tggtgcttac ctgtcgataa ggttgcgcct ggatggacga   1320
atggcatgca cacgacgttg ccgccgttca atgatgcgct tgtgtacttg ctgagaaagg   1380
gcgacccgga tatcactgat gaggctgcca tggcaaaaat tcgggcagtc cgggccgagc   1440
gagccaagat tttgggcgag gatttctgat gtagtggtgg agtgtacttg gactaggccg   1500
ccttcgggcg gtcttttctt tggtgcggcg tacattcgat tccggtggtg gccgagtgag   1560
attcgaaagc tatccggtaa ttagggtgag gtggcgatgt tgcattatgg aaagttcgtg   1620
gagggtggat cgaggatttt gtgtggtgat tgggtgaatt gtggaaaatc gccgattctg   1680
actggatttt tggggtcggc cgcgtcgagc ttaccggtaa tttacgaaac caggaattag   1740
ggtcgagcct tagtgccgcg tgggtttgaa gggcttaacc ggatactttc cggtttcgga   1800
tgcagccgca aaagtatact acagcgaaaa tcgattgcac aatcctaata gaaaaaatct   1860
atcacggacg ttacctatct ttaaaattaa ttaaattaat agtaatttgg taatttggta   1920
aactttagta ttgaaagcct cgcggcacta atcttgtaca tatcccgtca agtttccgat   1980
tccagccagc tcgcggcagg gtcgccggaa acttccggac ttccaatcca tgggtcgcgg   2040
caacaccacg gcggactaag cggcaaggac caaaactcga cgaacggaac cgggaatttg   2100
ggcgcacgac aaaatagctc agctggacat atttctaaca ttcgatttaa cactcctctc   2160
aaacgctcac caccatcgtc tcccgccaac cgccgactcg atcctcaccc accagcagat   2220
cgcccgtata acatcctata acaccaccta acactcattc atcatcaaac ccacccagac   2280
ctacagccca cccacaagca gcccatagac gcgatccctg gccccatagt acaatcgcgc   2340
catactcagt gtcgcgacag agcaccaggc cccatccacc aaccgagcca ccgcgacgac   2400
tccagaatcg aactcaggga cgcagcacca aatgaccaaa tactacagcc ccgacgatct   2460
agtcacgcca caggaattcg cagacccgca tttcgcggcg atcaaccaaa agcgattcga   2520
cctgtacatc gacctgcgcg tccaaggcta cagctcctgg cgggtcttcc gggccatctg   2580
```

```
gggcgaggag catatggacg gtcccgccca ggctcgcatc ttcgcgatgg agtccaaccc   2640
gtactatcgc aagcagttca aggccaagtt gaacgcgacc aaaacgtccg atttgtggaa   2700
tccaaagacg gcgctccacg aactcctcca aatggttcgt gacccaaccg tcaaggactc   2760
cagccgtctg tcggccatca aggaattgaa cgttctggct gaaatcacgt tcgtggacga   2820
gtctggcaag accaggatcg gtcgtggttt ggccgacttc tacgcatcag aagccgaggc   2880
tcagaccgcc accgtcgctg ctgcggccga agccaatggc tatgtgccgg aaggcgaaga   2940
gggagatttc ccgtctccga cgccggaacc gaccgaggaa gaccgcgcca accccattta   3000
gacataaaat aacatcgttc taggcccgaa tcggaccgaa ctaaggcgac ggtagcggga   3060
agggacgaaa aacgattcta gggcggttct aggaagtcgt agcctaaccc tcagaaacga   3120
caaagccccg gactctagtt cagaatccgg ggctttcttt tgggcgcctt attcgccagc   3180
ttcgatgatt tcgaagttgt atttgacgcc ttcgtgctcg aaagtcattt tgccagccgc   3240
cttcagctgc atgcggaagc ggatgtgttt cgaagaaggc aggccgaact cgatgaatgc   3300
tgcgttggtg gaccggaact cgccgcgctt gcctttgaca gtcacagcca cgccatggcg   3360
ctgagtgcgt ttcttggaaa cttccgggtc tttccaggag ttggcgatgg ctgccgacag   3420
gtctttggac tctttggctt tctccggagc gttcttggcc tcttcgcgca tcttccggat   3480
ttcttccagc gcttcctctt cggtgatctc ttcttcaggc ttcagattct cttcctcggc   3540
cttctcttct tccttcttct tggaagtgcg ggttttgtaa accttggccg gggcttcctc   3600
ttcctggaag gcttcttcct cggccggcag agcattcagg atggcgaggc agcgacgctc   3660
agcagtcttg cggtcagaga aacgcttgac agtcgcatcg gcgttgtggg cgttgtagaa   3720
ggcgaccagt tctttcattt ctgcgttctg gatgtcgccg aaggttttga tggagttggt   3780
cattttgcga tcctctgttt tggaagattt ctttcgggct tcggtttgtc gccccgttga   3840
aagagattat gcctaggtcg atgctgcgtg tctacattta tttcatcaga tttatcgcaa   3900
agccgacgaa cggttgtctg atgtgaaaac accgcagagc aggctgcggt gtttgttggc   3960
gagggcgatg gtcaagcgaa cggatcgccc agcatatctt cagacggggc acgttgcata   4020
tcgcccagct tgtctttgtc agttgccgga ctggacggga tcgcgccgga ccgaagcgac   4080
agagattccg actgcctgct cacctgcgga gccggaggag ccggaggagc cggaggagcc   4140
ggaggagccg gaggagccgg aggagctttt ggcgcagtag gggcaggcgg gaccggcagg   4200
cctggaggag ccatcggcgc catgggcggt tctggaagat caggaagact cggcgctatg   4260
ctgccaaagg accgctgcga ctgctgcgcc ggattgtcgc cgaacatttc ggcggatcgg   4320
ttgtccttga tgacttgacc tatggccgtc ttgtcgccgc ccggctctgc cggatcgaag   4380
cccgtgactg gcctggttac gcatcgcatg ttctgatggg tcggcagatt tttcagaact   4440
atggaatctg cccagacata cggattcttg tggttgccgg gtccgtggct gatgatctcg   4500
gcaggaatat ggccgttcat ggtgagccat tccgccatcc cttgccgagt cagcgggctt   4560
accacgatct gaccagtgga ctctttggcg atggcgaaca gatcaccgaa ttcgaatccg   4620
atgattgtgt agttggacct ggactcgccg acgaaagcca gagtttcgat gttgtggtgg   4680
atgtcttgtt cttcccagat gtacagcatg gttcgctcct caataaggtt gcttttggtg   4740
ttcgaccaga gacatgccgg ccggaacttt gaagcggacg tattcaatca tcagcgccgt   4800
gcgacgccga ttcgtgccag actcgtcgtt gacgaagagt tcgcattggt gcgggattac   4860
tcgcgtcacc aggccttcgc ctttcgagcc gtagaacttg atgtagaccg cgacgcctcg   4920
```

```
cgtcatgttc aggtggaccg tttcgcagag tcgctgcgcg gccgacgcgc tggacagatc   4980
gtttggactg accgtcaccc agtaatggcc actttgttct ttgtcggaca taagctgccc   5040
tccaatgaga aagcctctgc cgatccgcag aggctggttg ttgttagtcg cgcttcaaca   5100
gaacgacttt gtcatatgcg cgatatttac cgcgccagtc ttcccagtag tcgccggccg   5160
ggcaggtaag ctccagggtg atttcgtcgc gccagcattc gacagaaagt acaatcgcct   5220
tgttccttgc tgcaccctct gcggcatctg ctctgagctt aatcagaatt tcgtcgccag   5280
ttttcagctc atcaactctt acaactttgg ccatgacaca ctcctgtttg aagaggcgcg   5340
gccggaacca acccagccgc gccgatggat taacgtttgt gaaggatgga cactgcttcc   5400
acgtcgagga tgctgatggt acggcgacgg cgcggattgc tgcgttcatg gatgcgaatc   5460
aggttcgcag ctggagcttt gtcaaccacc catatatctt ccggcttctg cttccggagc   5520
aggaccgtca cttctgcgtt ctgggcgagg ccattgcaga tgaacgtgaa cttggacgag   5580
ggagtcctgt acatgtcgag attccttttt tggacttcgg gtccggcttt tcagtcggtg   5640
aagagattat gcctgatcat caccgtcgag taaagcactt atggaccaat tctccagtta   5700
aatggaacca cagcgcggta tcgctgatcg ctacgctccc acgccatggc ccttcttgct   5760
tacatacttc gaaccacaag ctgatttcca tccttgccag gactcggccg aaggattcga   5820
gccggcgccg gctagccagg atgtcgacat tcaaccgccg attgatttcg tatcggcgac   5880
cgttgatgac gaagactagg cgtagggtct gtccgtccag acattcccag tatttggttt   5940
catgccgaag ccagtagcgc ttgccagccg ggcctaccat ggtcatttaa tcgatgctcc   6000
tggccgcgcc acgcggtccg gtcggcggcg caggatcgaa ccgccccagg atgtagtcgg   6060
gccggcgcgc ttcctgagga cacacggcga gaaggcgcca tcctgcgtcc agggcgtact   6120
ggagttcgtc cgtgcagcag tcttccttga gcagcagacg gttgacgctc tggagattcg   6180
gaccagggat ggccgagctg gtgtgcgagt tccaaccttc gatgccgtcc accatctgcg   6240
gttggttgat gtagccttcg gacctgccag ccaaccggct cgcggccagc tccaggcgtt   6300
ccaacatggg tcgcagagca gcttccgggt caacgtcgtc ccatagaagg accagattga   6360
tgatggtgta cggatagtcc ttgtccagat cccaggccga agcggtcaga cggcccaggc   6420
cgatttcatt acacatcacg ggaacgtcgt tgctccaggt ggacggctcc cagttccgct   6480
caccaggatt cccgattgtt acgccttcca ggttccccag gagaacgtgg agtttgctga   6540
cgtattccgc ctccagcgct ttccgctctt cgtcggtctg gttgtggcga tagaaggatg   6600
gagggctgac ttttgcatgg tagagtttca tggcggttcc tcggtttttg aaggcttgaa   6660
cgttagagaa tggtgtcgca gtatttctcg aaaggactct ggcgcttctt ctcgcagatc   6720
gcgcaggtga tttccaggtc gggcagctcg ctgtaagtct tgccgagata cagccagcgc   6780
ttgcacagac tgtggccgtc cgacgtgaag aagtgagctt ttcgagcagc gccgggttgc   6840
gcccagccgc cttgatcgtt tttgcgcttg ctcatgacga tatctcctct ggatcgggaa   6900
tccatggtgt acgttcagtc acccaaactc catctacata gatcaggact gacagagcag   6960
tcgcgccaaa cccgaagcct acatagaatg aaccgggatc gatttccatg gtggcgctat   7020
tggtggtgct attgcaatcg acttcaaagt cgaatagcga atgaccaatc ataccatcac   7080
catgtcgatt tcattgacga agaaatggac atcgacacca tcggcgcggc cggtgtaacg   7140
cagccgagtc gtcccatcaa tgtgggattc ctcgacgccg atgacttcca ggatggtgtc   7200
gttgcagtaa agcttgacga acatcttgat gccggagcca atcgccgcga aggcgatctg   7260
cttgtacagg tcttgcttga tcatgctttg cgctcctgtt tgcggatgta ttctgccctg   7320
```

```
gcttcggctt cgagcttcgc ccaaagcgcg ttgtcgactg gaccccaggg accggtctga   7380
gttccgtcca ccggtgcgaa cttgccaccg gcgcgacgat acttggacag agttctcagg   7440
ccgatgattt tctcttcttg ggaatcgagt tgggcgatca cttgacacac ttcccgaagt   7500
agcaggtgtg gagtatttcc aggcctttgg agatagcctt cagcttgatg ccgaaattct   7560
tgatcgccca gtccagatcg tggtgataga actcgatgat gttgacgatt tgaccggcgc   7620
tgtagtggat gacgcgaatc ttgccattcc agcggaaatc ttcgcggctg tttacggcct   7680
cgacttcgat tgtgtcgttt ctgccgatgt tccatttgga gctagtcatg tcgcaatcct   7740
ctttttggag tgtttcgcgt ttcgatgagg taactatacc tcagtcacct catcgagtaa   7800
agcactttcg aacagattat tgaaatttct tgaagacaga tcaatcggac gcgtcatcga   7860
tatcgaacgc cgagcgcgcc aggttgatga tctctggcca ggtcaaggtg aaggctttgc   7920
cgtcatcacg aatgataatg ggagtccgca gcggctcgcc caccagcatt gtgtaggtat   7980
gtttctcgcc ggatgcggag ccgatgcggg tgcttaaggt gagcggggat tctttgtgta   8040
cggtgccgat cattgtttcg ttcctcggtg atgcccggag aatcgggctc gttggattag   8100
gctttgccgc gacggattgt tacgccgcat tcagtagtca ctcccttagc ggcaggatcg   8160
cgaacaagat aagcacaggc ggctttgaca ttcagagttc gggttacgcc gagtttgcag   8220
gaaagatcgt tcccttcttc gtcccacaga tgggcgatgc gagaggtaca gccttttct   8280
acttcggctt ctacagttac ggactggtca atgttgaata ccggcatcgc tttctctccg   8340
aggttgttcc gtttcaatga ggtgactata cctaagtcac ctcattgagt aaagcatttt   8400
cttcagatta tctgaaacct tttgaagtca ggaactgccg ccagagccag tcgatgtgtt   8460
cgttgcagta acgctcgcca tcggacgaca tagccagagc accatccttg atgccgaacc   8520
gggtaacggc gagccattcg aatccgaact ggagcgttcc tgggcgaggg atatgggaca   8580
tggcgtattt ctgcacggtc agtgatcctc agaaggtttc gcgtttgcga tagccgctac   8640
tttctgcata ccgaggcgat agaaatcggc ttctttcctg gctttggtaa gctgctccat   8700
ggcgtcgcac gccgtcttgt gctgggaatt ggcgttcttg atgctgccgt ccaggctctt   8760
gtctaactct tcccgaagag ccttctgcga tgctagctcg gcctccaaat cctggattct   8820
gagttgaagc tggcggttct gctcggcgac cttgtcttcg cgggctacga agttctgcag   8880
gcggtcgaca agacgagtat tttcgcgcac cagctgctgt ttggcgactt tggtccttcg   8940
cagttctgct cgcaatgcgg acaactccag cgcatgcaga tcggcgtccg attcttgcga   9000
ctctgcggcc tgcttattgc gcagatagta ttgcccagcc gcgaaggcga gcagtgctcg   9060
gtctgtatcc ttaactgtct tggccatgaa gtgggctcga tacagaggcg cgaacttgca   9120
ggcgtctggg tcccaggcca gattatcggc cacaggccag aatgcgcgaa agcttttcgc   9180
atcgacatgc gccttgaccg tctgcgatgc gcccgactct tcgcagatga tttccagagg   9240
gacataaatg gcgttcttga tgcttcggaa agaaatggtg gacataacac aatcctcata   9300
agaagtcgcg gccgggacca tcctggccgc gcatcgtaat cactcttcgc cttcgtccgc   9360
gctcagccac tcttcgaagg cgaaattcac cttcgactcg acccaatcct gcagctcatc   9420
ggcgaactcg tcactgtcga tgtccatggt gattcccata acttccatgt tccatagcgc   9480
ggcattcagt tcgaactgca ccatctgctc gccatcgact tccagcagga tgcggtctgc   9540
gacttcatag tcgtctacat cgaacagatg gccgcccgcc aggaggtgct gtacgaaagc   9600
ttcatcgagg ttggtgactt cgatctggac ttgtttggtc attttcgtat ccttacttag   9660
```

```
cggctttgaa ttgggctttg aggttggcca gttcagcttt cagatcgatc atcgcctgac   9720
cgcgcaggcc ttccatttca gcctcgctga ttgcgatctt ggctgcgcgg attttgtcgt   9780
tgatttgatc tttagtcatt tttcggcttc cttttgtttg aagggtttcg cgtttcgatg   9840
aggagattat gccgatagtc agaatggaag taaagtgtct gagtgaagaa atttctgtac   9900
accgacgaac ggttgcgctc gaccgtctgc tgcggtgtcg atatactcgg cctattgcga   9960
acaatggact gattaaatgt tcaagctcaa tcctgcactg cgagcggtct ggcgaactcg  10020
tgcccgttac aaagtcatct atggcggccg ggcgtcttcg aagtcgcacg acgctggcgg  10080
tatagccgtt ttcctcgcgg ccaactacaa gctcaagttc ctctgtgctc gccagttcca  10140
gaaccgcatc agcgaatcgg tctacacatt gatcaaagac aagatcgaaa actcagagta  10200
taatggcgaa ttcatcttca ccaagaactc catcaagcac aagattaccg gctcagagtt  10260
cctgttttat gggatcgccc gtaacctgtc ggaaatcaag tccaccgaag gcatcgacat  10320
tctctggctt gaggaagctc actatctgac ccaggagcaa tgggaagtca tcgagccgac  10380
catccggaaa gagaactcag aaatctggat catcttcaac ccgaacgaag tgaccgactt  10440
cgtgtatcag aacttcgtgg tcaagccccc gaaagattcc tgcgtcaaga tgatcaactg  10500
gaacgaaaat ccgttcctca gtgagacgat gctcaaagtg attcacgaag cttatgagcg  10560
cgaccgggag caggccgagc acatttatgg cgggattccg aagactggag gcgacaaatc  10620
cgtcatcaat ctcaagttca ttcttgcggc catcgacgcc cacaagaaac tcggctggga  10680
gccggccgga tcgaagcgca tcggcttcga cgttgcggac gacggcgagg atgcgaacgc  10740
aactacgctc atgcacggca acgtcatcat ggaagtggac gaatgggacg gcctggaaga  10800
tgaactgctc aaatcgtcca gtcgcgttta caacctggcg aagatgaaag gcgcatcggt  10860
cacttatgac tccatcggcg tcggcgctca tgtcggttcg aagttcgccg agttgaacga  10920
tgccagccca gacttcaaac tgatctatga cccattcaac gcgggcggcg ctgtcgataa  10980
gcctgatgac gtctatatga agctgccgca cacgacgatc aagaacaaag accacttcag  11040
caacatcaag gcgcagaagt gggaagaagt cgcgacccga ttcaggaaga cttatgaagc  11100
ggttgagcat ggaaaggttt atccatttga cgaattgatt tcgatcaact ctgaaacgat  11160
tcacccggac aaactaaatc aactgtgtat cgaactttcg tcaccgcgca aagacctgga  11220
catgaacggc cggttcaaag tcgagtccaa gaaggatatg cgcgagaaac gcaaaatcaa  11280
gtcaccgaac atcgctgact cggtgattat gtcggccatt ctgccgatcc ggaagcccaa  11340
aggcttcttc gacttctaaa catagaaaag cccggatcgc tccgggcttc gggtcttact  11400
cggtgcggtt cctggcgctg agtgtcgacg caacggcctc gccgactccc agggcttcct  11460
ggccggccgc gagcgcttcg gcttccgact cgacgatgaa atcatcacct tggccatcgc  11520
ctggcggaac ctcgaccagc acggcttctt cgccttcgaa ccgcaggtca taggtctttt  11580
cgacggacag accgtaacga gcgttgagcg cgtcccagag ctgggcctca taggtccgca  11640
ggtcttgcag agctttctgg tggctgagca tggccatgtc aacggcccgt tgcagggttt  11700
cgtccaggac gttgaatcga atgcgaagag aacgaatccg ctcgacgact tccgcatcca  11760
ctacatgtct ttcgatcatt gcttttcacc tttgctgaat gtaacgttgt agccgttgtc  11820
ggccaggtag gtcagggcgc cttcgaagga agttccgacg aggtgcttta gcttcatttc  11880
gcgttgcgcg gccagccaga atgcagttcc ggagaactcg gcgcggcctt cggccaagac  11940
cctgccatca ggcccggcga tccgtacatt gacggaagat agcttgatcg gcatcagtga  12000
atacctccac tggcttgcga cggcatgctt tcggcgcgag cagcttcgca gtccgggcag  12060
```

```
ggacaggctt ggcggacgcg ctccagctcg tcggcatcca tgacatagag cttcccatcg  12120
gcagtgtcgt gtgccatggc gatgttcggg aagtcggtgg cgctcaggcc ggcgacagcg  12180
cggatttcgt cccagagcac cagatgctcg gcattcaggc gggcggcgag cgcttcatgc  12240
tctttagcga cgcgcgccat gaactcgtcc atccggaatg cgaattccgc atcgatggca  12300
cgggccgagg ccatggagct gagtcgaatc ggttctttct tcatgatgat tctcttttgg  12360
ttggtggttg ttcgctgccc aggcctattc acggcctggg cagcacgatg aagatgaaca  12420
caaaggctgc aaacgccaat agcgttccgg caagcatttt ggaatgactc tgcatctcag  12480
cgtactgctt agtggacatt ccgtgctgcg ccgcctcggc cgcgaagcgg gctttcgcct  12540
cgataacttc cgggcgcagc gacaggacat attctaaggc ctcttcccgc gctttttcgg  12600
cctcgaccga cctagggtcg cgggccgaga cttcgctgtg ccctggcctc gcgggatggg  12660
cttgcagcga tggagggagt tcagccgcca cgactccata gtctgcgcag gcccaagcga  12720
tcccgatgag gatcgcgagg atggattgga cgattcgcag catcactttg tcgctaggga  12780
agttcatgat caatcctcca ccgaccgaac gatttccatg ttacgcccgg cattggcccc  12840
tgcattgaag gcgcgccgac cgtcgctatc gtccagacgc atgagcttgg cgacattcga  12900
cttcttgtag ccaggatcgc cgaaatgttc gtgaaccgca gcttccttca ccacaaccag  12960
agacgttccg gcagaagata ccagctccat acgcttcctg gtgatggact gaaggcgata  13020
gctgatttcc tgggtcgcgg ccagtttgaa ttgcgcggca acctttacgt tgaaacgttc  13080
gtacccttga gccttctgat actcccgaca tagacgatca atggcctcga ccagggagtt  13140
gaacatattc accgccagct caacgtccga cttgtagcct ttgaagcgta cggcatgacc  13200
ccagcgcttg gtagtgcttc cgtcgcgggc gcttctggat gccttagccg atgctctgtg  13260
gttgttgatg ccaccggcga aatccatgat gcagtcattg tacgtcgcca cggccactga  13320
gaaaaacttc atccagttcg ggattgcgga atagtaacga gtggcaattt gctcatcgaa  13380
ctcttcgcga atctcgccgg tagcttcgaa gtcgtgaagg tcatatttgt ccttcaactt  13440
cttcacacgc tcggctgcga tggccgcttc gtgcggactg gaagagtcgg ctgccatggc  13500
ggtcagtttg cggatgcggt ctttcgcctt ctcgatggct tccggagtga attcgttctg  13560
gtcggtcatg gtcggttcct tttgtctgaa gggtttcgcg tttcaatgga gctattctgc  13620
cttcactcag aatggaagta aagcactttc ttccactatt tcggcatcga ctggaagaaa  13680
ttccagatcc aatcacctgc taccagcaag aggatgaggg cggcaaagaa caggacgacg  13740
gccgcgagct gtgcgccagg cttcagcttg ggatggctga gctttggttc tgcgggaacg  13800
gattgagtgc tggcgctgcg accgtcttct cccaggccgt agccgatgcc gcattcacgc  13860
gcctggagcg gcaccaggga tttcagatac tcggtctgct tttgcgactc ttcgtagatg  13920
ccggcgacgg cgaaccagag ggcgaacacg acggacgtac acacaaccca ggcgccggtc  13980
agcaggaggg ccagcgggcc gatgacgaag acggtagcag ccaggacgat tgcgccgccc  14040
cagatgatga agccggccag accattagtg atgtcgacac agaacttttt cattttcaga  14100
ttccttcggt tacgggatgg aggggatttg aaactctgcg ccgccgagaa catcaatgac  14160
gacctcccag agcgtcggaa cagaccactg gtaacggtcg aagtcggttt caggatcgac  14220
gcccagcgtc acataggaag tggcaggcca tttatgaaca ctgcctttcc gcatgagagt  14280
cgccacgcgg ccgtcaccga gcggattcgt cctgtgcgga acgtacgcag acatcgaata  14340
ttgctgcccg gcgtcgacaa caaatctttg cctctggcgc agacatacag agcccacagg  14400
```

-continued

```
attccagccg cgaccgccgc aagcctggcg agccgaagaa tgctcataac cttcgtgagt  14460
catttcgccg aggcaagccg agcgatcctc gtaatagttg atgttctcca tcgatccaac  14520
cagcaccaga gactcgaaat cgaatcgatg atcgtggatg gccgagtgat tgaagcaaag  14580
ccgacgcggc agctccgggt gccaaacatg gaggcgaccg gccggaagtt ggacctgaat  14640
gaaccccagg ccgtgcagag tgatcttgtc cttcatcggg tcatggacgg tgctcatgga  14700
taatcctcag tagcagaaat gtattgtgag agttacgatt gacaagccgg tcgcccatag  14760
aagggcgaac caggccatgg ctttgattgt cgtgtagatc atccgaagaa ttttccggca  14820
cagatcgggc caatgcccat ttcgatggat gcgtggttgg tcaactcgcg accgcagcag  14880
gagcactgac cagtcttccg accgtaggcg actgccgatt ccatcggctt ttcgaacatc  14940
ttcagaacgt cgtcgtgctc agtatcggtg cagtcgcgac tcttgatgaa tttgccattt  15000
gtgatccggc cgaggtagat gtcgcccagg acgtacaggc taccggcgtt ccggctgtga  15060
gcgctagcct ctttcacgac aacgatgagc ggctcctcgc cttcgccagc taggcggatt  15120
ttcgggcgct tgataccaga ctctttcgcc ttctcaaacg ctttctcgat gccggaaatg  15180
tccagagtcg gcgcagcagc ttcctgcgcg gccactttct cgcgatactt ggcgaggttt  15240
tcgatggcgc gcttcgcagc agcgatctga ttttctgtca aggagccgta tttatacaac  15300
gactcctgaa ggctctgagc gaagctgaag gaatttccag tccaccactc gatgatatcc  15360
gggtgcgcgg cttcgaaagc cttaattttg aggtcgcgtt cttgcgcagc gctacagatt  15420
ttctcggcgc gcttttctgc cgccttggca cggctcttgg cgcgctgctc cgggctggtt  15480
ttgtactctt tgtatccgac accgccgcag gcaaagcagg cgcgaccata agatgaaggg  15540
ccacggtaca ggccggtgcc tgcgcatttg gtgcacttgt cgcgatacag cttcacttcc  15600
ttccgggagt tcgggcgggc gcccatggac acatcttcca gcgtcttcgg cgcttcgtca  15660
gtgatcgcta cggtagcgaa gtcatcgccc aggtcttcga agcctgtgaa cagattctct  15720
gctgcgttca tatcgattct cctgtttgga aagttcgttt cgatgagttg actatacgcc  15780
agaaatggaa aaacggtagc gatttctcac taccgttcgt cgggtcgaag acaatcaata  15840
aatgtcgcta ttgatctcga acccatgctc agcgccgtcg ttgtagtcgt actcagcata  15900
gctgtcgcag tagtcgttca aatgctgaat gatgcctaga acatcgttcg cggccttgtg  15960
ccgtttcgcg gcgatggtct tggcgatgct gtcgccgact tccagggttt cggccgtccg  16020
gcgatggatc agcagacggc tccaaagata gagccggacg cgacgaatga tgtctcgatg  16080
gcgctccagt cgtccgtgca actcttcaat ttcttgctcg cgagatttca ctactcgtcg  16140
aagctgctga acttccagtt ccaaatcggc cttagtagcc atgttcacct caaaaaggaa  16200
aatcgtctgg gactccagga agttcgacga ttattgttga gcctgatcga tccagaatgc  16260
atccgaccga gccggccctg tggggatagg gtctacacga actataacag gtgacttccc  16320
tgactattcg ccaggtcgat cctccacacc atctgcaaat tggcgggcgc ttcgacttca  16380
gttttcgttc gtccaggacg gcgcgtctgt cgcaggaaag gcagcgtgcc ttaaccgacg  16440
taaccatggg tatagtcgat cattcggatg agctcatcat cctctgattc tctcgacttc  16500
agaccgccca aagagtccga ctggccgtcg catttcgcat cgatatccat cgaagacagg  16560
aatcctgccg atactgcggt gatatcaact ttgtcgccgg ctttcttgaa gccttcgcac  16620
tcagcatcga gggccacaat tgcactcgcg gccatgttca catgactgat gaggtcgggg  16680
aagatcacag gaacttcacg cgacatgcca cggaccgtca gcttcaggac tacatacttc  16740
atactcacta tccctttgt atgtgaggaa agaacttgct gttttccgga tggtgaaaac  16800
```

```
gctcggtcgc aggcggtctt tcttccggac attgaatcgt cgaaggcggg aaaaccgcgc  16860
cggcgataat cgccgcgagg agtgcagcgg atgtcgacat ccagagggcg gtttccaggc  16920
tcacccgaac ttccggacgg cgcggcttca ttcgctccac cctcttcccg gttcatagga  16980
tggtagactg ccgccgcgaa cccagttgtc ccacatatgg ttcagaccag tcggtggctg  17040
gggtggcgga ctgtagaatc cgggagtctc agtgctgctc aggaaataag gcgtgcaaac  17100
ggcctggacg accaattggt gccgctccca catcttatca atcgctctta gcatgacgtc  17160
ttcgcactga gccttactgt cgaaccgtct gctagtatgg tccggcatct ggacgcagcc  17220
gtctccagtg caaaggaaag cagtagcaat ccatacggtg atactcgcca tttcgtcacc  17280
ctctttagtt gatgagcaga gtctattcca tctgctcgcc aggagtaaag cgcttttcgt  17340
cgggataaat gccgatgatg tctgcgtcga gcatccaaat ctccacggac ggatcgtcgc  17400
tgctgatgtg gtacaggttg tacagctccc gtccgccgac agcgcgctcg cctcgcggct  17460
caaccgccag aaccttgccg tgcccttctc cgtgctcgtc caggtatatg acgtgatcgc  17520
cgacttcata gctttctttc gtgacgaggc gtgaacgcga gctgttctgc gattccacca  17580
cccaggaatc cagcacgccg cctttcatgt cgcgaaacaa tcttgccgat ttgtcgcaat  17640
cgaatacgcc cagaacttct ccgtctttca acacgatatg tacgattggc aaaagagtat  17700
tcatgtttaa tctccattgg ttgataatta gagtctaatc tgccgaaaag ttcccgtaaa  17760
gaattatttt ctcacaactg attagttgca actgttaatc tgatgtatat gtttgaatct  17820
cttttgaacg tttgatgttt cccctataat aagcgcacac agccaacaac cacgtggaac  17880
tacaatgttt aaactttcct ggatattcgg gcgcaaaaag gataatgctg cctgttctga  17940
atcggcgccg gagaaagtcg cacaaatccc tcaacacgat ccgctcgacc ccatgatcaa  18000
gctgggaagg attcgcggct ggaacgtcga gccggagaaa gccccggtca ttcgtagtgt  18060
gaaagatttc ctggagccgg gcctatctgt cgcaatggat agtgcgtatg gtgatggacc  18120
aaccccggcc gcgaaggctg ctgcgggcgg ccagaatccc tatgtcgtcc cgactatgtt  18180
gcaggactgg tacaattccc aagggttcat cggataccaa gcttgcgcaa tcatttccca  18240
acactggttg gtggacaaag cttgttccat gtctggggaa gacgcagcac ggaacggatg  18300
ggaactcaaa tcggacggca ggaagctatc cgatgaacaa agcgcgctga tcgcccggcg  18360
cgacatggag tttcgcgtca aagacaacct cgtcgaactc aacagattca agaacgtttt  18420
cggcgttcgc atcgcgctgt tcgttgtgga gtctgatgac ccggactact acgaaaaacc  18480
gttcaatccg gatggaatca cgcccggctc ctacaaggga atctcccaga tcgatccata  18540
ctgggcgatg ccgcagctca ctgctggctc gacggcagat ccgtcttccg aacatttcta  18600
tgagccggat ttctggatta tcagcggtaa aaaatatcat cgcagccatc tagtagtcgt  18660
tcgcggaccg cagccgccag acatcctgaa gcctacatac atcttcggcg gcatcccgct  18720
cacccagaga atctatgagc gcgtgtatgc ggcggaacgg acggcgaacg aagccccgct  18780
gcttgccatg tcgaagcgaa ccagcaccat tcacgttgac gtggaaaagg ccatcgcgaa  18840
tgaagatgct ttcaacgctc gcctggcgtt ctggattgcc aatcgcgata accacggcgt  18900
gaaagtcttg ggtactgatg aaagcatgga gcagttcgac acgaaccttg ccgacttcga  18960
cagcatcatt atgaaccaat atcagctggt cgctgccatc gccaagaccc cagctacgaa  19020
gctcctcggc acttctccaa aaggattcaa tgccactggt gagcacgaaa cgatttctta  19080
tcacgaagaa ctggagtcca ttcaagagca catattcgac ccacttcttg aacgccacta  19140
```

-continued

```
tttgcttctg gcgaagtcgg aagaaatcga tgtgcagctg gaaatcgtct ggaaccctgt  19200
ggactccaca tccagccagc aacaagcaga attgaacaac aagaaagccg cgaccgatga  19260
aatctacatc aactctggcg tcgtgtctcc ggatgaagtg cgcgagcgtc tgcgtgacga  19320
tccgcgttcc ggctacaacc gactcaccga cgatcaggcc gaaaccgaac cgggcatgtc  19380
tccggaaaac ctggccgaat tcgagaaggc cggtgcacag tcggccaagg cgaaaggcga  19440
agccgagcga gccgaagccc aggcgggcgc cgtagagggc gcaggcggcc cggttcccgc  19500
cgctccacgc gggactaagc ctctcgcgaa agcggccgag gaaggggcca gcgaggccgc  19560
tgaaccgccg tcgaggccgg accccaaggc cgagctgcgg aacttgttgg tcgatctttt  19620
gtcgaagctc caagacctgg acgacattaa ggcgccggac ggcgtagaca tagagcacaa  19680
tgatgcgcct ggcttaaagc gcacatccaa acctggcgtg tctggtatgg agccttcggt  19740
gttttcgtcc aaccgcatcg tcgggcctcg tgatcattcg gaactccaga gaatcaaggt  19800
gaatggaata accaccctga tcgaaaatcc gcgcggaagc attcgacaag gcaaggatgg  19860
gagttggcga gttcagatga aacaccacta cgggttcatc aagggaacga aaggcgctga  19920
tggggatgaa gtcgattgct tcgtcggtcc gaatctggga tccaaacggg tcttcgtcgt  19980
caaccaggtg aacaaggaag gtcagtttga cgagcacaag tgcatgctcg gcttcaacaa  20040
catcaacgat gcgaagtctg gatatctgtc ctgcttccgc ccaggttggg atggtctcgg  20100
ctccatacat gaagttgacc tacccgcgtt ccgtcgctgg ctggcgaacg gcgacacaac  20160
caaaccgttc gggggcgagt gatggcattc aaggcctcca aaaagcgcga acgccgggcg  20220
cctcttccag tcggaagagg gaagcccata attccatcgg caggaatcga ggcctggtat  20280
cgaaagcaga tgaaggatat gtccaagctc atgatcgccg actatcgaag cgagattgag  20340
aatgcactgt cccagcctgc ggccgaacgg ttcttcgcca gcgacgaatc cgttaacgtt  20400
ctgttcaaga tgacccttcg aagcctacag cagcgatgga gccgcatttt tgaaggcttc  20460
gcggccaaga tcgccccgga gtttgttaac cggaccgaag aagcggccac cgccgcgacc  20520
ctgcacagct tgtctgtggc cggcgtcgat cagccaagag ctgcgtacaa tgagagcgtc  20580
aggaataccc tggaggcagc aactacttac aaccatactc tcatcaccag gattcaagag  20640
gaagtccacg agaagattta cacatcagta atgttgtctc tgacttcccc aaatccggaa  20700
gagcaaggaa cttccggcat aacgaacgca cttcgcaaag tcgggaagtt ctctgaagat  20760
cgaatcgaac tcatcgcaag agatcaaacc agcaagcttt acagttctct gagcgatgag  20820
agaatggcgg aaaatggagt cgaggaattc gagtggatgc actcttctgc cggcaagact  20880
cctcgccata cccacctgga gaaagatggg aaaaggttca agctgaatga ccccagactt  20940
tgggagggtc cgaaggccga ccaggggccg ccaggatggg cgattaactg taggtgcaga  21000
aagataccaa tcatttgata tcgataggag cgctatatgc cgttagttca tggcacttcc  21060
aatgaggctc gttctgaaaa catcaagcgg gagatcgaag ccggtaaaga cccaaagcag  21120
gctgcggcca tcgcttactc catccagcgc agtgagaaag ggaagacggc gaaagattgt  21180
tcgcctgagc tcgttgccga tcttcgcgcc ctggtggaca ctctgtcgag gctcgtgaaa  21240
tgaaccgcaa gacatgccgg cgccgactcg tggtcgatgt aatcagggcc aatattcacg  21300
gcggattctt cagcctgaag tttgccgcca tcgatttggc aatcatcggc gtcgccatct  21360
tgatgacttt tggccgataa tgctgagaaa atctggattc tgactaaaaa ttctagtccg  21420
gatagccgca agttaccgtt tacggaaaat agcagtaatt tggaaagcct actgccgcga  21480
ggctttaaca gagccagttc ctaatttccg atttagccgc gtgcttcaaa agtatatagc  21540
```

```
ctgggaaatt agaagtaacg ttccaataga attcatctat aagtaacgtt ataatataac  21600
gtcaatctat atgctctaga cgtattgaaa ttcaattttt aattggtaaa ttggtaattt  21660
ggattagttt aggagttgaa agtctcgcgg cagtaggctt agacaaatcc cgtaaagttt  21720
ccgagaccaa attaccggat tttcgcggct gaggaaactg gtaattagat cataatacaa  21780
attataatgt aagttaacag tcgcggctac atctaattat tgttccgctt atttaccctt  21840
agatgtactg cgtatataat acagccatag tccacgactc ttcgaattaa cgatgacaaa  21900
gtcgaaaaga aaaattgacg aaaatggata tatgaccatc gagggctgcc cgatcagctc  21960
ttatggcgtt ttccagtatt ctgctggtca actcggtctt ccgggcgatc cgacgcggat  22020
tgtcaacgta tatcgcccgg agtctgccgt cagcgatcct gagtacatcg aatctctgaa  22080
gaatctcccg ttgatcgacg agcacgaaat gctgtcggga ttcgacgacg atgacgacag  22140
cgtggccccc gaagacaaag ggtggagggg catcatcacc tccaacgctt actacgaagc  22200
cccatgggct cgcggcgata tccgcatcta ttcccgcaac atgcagaatc agctggaaag  22260
gggcaaagaa gacctgtccc taggctatag ttgccgctac actgagcaac ccggcatctg  22320
gaacgggacg ccttatgaag tcgtccagga caagatgcgc ggcaaccaca tcgccctggt  22380
aaaagagggt cgtgtgccgg gggccagagt attggatggt ctgtgttttg accatctcag  22440
ttttgatttc agaccatccg atgagggtaa tgaaatgagt ctcaagaaag ccaagcggaa  22500
gcccccctgtc cagcgcgtag ggcaagctgc tgactcggcg gtcgaagagt tgcgcaccct  22560
gtggccgaaa ctctctgcgt ctgtccagaa gttcctgggc gaagaagagc aggagccgga  22620
gcatcaggaa ggtgccgctc cggccgaacc gaccgacagc gagcacctga ccgagcatcc  22680
gactctggaa ggcgcccaga aggacgacga agagcaggaa gaggagcctt ccgttgtcga  22740
tccggccgtg gccgccgtcg agccggagca tcaagaaagc gccgcatccg aaatgtccgg  22800
tgaaggcgaa gtcgccgaac tgatctctca ggtcaaagcc attctggctc gactggaggg  22860
aacggtagcc gaaggggcag acgaagagca tggcgaaggt caagatgtcg tcgagggttt  22920
ggaggagcag agcagcctca gcggctcgca aaccgccagc gacgatggtg gtgagagcaa  22980
ggataacagc gaggaacttc ctgaaatggc acagaagaac gcgcaagatg ctgcaattcg  23040
cggtctctat cgcgacattg ctgctaaaga tcgcctctac aagcgtctta gctccgtggt  23100
tggtgcgttc gatcaccgag ctatggactc ggctgaagtc gctgtttacg gcgtgaaaaa  23160
gctgaacatc agctgtgcga agggccagga agctctggcg ctcgacatgt acctgaaagg  23220
cgtcgaagcc tcgcgcggcg cggccagccg tcaatcgaaa gcccaggatt cggccggttc  23280
tgctccgcag tgcgccgagc tggacagcta cctgaagggg gagtaactca tgttccagaa  23340
acaagtttac cgccagtaca ctcctggttt tccgggcgat ctgatcgagg acggcccgaa  23400
gcgggcgcgg ccgggtcgaa tcatgcctct gtctgccgta aatccggctg ccaccgccac  23460
cggccccaac cgcatcagtc gcgctttcgg ttacgccggt gacgtcagcg ccctcggcga  23520
aggtcagccg aagaccatcg cggctcgcgc ttctgaagtc gtgatcggcg gcgccaactt  23580
ctttggtgtc ctcggtcatc cgaagcacta tgcgctgttc ggttcggccg gagactccct  23640
ggctcccagc tatgatctgc ccgatggcgc cgaaggcgag ttcttcgaca tggccaccgg  23700
cctggtcgtc gaaattttca acggcgccgc aaccgccctg gacctggact atggtgacct  23760
ggtcgcctat gtaccaaaca acctgcctac cgccgacaac gcgcttggcc tgccggccgg  23820
cgccctggtt ggcttcaagg ctggctccat gccgaccggc ttggtccaga ttcccaacgc  23880
```

```
acgcatcgtt aacgccatca gtctgccggc ccagtcggcg gggaatctgg tcgctggcgt  23940
taccatcgtc cagctcacgc agtaaggagg cgtcatgagc cagatcagca agacccattc  24000
gcgcctcgca ggccgcaatg cgaaaccttt cgacctgaaa aacatcacca atgacgccgt  24060
ggcgtctctg cgccgcatcg gcctggtatt cgatcacgcc gtcgtccagg accagatcaa  24120
ggccttggcg aaggccggcg cgttccgctc cggctcggcc atggacagca acttcaccgc  24180
cccggtgacc acgccgtcca tcccgactcc catccagttc ctgcagacct ggctgccggg  24240
cttcgtgaag gtcatgaccg ctgcacggaa gatcgacgaa atcatcggca tcgataccgt  24300
tggctcctgg gaagatcaag aaatcgtcca gggcatcgtg gagccggccg gcactgcggt  24360
ggaatacggc gaccacacca acatcccgct gaccagctgg aacgccaact tcgaacgtcg  24420
caccatcgtt cgtggcgagc tgggtatgat ggtgggcacc ctggaagagg gtcgtgcctc  24480
ggccatccgg ctgaacagcg ccgaaaccaa acgccaacag gcggccatcg gtctggaaat  24540
cttccgcaac gccatcggct tttatggctg gcagagcggc ctgggcaacc gcacctatgg  24600
tttcctgaac gatcccaacc tgccgccgtt ccagaccccg ccgagccagg gctggtccac  24660
tgccgactgg gcaggcatca tcggcgatat ccgcgaggcc gttcgccagc tgcgtattca  24720
gagtcaagat cagatcgatc cgaaggcgga aaagatcacc ctggccctgg ccaccagcaa  24780
ggtggactac ctgtcggtca ccacgccata cggcatttcg gtttctgact ggatcgaaca  24840
gacctatccg aaaatgcgga tcgtgtctgc tccggaactg tcaggcgtcc agatgaaagc  24900
ccaagagccg gaagatgctc tggtgctctt cgtcgaagac gtgaacgcgg ccgtcgatgg  24960
aagcaccgat ggcggcagcg tgttcagcca gctggtacag agcaagttca tcaccctggg  25020
tgtcgaaaag cgggcgaagt cgtatgtgga agacttctcc aacggcaccg ccggtgcgct  25080
gtgtaagcgt ccgtgggccg tggtgcgcta cctcggcatc taaccgatgc ctattcacca  25140
aaggccgggt ttccggcctt tgttcactct gactctgact cggttgtagg ggccggttag  25200
ggcataatta ctaggactac gccaatgact gtttacatcg tttccgccat gactcaatcc  25260
gtgtcttaca atgcgtatga cacctctgat ccgtccaatc ctcgcctcca gcgaaagatt  25320
ctgattcgtg gccgcgccgg catcgcatcc gaaacttccg gcttcggcga catgatttcc  25380
gacgcggccg ggcgtccgat ctggaccccg cagggcgatt gcactgccgt gagcgattcg  25440
gatttcgagc tgcttcaggc caataagatt ttcatgcgtc acatggagaa gggttatctg  25500
cgagtcgtga agaccgacat caccagtgac caccagcgga tttccaaaga gactcgcacc  25560
atggagcgtg atggattcca gcctctggac gctactcgcc tgcagcagaa aatcaaggtg  25620
accacagcca gcgcttccca ggaacaagag ttccggattt aaccgagggt ttcggtatgg  25680
tgattttcga cgaaaataag tttcgcacgc tgtttccgga gtttgctgat ccagccgctt  25740
atccggacgt gcgcctgcag atgtatttcg acattgcgtg cgaattcatt tctgatcgcg  25800
attcgccata ccggattctc aacggcaaag ccctggaagc atgcctgtat cttctgaccg  25860
cccacctcct gtcgctgtcc acgatgcaag ttcagggcgc ggctggaggt ggcgtcacag  25920
caggtgggac tcaaggcggt ttcatcacca gcgctactgt cggcgaggtt agcgtggcta  25980
agctcgcgcc cccggccaag aatggttggc agtggtggct gtccgggacg ccttatggcc  26040
aagagctgtg ggcgctcctc agcgtcaagt ctgtgggggg attctacatc ggcggccttc  26100
cagagcgtcg aggattccgg aaggttggag ggacgttctg gtgatccctg gagcgaatct  26160
cctgcgcatg gccttcgggg tcattggcac tcaaattgtg agatatcgca agtttgagca  26220
gcgagtgaag aatgatcaag cccagtacgt atccatgttc ggggagcctt tcgacctggc  26280
```

```
agcgtctgtc cagcgagtcc gacgcgatca gtatgtccag tttaatctgg agttccaacg  26340
gaattatgtt atgatcttcg ccaactttga gatggttgac ttggatcgcg atgtggccgg  26400
tgaccagttc ctctggaccg gaagagtttt tcagctggag tctcaaggct cctggtttta  26460
tcaagacggc tggggagttt gcctggccgt ggatatcggt gctgccaagc tcactgatga  26520
cgggaaaccg actttctagg tgatgtatgt ttgacggcga actgatagcg aaaatggttg  26580
tcgagctgaa tgcggcgatg acatctgctc aagaggcttt gcagttcccg gattttgaag  26640
tagtccagaa agctcagccg acccaacagg gaacgtcaac caggccgacc atctttttcc  26700
agaaactgtt tgacattcct cgcggctggc ctgccaccga ttggcacctg gacaacacgg  26760
ctcgcaaata tgtagaaata actcgacagc atgtagagac gactttccag attagttccc  26820
ttcattggca gaatcctgaa ataactcacg tggttacggc ttccgatatc gccaactatg  26880
tgagggctta tttccaagct cgatccacga ttgagcgcgt aaaggaactg gacttcctca  26940
ttcttcgcgt gtctcaaatt tccaacgaag cattcgagaa cgacaatcac cagttcgaat  27000
tccacccaag ttttgacatg gttgtaactt acaaccaata tattcgcctg tacgaaaacg  27060
cagcatattc ggccgatggg gtattaatag gcatatgagt ctgaggcgcg attcagagct  27120
aatcgccgcg cacctccaga tgttaagagc catgcgcggc aggtccgttt cagccggatg  27180
gtattccacg gctcgatatc ctgacaaggc aggcgggtcg gtcggaatac aagtcgcgag  27240
aatcgcacgt ctcaatgagt acggcggaac tatcgaccat ccgggcggga ccaggtatat  27300
tagggacgcc attgttcggg gccggtttgt tggcgttcgg ttcgtcagaa acgactttcc  27360
gggagaaacc gaggtaacta agcctcacag aattaccatc ccggctagac cgtttatgcg  27420
atatgcttgg aacttgtttt ccgcagatcg cgccgcaatc cagaaccgga tagccatgag  27480
gctggccaga ggacagatca ctccagatca agctcttgcc cagatcggcc tggcgttgga  27540
aggatacata gccagaagca tcaggaccgg gccatgggtg gctaactcag catctacggt  27600
caggagaaag ggattcaaca gaccgctggt cgatacggcg cacatgcttc aatcgattag  27660
cagcagagta acataaccag gagatcatcc agtgatcagt cagagccgtt atatccggat  27720
catttcgggc gtaggcgcag gcgctccggt cgcaggccga aagctgattc tgcgcgtcat  27780
gactaccaac aacgtcatcc cgcccggaat cgtcatcgag ttcgacaacg ccaacgcagt  27840
catgtcatac ttcggcgcgc agtcggaaga gtatcagcgg gctgcggctt atttcaaatt  27900
catcagtaaa agcgtgaatt cgccgtccag catcagcttc gctcgctggg taaacaccgc  27960
catcgcgccg atggttgttg gtgacaatct gccgaagacc atcgccgatt tcgccggctt  28020
ctcagcaggg gttctgacca tcatggtcgg cgcggccgaa cagaacatca ccgccatcga  28080
tacgtccgca gcgacttcta tggacaacgt ggcgtcgatc atccagaccg aaatccgcaa  28140
gaacgccgac ccgcagctgg cccaggctac cgttacctgg aatcagaaca ccaaccagtt  28200
caccttggtc ggcgccacca tcggcaccgg cgtcctggct gtggcgaaat ctgccgatcc  28260
ccaggacatg tccactgccc tcggctggtc cacctccaac gtcgtcaacg tcgccggcca  28320
ggctgccgat cttcccgacg cggccgttgc caagagcacc aatgtcagca acaacttcgg  28380
ttcgttcctg ttcgccggtg cgccgctcga caatgaccag atcaaggccg tgtcggcctg  28440
gaacgcggct cagaacaacc agttcatcta cacggtcgca acttccctgg cgaacctcgg  28500
cactcttttc accttggtga atggaaacgc cgggaccgcc ctgaacgtgc tgtcggcgac  28560
tgctgccaac gacttcgtgg agcagtgccc cagcgagatt ctggccgcca ccaactacga  28620
```

```
tgagccgggc gcttcgcaaa actacatgta ctaccaattc cctggccgca acatcaccgt  28680
ttccgacgat accgttgcga acaccgtcga caagagccgg ggcaactaca tcggcgtcac  28740
ccaggccaat ggccagcaac tcgcgttcta ccagcgcggc attctgtgcg gcggtccgac  28800
cgatgctgtg gacatgaacg tctatgccaa cgaaatctgg ctgaagtcgg ctatcgctca  28860
agcgctcctg gacttgttcc tgaacgtcaa tgcggttccg gcgagcagca ctggcgaggc  28920
gatgaccctg gcggtgctgc agccggttct ggacaaggcg accgccaacg gcacgttcac  28980
ctacggcaag gaaatcagcg ccgtccagca gcagtacatc acccaagtca ccggtgatcg  29040
ccgcgcctgg cgtcaagtcc aaaccctggg ttactggatc aacatcacct tctccagcta  29100
taccaacagc aacacaggct tgaccgagtg gaaggccaac tacacgctga tctattcgaa  29160
gggcgatgcc atccgcttcg tcgaaggatc ggatgtgatg atctaatggt ttgcggcgga  29220
ctcgatccgc cgcgaccttc cataaatgga gtgaggaata agcaatgatc aacatttctg  29280
cgttcggctc gatctgccag ttcacggcaa gcagaacttt cccgaacgga ttcaccgtca  29340
ccgagtttgc cgacgatgcc gatcccatcg acagcccgcc gttcaccgct gccgataccg  29400
gcgtcggtct caacggtgac atggtagttt ggaaccgggc gaacatcctg gaagtagtcg  29460
tcaacgtcat tccgaatacc gagggcgagc gcaacctggc agtcctgctg gatgccaacc  29520
gcaccggaaa ggacaagtcg ggcgctcgtg atgtcgtcgg tctggtcgtg gcgatgccgg  29580
acggcagcaa aatcacctgc accaacggca cccccatcga cggcgttctg atcaacgcgg  29640
tggcaagcgt cggccgtctg aagaccaagc cgtatcggtt ccgatttgaa aaagtgatca  29700
aagccggtac tagctgatga agaaaattcc gctgacagca gtccccaatc aagcgatctc  29760
atttaacgcc ggcagcagct attggaagat tcgcctgtac cagaacatgg acatgatgaa  29820
tgccgatatc agccgcgacg gcgtgatcgt ttgccatggg gtccgctgct tcggcgggat  29880
tcctcttctc cagtacagcc atcagtaccg acctgactat ggcaatttcg tcttcgaccg  29940
cgacgccgat tggacgttgt tcggcgacgg aatcaacctg ttctatctgg acggcgccga  30000
attcgccgag tatcaggcgc ttgccacgag gaaagaatga gcacatcaac gatcagaacc  30060
gggacgaaca acgatatcct tttggacgac aatggaaaca tggttatcct cagggatgtc  30120
gaagcgtgcg cccaggacgt tcgggcggcg atgctcatgc gcaccggcga aaacattttc  30180
gatgtgaact ccggcgtggg atatttcgaa tacatcttct cgccgcagaa aagctatgat  30240
gacgctcgca aatccatcgc ggatgcaatt ttatcctcgc cggatgtgac cggcatcgag  30300
cagcttgaca tcgacataac cggggaagtc ttcggcgtcg atgcgaaagt catcaccatc  30360
cacgggcctg ttaccacagg agtttgaaat gagtaccatc cgcatccaat acgccaacgg  30420
cacccaactg ttcctggacg gcaaaaatcc gccgcccctg gacccgctgc cctcgtttaa  30480
cccgtctgtc gaagatctgg aaggcctgga ccgcgaaaag aacatcgaca agggcgactc  30540
ctcgccggcc ggtcttcccg ttccccggt aaacgtcgat tccaatgtcg acaacggcgg  30600
aaccatcccg gctccggtat cgaccgacgc tgctgcggcc gaatcggccc cggaaggcgc  30660
ccaggaagct cctgcagcag gccaaggcga cgagaaaggc gccgaggaag ccccgactac  30720
agcccctgta gaaaaggccg aggaaacggc ctcgccggcc gctgaagagg aaaccccggc  30780
tcccgccaag gccacctctc gcaaaaccac cagcaagtaa ggactcgaca tgatcaacgt  30840
cagcggcttc ggcacaggaa ttgtaatagt ttccgcctca tcgttcccga tggggttttc  30900
cttgtcgaag ttcgctgatg atgagagtcc gatatcctcc aaagagctgg agccgttcgg  30960
atatgagatg ctttatgacg gcggcctatt cgcctttgac aaggctgctc ctctggaagt  31020
```

```
atctgtatcc gtcatcgcag ggagcgagga tgatattaac cttcgcaccc ttctcaattc  31080
caaaaaggga tcattcagat ttcttccggg cagcatcccg gatatgacga ctctcgtggc  31140
cactcttcct gatggcggcc gcaccgttct gtccaatggg actatcatca agggtccggc  31200
catcgacacc atacagaaca ccggacgacg caaaggcaac acgtacactt ttgttttcgg  31260
tagctatctt ggcgcccaga ctgcgcgtca agccatttct aacgttatcc aatcggtact  31320
ggaggtggtc tgatgttggg gattttcacc agcctcctaa gttcgcgatc tttttcgatt  31380
gtggaccaaa acacaaacca gctagttgct gcggatttga ggataagccg ggtcaacacc  31440
cggttttctt ctgtagggca acgccacatg ctggaagatg gtacgaccaa gatggattcc  31500
agaacgatcc accctatgga aatcatcgtc gaagtatttt gcccttcaat tgatgtcgtc  31560
gatcagatca atcaattgct cctggatcgc gacacactgt acaaagtcat cactcgcggc  31620
atggtattcg aacggatgat gtgtaccagc gaagcgctca atcagactcc ggatatgata  31680
tcggcgactc ctgcgcggct gacattctcc caagttctcg tccagaatcc caagcctata  31740
atgttcagaa atgcagggga ctcttctatg atcgaccgag ggctggccct agctgaagac  31800
gtggttggct cggccggcga tctgttcgac tacgcagtaa acggcgtcca gaacgccgca  31860
gacttgttct gaggtgccaa ttgaactctt tcctcaagtc tattctcaac acgcctactc  31920
tcaccatacg cgatgatgtt accaaacttc ctgtctggaa gagtcttcaa gtcaagaaag  31980
tggaaattta ctcgccggct tccgtagtgt cgaaacctct ggcgacgaaa gaccagacgg  32040
aagctcaagt gtacaccgaa gctctggaca ttgatgtgaa gaatggaaag atcatccaac  32100
cggtgcgact ccgcatcagt gctatctgtc cggacctgtc caccgttgaa agtatcatga  32160
acgctttcaa tgataacacc tcgactttcg ctatcacttc taagtcgata ttggccgata  32220
aaatggccat catgacgctc gatgtagatc agtctccaga catgttgaac gcggctgaga  32280
tcaatatgga attcgagcag gttgagcctc cagtattgaa taaattcgat cctgcgttcc  32340
ctcaagatag tccgacttat ggggtacaga ttcaatctct ttctgatgct aatttgctgg  32400
atttgggcgc catcggcgat tcgatatctt cggccgcaaa atcgctatat aatcgcgtga  32460
ccagctactt ctgaggatgt atcatgcttg aaatcaatct tcccgatggc cgtcaaattc  32520
gcgtacaaat cgaggcgtgg tcggcattgg atggctggga actccagcgc cgtttcgtcg  32580
aattcgctgt cagccaagat tccgacttcc gccgctcttt caccatggaa atcctgggct  32640
atgcgaaagt gctgcttggc gacgatgaca ccggcattcc gctgaccacc gcggcagtca  32700
tcaacaacca cctcggccac tggaagaacg tggaactggt tttcaactct gttctcaagc  32760
acaatggcat cgacccggcc acgcacgccg accggccgga ctattgggaa caagtcggat  32820
cgcagatggc catcgcattt ctggccgagg cgtccaagct cattggtcca gcaatgaaga  32880
tcgccgaagg actcgccaac aagccggagt gattcatgtc tagtgatttg gatgaattca  32940
tacttcggta tgaggccgat actgccagag ccgagcgcaa tctggagcgc ctccagaacc  33000
agatcaggcg cgtgaacagc gcatcgacga gtggccttca ggatttgcgc cacttcgcag  33060
acggcgcggc cactgaactc ggccgagtcg ttccgcagat cgattctgtg acgagcgcga  33120
ttcgcgggat gaacgcgcaa ctggcgatag gcgccactgg cgtggccctg gtcgcggccg  33180
gcgtcaaggc gttcatgaac accagggacc agtacaatca gcagcgcatc caggcgatgg  33240
acatcggcat cgccccggca cgcttggaag agtaccagag aaaattcgtt cgccagtccg  33300
gtggaaccat cagccgcgag cagggcgcgg agatgaccaa aaatctggca gacactttcc  33360
```

```
ggcgtgctta tcgcgatatc gggcgagtcg gcccggaagc gcgaattctg cgtatggccg  33420
gcgttgatgt cgggagcttc caaaagggca tgcggccgct caacgacatc attactgatc  33480
tggccacgaa aatggccaag ctgaagccgg acgaaatttc tgcctacgct gatgcccttg  33540
gcgtctcgcg agactacctg agcaccctgg ctaagatcgg cccggccatg ggaaaagtca  33600
ccgagatgac gactgcggaa ctccagtcca gggtccaggg cgagtccaac attcagaaat  33660
tcaacgatgc tctggcgaat ctcaaccaga cgttcaccac cctggaaaac cgagtcggcg  33720
aaaagctcgc gcctgcgttc accaagctga tcgaaatcat cgacaagata gtccaggcta  33780
ttcccaatga agtggaaagc ttcgcgaagg acaccaaatc ccgttgggaa gatggagtgc  33840
tcgggaaggc gaccgttggc agtgatatcc tatccctcct cagccccggc gccctgctcg  33900
gtcgcctggc agcgtggggg actcgtcgcg gcatggaaga atcagggctc atcgacaagg  33960
acaaggttcc cggcgctcaa accagcgaag acctggccaa gaaacaagaa gaccaggaca  34020
aggctactaa gtccatgaaa gagctagaga agctggctga ccagaccacg aagtctacca  34080
atgattttgc ggtggcgatc aacatgttca gtggcgcggt atcgtcgttc gcgaatgccg  34140
ttgacgagcg ccaagcttgg gcagcctggg cgggggaaat tggtcgggcg gtcggtatgg  34200
gaagcaccgc gccgacttcg cgggccaccg gcgtctatcc gcacgcgatc tatgatcagt  34260
cgaagagtgg cgcggccgga caggtcttcg gcgagccaat cggcgcccag tctcttcgca  34320
atcgcatgtt ctcgccgcag cgcaaggccg aaccggtcac cgttccatcg tacatcaacg  34380
atatcatcaa agatgcttcg aagatgtaca acattcctga gctggacatc aagaaactca  34440
tatacaccga aagccgattc aacgccaggg ccaccagcga agccggagct aaaggcctca  34500
tgcagctgat gccggaaatc gccaaggcgt atggtatcac tgacgtatat gaccctcgcc  34560
agaacatcct cggcggaacg cgcctactgc gggaaaacct agatcgagca aatggcgaca  34620
tgcggttggc cttgacctac tatcatggcg gactcgatcc gaagaactgg ggtccaagga  34680
ctcgcgcata tccgggtttg gtaatgagcg ctccaatcga gctgatggaa gaggctcagc  34740
gcaagcagaa ggctgcggcc atgaccgtcg ccagcgagac gttcgccccg gaaggcggcg  34800
acatggacat tcgtccctat gatggcgggc gactggaaac cccagaccag ggcaagaagg  34860
aagatgagcg ccgcgaagcc cgtcgatatg acgacagggt tgtgcgaccg gaaattcgca  34920
tcatcgaccg catgccagac cgcagcgacg gcgaaatcct caagatgtct agacgtcaag  34980
aggccgaccg ggcagattct ggattccgga agttcccgaa tcaagttcgc ggcgagacca  35040
agcagaacat ccaggctcaa ctcactgcag gagccatcgc gcaagtgatc ggcgttaacc  35100
ccaaccagat catgcgccgc gaaatcagcc gttctgactt gctgttcgga tacaaccaag  35160
ccatcctggg caagcaacag gagatcaagg ccgccgcgac cgaagccaac aacgtattcc  35220
tgtctccagc caagcttgcc gaagccacgg ccaaggtgaa cgcagcatcg cgagaaatgg  35280
atattctcag gacgtatggc gagcaacttc tgaagagcgc tccagagcgc ggccaggagc  35340
tgaccatcgg tcgaatcgac atgttggtca acgtcaccgg cgcgaattct ccggaagagg  35400
ctcgcgagat attcagtaag cagactgcag accagctgac tacggcaatc caggacgctc  35460
aaaacgattc cgcaactaag atactctact gatgaaaaag agaattctgc gagtaacatt  35520
caacatgcct tatggacccg aagtcatccg cgaagatctg gatgttcggg tccggattat  35580
gaaggctgcg ttgcggattc agaaccgggc gacgatggaa attttcggcc tcaccactca  35640
gcttcgcgag tctcttctgt cgcagttcac cgcgtggaag catcggcaac gtcaagtggg  35700
catggaagat gaattgatga tcaaggtgtc ggtggaagcc ggctactctg accaggggcg  35760
```

```
cgagcaagtt tccagagtct ttgtcggcga agtcgccatt gtcgatatca tttctccgcc  35820
accggacatt ggaatccgca tccagtgcta taccaggcaa atcgacagga cgaagaccat  35880
tcggaatatg ccgcccgcca acacgacgtt tgtcaagttc gtcgagtggg gcgcgaacga  35940
aatgggattg aacttcatct gcgataccag ttacaacgat caagttctga agaatccggg  36000
ccggtctatc actgtcgcgt cggcaatcct ggcgtcgatt caggatatgt acatgccgga  36060
cgtggccgcg ttcgtcgatg atgacatatt gatcgtgaag gaccgcgata aagtcattcg  36120
tccggatgag gtgaccaacg tcaactcgtt tgttggaatt ccatcttggt ctgaatgggg  36180
cgtggaattc cagtgcctgt ttgagccatc gattcgtgtg gctggaggcg tagcggtcga  36240
atctctcatg aatccaagtg ttaatggtaa ctatgtaata actgctctgg aatacgattt  36300
ggccagtcgg gatcggccgt tctatatcaa agtcatgggg agtccagcag cataatggcc  36360
agggaaatca aatcattcaa catgttcgga gttcactata cttcgcggca attctctgct  36420
gtcgatgggc tcagcatgat gtcggaaatt cagagcgtgc cgccagaaga attgctcaag  36480
ggtactgatg tattggcgca tccggaagac catccggaag gcatctggct tccattgact  36540
gctgcgaaca tcaatcttta tgtcgttgat cgagcgaaag taatagctcc cgtacaagtt  36600
cttgcacttc tgtccgaagt ggtaatcgac tggaattttg gttttctcaa agactggacc  36660
ggagtcaaga ttccatccag atttgtcgaa gatatcaaaa gcgtgaagac ggcacattca  36720
ccttctgtag ttgcgagttt ggtggcgaac ggttcggcct ctatgcgcga gttggaagag  36780
tattattcga ctcaagatgc ctttaagatg atagatatca tgacggcgaa gagcgtgaac  36840
gaggccttgg cgtccgaagc atcgcacaac agaatcaaaa agggataatt cctaaccggg  36900
cctgggaagg ctatactaga cctgccaaat cagaggcttt cccatgtcca atatttctct  36960
aacatccgca aaagctcccg acaggacgcg actgatcgcc gctcttgacg ctcggtcgcg  37020
gcgggatgct ctagatttcg aagtaatgat accggctcag gttgttcaat atgaccgggc  37080
cgagaatatc gcgacgattc aacctctcat cacctgggtt gacacggaac acaacgccgt  37140
ccaaaggcat cagctggttg atattcctgt aatttccatg gggggctggcg gcttccacat  37200
aagtttcccg attcagcaag gtgacatagg ctggatttat gcggccgacc gcgacacatc  37260
tcagttcctg gagtcgttgt caatgtcgaa gccgaacacc ggccgcatcc ataagttcga  37320
gcatggcctg ttcatcccgg acgtattccg tcgatacacc atcaattccg aagattcggc  37380
cgctatggtc atacaatcga cttccggagc gaccagaatt tcgattcgcg gcgataacat  37440
caagataact gcgccgtcga acgttactgt ggatactccg caggcgaact tcaccggcaa  37500
tgtgactatc gctaacaccc tggtcgtaaa cggcatcaac gtgaacaacc acggccacct  37560
cgaaaacaac ccgcctgatg cccggacgaa aggcggcatg gttgcttaag gagattttca  37620
tggcaagttt tgatttttct gatttaacag cgggggggggg ttgtaatggc taactacaac  37680
tacatcgtcg atactggtgt gatagtcgca gataccgccg acgttctgag cgacgttgag  37740
gccgagttca gcgccgccct cggtgccaat atcaacttgg ccgcgagcac tccgcaggga  37800
tcgcttgtcg cggccgaggc catcgcccgt tccagtgtca tgcggaatga agcgcgaatt  37860
gccaatacca taaacccgaa cgtttcattc ggaacgttcc tggacgcgat ctgtgccttg  37920
atggggatcg agcgcggttc tgatctgtca accttcggct atggagttca agtcaccggc  37980
cgcagccaaa cccgcatttc caccgggtct agggtccaga ctccggccgg cgcgatcttc  38040
acagtgatga gcgatgtcac gatccctgct ggtggtgtcg cgaccatcga tatcaaatcg  38100
```

-continued

```
caggagtatg gcaacattcc tctgccggtc gggaatctca tcatcatcga cggaacaatt  38160
ggatggtccg gagcaaaagt catcgcctcc actcgcgtcg atccgggcag ccgccaaatg  38220
agcgatgcag agttgaagaa tgcccgcgtt aatcgattgg ccatccaagg ccgcaactcg  38280
actatggcca tcaagtcgta tgtgagcgcc gttccaaacg tcacgtcggt gaacgtaatc  38340
gagaacaaca ccggcgccgt tcaagtggtg aatggagtct cgtttaccct tccgtatgct  38400
gtttgggtct gcgtcgccgg aaacccggat aaacaagcag tcgccgatgc gttgtgggcc  38460
gcccataacg gcggaactcc atgggactat ggtgcgacga acaacggcgt cccggtggac  38520
ggtccgaatg gcgttcctgt gcgcgatccg gcgtccggtc gaaagtatgt cgtgaagtgg  38580
accactccaa ttatgtacga tggatatgtt aacgtaacag tccagcaagg ttcctcctct  38640
gtagctccgg aagccattca gaacgcagtg gtcaattacg cccaggggaa agtggaaggg  38700
gaagaggggc tggtggtggg cgcgagcctg tcggcattcg aagtcgccgg agccatcgct  38760
cgcgaaattc ccggcatcta catcaaactc tgccaggtcg cgtgcgtcgc ggctggctcg  38820
ccggctccgg ctccgggcga tttcacttcg gaatacgtca tgagcgcatt cggccaggct  38880
accatttccg ttggtaacgt tcgggtgact ttcgtatgac tctgcctgcg tacaattcgg  38940
acatccaaca agctctgaaa tggctccata accaggcgcc tggaatcacc ggcctgatcc  39000
agagaaaggc gcaatggtat gacagattca gccgccaatt ctgggccaac tgggagcgcg  39060
acgttttcaa cttgaagacc gccaacccgt tcggccttat ggtttggtgc atcatcctcg  39120
gcacgccttc gaaagggttc ggcctttatc caaagaacag ttcttgggca ttcggtcggc  39180
tacgccagaa cttcatctat agcggtacac aagtcccgcc accggcagac gcatcgcctg  39240
gaggcaactt ctacggtggc ggcaatgccg aaattctcaa cttggacgaa atcaggaaag  39300
tgcttcagct aagatatgta gcgctgattt cgaacggctc gattgcatat atcaatcgca  39360
tgcttcgtta catattcaat gatgatgagc catgggacga ggcgaccggt ctgtacttct  39420
atctcatgga ctcaaccggc gagaatggcc ctgtggagaa cttggcagta tatcggaaag  39480
attgggaagg tatggtgctg ttgtccagtt cgcccagaac gaaccacgtg ctgacatcga  39540
cccctgccag cgacgccgat tggccgggag tcgatccggc cgcgagcggt attccggtaa  39600
cggtcgaaac ggcgtccgct acggccccgg acggctccgc tacggtgtgc aagcttacta  39660
agccggccgg gagtaccgct tacgtctccg cgccgataga tgggccgctg gggtccggta  39720
gcactgtaac gttctcgttc ttcgcgaaag ccggctccac ccgtttcatt gcaattcagt  39780
cggctgccga tttccccagt cgagccgatg ccgttttcga cctggattcc gggaacgtaa  39840
tcagcgatca gatgctggac agcagcgtgg taagcgcccg aatgattcgt ctggaaaatg  39900
gctggtggcg ttgcgttctc acgaccaaga ccgtcagctc ttcgttccgc gcggcttaca  39960
tcgctccggc agaaaccaac ttcagctgga ttgattcgaa ttccagcgcg gcgattgacg  40020
tgcttatctg gggcgctcag atcgaactgg gtgatactcc aaccggatac ttggagacta  40080
ccggaacgcc cgtcaccatc accgattacg ttctgcagag cgcccagacc ggaacggtca  40140
agttcacaca gcctcttccg accggagtag aagcgtattg gactggagac tggaaaggtg  40200
ggtctgcgac cgagccggcc agattcgcag taggggatgg gactcaagat acattcaatc  40260
tgtccagccc tgcatacatc ggcctaccca ctagtggggc gttcaagcta gaatacagag  40320
ttggtccggc gcttaatttg tcgccgcaat tgatcaacct catgaatgac cgggcggtcg  40380
gtatcatgcc gacttgcgcc ggttgcgatg taaaagtcat tcaggagtaa tgacgtgatc  40440
acacccgaac tgatacccag tccgtttgct gcgcagggcg acaaagaccc gattccacaa  40500
```

```
acctcctcca ctggcttcgc aaaccttcgc gacggctata cgccggacta cgaaatcagc  40560
ctggcgtcga acaacccgca ggccaaagcg gtcgagcgga aaattcaaaa ccaactcttc  40620
ttcatcgcga cccagaacgc acaggcgtgg cagcgacaaa tggcgccgcc gtggtttcag  40680
ggcatgcctg gcggctacga acagaatgca gaagtcgtgc gcgtcggaaa tgacggcata  40740
atgcggcgtt atcgttccat ggtgaatgcc aatgcgagcg accctctcag cagcacgact  40800
tgggaagaac aacccgcatg gtcggcgatg cgctccaaca tcccgatgcc ggccggaggc  40860
ccaggcctat cttctggcgg agaagtcatc acgaccggcc gcaacttcaa cgacctgtta  40920
aatgggacgt gggagttctt ctctgattca gtggttatcg cttctcagaa tgcccccgta  40980
tatccggctt ccgctggtgc cgctgctggc atgttggagg cgaaatcttg ggtgtccgga  41040
gccaatacgt tctgcgtcca acgctacact gatcgcgtcg ggaacgtcgc tgtgcgcggg  41100
cttaatgccg gagcgtggac caactggatg tatgcggtaa acgtcatggc tcttcaacaa  41160
ggtcgggtca cctatggagt cgcggccgga tcggcgaacg cttacacgtt gacgctagtt  41220
ccgcagctcc aaggcggcct ggtggatggc atgattcttc gggtcaagtt caacaccatg  41280
aacaccggcg cctccaccat caacgtctcc ggactcggcg ccaaagccat cgtcggcgcg  41340
gccaacttcc ctctcaccgg cggcgaactt ggccaaggac tcatcgctga gcttgtattc  41400
gacgcagcag gcgaccgctg gagaatcctc gcaggcgcgc cacgcatcca agtgggcaac  41460
gcagatcagg actaccaggc ccccagctgg aaacaggtga aggactatgt agcgtcccaa  41520
aagctcaccg aagtggattg ggccgatgtc gtcaacaagc cgaacgtcgc catccaagac  41580
accacgccgt ggttcgccaa tctggagctg tctgacgctc ggcctttcat cgattttcat  41640
ttcaacaata accgcgccaa agacttcgac tatcgcttta tctctgaggc tgatgggtcg  41700
atggcattct attctcgcca ggggtctgcc ggtcctaccc aggacatcct gttcagcagg  41760
tcgaatgtaa cattcctcca gccgcgactg gatgttgcga aaaacctcgc gtacatcgcg  41820
aactctggcc ccctttggca gaacaccaca gccgatcagc ccggctggaa attcaccttc  41880
gcacaaggcg tggacgcgaa caacaacgcg gtgatcgcag tcaataccac caatccggac  41940
ggttcctatc gctcacagat catgcgatgg gactgggctt ccacgaacgt catattcaat  42000
aatcgtccgc tcttcgccgg tcaatacacc ccttgggatt ctgggaactt taatccttcc  42060
accaagttga ccgtgaatgc cacgaaccaa atcgccggcc cgaccgggat tcggaataca  42120
aacggcaaca ccggcaacat gaacacatgg ggttccggtt ccacaacggc atcctatggt  42180
aatgctgcca ttcaaatctt cgggaaaggg agtggtgagc ctgccgcgat ctatttcgac  42240
aactcccaga caggatggta tctggggatg gacaaggatg gacagctcaa gcgggccggc  42300
tggtcgctcg gcaataacgc ctacgtgatt accgacgaat ccaacattcg tttccacgtg  42360
aattccatgg ctggcactcc tgtttggggc ggaaacgaat tctgggggcc gtggaacttt  42420
aatccgaaca ccaagctgac catcaaagcc ggcacccagg aaactagcag cactgcgata  42480
ttcagcggaa ctatgccatt cgctccaatc gcatcgctgt ccgattattc tcaggcccct  42540
ttgacggttt acaacgcgcc aaccggtccg tctgcaaaac cggccgtcat cgcgttcatt  42600
cgtcctggta actggggagc attcttcggc atcgataccg acaacaagct gaaatggggc  42660
ggcggatcac tcggcaacag ctccagggaa atcgccgatt caagcaacat catgaatctt  42720
tgggcggcca acccgaccgc gccgtcctgg aacggccaaa ccatttggcg atccgggaat  42780
tttgatccgg caacgaaagt ggatttgaac gccgcgaacg ccaccaacgg aaacatgatc  42840
```

```
ttcaaccgca tcgccggaac tggtagcggc atagcttcgt ccggtcgagt cggtgccatc  42900
aacctgcaga acggggcgca ttcggggcaa gcggcagcag tcactttcga gcggggcggc  42960
agtatcttcg tcaacttcgg cttggatacc gacaacgttc tcaaagtagg tggcggaaac  43020
ctgggggcag atgcctatcc ggtcatccac gccgggaact acaataacta catcaaccag  43080
gcgctggttc aggtgggtct tggcggagtc ggttcctatg gaattttcgc ggttctggat  43140
tatgccgctc caaccgcaac cgttcaaccc ggagtggtcg tggacggttc cattctcatc  43200
tactcgtctt gcgccgcaaa ctacaatagc ggtaaaagac ctgccggaac ttggcgctgc  43260
atgggatatg tagtcaaccg ggatgccaac accoctgact ccgcgaccct tttccagcga  43320
gtgacgtaaa aatgaaatgg acgcggatca gaaacccacg ttggctggac gcggtaaaca  43380
tccacgccat ggttactttc gaggggattg gagaagttcc tttcaccgcc aatccgcacg  43440
acgtggaggc ccacggaagg gccattcacg ctgcgatcct gtccggggcg cacggaccta  43500
tcgccccagt agactcgacg cgggagcagg ccttgcagga cgctatacga gacagggaaa  43560
agcgggctat ccttcgcgat acccgatggc ccatagatcg tcacgacgag cagaggcggc  43620
ttggtatcga aaccacggac gggcctgggc tgatagcagc ccttgttcac tggaggcagc  43680
agattcgcga ttggaatagc ggggatcggc cgcgacttcc catggctctg aaaacaatgt  43740
tcaaaaatca ggagtattga tgaaaatcac gaaggatgtt ctgatcaccg gaaccgggtg  43800
caccacggat cgggcgatca agtggctgga tgatgtacag gcggccatgg acaagttcca  43860
catcgagtca ccgcgagcca tcgcggccta cctcgccaac atcggcgtcg agtccggcgg  43920
actggtaagt ctggtggaga atctcaacta cagcgcccaa ggattggcca acacatggcc  43980
gcgccggtac gcagtagacc cgcgagtccg cccgtatgtc ccgaatgctc tggcgaatcg  44040
tctggcccga aacccggttg ccatcgccaa caacgtgtac gcggatcgca tgggcaatgg  44100
atgcgagcag gatggcgatg gttggaagta tcgcgggcgc ggcttaatcc agctgaccgg  44160
gaagtcgaac tattccctgt tcgccgaaga ctccggcatg gacgttctgg agaaaccgga  44220
gcttctggaa actccggccg gcgcgtcgat gtcttctgcc tggttcttct ggcgcaatcg  44280
ctgtatcccc atggcggagt ccaacaactt ctccctggtg gtgaagacca tcaacggcgc  44340
cgcgccgaac gatgcgaacc acggccagct ccggatcaac cgctacatga agaccatcgc  44400
cgcgatcaat caaggctcct gatattcgcc caaaagaaaa ggccgcttat tcagcggcct  44460
ttttgctttc cggctttgcc tcttcaacca gcttgacttc aaccggcgcg gcggactctt  44520
cctgagtgac cgaatccaca tagttcccta gtgaactcag aacgccgatt aacagcgctc  44580
ttaccacctt gtccttgact gtctcgccta tgatcttggt cagaacggat atcaactctt  44640
cccggagtct tgggctgatt cttggccgaa agcgcttgcg atgctctttg cgtttcatgt  44700
ttagtcctct gtctgcggtc ttctcctcac cccgataatg gcttggggat gcgttgtgtt  44760
aatcggaagg gtcgggcgct attataaccc gtcgaaaatg ctcgcgctta actgtttaac  44820
gatacgcacc gcgatattaa atcgccttct ttctggccaa ggaactctgg cggccgggtc  44880
cggtctaagg cctaatttgt cgacattaaa acgagaaaac ccggatcgcc tgtagggtaa  44940
ggcgtccggg tttatttcga tctagtgtcc gctagaatca gtggcttccg ccccatccgt  45000
ccagccagca atcgaagacg gcgtgtctcg gcttgtcctt ggcgccatgg gagaagtgct  45060
tgaatcggat gacctggccc ttgaggtatt ccctgtcatt ccagcggcgc tgtttctcgt  45120
cgtgggtcag gctggaggcc gacacgttga aggtgactcc aggccacaga cgttcgttgc  45180
ggcagacgaa cgcaccgacc attccggacg gcgacaggtt ttctgcgtgg ctggagcggg  45240
```

```
ccgtgtggcc aagttcattg atgaaagctt cattgttgtt gtgcatcaac tcttccacgt  45300
cgatgatctc agcttcatcg tagtcgtatc gcttgacttt cacacagtgc ccttccttgg  45360
cagtcgagcg accgaacttg tacagtccat cagcgcgctt gcccatggaa ccttcgaatc  45420
ccagcattgt gtggcggcgc tcgacttcgc tgaactgttc gatggaagtc accagttcct  45480
gctcgaccag gtgaatcctc tcatagccga ggcagtgacg aaggaagttc acgcgctcgg  45540
ccgccctggc taggcgatct tcggtcggtg cgcgaggatc ggtgaaatca tcgaacacat  45600
ggaaagacca gtccggctca ccgctgtggc ggcgaagatc gccggacgac ttctggaaaa  45660
ctttcgggtc gctgatgtcg ccgcagacca gctcgccgtc caggccgttt aacagtttat  45720
cgctgaggta ttcgtagatc gattgattgt tctgccgctt gagttgacga gtcagcgcct  45780
cgccttcgaa tacgaagcag cgaaatccat cgatcttcgg cgagaaatac atcggcagtt  45840
ggccttccag cagcttcggg tcaaaattcg atgcgagcat gggtttcata cagttctcca  45900
gaaaagaagc ccggcgaacc gggctaaatg gcggtaagcc ggctcagatg gtttcgttgg  45960
cgtggttcag ttcggccatg atcgacgcat agcgctcgtc cgactccttg atgaacacgc  46020
cgtcgtacat gacgcctttg cgatccttga tggtgtcgta ggccgcagcg tagcaggcga  46080
gcatggtagt gtcgtgctct tccgtcacat cgaacagagt catgacggcc aataccaggc  46140
tcttgatggc taatccatga tttccgcgtg ccagcgcgcc ggccagatgt ccgaggtgct  46200
gcaaatcgtc gccgtaggtg ggatgaactt cgacagtctc gctgaagacc gatagatgat  46260
cgaacagatt ttcaccgagt tgcgcggcca tgatcgtggc aaccaccatt acgtcgccga  46320
tgccgtcttt cacctcgact ggtttgttat aaacccaggc ttcgcaaact tctgcgaact  46380
cttcgaccaa cttcaggaat tgatccttgg ccgaagagcc tttgatcagg ttccggtcgg  46440
aaccccattt aacaaccagg tcgtgaagtt cgcgactcat gatttgttcg atattcattc  46500
tttcgattcc ttttggattt gggattttac tgcgttgatt atggacgccg tgctctggcg  46560
cgatccatcc ttggtggtgc cgaagtagaa ggccattacc gacttcagct cggcgaacca  46620
atagccgatg atggtgccga tggcgaccga ggatgttggg tccatcagag cctcgcggcc  46680
gaatgtgaag attgcgatga tgatgagaat ggagcctgtc agaagagcga atgtgatcgc  46740
cgggcgaacg aaatcgttct gctgcgccgc aagcctcctc gcagaatccc tgtcggccgc  46800
ctctgcggcg aactggctaa gctcggcctg gagctggttc tgctcagact gaaggcgatt  46860
ttgttcggct tgaatcgcaa gctcctggag acgaacgcgc tcggcgctct ggagttcggc  46920
gagacgcgct agagcttccg gattcgcgtc tagagcgcta gcgaccgagg ctgggtcggc  46980
cttcgacccc agcgccgtag cgacgatagc gccaacggcg gcgcctgcag gcccacccag  47040
gagcgacccc agagccgggg cagccgcgcc gatcttacta cctatgtctt tccagtccat  47100
ttcgactcct caaaagaaag gcgccattac agcgcctttc tccggccggt gatttagaac  47160
tcttcggctt cggtcgcatc gccgacgcca ccggcgtcac tgcgaggctg ttcctgcttg  47220
ctgtagtcca ccttcacctc gccgccgacg aacgacttgt acaggtcggc cgcagccttg  47280
aagtgatccg ggttcttcac caggccttcc agctcgaact ggacgccgga ccagctaccc  47340
ttgtcgttcg acatgcctac ggtggtcatg cggaccaggt tggcgaaagt cggcggggtg  47400
cgcaggccct gcggggtctg aacctttttc tgggacagcg cggtcatgag cttcttcgag  47460
gccttgatct gcgaagacga cagggagatc agagcctggc cgaaatcgcc ggtgtccgga  47520
tcgatgacga tgacgtaatg accacgggtg tcggcgaagt agtcagactt cttgtcgctg  47580
```

```
accgaaccgt cttcgttcgg cgcgtacagg cgtccttcga cttccttcac cttggtcggg  47640
tctttcatca tttccttgaa gtcttcgacg ctgatggcgc ccttgaaacc gccctcggcc  47700
tcgcgacctg cccagcggat gaactcgcgg cggtacgcgg ccggaatgat cagcaggccg  47760
gtcttgccgt cgtaaatctt gccggtgacg gtgttcagga acatgccggc cttcgcgcct  47820
tcgatgtact tcgggtcatc ttcatcgacc tggggagaca tcttctgcag aacctggatg  47880
aaggggatgg cataggactc ggcatcggcg ccttcgaagc ctgcgccgtc atacgatccc  47940
aaatccatga agtcgggaac ttcggtagtc gcgacggcgc cgccaccggt ggcaactgct  48000
acggccttgg tttcttcggt tgcttcggaa gtttcggttt tcttaccagc catgttaggc  48060
tccttgtttg tcgaatttca gttatcgcta actgtgggtt tataataacg gaagttgcaa  48120
ctaagtaaag caaattacat atcaagattt gctctttttc accttcggtt tcgtgatctt  48180
ggcctctttg tattcgtgta cgccgatgaa atctggcagc tcttcgccct tctccaggta  48240
ctcgcgaccg aacgcctgga gggtctggta atggacatcg cggttgatgg tggcgtcata  48300
gccggcttcg atgatggcct cggccgcctt cttcgcatct tccatttcgc cgcgaccgaa  48360
ttcggccaga accttggtct tgatgatgcc gtcgttgtcg gtgtcttcca gccacttcca  48420
gaacttcgat ttgttctctt ccttgacgga aatgatggcc ttcggctcta cttttaccgt  48480
gcgaccgtcc gccagagtag tggtcttctg accaagctct tccaacagct ccggaatggt  48540
gttacgcttg agggtcttca gctcctcttc cttttcggcc agcgcctttt gaagatcgag  48600
gatttcgccg tccagctgcg aggccttgtc caccaagttc agcagtcgat ggccgatgtc  48660
ggtggcttca accgccattt catccatgac gccaaaatag tcgatttcgc ccggcgcgtt  48720
ctctttcaag tattccggga tttcaagctc ttgctctttc atgtccgcct ccaacttagt  48780
gatgttccct tacttgaacc aagtattgag tagatattat gccgcatctt ccttgatacg  48840
gctactgatt tacatattaa atttcgtcgc gagtgctaac gtcagcctca aacacgccat  48900
caacgacata acttgccagg ttgcgtttcc actccaagct gacctggatt ttctcgtcga  48960
tggaatccag acagatcagg tcgaagtaca gaaccgagtt gacggtgccg attcgatgat  49020
ttcggtcttc ggactgcatc cgcagctcgt tgtcttcgtc ggtcgtgtag tagatggcca  49080
cgtctgcggc ggtgagcgtg atcccgatcc ctgctgcggc cgggttgccc aggaacacct  49140
ggacgcgctt ggcctggaaa tcgtcgatca atttttcccg ctcggcctct ttggtctcgc  49200
cgtagtatgt gccaaacgaa attccttggg cctccagata cgccttgatc tggtcgattt  49260
cctgaatgcg catggcccag atgatgatgg agcgctccgg gtcttcctcc agcagaccct  49320
ccagaagatc agtaaacacg gcgaatcgcg ggttgtcttc gggcggcagg atcaccggct  49380
cgccatagac gttgatatag ccggatgcaa cttgcttgag cttcgaacgc gctgccgcag  49440
catcgaaaga tacgtccagc atgaagtctt cgttcttgag aacgaagtgg tagtcttctt  49500
ccactcgctg ataaaccttc ctttgctcag gcgacatttc gaaatatatg cgcttgtaaa  49560
ccttttctgg caggaatggt aatgcctctt tcttcgtgac ccggaagctg tgcggctcga  49620
tcagggaccg cagtttgtcg agatttcgga atactggtcg tccaagatcg tctttctcga  49680
cgagctgagg ggggactgta ctcttcccat ccaatttgcg catgatggcg accattcgcg  49740
gatcgtcgct gggaaccaga acggaaaatt cagccacgaa cgcccgatag gatttcgtgc  49800
caagaatgcc atcgcgtagg aattgaaact gcatgaacaa gtccgtaggc gctcgcgtca  49860
gaggcgtgcc agaaagtatt cgacgtgcca cggccttctc gcccagcttt acgatctttt  49920
tcgcgcgttt tgcttgtggg tttttgatcc tcgtggattc gtcaacaatc gcgcacactc  49980
```

```
tgaacgtctt gaggaatcgc tcgacttcgt catagccaga ctgatggttg atggcatcga  50040
cgttgatggc aaagacccgg agaactttct catcggcgaa cgtctcggca tacagacgat  50100
ccaaacgcgc cctggccttt ttggaagtcg gtctgccgcg ccaatccacg cacagagtct  50160
tgactgcgac gtgagtagga atttcgcgca gaatccagtt agtatgcacg cctttggggg  50220
cgacgatgag cagcgcgtca acccttcctt gcaggaagag cctaactgag tctgccaaag  50280
tagtccatgt cttcccggtg ccctgttcca tcaggtaggc gaaatttctt ttgtttaggg  50340
aagctgccag ggcattgaac tggtgctgca tagcctcggt cttcataccc ttgactggaa  50400
aggttttggc tttcatttgt tctccagatc tgcgaggaat tggatgatat tgtccagtcc  50460
ttctgcatga ctcgcgactt ccaccaggtc gcggctgtta agatcgaaca gatcgagcat  50520
gggattcaga agcagccaat cggttccgat ttttgccagg acgaagccgc gaccacccca  50580
gccaatccgc tcccgaagga aagggatttg cccaggctcg aaacatcttg ccattgggca  50640
ggtggaggcg cgtttcggcc actcctccaa cgccttgaac tcgacccaga actggacacc  50700
tcgacgattc aggcaaatcg aatcggacat accagaccgc cgcgtctcca gaaagtcgat  50760
caggattcgg ccgagcgagc gctgcttaaa cgcattcgcc gctttcgtct cgcgatcatt  50820
catcgccttc gccctctttg gaaactttct tagtttgctc ttccagtttg gccttctcgc  50880
gctcggtcaa tatccgtttg atggccttca cgatgaacat gtcgatgccg ctgagcttcc  50940
agcctttgat caggaaccaa gagccggtcg gcgtcccttc ggcgatctgc tttccgtatc  51000
gcagatattt ctcaggcctg atacggaatc ggatttgttg atcaaccgaa tcatccacac  51060
acatgatgtc gaggaactgc gactggccct tgtacaccgg gtttttccct tggtcagccc  51120
tcttcttctg gcgaatcggt tcgttctcat ctgacagaac tttcttcacc atcttgacaa  51180
taaccaggcc gtcgtcgcca tcgcggatat cccgaatgtt ctgaatgggg tttccggaag  51240
ttactccaac cagctccgga ttgtcataag catgacccca gagcgtgtga gcttcgttca  51300
agtctgcgaa ttgaacttca gaattcgaca gactcgcggc gactttctcc caatcctgaa  51360
gcgtcttcag gtgggagccg gccagctcct tatattgggc cttcagctct ttcagatcgg  51420
cctttagctc cttcagatcg gccttcaaca gtttctccag ttctttgtct cggctgattt  51480
tcgccgaaag aatctgggct tccagtgctg ctacatcagc ctcctttacc tccacatcct  51540
gcgccgatat cgggcaattg gccagggcga tccttgcggc cttgacttcc tcgcgaaggc  51600
gcaggaacct ctcggccttc gccgggccga agcctttggc gttcatgatg ccgccgatca  51660
ggcgcccgtc cgccaccacc cagttgagtt cggaatgctc cgggtccagg gccgtatatt  51720
ctacgccttc tttggccaat tcgcgaagga tagacacagt ttgctggtcg tccttcgccg  51780
cccgaaggca cgcggccgcg tattccaggc gatgataccg cttcatgtag caggtccagt  51840
acgtcaccac agcgtagctg accgagtggg agcggttgaa tccccaggct ccgaaagtca  51900
ccatttcctg ccacacacgg tgagcatcgt ccggggcgac gcctatggtc ttggcgccct  51960
cgatgaacaa ttcccggcgc ttgttgaaga actcttcgcc ctttcgcgca gacatggcct  52020
tccggattgc cgatgtctgc tcccagtcga actgtccgat gtccttgacg atggacatga  52080
tctgttcctg atataggaag acgccgtacg tccctgacag atattgctcg acctgcggaa  52140
tggtataggt cacaggctcg cggccggcca cgcgctcgat atacttggtg gccataccag  52200
aagacaacgg acccggacgg gcgagcgccg tgatatggtc gatgttttcg aacgcggtga  52260
tattgatcgc gtttgcgacc gaacgaactg cctgcccttc gaactggaaa atgccggaca  52320
```

```
ttttgtcttc gttgagaaca tccaggaccg ccttgtcgtt caaaggcaag tcgtacaact  52380
cctgcgcagt cacacagttc gcgtcctgga tgacgcccag agttcgaagg ccgagcgcat  52440
cgatcttgag gagattcaaa tattccgaat ccggcttatc gagctgcgcg acgccttcag  52500
aagttaccgt acagaagtcg ataacttcat cgttgcagac caggatgcct gccgcgtgga  52560
ctccagagtg ggatgggtga atttcgaggt cgcccatgca ggcggacgcg atctcatact  52620
tttcacggaa gtcgcggccg ggttgagttt tttcgaaagt gtcctccaat ccttttccat  52680
accgttcgtc cgccgacgta tattcaatga tcgagttttt gatgttgtcg gtatcgtgga  52740
aggggatgcc gaagcgcttt ccgacgtgag cgataaccga cgcggccttg agcgtattga  52800
tgttgcccaa cttcaccacg ttccaagtgc catacttctg ctggagatat tcgaacacta  52860
gatagcgatg ggtatcggcg aagtcgatat ctatatcggg aagatcggac cgggaaatgt  52920
cgataaagcg ctggaagaga aggcgatgag ggagcgggtc aacctcggta atgccaagga  52980
gatagcagac caaagagcct gccgaagagc cgcgagctgg gccgaccagc atatgcttct  53040
tggcgaacgc gaccagatct gccacgacca ggaagtagct gtcgaaatct ttcagctgaa  53100
tctgcttgat ctcttcttgg aatcgatcct catactcctg ggtccattcc ttgatgtggc  53160
cgcgactgag gcggtaggct tgcccctcgc gagccagagc gacgatatca ccatccaagt  53220
ggatcatcgg cgccttcgcc agtttcacat ccgccaaccg ctcgactacc gcacgagtat  53280
tggctgcggc agtatcgaac tcttcgcgag tcatgatgtg gcgtaaacgg ctccacagct  53340
cctcttcggt ggcgatgtgg cgaaggccga ccgattcccg caccttccag gccgacgcga  53400
aatcagcatg gtcgatggac ggcatgtcgt tgtaagaggt aattaccacc ggctttccga  53460
atgccctggc cgtctccata gcgccgtgcg cggcgaccat cgacgcggga ttgatgtcaa  53520
tgtagtcgat tccggccaga tccagatggg cataggcctc gccagcgaat ttgatgacgc  53580
cgtcagcttc ctggaattct tgcggagtca atccttgatt ctggaccgac ttggaagtca  53640
agcggtagaa cttctttgtg tccttggcga gcacccaggc tttgagcttc agctctttct  53700
cgccatcgtc ggcgcatttg atcgggattt ccatgccgaa tccgcgaggc agttctgcct  53760
tggtagcggc ttgttcccaa cggacgtggc cccatgttcc atcatcgacg atggcgacga  53820
atggggattc gatctctttg gcgcgctcga tgatctccgg gaatcgacca tatgcggcgc  53880
cgtaggagta accagagcga acgcggagct gagggaaaga catcatgcgg cctccattgc  53940
ttgatacgcc cgatacactc ccatgcgctt gcagacttcg tggagcagcc gcacgtcgtc  54000
gagcgcccgg tgtttctgta catatgggcc gcagtagtgc tcataaagat gttgcagccg  54060
catgcggtgg ccgaacaacg gcgccgactc ttccacagta cagatatcga gcgatgggaa  54120
attgacttcg tccaggccga acttgccgcg agccagatcg caggtcagca tgaacttatc  54180
gaatggcagg ttgtgggcaa tattcgcgtc ggctctggaa aagaagtcgc gaactttctg  54240
gcgctgatcg aggaaagatg ggtgcttgat caggtcttcg ttctgcaacc cggtgatctt  54300
ggtgatgatt tcctcgataa cgattccagg attgcagatg aactctactt catccaaaat  54360
cttttcgcca tcagttatca cgccggcgaa ttcgatgatt ctcggctgct ttctcagact  54420
cacccttttgg tggaacggga gtcctgtggt ctcagtatcc catacagcga atatcatgtt  54480
tgttccctct tatgtcgaaa ggccggctgc tttcgcgacc ggcctgagga gtatatcgcg  54540
acggctgaag atttacgcct tctgtccgtc tttcggcgtg atgcggctgg agcgcatggt  54600
ggcgtgaaca aacgccgaat agttgatcaa gtccaaggcc gaatcggcat ccttgaaccc  54660
gctattcgcc aggcgagtga gtttacccac catgtgcatc acgaacaggg cgagtcgatg  54720
```

```
atcatcggcg gtcttcgcca ccaggccgtt cgggaagagg atttccatga tctttccgta  54780
catcagatca ttgcgaccat aggtgctctg gcgggcgcgg aagacttctt ctgctgcgta  54840
cagattgttg agaacatctt ccgcgaaatc atcgggatgg gaatcatctt cgcccggcca  54900
gacggatgcc atggcgaacg gcgcggcgtc ttcggactga gccgtttcag cgagcggaga  54960
cggggctttc gcaaaagcct cgtcgagggt aggggcggag ttcggggcgg ccgggaacgg  55020
ctcgcctgcc atgtcgttgg gcgcgctatc ggggtcgcta tcggccgcga cggcgaagaa  55080
cggcgcatcg caaccttcca ggttcaggat gtaggagtcg atccccaggc tattgtaggc  55140
atcgatgatg tcctggcgat catcgaacgc cgcgacgatc ttggtgacgc cttcgatttt  55200
cttcaggatg tcgagcgcga ctgcccgctt gaactgaggc gccggctcgg tgttaccata  55260
cggccgcatg atgagttcat actcgcgatg ttcggcgatg ccgagttcgc ggtggagctt  55320
ggccctggtc tggaaaaagt ggttgtcggt tcggccggtg acgaagaaaa tcatgaggtc  55380
ggcgtcgatg gcattcctga tgcgacctac agcgtgcggg ttgagagtgt ccttgtcgag  55440
acgagaatga tactcgtccc attgccgttc caaggcgaag ctcttgcggt ggctatcgtc  55500
gaatacgcag ccgtccaggt cgaagatgat gatgccattc tttggtttgc gttccatatt  55560
cagatttcct cgctggttgc tttctgggtg acggttttat cgatgaacgt cccatcagaa  55620
gtgaggcgga aaacttcgcc attctggatg aaatcgaacg attgcacgtt catcgtgatg  55680
cgaatggatt cgctgccgtt ggtcacttcg acttgtgcga tgtcgccaac tttctcgaca  55740
atgatcttca tgttacatgg acttcccgtt gacggccaca gggttggcct cttgtttttc  55800
cgatccccag aactcgcggc gcagttcttc ctgctcggcc gagcgatcca tccaggggcg  55860
atagaactta cactggtaga taggttccaa cggaacatca accacaggaa tctggccggg  55920
cttcgtctcc agagcggaca tgaaccggtc ataggatttc tgctggattt cctcttcatt  55980
catcaccttc gacccatagc gcgggaaggc gcaggagccg gtggcgacgc agtgcggctg  56040
gagtaggctg tcgaacatag gatagacttc cagaaccagc cggcgcattt cgcggaatac  56100
ttcctgatat tcaccctggg tccgaacgca caggcgaacc ttcgccatgt cgctgagagt  56160
ccgcagattg aacttggccg cgatcttcgt ttccatgttg gaaggaatga ttgcacgagc  56220
gtcctggagc gacgcgccgg cctccagaag cttctggtag ctggtttgcg cgtcggcaat  56280
ggcgtcatgc cacagacggt tcagctcttc gcggacatgg taggtcgggt caggctcgcc  56340
atttaccgta gccggttcgt cgaattccca gcggaaagct tctggctgaa cgacggcgct  56400
gatttccaga gcgcgactgg tttcctgctg gtaagccccg gtacgagtcc gaacgagttg  56460
atgggtgaag ttcttgctga caccctcgat ctggaagatg aagtccacga actcgaacgg  56520
cgagcggatg gtgtccagca tgtacttcca gtggtcgagc ttttcggcct cggtcatggt  56580
cgccgggtct tggccgcgca tgcgggtgga cttcgttccc aagagcaatt cccaggcgtt  56640
ctgggtgtaa ctaatcagag aaatcttcat cagaaatctt ccggaattgg cgtgaagtgg  56700
aatttttcgg tgagagccag ggccaggcct tgggcttgct ccctgttaag gccatactgc  56760
tctatctctt ccttgagcag ttcgcaggcc tccagacgcg cctcatactc ttcagcctca  56820
tggacggatg agaagacggc tccatcagag gttcggtaca caagttcgat cgccatggtg  56880
acctcagtag cagcggatga tttcggcgcg gatgtcgcga cggtcgaggt agtgctcacg  56940
aatcttgtcg cgggcacgct cggcctcttc gcggctgccg aacgacaggt tgaacgacgt  57000
gaaaggctta tcgtccagtt cagcgccggt ctgatacagg atgcctacca gaacgaaaga  57060
```

-continued

```
cggcgcggtc ttcggctgct ggtcggcttg catttcgagt tcgaggaagg acataggaac  57120
ctcttcagga tgatctggtg cgtaaattaa tagcgctcct gctgagcagc tacggtttcc  57180
ggctcgtaga tgagcatgtc aacgatttcc gggcactggc ctttcaccca gtcgatggcc  57240
gcgaccagtg tggtggaagc ggagaaagag aaagtgcggt aagactcatg gatgtacggc  57300
gaccccatcg aatcgcgctc ggtcgtgcga gaaatgactg ctttgatatt aacgatccgg  57360
cccatcttcg gcctccactt tagcgattat atcggacagg cttaacttct cgccattcag  57420
gaaataactg gcgcgaaact tcctgtcgcc ctctggcccg acgattcggg ccgttatggt  57480
gagactcccg ccgccaaggg catcggtgtc cctgaagaaa gtcagcagcg cccgcttgag  57540
cgctgcctcg cgaggatcga cggccattaa cctaccacgt tccagccgtg ctgagcgcac  57600
caaaccgcac cggtccctgc aggaaggcta ttcagaagga acacaggagt caggcggcca  57660
tcctcggtca tatggatgaa gtagcgggcg cattcaccta gccattcggc cttggcaata  57720
gcgcgttcta gattggcctt ggtggcgtag gtcttggtgg tgtttttgtc ggtggagaag  57780
attacttcgc gggccatttt gtcgattcct tttggttgaa gggtttcgcg tttcgatgag  57840
ggaatactac gcccacctga ctcagaagta aagcaatttg tgtaaattac ttcacgaaca  57900
ttttcttggc cttctgataa gacgaagaag tcatcaggcg ctcaatgacg tccatgtccg  57960
aaaccagatc gtccagaagg acgttgcgcc aggtagcgaa ccgaccgagc gagaagatgc  58020
cggcttcatg ggtgagattc cagatcatgg attcgcgctc gtcgcgaccg agcggaatga  58080
ttttgccttt ggtctggatg gtcggctcgc catcttcgat gagatgcctt ttcctgatgc  58140
cgaaggccgc gcaaacgtaa tccatatccc agtcgctgtc ccattcgatg gtttcgattt  58200
taccatctaa agtctccact atccccttag tgatggattc gacgatcaga gtatcaccgg  58260
tgatggacgc tcgaaacgtt cccactttag gaccagggaa atacacggtc tggaagacat  58320
cacaggggat ggaaagcttg tatcgactca cgatgatgga ggttccttca ccgaatgacg  58380
ggtcgattcc caggtccagc cctgccgcag ccagattggc gcggaacggc gcggtgctga  58440
tgatattcac gtggtcatct tgccggcgaa gatactggaa gaaagaggcg tcgaaaggac  58500
ggctccaagt gatgcggttc gctagcttag ccaccagctg ctcatagtag tctgccggtg  58560
cgatccaacg cttttcagtc gccagattcc agatggaccg gtccgacagg ccgcccgtta  58620
ctttcctgga gtacatattg cagtggtcga tgcgcggctg ggaaatgaac tcgccgtcga  58680
tgtagatagc cttgtgtaca gtgacttcgc ggaacgggat gccggttagt tggccaatca  58740
ctggcgagcg gaatcgcaga agtgcgttgt ggcgctcctt attctccggc gtcgccgcgt  58800
cgatgatttg ggcttgagga aagcgatgcg cggcgatcag tccggcgagt ccggcaccta  58860
cgatgattac tttctgatca ggaatcatga tgtgtccctt atgagtgtac aaaacttgag  58920
aggataaaaa agggacccat tttcatgagt cccttgaaga gctagacgat tcggtctcag  58980
aagagcggcg gcttactctt cttcaccatc ggaaccgtcg gcgccctgac cttcaccgtc  59040
gtgctcctgg ccttcatcgg ccttctcgtc atcgccctgg ccagcttcgt cttccttcga  59100
agcgatggcg accagatcga cccagcccat gatttccagc ttgctcagat agctgcgaac  59160
cgaggtgccg tacagcaggt gggccacctt ctcgccgaag gattcgattt cgaccggctc  59220
accaacggtg cagtgctcgt tgatgtaagc aaacaccttg ccgcgagtcg agaaggcctg  59280
cggggttcca tggccgtcgc cggtcgggat gaagtgagtg gcgcgggggc gacgcgagcc  59340
gttggacttc aggtcttcgc ggcgggcttc ggccttcgcg cggcgctctt cctgctcttc  59400
cttgcggcgc tgcttctcgg cttcgcgctc tgccttcttc tgctcggcca ggcgcttgcg  59460
```

```
ctcttcttcg cgtgcggctt tctgggcttc ctgcgcggcc ttcttctctt cggccttctt  59520
ggcgcgctcg gcttccttct cggccttctt ctgctcgcgc tcggcttcct tcgccttcgc  59580
cttctcggcc tgctcggctt ccttcgcctt ggccttttca gcgcgctcgg cttccttggc  59640
ggcggccttt tccttcgcct tctcggcgcg ctcggcttct ttcttctcgc gctcggcttt  59700
gcgcttctct tcgcgctcgg ctttcttctg ctcggcttcc ttggccttgg cttcggcctt  59760
ctcggcgcgc tcgcgctctt tacgttggcg ctcagcagcc ttctcggcct tgcgcagggc  59820
agcggcttgt tccttggtca gctcttcgcc ttgggtctgt tcgttctggt ccttctgttc  59880
catgttctta ctccgggaat gtttaaaggg atggcttatt ggcctgtgag aggattatct  59940
ctaaactaat tgaagaaggg aataccctta gcctgaactt tcctaaatat tttctttcgg  60000
gaaagtccaa actctaggga acttatttat gttcgagaag ttcctagctt ttacgcaaga  60060
acagtaagta ttcgattgcg cgagttatcc cagtatacat caactgacta taagggatgg  60120
acggcaagtt ttcttctaac atggcaaccc gtttccattc tgaaccctgc gacttgtgga  60180
acgtcatcgc ccagccgaag tcgaatccgc caatagcctt ctgcgcctcc agccgcacgt  60240
cttcctcgac cgaaaagctc agagggttga acttcaccca gcgttcatag ttcgtgccga  60300
taatgcgaac tttggcgaac aacatttcat caggctcgtc gtcatcttct tgcccttcag  60360
gaactggctt gaagtccagc agaatggctt gttcgccgtt catgatgcca tattcgtgct  60420
ggttcccagt gcacaccagc ttctcaccga ttcctggctg cacgcctttg tagccgagga  60480
ttcggcgagc gcgtgcgttc aagcggcggc gagtattgtt gtaggcacaa agaatcacgc  60540
catcgtcgtc caggaacgtt cgcatttcat catcagacat atcgaagccg gcccggacca  60600
atatgtcgtc atactcgcgg cagggcaggc gcttgccctg tcgcacgaac atcgacgccc  60660
gaacgatgtt gccggcatta cgctcgattt cggtcatgat ggtgtcacag ctgttctcgt  60720
ggaaaatttg gacgccgcgc acaggaggaa cttggccaaa gtcgccaatc tccaaaaccg  60780
gaattcggtg cgacagcaag cgctcttcat cccactcgcc gatcatggac gactcgtcga  60840
gcacgaccaa cttcggcttc tcgtcgagcg agtctttgtt ggcaaacatg atttcgccgt  60900
cttcatcttc gccaatcggc cgatagatga agctgtggag ggtccgggca ttgatgcaac  60960
ccttctcgcg aagccgcgct gctgccttcc cggtcggcgc gacgaagacc gtccagtcca  61020
tcgagcagca aagttcggcg atgatcttcg cgatggaagt tttaccagtg ccggcgaatc  61080
cggcgagtcg atagacctgg cggcggtgcg cccgatcaca ccaaccgcga taccagttca  61140
caacggaatt gatcgcgtcg atctgctgat tgtttggccg aaagccgaat cgctcttcga  61200
tctgatcgac ggtgaaacta gatgctgaca tatttgcgtt ctccaacgct gggtttaatt  61260
gaatcgaggc taagtttaag cacgccatcc acagaccatc cagtatcacg acgatacttg  61320
cggccttgcg gatcgacata gaagttcttc gtgcgccgca gcagtacata atgccaggca  61380
gctcccagcg catgaactct tcctttataa gggaaggcct tcgcctgctc tgcggcctcc  61440
ttggccccag ggagccagcg gacggtcgaa aggaccagga ccgcaccctt gacagcctgg  61500
gaagcggcgc ggccgtcctg tgggctatag cgatgtctat cggggtctac ccagtggtgg  61560
ttgccgcgcc ggagcttcac cgtccgggat cggccatcga acaccacagt gccttcgtga  61620
gtaaaaatgt gttccgccat cggatgttcc tttataacgt acagttatgc tttacctctg  61680
cgcaggaaga gtatactatc agctgactcg ccaaagcgag cgaatttaat ccaactttac  61740
ttcggcagga aagtggccga tactagcgcc gccgcctgta ctgccctcca aaacagagga  61800
```

```
tacattaaat gcaagaatgc aagatttccc gcgaccaact cccggtcggt aatccgaatc  61860
ccaatgtcga caagacccgc gacccaaacc tgaagcccgg tttcctgcgt cgcagccgcg  61920
agcttgaccc ggcgctggcc gttcgcattc gtcgcgagct gatccatgcc gaagcatccg  61980
acttggccaa ggccggatgg gtcaattcac agtccagcct ttatggatcg aaagccttcc  62040
cgcgccattc tgtcgttcgc gtgaccggag ttccggaaga tggagctttc atcggcatgc  62100
tgatcggctt catcgagcat cgcgagcatg gcgaatgggc ggtcatggaa gccggaacga  62160
aagaaggcgg cgccgtcatc attccagtcg atcacatcat gcgagcgtca ttcgccgaag  62220
ccgaagagtt cgccgaaaag tgggagcgga acttggggtg gcgtctcctg cgccaactcc  62280
gcgagtgcgg cgccctggcc gggactgaag acgagttcct gcggcggatc atcaatcgat  62340
acgttcgtga tcgcacgatc ctcgatcacc acaaagtcgg cgcggacaaa atctacactg  62400
atgcagtgct caaaagcatc ggtgaaacat ggccgaaaat tccttcgggg aaattcgtcg  62460
gacaccgagt cgcgcagctc ctgatcggcc acaagctagg tcgagcgggg accatcctga  62520
atgacctggt ggacttcctg gagaagttcg cggccgggcg cgataaagtt ctcaacatcg  62580
ccatctgtaa ttgaggtgaa tgatatggaa gatttgggaa agcccagcat tccggagttc  62640
gagaagatcg acgccaaaaa actttatgag gctctggaga cgattgcgga gctagagaag  62700
aagtgggacg aatccgaaaa gcgcacacgc gatctggcag aagtggaacg gccagaggta  62760
gtcggctatc gcagcgcggc ttctcgcatg gtctatgaaa aggactatgg actgcagaat  62820
cctgagtcga tgatgcttgt ctcccagcac gaccgcatag tcggggagct gctgactgca  62880
ttaacctcga tgactgaggc gcgcaatcgc tacaacaacc tatggaattg cgctggtaac  62940
cgcctagctt tggcgcaagt tgaaatccgc aaagtaacat ccgagcgcta cgcagccctg  63000
gccaggatcg ctgagctgga aaaggaattg gccgaatccg aaaagcgcgg gagcgagctg  63060
gccgcgagct attgtgacgg cgtagtaggc gatgaatacg gccatcctta ttgtcgttat  63120
aaagtggaac gcgaagtcgc gctggccgaa gtcgagcgcc tgcgagaatc aaaaggcgat  63180
ccttctggca gcttcgacag atgcatgaag atgatgtatg agcgagacga gaacgcaaaa  63240
cagctagaat tcgccctggc cagggtggcg gagctggaga aagaactggc gatggcacgc  63300
gacgcagcag caaagggtga tgctgcccgc cacgctgctg gcggcatgga aatggagatt  63360
catgagctga agacgaagct ggccgagctg gagaaacaag agccggtggc atggggagcc  63420
ttccatttcg gcgggaagcg cgacggcaag ctgtatgcgc aatgcgaaac tgaggctcag  63480
atagaggcgt atatcctcga catgcaccga agcagcgact cattgacgct caggaaaggt  63540
tccctctaca ccgcgcctgt agtccaggct caacccagcg tgcctgatgg gtggaaaccc  63600
gttccgatgg aaccgacgcc gcaaatgaca ttcgtcggcc agtccctgcg ttatgactcg  63660
gtaaacagca tcggcgagat ttaccggcaa atgctcgccg tagctccctc acccatcgat  63720
ccggctgcgc atcctcagcc gtgccaacaa ccacaggccc atcctgcccg ctgcgggtgc  63780
gagcggtaag tgccaagtaa ggagtttatg taatggaaca gcagaaacct tcggaagtag  63840
atggagccat cgtcatgacc gatctcgata ttcgcattct tcgaaaggcg aagccagaag  63900
cgcaggacga gtgcgccgtg tccatgttcg caacggcgat ccgccagaaa ctgcagcgct  63960
cccgcgataa aggccgaggc ggctggatcg actgcgacga agatattctg atcaacggat  64020
tcgccgaaca tgcgctgaag ggaaatgaga acaacctctt ggacctggcg acgttcctga  64080
tgttcatgtg ggtgcgcggc atcgacgatg cgaagattcc cccggcgctc gaaaaggcgc  64140
gacagcacaa gatcatggaa gcctggagtc gaatccatga agacggcctg aactccgcca  64200
```

```
gaaaggcgag tgctgcgcga cagttcgtgg aagtgccacg acgcaagggg cgcccggagc  64260

gacttgcatg aagcctcacg aaataagact ggcccaggcc gaagagttcc tgcgcgaact  64320

cggccgaggg attccggacg acgaacgggt gatggtcggc tacgcggaag aggccacagt  64380

ccagaccgac gagaacgggc gcaagctcaa cgccggatgg tggcccgtac cctggaagga  64440

agggaaatac atcaactcca gatccaacgc ctacgcctgt atatcgtcgt ccatcaagac  64500

gcccaacccg aagaccggcc agatgcggta ctggcgcggc gaagcctctt tcggccacgg  64560

cctggcgttg atggtcgatg acatcggctc aggcaaaggg tccaagggcg acttcgaccg  64620

cgacgagttc cgagaacgac tggagccgac cgcgattgtg gagacttcgc cgaacaacta  64680

ccagttctgg tatttcttca aagagccgat gtcccacatg ctccagttca aggcgctgct  64740

ctattcgttc gtggaccagg tgctaaagaa aggcggcgac aacacagtca aggacgtcag  64800

ccgttacggc cggatgccat tcggcttcaa caacaagcgc gggaaagacg gcaagttcaa  64860

atatgccgac gaaaacggca agcccgaatt ggtgcgcctg tacagcgccg actattccaa  64920

gcgctactcg ccggaagaga ttgcccaggc attcggcgtc cgcatcatca tgccgcagat  64980

gaagaaggtg gagataaacc gcgatgactg ggtgtatgac caagtatggc tgaagtatgc  65040

cgagcacatc tgcacgaaat acaagatggg agaagcggca ggcggccagg tccagcagaa  65100

tatgtccggc aaataccgca tccgctgtcc atggggcgac gagcacacca acggcgatcc  65160

tttcggcgca tactttcgcg gaccgatacc tggagccgag cacgaatatg tgttcggttg  65220

cgggcacgat acttgccgca aagagcatcg acggacgtgg gcggccttca ctgatgaagt  65280

cgtcctgccg tacattgtcg aacaacttga acgcatcaac cgccgccata tcggcgagga  65340

gtagtaacta tgcaaaatga tcctggaatt ctgattaccg caatcggctc attgcttctc  65400

ggccttctcg tcttcttcga aggcctgaat ggctggaaaa taccagtagc gaactttctc  65460

gcgtcgcttc tgtgcttctt cgtcggcctt tctgctttaa cgtgctggtt cgtcttggcg  65520

tttgacgtgt tttagtcgac gaacggtccg gaaattttcg gatggggacg gaacttatta  65580

gctctgccgg tttaggtagg agataatagc cgtccctttc gcctcaatat gtagaggcag  65640

tgttatatcc gatcatgtaa agcagaaggc ggcaaaccta acatgattat cgacgacgat  65700

aacattcttg atgacgaatc ggggtccagt gagtttgatc tcgcgcagat agaagatgct  65760

ggaatggacc ctttgatgac cgccgcaagt aaagcggccg acgatgcgat tgcgaggaat  65820

gagacttacc gagcgcaaaa ggcagcaaag tatgcagagg cgtatgcgga accagatctg  65880

aagaagcgag cgcgattgtt gatgctcgat caggcctttg atctcccggt cagccggttg  65940

gtgaaaggac cgttcgacga cttcatcacc aagtacagct cgacttcaga cagcaactac  66000

ctcgcggtct atgatacgtt gttc                                         66024
```

```
<210> SEQ ID NO 3
<211> LENGTH: 45333
<212> TYPE: DNA
<213> ORGANISM: Bacteriophage P1792

<400> SEQUENCE: 3

tcaaaaggaa gaaggaatct taagagccta taggtctatt atactacatt ttggatacct     60

tgtcaagtac tttttgatat ttctttgata atcacatgat ttacccgacg aacggtatga    120

tagggttcta taggtatacc ctaagactac ccttcgtagg ttgctggtaa ggggtaagtg    180

gcatagggtt cccttgatcc aggttctata ggtatacccc tagactacct ctgtttgcta    240
```

```
tgtcctggcc tattgcccct ttatccagta atataccaac aggtatcgga ggttgccttt    300
gatccagggc ctataaccgg gggttacccc aaaagtctat tttatcctcc ggtgtatctg    360
gggaatatcc ccccaggagt cccccagata aagtgggggt ggcctatccc caggggtata    420
gcccctagcc cctccctagg ataccatggg attagtccgg gggtcaaccc cttgagatac    480
cgttcatcgg gtggacccta gggtattcat aagaaaaatc ttagggtatt caggggggtgg   540
atcgggggga atatccctta gactccccct tgacagtctg ctggctaatc tgatactcaa    600
gacttctatg tccgggggat agcgccccag ggtatagccg aaaggctgta tgaaaaacca    660
gtagacaacc ccgtaaagaa tatggcgtaa tggcgccgcc ttgagggaaa ccgataggca    720
ccgggggaaa ccccaggggc ttgacaaacc ccgcggaacc gggtctaatg gcccccacgt    780
tctacctagg ccaccatccc tcaagtctac ggacacatgc gggggctgcc aaccaagggg    840
gaatgcctaa gtcacccaag tgtaaggccg gcaggcatcg gggttgaca agggataggg     900
gaagcggtaa gatggccccc aagtcaacgg cataacgtgc atgactcctt cgggattagc    960
gtagccttga caataagcgg atgtgttgat ccggggcggt gtagataggg cgccttgttt   1020
atatcctaac tacaaagcta tgactctagc cgataggatt ggtccaccac gtaaatacag   1080
acggaccact tagcaacaag tcgagagact ataaagcgcg atattgacaa gccaagccta   1140
aggctctaac ataggcaccc gtccccagcc atctacggat ggttgagata caagccccca   1200
ggtagggcag gcattgggga atgccgatag tttaagctag accattcaac aaccgagtat   1260
cttaggtcta accaatcccc ccggataacc cgcttgattg cggacccagg aacggcggtt   1320
agactattga aaaaggttgg gtcaaaaggg tagccatccg agtccctact actagcttat   1380
cgtgactggt atgcgagagt cctttgggca agacgcatcc ctacctaaca ggtaaggtta   1440
ctccctacga tagccatccg gctccctctt acaagtaacc tcggagttag gtaggatata   1500
ttacaaagga ctaacccttt gcaatgtatc ctctagaggg aattaaagtg aaaggcaaac   1560
cgaaacaaag gaccgcagta tacaaaggcg gtcgcaagac tgctaaaact gatatccatc   1620
gcaacaatcg gaagtcggtc tttggtagcc cacgtctggg gcgtaacccc cttgacattc   1680
tccttaactc ctgaaacaaa aggaaatact tatgaaaact gtactcaccg cagacaaaat   1740
cctcggcaag gatcagatca ccgctggtct ggtagctctg aaatcgttca acaaggcttg   1800
gaacgaagcg acccaacaac tggcggcctc ggctaccgta ctggctcacg agcatggtga   1860
tgttcgggct atccgtgcga tgctggccat gatgccgaag ggcgctaaga ccaacagcct   1920
gcgccgctac ttcgagcgct acgcaccggt caagtggtcc gaactcaaga aagagttcaa   1980
gttcgacggc aacaaacagc acaagggcgt tcgccggggg gaaaccgaag aagacttggc   2040
attgttctcc ggcatcctga acacccactg gtccgactgc ggcccggcgg aaaccgctga   2100
caatttcaag ccgatcgatc tccaggcacg gctcctgcgg ctggtcaagg actgcaacaa   2160
ggaactggac agcgagttca aggaccagtc caaggtaact gctgaccagg tgaatcagct   2220
gaataccctg ctgcgccaga tgttccccaa cggcgaggcg gcctgatgcg agtagtgggt   2280
ggcgcttggt tcttccccaa ggttactaag cgcacccctc accagcaacg aatccgaaag   2340
tatctgtcca tggtaaaccg tgggcaggta tctagggcca agcggtacgc tgaaaggcat   2400
tgcctatgat ggccaggggc gtactatgac gcgccccagg tctatcccta gagtgcatgg   2460
taggtccgtg cattgtagcg atagactatc aggaggtttc catgggttac tgtatctttg   2520
ggcaggctcg ttccatccaa gatcggggtt atgtgtctgg tttctgcgat gcaagggtag   2580
gctggcaagg gggtattgtt taccgctgga tattcaagga cggtaaattt gcctgcggtg   2640
```

```
tctactctac ggatggtatc cgtctgagcg tctgcgggtg ggtcaaatga agtcacccta   2700
cgaagcggcc cacgaaaggg cactcatggt taatcggttg cagaagctca cgaggatgct   2760
gcgggttcac cccgatccca agtggaagca agaacaacag gaattgatta agaggttgaa   2820
gaaatgacta tcgctatcgt ggtgtcttgc gtaggcatcg gatacttctt cttccgtgac   2880
tggaaggaag agatgggtat caactgaccc aactgatgag gccatggtga ttcctggccg   2940
aaacccccac cggacctatg gtcgcaggct ggggagtctt gggaaatcag caaaggaaac   3000
catcccgtga aacgcaacga ctatcgtaag gttagccgca acatgcaagc tatcgaggca   3060
atcgaccgca agattgccaa ggtaactcgt gagttgacca actacagcgg caatcacctt   3120
ggtaaaaccc tggagttgaa caagctccgg gcaaagcgtg catcgctggc taagaacagg   3180
gcgcggtaat gtcatggaag tatattgcat gtgccgccat acgctcacgt tccaatgggt   3240
tgttgctggt agcgtgggtg gttctcttcg tcctgtcctc gaccttggac agcatccatt   3300
ttgcatcgtg aggtagtcct atgaatatca aggtgtggcc acgcaacgga gtaaccctca   3360
gttctctggt taagtcccaa accttccgta taaatgaggg tgtgtacatg gtctgcgaac   3420
tccgcagcat caggatgcag ggtgaatctg atgaggttgc cgttgttaac cttaagactg   3480
gcaacgtcat ttacatgcct ccagtgagtc tggtataccc agtaactgcc gagctgaatt   3540
gctacgaggt gtaacatgaa actccaatac aacatgatta ccagtaagat caaggttgcc   3600
tcttgggatg atctggagtc ggggcgtctg tacatccgcc aggacgagga cggggctgca   3660
aacccgcgtg tctttatgta catggaagtt gcagatgaat tcttcatcgt ggatatcttc   3720
ggtggacccg tgggtgccgt atacttcagc ggcgatgttg actgcgggtt ctaccccgtg   3780
accatcaagg ctgcgtccat cgaagtccat cggttcggcc caccggccta gggtgtgtac   3840
tatgacgctc gcccgataca tctaccactg gttggtatcc aaggttgtca tccgtcgata   3900
ccagcctaac cccaaactgt accccaactg gtccgttact catatccgtg tgtcgatctt   3960
cggcaaacgt gcaggtatcg tctatgaaat ccactgaacc acaagtctat tggttggcca   4020
gtcccgatgg tgaattccac ctgaaggtca tcaacttcgg ccagttcatc accgaaaccc   4080
tttacgaact cggcattccg gtggaccaca aggttcatcg ggtccactga ggtgacccat   4140
gacaaacact accttcactg tagcagcaac ccgcccccgg aacgaccttc acatcagtaa   4200
gcgggcggat ggggtttatg tgaaccctaa aaactctggc gatattgcct tcctcaagga   4260
aggtaataag gttgtcgtcc tcagccagag cgggttcagc atcctcgaag cccagaccat   4320
gcccaacatc ggggaactct acccggctaa ggaggtccat gtatccgcca aggtgtgggg   4380
accgtatgaa gagtaaacca atgatcggcc agataatggc ccaggagcgt cgcatgaagc   4440
gtcgggtaga gaaacgagag ttcaacatga ctcatcagga aggcccccag gagccccgtg   4500
gtgagcttgg tttcaccctg gcagccgtag gtgtggagtc gagccgatcg gcttacctgc   4560
ggcacgccag ggaggctatg atccaatctg gtgagccttg cccccactgt atgccagtct   4620
tcggtcccaa agagggccgt tgctgcaact gcgcgaggga ctggtgatgg atttcggtaa   4680
tctttggtgt ctcttgggcg tccatcggta caaatggtcc gcagcaaatg atgacatacc   4740
tcctgataat cccagcgatc ctggcctaca tgtcggtagc cctcatcaag tcaaccaaac   4800
gactaatcaa aggagattac taatgcaccg cagagacttt ccctcctgct gtaccgcaaa   4860
aatctacatc ggcatgggcc cctcgggtac cgctgaccat tacgccggcc tcgcatccaa   4920
cgggttcagc cccgtggttt tcgcccagga actgatcggc gccatccgtc gtgagtacaa   4980
```

```
cgagggccac ggtacgatgg tcttcacggt gaacagcgag caggtggtag cagataccat   5040
cctccgccgc atgggcagcc actacaaccc ctgggcatcc agcgacaacc actcgaccaa   5100
ggtccgggtc cacgtcatca acgtgcaagc tgcggcggag atcctcatct accacggtgt   5160
ccccggtact gtcgagcact cggaatacct cgacaagctc tgtaaaggtc tgtaacatct   5220
aggccttgac attctgctgg aagtgtggta taataacctt aaggtgtccg ggttgctct   5280
tatacctata ggatacctta gggtctacct ttatctctta cttattattt gaggtatcaa   5340
atactcaaga tgtatacccg gactatgctg gtggctatcc ccctgtgggt tctttacctc   5400
ctcgtcctcc cctacctgat gacctcggat tcaacctcgg ctagcgccct gggtgccggt   5460
ctgatggttg catccatctt ctatgggctc ttcttcttga agtacctgta caactacagt   5520
aagcggctgg agaaaaaggt caagactttg gggtgggaa atgggtgagt cgaaggaacc   5580
tatcgtcagc ttcgagaagt tcatgcaggt catgtatgac cgagacgagt acgccaagcg   5640
cctggaagta gcaacggcca agatcgagga gctggagaag tccttggcaa tggcactcga   5700
cgcagcagcg aagggtgatg atgctcgcca tcagtgcggc ggaatggaga tggagatcca   5760
ggaacttcgt gatgaattgg caggactgaa aaatgaagta aaggcgagta agcctcagca   5820
tgtcacccct catttctggc gacaacgggg gggtggtcga atctttgtgt caggtaactt   5880
taacctggac accgagacga taccccttcat ctgcctggag actggccaaa gctgggacat   5940
tcaggagggg cgggtagagt atatcttcga gttactcccc aagggccata ccttcacggt   6000
ggaggtctga tgtactatga cgaacagcaa tggggaccgc acccaagggc gccgccggtg   6060
ttaccgtacc agtgaggtaa cttcggacat atatgacgcg atctacaata tcccagcaat   6120
cgctggatcc cccaagaggc caccggatga tgattgggta tactacctcc tgatggtagt   6180
cctcttcatc agcttgtgca tggccttcct tactcccctc atcaccagca aggatacagc   6240
ctattaaagc caaagtcttc tacgagcgac tgaaaacctc cggcgagctg accctgaatg   6300
gcggcatcta caaggccacc aaggttcctg cgccccacaa gggtaagcag cagcgtcgcg   6360
gccccttcta agaggtcgct agtaataccc ctagtattcc tgtcctgggg gtattgctgg   6420
ataactcaac aaaggagaaa acaaatggca cgtatcaagt acgccttcgg tatgaagtcc   6480
aagaatggcg aggataaagc cctcaaggtg atgacctcta cctcctgctt cggtacaatg   6540
gaaggtccgg taacccacgg ctataagctc gacggttgga ccttcatctg ctcccgccga   6600
agcaagaagt tcatcgatgt actcaacaag tgtacccaag gtgaactcaa gaccatcacc   6660
atcggaggca aggccttcaa gatcccgaag gtccacttct ggtcttacga aagcaaggcc   6720
aaggattccc ccttcgagaa gtattctaac gggacggaaa tgatttcccc cacccatcac   6780
ggaaaggaag gggtctgcgg tatctacttc aaccccaagg tacacaccct ggattcctgg   6840
taccccatca tgaaattcct cttcaagatg atctccagcg gactcgacta ccaaggtcgt   6900
gaagaggagg ttcacctgaa gcttgctgag aagcatggct tctggaagtc ctacctcgca   6960
atgtccttcc acgggctgat agccaatggc tacaccgggt atccgatctc caactacatg   7020
ttcagtagtg attgggatga tctcaagaag ggagatatcc acatccaatc cgctgacgag   7080
tctatccgat tcggtcgttg gatgcccaat cgggatgccc caggtggacg cgagtgggta   7140
aggggcacac cctggcggtc tgaattcctg aagattcagt tggacaaggt ggaggtggtt   7200
accatagccc ctcagccaac cgtcttcgga aagaaagatc cctacatgac cgtagatagc   7260
gaggtgggag ggttcctacg gcttactccc actagctgtg aaaaacacgg agtggtaatg   7320
ctggggatta tgggtgaaat taactggggt cgtgacataa aggatatctt actggccctc   7380
```

```
gaagacttca tcgagaaaaa cttctgacaa ccaaggagaa atcaaatggg aatgtatgca   7440
gcccataatg tgtactatga cgccgagggc tctattgtac accaatactc ggtcaagagc   7500
atgaccgaat atacaaactg cttcggagcc tattgcgacc ggacctccgg cgttagtggc   7560
gaccggtggg ttaccggggt tggccacctg ctggtatcta cccacgagaa tacctctggt   7620
aaactggtgg agttcttgaa cagcgatctg gtcaacagga ttaccgacgg tggtattctc   7680
tcggcttcca tcgactggcc tacccgttgg tgggattaca acgatgacct caagaaccta   7740
agtgatcccg accacttctc tcccccagga cgccggcagg cagtgtatgt acgggtggac   7800
ctcaggaaga acgcatcggc catcatctgt gccctccgaa tgggcgatcg cttgtggtgt   7860
gtaggtgatt ccatgcgtcg ctatacccag gaaaaccggg ataaggtcct gggatgcaat   7920
gcagagatcc tcaccctcgc ggcttgtgcc caggtaggta gcactgctca ctgcgacagc   7980
tatcctgcca tgttcccggt gactgccggt gaataccggg aaggatgcga gagtcacgga   8040
tgggaagtgt atgacagcta catcagcgaa gtcatggatg gtatcgtagg tgggtacaag   8100
gagatcacct acttcgatat caagagcatc catgggcgga ctcgcgaaga gttcaaggac   8160
aaactcaagc atcacgacgc tgagttgtgg caagggtata ccaaggacga ttacctgatc   8220
gaatgcgacg ggctcgaagg tgtacacaat gatcggatcc tctccatcat ggcacctatc   8280
actatcgacg taggtgacca aggtcgggaa aggtctgaga ccgtacccac cagtccctac   8340
agcatccccg aaatcctcga aaaactggag actatgcaat gaacaacgca atccccctga   8400
tcggtgcaga tcccgaagtt ttcgtcggct acgaccgtaa cccccagagc gtcatcggct   8460
tcatcggtgg aaccaaggaa gccccccttgg ctgtagccgg tggtgccgtc caggaagaca   8520
acgttcttct ggagtacaac atcgacccgg ccagcaccaa ggaagagttc gtgaagcgta   8580
tcgtttccgt tcgactcctg ggtgcccaga tgctccaccc cttcggcatg aacatcatcg   8640
agaacctgtc ctctcacctg tacgacgagg aactcctccg cagcttcggt ccccaggctt   8700
acgtcttcgg ttgcgagccg gactacaact gctggactcg tcgtcagaac gtgatgccga   8760
aggatgcccc tccgaccctg cgcactgctg gcggccacgt ccatatcggc ttcagccaca   8820
tcgagcgagt taccaaggct accacccgcg aggtcatgca gatgtgtgac tacctcctgg   8880
gcctggcctc tgtcatcctc gatggtgaca cccagcgtaa gaagctgtac ggcaaggctg   8940
gcgcaatgcg ctataagccc tacggcggcg agtaccgtag cctgtcgaac ttctggatct   9000
tctctgtaga cctgaccgag tgggtctatg aaatggcagt acgggcttac acctccaagc   9060
acctcctgga ggagtacaag tccatcgtat ctggcgatga agtccagcga atcatcaacg   9120
agaacgacgg cgccgcggcg gtagctgcac ttaaagcgct gggggtggta tatgaatgac   9180
ctgaataatc gccatcggtt ggccggggac ttcaacatgt actactcctc cacctatgcc   9240
ttcttccggg tggacggaga gcctcgggta gtgtacgtgg acgataccga gtccattggt   9300
gacgaccgtc aattcgacgg gtttcgtctc cttggcaacg tgtatcgccc cgacggcagt   9360
aactactacg gaggggttgt ctacagcgag gtagaaagcg tgcggccctc cagtgggtac   9420
tatgacgtct ttggtcgtgg ggttcgtgat acctatgtat ccttcctcgt gaacaaccgt   9480
acccagcgca agggtgtaga tccccggaac atcttgctga atcatggcca acaggctatc   9540
accggcgaaa tgatgatccg aatcttcacc caggccgagg aaatgatctc tgctccctcc   9600
caccgggact tcttcatcaa ggatggggtt gtccactgga agggcgtgaa ggtcggccag   9660
atggtggatg ggcggctgtc cgcagatgaa caattcaaga accaggagga cttgctatgt   9720
```

```
cagttattgg cacacagata gggttccata agaaccagat catcgccccg gaacaccacg   9780
aggaacttcc tgcggttgct tccttcgggt tcgaagtcga actggaaggc ctcaacaact   9840
ggccagaagt ggatgggtgg gatctgaagg gtgacggctc tctgcggggg ggtatggagt   9900
atgtcttctc cggtcccgcc tctggccaga gggcaatcac tcgggttgaa tcctttgtaa   9960
gtgcgatgga agaaacccct ccggctccta ccttccgatg ctccacccac ctgcacatgg  10020
atatgcggga cgtagagtgg ccggtgtacg aacgaacggt cctgacttac atggcattcg  10080
aggatgtttt cttcgatcac tgccagccat atcgtcggga tagtaacttc tgcatcccgt  10140
tcttcagcaa cgactggttg gcccagacct tcggtcgccg tatcctggcc ccggaaggtg  10200
accgagagaa agtcttgggt cttacctcct ggcccaagta ttcggccttg aacctccagg  10260
taacccacaa cttcgggtcc atcgagttcc gtggtgctca cgccctgact actcgacagg  10320
aaatggtagg cctgatgcag cgtatgttgt gtctcaaggc cttcgccatg gctcacgcag  10380
aaaccccct ggaagagttc ctcaaggtgc tctccgaggt gaatctccgt gatgtgttct  10440
tcctggggt atctccggac tatgaaatgt ctccgggtgg tcgtgaaatg ggatcgcca  10500
gtgctactct cgcggtggca accatgggct ttgttcgctc cggggtagat cctctggagg  10560
atgaacagaa ccgtcagcgt cgtctccggg agcaggaacg tgagcgtcag agggctttgg  10620
atcgcaggct gcttttggct cgatctacta cctccagact actcgatggt gcagcagagc  10680
ggtacaactt ggcaatggtc ccaggtaccc aggttcgact ggatacggcg attactgcgg  10740
taacttctct gcgtcgtatt ggtcaccaag tgcgtgtacg agaccttctg gaggaccaag  10800
aggctcttca agatgccttc gtactgctca tggataaccc gcagcacctt cagcgccata  10860
ccggcgtaac aatcgaacca gatatgtact aaggagaaat acaatgtgtg gattggtagg  10920
cttctgtgcc acaactaacg cgagtgataa cgaaatcgct cttctcaaat ccctcctggc  10980
cgtggatatt atccgtggtg ctcacgccac cggtttggcc aagatcgacc cggttaagaa  11040
cgaggtagga attcacaagc gggcagtaga tgcctacgac ttcctggctg atcctgaaac  11100
caaggagttc ctggacaagg gtcgggctcg catctacatg ggtcacaacc gttacgccac  11160
gatgggcgac aagacggacc atggtaatgc ccaccccttc caggtagacc acatcaccat  11220
ggtacataac ggaaccgtag atacctgggg cctgcacctg ctggacggca atgataagta  11280
caacgtggat tccaacatgc tgtgcgctac cattgccaac cacggtgcca agaagacgtt  11340
cgaggagaag ttctctggtg ctgctgcggt tgtctggtgg gattccaagg aacgtagcct  11400
gaacttcatc cgtaacgagg atcgtcctct gttcatggcg gttaccacca ccgggaccat  11460
cgtatgggca tcggagcctg ggatgctcaa ggttttcctg gagcgaccca atgctaagat  11520
ccgcctgcgt tctcctatcg ctgaactgaa ggccgaagtc ctggtaacta tcccgttcac  11580
ggaggccgga gtgcgaaagg gtgcagaacc ccagaccact ccggtcacgt ttctggacct  11640
cccgattccc gaaagcgaaa ggcaagcagc ggcatggtgg agtcgttacg tcggtgtctc  11700
ggactacgat gactacagcc gaagccaagg cagccaagcg ggaacgaaag gcagccaagc  11760
gggctcgtcg tatggaacgt ctggcgatgc gtacgcaagg aacaccctcc ggatcaacaa  11820
caacctcgac gcagcaggta gcaccttcaa gcaccggcaa ctcgtcacct tcgatgttgt  11880
caagatcgag gcctacgcaa acggcagcga gtacggaact gtcactggaa tcgagcgtga  11940
agaaaacctt ctcatcgaag ctcatggcat caacgtcgcc aaggtccacg gatacaccgt  12000
cctccgaggg agtatctcca atgcctactt catcggccaa gaccgtgatc tcaaggttac  12060
tgtcgaggat ctggcggtaa gctgcctgga cccaaagcat cggccgactc ctggggagac  12120
```

```
taccccagtg ttgaggattg gaacgatctc atcggagacg aaatcccatt ctaaacccag  12180
ggttcaagtc ggcggcacct cggggaacac ccctccggcc aacatcacct accccctgaa  12240
ggtgcaaggc cacaccttca acaacgtgca tgtctttcgg gacttcgtgt cccagggatg  12300
tgcatcttgc gggaagatcc caaccgcata tgaccagcgt aatcgtcatc tgacggtata  12360
cgaaggtgcc aagttcactg gtagcctgga tgagtgcgag ttcatctgtg gtgagtgtgt  12420
aatcgaaaat aaataggagg tcaaaatgac ccaagtaacg atgaagcgtc aagtagtgat  12480
ccagatggag accgacgcaa cccgtaagta tcccttctcc cgtgacaccc tggacaagat  12540
ccagtcgatt cgtcgagtca aggagcagga actcaatgat gccaacccgg acgaggaatt  12600
cctggtaccg gccccggtag tcattgcgga agctatcgac cgactcttcg aagactactt  12660
cgagtaaggt agtgcgttag taatagtccc tggccgaccc atgccggttc ctaagatgcg  12720
tacatgggat ctaacttagg attccagggg ctattgctgg cttcactacc ctcaacagaa  12780
acaggagatt tgccatgttc tatatctata aaggtgcccg cccctctgct ggtgctgtag  12840
cccttcgtaa cgccctgggt gctcgaatcc ttcgctccga ggggtctacc tatcggggtc  12900
gtgcgggtac tgcggtaatc aactggggta ccgttggtgc agaggctcac cgactccggg  12960
atattgcccc tgtgttcctc aacgacccgg cagttgttca ccgctgctct aacaagctgg  13020
agttcttccg ccacttcgag gccaatgctc cccacctgat tcctcgttgg accgagcgct  13080
gggaagatgc cttgggtgta ctcaatatct ctggtcgcat gtatgcacgt accgatctga  13140
acggccatag cggtcgtggt atccatctgg tgtgtactgt caacgatgca gaagttgctg  13200
caatcgatgc tctccgtaga cagggccact acccggtaca catctacggt cacacccaca  13260
tcccggatgt tatcaccagg gcacaactgt tcacccaggg aatcgtcggt aagcgtaccg  13320
agtttcgagc ccatgtgatc cgtggggaag tagtacttct ccaagtcaag ctccgccgtg  13380
ttgccaatga aatggtgacc aacgaaggac aaagcatcgt tcgtaacgta gctggcggct  13440
gggtctacgg ggttaacgat gcaatggacc gtgatggtgc tgagcaggct atgtcggcag  13500
cggcagaggc tatccaggta gctggactgg acttcggtgc agtagatatc atcttccagc  13560
acgccactgg ccgggccttt gtcctggaga tcaacaccgc cccaggtctg gacgctgaag  13620
gcagcgccct ggaggcatac gtcaagggct tcagcaaaat cttcgaggag actatctaat  13680
ggctgttcgt gttttcgttt atggtactct cctgtcaggt ttgtacaacc actaccttct  13740
ggaaggggcc gagttcatag gcaatgctgt atcctgcgag cggggtctaa tgtactccgc  13800
tggcggcttc cccatcctct ccttcgcctc ccgtgctgac ctcatcgtag gcgaaatctg  13860
gcaactcccc gagggcgaag cgggggatga aatgctggag aacctggatg ccctagaggg  13920
ttatccgggt tggtatgatc gtaccctcaa ggatttccga atcaatgggg aacgcatcaa  13980
ggccctggtg taccatcagg atagccacat ggcgatggat atcgtcaagg atggcgactg  14040
gaaggcacac ctggcaaaac gacaaggagc agtataatga acgaaatgac cgtagacaaa  14100
gcagtagaag tctaccgcga tactccgaat acattcggac accaagagct acatgcccag  14160
aagatgcttc tcaaggagat cctgggcctt gtagcttccc agcgacacct ccaagactct  14220
atcgaggtct ccaagattcc ggaggcctcg gatagtcccg agaccagcta cggtgggtac  14280
tgtgacgaat ccattggcat tcgcttcatg tgggagcgac tgaagaaaat cgaggatcgt  14340
cttcgggaac tggaggaggt ctacggtacc ttcgtaacaa ctccttataa aaccctaccg  14400
ggcaacgtga atgctgtacc aagcctggtt ctcaagagtc aactggaggg gtaagtgaag  14460
```

-continued

```
aagatcatcg gtgatacggc ttgtccgggt tgccgagcta aaggtgggga taaaacagga  14520
aatcacctca tcttgttcgt tgatacagaa aagggtactc ggttcggaag ttgtaaccgt  14580
tgtggtcact acgaagtcct cgaagagggt ttcaaggtgc cagagcgtaa ggagaaatcc  14640
gaggaggata tcatccatga agtcaacgaa gtccttgagt atccaattaa agccctcgat  14700
actcgaaaga tcagcaaatc aatcgctgaa cggtacgggg tacgtgttgg tctatcacaa  14760
gagaatggtg aggacgttat cgagcattac tatccacgca ctcgcgaagg ggagtaccga  14820
gcgttcaacg tccgaatcct agaacctaag gctttctact accgtggaag ccccaagggc  14880
ggtgtagacc ccttcgggta taacaccctt cggcataagg atatgggaca cctgcggtta  14940
gtcatctgcg aagatgaact gtcggctatg tctgtggccc agatcatgga gtcgaaactc  15000
ccggagaagt ggaagcatct tcgtcaggca tccattagct ggtcctcggg tgttggttct  15060
gctggacggg acattgcgtt ccttaaggag tctggtgtac ttgagcggtt caacgaggtc  15120
atctattgcc acgatgcgga cgacgaaggc cgtaaatcag tagaaaaggt acgtgccctg  15180
taccccgagt gtaagtttgt cgagctcccg ctgaaggatg ctaacgacat gctcatgcgt  15240
aatcgggggg atgaggttta ccagatgata cgtttcggca gcaaggtcaa gtctccggac  15300
tgttccgtta ctgtcgatga ggtatacgct gaggctctgg aaccccccaa gtggggcaag  15360
agttacccgt gggaaggttt aaccaaccta acctatggtc agcgggatgg tgaaatcatc  15420
ggggtaggcg gtggtactgg tatcggtaag accctgttgg cccacgagat tgctgcctgg  15480
aattgcattg agcacgggga gaacgtaggg acattcctgt tggaagagca ggtagccatg  15540
acccttaaga atatcgcggg gaaggttgcc aacgtgccct tccaccgacc ggatatcgag  15600
tgggatgagc aagcctttaa agatgctgct ggtaaactcc gtggcaaact cttcatgtgg  15660
aagaacaagg gtcagaacga ttgggatcat atcaaggagt gtattcgctt ctgggctgta  15720
gccatggatg tgaagactat ccttctggat aacatgaccg ccatgaccaa ccaccttagt  15780
ccttctgaaa tgaacacgga gatagcccgt atctgtacag aactcgcagg gatggccgac  15840
gagctaggac tgcggatctt catcttctcc caccttaacc cacccaaggg taaccgtacc  15900
cacgaggagg gcgctgaagt aaaggaaagc cagttcactg gttcccgagc tatgcagcgg  15960
tggtgtcagc ttatgatcgg cttcgagcgg aacaagcagg ctgacgggga agagaagcac  16020
gagagtcgaa tccgtgtaat caaggacagg aactacggta acactggcct agtgttcacc  16080
aagtataacc ctgagacggg tcgcttggtt gagcgcgagg gcagttacga cgaggtacct  16140
gctgacgatg acaccccaat ttgattacgt gatctatgac cttgaggggg acggcctctt  16200
caatacggtc acaaggcttt ggtgcgctgt tgttgtagac attccgactg gggtagtccg  16260
gggattccgg cccgaggaaa tggatgtgtt ctacaggatc atcgcccatg caaagttcgt  16320
agtcggtcac aacatccttg actacgacaa ccgggtcctt gagaaacttc atgggattat  16380
catacccccca gatcgaagct acgacacctt ggttgcatcg aggttgactt ggccagaccg  16440
accccagggt cattccctgg gtgcctgggg tagattcctg aagtgtcaca agggtgattt  16500
taacgacttc tccaagttct cagaagaaat gtttgagtat tgccttcagg atggagtggt  16560
cagtcacgca ctgttcaact acctcctccg ggtactcggc atgacttggc aagagcttgt  16620
tgaatggagg actgtagatt ggctaaaaag cgagtgagga actacaagcg tgaaagggaa  16680
ctggctattc gacgcggcga aacgggcgtt gggtctaagt ctggagatgc tcagcggcac  16740
cgagcccgcc gaaaggtgga aaagcgtctt ggaaggaaac tcggagccga cgaggttgtc  16800
gatcatatca aacgtgttaa agatggtggc ggtaacgggg attctaatct ccgcgtccgt  16860
```

-continued

```
agtcattctt ctaacgctgc tgatggtggt cgtgtgggca atcgtaaggc caaaggcatt  16920
cgtaagaaaa agtaactaag gaggggcctt cgggcccccg aggactctct atgttcaatc  16980
gaaagcttag catcagtaac atcctcagtt ccttcgataa ggttctggtg aacctgaaga  17040
ccttcatcca agagtcttcg gaggaatctg agcgcatcta caacgagatc agcctgctca  17100
aagctgagcg tacccaggtc atgcaggaca acctgaaggc ccagaaggta ctggctaatc  17160
tcgaagagct tctgggaggt aagaatgaag aagtatcggg ttaacgtggg gttccaggac  17220
accaaggtgt tcactgcgga cttctatcga atagaactgg atatcattcg gttctactcg  17280
ggtgattctg atgccaaccc attgaccgtc cgggcctatg aggttggggc tgtccgtgga  17340
tgggtttctg tggaggagat taacgatgga gagtaagaag gaaagcctgg aggatcaggc  17400
acggaaggag attgccctgg agaaggagtt ctctggtagc tggggtggcc ccgagatcga  17460
tgctgatgac ttccccttgg gtagtgcctg tggcctagat cccgaggtct gcgagtcatg  17520
cagctgagtc agtgcgcatc atagcaggag atatctggtg agtatcctag cgcaagtgct  17580
tgtcatcttc tggagtgcat tcttccaggt attcctcctg ggattgaact ctaagctgct  17640
ccgggatgac aagatcaagg ctgggttcgt agtgtcttgg tgtatcacgc tggctcagtt  17700
tgcttacatc aaggcggtag cctcctccca cttggatatc ggatggttta tcttcgtgtc  17760
cgggtgggga ggtgctattg ggattacctc tgctcaatac ttctacaagt ggtatgacag  17820
agttttccac agatagtctt gacaaatcca gcaaagtgtg atataataac cttaaggtgc  17880
cgggggttgc tttaccccta taggagatac aaatgagtga ccatgtaagc tactccaaac  17940
atgtccgtgg taagtacctg tgtaatatgg cttctgccct acataagagc atggaggtac  18000
aaaggactaa catccggaag ttcctcagca gtccccacat taccctacgg gagaagcgtc  18060
gggtgttcct gagcctgcca gagggattcc tgggggtgag ctacttcaca ggctctcatc  18120
ttaacctgag ttcctactcg gatcgtcgaa acgcccggat tcgtgacaag gatatgagcc  18180
tctacgatga cttctacgtg gacaggggcg cccagctgga ccctcgggat gtcctgctta  18240
cctcccaaga ggagaagaag tgggggtttc aattccttaa gaagaggcgg ggtggtgtct  18300
tcaacctgtc cgacgaagag ttgagcgatg ccaaggatat ccagcgcaag cttgacctgt  18360
cctggtacct ggtggacctt gcctgtgagc gtgggtgttc ctacttcatt ttcgactggt  18420
gataacatga gcaagatcaa gagtgttctc atggagcggg tagatgactt cctgctcaag  18480
caagttgctg tagcgttctt ggaacagcaa tggcgactgg accgaagcgg aaccgtggac  18540
tacctctcct acctggaggg tatctccgac gaggcagtgg aggtagtcat agagaatctg  18600
gcggagcgtc ttaaggggga ttaagtggat tggagaaagt cactgttcgt tgagcacaag  18660
gtagctgata tcatcagtcg ccagagtaaa cgtggagtcc acttcaagac tcagcgggcc  18720
aagtggctga tccatgtgct taccgaacga atcctcaaga ttgaccttga ggccgtcccc  18780
cagatgccga tgatgatcgt aaaggctggg gccttcagca agccattcct aaagagtggt  18840
aagccgaacc aaaggctcca gtccttatgg caacgtcttg ggcacttcga ggtatctgga  18900
ccattcactg caatcgagta catacccttc gaccttggta agactgccaa gttcaaggat  18960
tggatgctgg atcagggatg ggttcctgac caatggaaca tcaaggatat tactgtcggc  19020
actgatggca agaagctacg tggatccgac cttaatgaat ccttgaacaa gtacattgaa  19080
gacctccgac agagtaaatc tggacgactc cgaatgaagc tccagggtat catccctggt  19140
aagactacaa tcggagaggt caagagaaag ctagaaaggc aacgaaaggt actaacgact  19200
```

```
cctaagatga ctgaagagtc gatggatacc gtccagggag acctgggaaa gctggtgatg  19260
cagcgaatgg tttgggccca ccgtcggtcc ctcttgcagg ggctggtaga tcaggtgagg  19320
cccgatggac gcctagaggg gagtgctaac ccctgtgcaa cacctacggg ccgtatgagg  19380
caccgtgtag tagttaatat ccccgctgct cgttctccct ttggaccaga aatccgaggg  19440
ttgttccagg ggacacctga tgccggtgaa tggaaatgga ctgtcctccg ccgagacatt  19500
ggagagaacg aaagggttag gcccttcact aacatcgtgg aggaactcaa gaaaggtaag  19560
tggaagcctg taggaaagca caagatatac gtcccagcga atcaaatgat cttcgtgggc  19620
tatgatggtg ctggactaga gcttcggatg cttgcatcct acatcaataa cccagagtac  19680
accaaagagg tggtcgaggg tgatgtacac acggccaacc agatagccgc agggctccca  19740
acccgtgacg atgctaagac cttcatctgt gagatatgga tgacttgggg gaaacccctc  19800
gattaaaact gggtgaactc agggaaccct ttaatatggg aatcctgagc caagacactt  19860
gacatttccc gtagaatgtg ttatactgat attttatggg aggtgtttat gaagtaccca  19920
aatggatggt ttaagattaa gaactgtaga aagtgctcct cggagttcca gcctactgcc  19980
cctagccacc actactgctc agacgagtgc aaggagtggg gtaggatcaa tgcctactac  20040
accagagtct atggactcac gtatgatgaa gtaagggcta tggctgatga acgagaccac  20100
aagtgtgata tctgcgggga gaagggattc ctgatggact cctctaagca cattgcattc  20160
ttagtcgttg accactgcca tgcaactggt aaggttcgtg gactcttgtg tcacaactgt  20220
aacagagcat tgggactgat gaaagattct ccagagcttc ttcggaaggc tgctgagtat  20280
cttcaagtgt aaggtgcaga gactattatg taggacccaa gcgggttcga agcgcccagc  20340
ccctggaaga cagggtgatg atatagtccg atccccaggg gaaaccttgg ggcagccgag  20400
aggcgggcca gtagtagcga cactggttga acttttgatg cgttcatcta cggtgctggg  20460
gatgccaaga tcgggactat cattggaggc accagggcag acggggctag gctccgggcc  20520
cagttccttg aggctaaccc tgatcttgct gcattgattg agagggttaa gcaggaagcc  20580
gagagaggtt atctcgaagg gctagacgga cggaagctaa ccatgcgacg ttctgagtct  20640
ggcgacgtga tgatccataa ggcattgaac accctcctac aagcggcagg tgcaattgtc  20700
atgaagtggg ccatggtgct cctagatgaa cgggtccgga ggttgaacct tcgggcttgg  20760
aaagtcctgg atatccatga cgaaggtcag tgggaatgcc acccagagga tctcattgcg  20820
ctacgtggac agatggaaat ctgtgtccgg gatgctggag ttctccttgg ggttaactgt  20880
cctttggcta gtgattccat cgctggtcgc tcgtggtatg acacacactg atacatctgg  20940
gggttgactt tcagccccct ttgtggtata ataccttctt ccctacgaga ggtttaagat  21000
atgtctaaga aagtatccca acgattcacc ttcccggtag cgaagctgat cttcccctac  21060
atcgtaactc cggacaccga gtacggtgaa gtctaccaag taaccatctg cattccgacc  21120
aaggaagagg ccgacaatct ggtacagcag atggagtcca aggatgcccg actgaagggt  21180
accatcaagt accaagagcg tgacggagag tacctgttca aggtcaagca gaagaagcac  21240
gtggattgga tgcaagacgg tgagcgcaaa tctgccgtga tgaagccggt ggttctgacc  21300
tcggacaaca agccgtatga tggccccaat ccgtggggtg gctctactgg tgaagttggc  21360
atcctgatcg agacccaaaa gggcccacga ggcaagggta ctatgacggc cctgcggctg  21420
cgcggtgtac gactccacga gatcgtatcc ggtggtgacg gtgaggacga tccgctgttc  21480
ggtggtgcct tcaccgagga agagcccgag gatgtattcg acgaggtgtt cgatgacgaa  21540
gacgctccta tctaaggggt tgggggatca cgaggcgggg gtatgcccac ggggctgccc  21600
```

```
ctactgctta atcgaattcg aaagagtgtg gggtgtaagg gtggtcagtt ctacagctgc  21660
atctaataat aaagtagagg tcgatcctaa tggaatcaag ccgggtgagc cgggcgctaa  21720
acttgatagc ggcaaggtgg atgttggaat catcttcgaa gcgttcccga gggctctata  21780
tgcagtggca caagttgcta acttcggagc cagcaagtat agtcgcgggg gttggaggtc  21840
tgtcgagaac ggagtccagc gatatgatgc tgccttcggg agacacctcc ttgagcgaca  21900
caagggtgag gctttggacc cccaaagtaa actaccccac cgataccacg aagtgtggaa  21960
cgctctagca tccctggaac tagtcattca gcaagaggag gactccaatg gaacttctgt  22020
tggatccaag ggctaagact gttcctagca actactctgt aaaaggcgtt gatgtagacc  22080
tggggcttcc cccaggctac agcctaacgg aggaagctat ggacaaggcc aagcgtcaag  22140
agagtgaata ttacgactgg aagggctacg aagcactggt taatccggtg gtagagcacc  22200
cagagtatcg agccaagggt gaagcctttg ccctccgtgt attctgggaa gagaagctca  22260
aagagtctca ggtcgtagaa gaggtaacgt aatgattgct ggtatcgatg gtgacgttct  22320
taggtatgag ctaggccacg tggctatgtc gaaggaacac atcttcgata tccaggtgga  22380
gaagccatgg cctgaggaag aagtccacaa gctcgtcgat gataaagtcg aacaaattat  22440
caaaagggtg aatgcagatg agtgtgaaat ctaccttact ggccaaggaa attttaggct  22500
ggagcttgcg aaaatcaagc aatataaggg tactcgaatc ggtcttgaaa agcctcatca  22560
ctgggaaacc gtgtcagcca gacttaagga caagtgggga gcaatcactt tccacggtat  22620
cgaggctgat gactggctcg ggattcgagg gactgaagag ggagataact ttacagcgtg  22680
ttctagagac aaggatatcc gccaagtccc aggatgctac cattacagtt ggccctgtgg  22740
agattcccag ccggagttgg gaccgtttca agttgatggt cttggaagag tctccgcttc  22800
ttggagaatg tatggcgtta aaaagccgca gaaatcatgg aagcttgagg gcaacggtac  22860
ggcattcctc tacgggcaac tccttgttgg tgactctgtg gataacatac caggcctccc  22920
agggacggga ccaaagacag cggcagattt gcttggggag ctttctagtg agagagatct  22980
cttcgcagct tgcgcttacg cctaccaaca gaagtacgga gataattgga aagagtacct  23040
tctggagaat tttcgtctcc tctacctcat tcgggaccgc tcttggcttg atattcagca  23100
gtccggtaac gagtatcact gctcactgaa gaaacattgg gagattccct atgacgatga  23160
agaaatattc tattgaggaa gcacagaaaa tctgtgaagg cctctttgag atccttgagg  23220
gtcttaactt tactgactac aaggtcgctg gtggtttcct tcgggatgca gacaacgggg  23280
ttgcacccaa ggatatcgac ctgtatgtcc gtaggcccta tgtggaggac cccactgata  23340
ctcggcgtag tcgctttggc ccacggttga tcccctgtga tgacgatacc ctagaggtag  23400
aggtcactcg gttctacaat aagctgggcc acaagaaagt ccggtgtagg actggggata  23460
agcctgatgg gtatcctgcg gggtttgatg tgtgggaatc cattggtgtt gacctacccg  23520
tcaaccttgt cgtgagtact cactcccatc cagcagagtt cgatgtagga ctgtgtgaga  23580
ttgcatgctg gcccataagt atccgtggac tgaaatctca aatctaccgt tcaagggctt  23640
atgagtttga taaagaagag aagtgcatta ctcttaaccg agtcctagac cctcttctgg  23700
atcattctca accccctaact gacaatcaag ttgaaaaggt tgtctctcat atccaacgta  23760
tcaaactgaa gtatccggag ttccgggtgt gcctgggggga ttggatctgg cttctggttc  23820
gggctaattc tatcctgact gaagggacac tctcggttat ctggaagctt caagaaggag  23880
ggctcattgg caaagcaggg gagattcttc agacccaaac tgaagtcatt gattgggacg  23940
```

```
aagtacgaca gcgaaaccga gaagatcgtc cacgagacga tgccctggat gcagttcaag  24000
ccagacccgg tgagctacgt catacagcac aagtacaagc ccgacttcaa ggtatcgacc  24060
tcacaacctt gtggatcgac gaagcacctg ctggtcgagg tcaaggggta cttccaggaa  24120
gcctcggagg catctaagta catctgggtg agggaggctc tccccccaga tactgaactt  24180
gtgtttatct tcgagcgtcc taacacagct tgccattggc ttagtaagcg taaagatggc  24240
acaaagcaat ccatggcgga atgggccgaa cgtaatggct tccgctggtt tactctagag  24300
actttcaagg agtccttccc taatgagtaa gaagtataat gaagacactc tcgtcattgc  24360
ggacacccaa gttcgatccg aggtcaacat cgatcacctc gggaaccttg ggagtggat  24420
cgcacgtaac cgccccaagc gaattgttca tattggggac cattgggaca tgcccagtct  24480
gtcaagctac gaccgtggta ccgctaagat cgaaggccgc cgagtcctcg ctgacataca  24540
agctggtaat gatgcgatgc gagttctgct cgaccctctt cgccgcctac agcaacacca  24600
agcgggttgt aagaagcgta tctaccgacc agaaatgcac ttcttcatcg gaaaccacga  24660
ggagcgtatc aagcggtatg aaaattctaa ccctgctctc caaggtttta ttgggtacga  24720
tcattttgat ctgtccgatt ggattgtcca tgatttcctc gacgtgggtg ttatcgaagg  24780
tgtcgccttc gcccactact tctacaatcc caacagtggt cggccatacg gcgggagtgc  24840
cgagcatcgc ctcaataaga tcaagcgcag cttcgtccaa ggccacgaac agggattcaa  24900
gtaccacatc gaggcagtag gcaagaagcg aatccacggg cttgtagtcg gtagcttcta  24960
cactcacgat gagtcctaca aagggcccca gggtaacgac cactggcgag gtgtagccct  25020
cctccggaac cacaaggacg gagagtatga cctcaagctg atgagtgtgg aggagttcct  25080
gtgagtaagt tcttgccaga cctgtactac attaagtctg agcatgactt cggtcaacgg  25140
gggttggcgt ttaagacgcc gatctccgca gaactctggc tggatatgaa gtttgggaaa  25200
ggtggtgctg aggatgggct tagacgaggg atgtattcca tcgaagtcct ggagatcctc  25260
tacatcccca gcgttcacct tccggatatc ttggggtaat ctatgaaaga tcgagtggga  25320
cgtaagctag aggtagggga cagtgtagtc ttcctggtcc acaggaacac ctcctcccat  25380
ctagccattg gcaccgtcga tgggtttacc cccaagatga ttcggatcaa atgcccgacc  25440
atgagttgga ctattgacgc tgagtatgtt ctaagaagca gtgacaaggt ggtgtactat  25500
gacaaaggct gaactggaga aagcacttga agagacgcaa agcgctcttg cgaaggctga  25560
ggcgaaggcc ttttcctttg aagaactggc tgaagaagct aaaagacaga ttgaattcct  25620
cgaagggatg ctagacctag tagaccttag ggcttctgta ttctacggag attggagggg  25680
ttatgcagaa agatcaaaag ggtaagggtg gattcccttg gacctacatt gcggtagcag  25740
ccttgtttgc cctgctggtt tatgtaggat atagctgact gatgttactc ctgaccctgg  25800
gagaaatatc cagactcctc atcgatgtat tatcttgggc aggttcactg taggtatcca  25860
tcgagtaacc aaaaaaaagg ccccaagggt atcatcccaa ggggccttat ctttagctcc  25920
gtagagcgtt cagcagtgtg ttgaacttat caacgagtgc ctcgtgagta tccgtatagg  25980
aagccacggg gatctcaact accttaccct tgacgtaagc cgcaatggct gcatctaggc  26040
cactcacttc gctagccttg ggtttccagt tacctggttt agcctcgcta gccttagcac  26100
ctacctccag aagctcaggc ttcccctcaa tatcctccca tttcactggc tcaaagtctt  26160
tcgggccaat gacttgtcga agggtcccat cttcattacg tacagcaata gccttcgatt  26220
gaataacgaa tacactgttg ccgtcgttgt cagcgatata acctgccata atctaactcc  26280
taattaaact gccgatttga aggtacccac ggtaccaccg aaaggataca ctcggacagt  26340
```

```
gcattcccca aattgaccat cagtctccgt ctgattaccc ttagcatacc aagccttgtc  26400
cggagataca gcgaacttga tcttagctgt agacccttgg ataaagtgga agtgacaacc  26460
tggggttaca tccggaccaa gagtaacggt aatatccgta gtcccctggg acatgaagaa  26520
ccaaccagac tgctgcttag taagggtaat gttctgggtg agttgctggg tgttgacaac  26580
gttaccaccg aggtgagtag tcaccagtcg gggatccagg tagttctgtt gaagagaacc  26640
aatgttcttc acaggaccac gcatgtcgtc aaactgctcg ataatgtaat ccccgatggt  26700
accaccgttt tggtcatccg ggccaatcac gtgcttaata gccacgtaaa cacccaggtg  26760
ttcccgtcga gggtctactc ggaattcact accgaatgca gtaccgcaag gtgcctcaat  26820
catggtctca gagaacagac caatcacgtg gccagggtca cggttaccac ccgaggtttc  26880
tccaggagca cccacgaggg tattgaccag gacagagggg ataacggcct ctgagggatt  26940
ctccgggaag gaggctgtaa cgttctctac taccagggct gcgttctcct taactgcata  27000
atagtcaggg aggaactctg tagcggtaac gatgttagta tttacccgac cggcatccga  27060
ggtaatctca atgagatcac catcggcatt acgtcggaag acttttggaa catcaaccac  27120
gtaggcacgg ccaccaggac cagcggcatc agtttctaca taagttgcca tattacttct  27180
ccttaaagat ccagagcatc ttccatcgct tccataccgg caacgaaagg acgtgctgga  27240
gtttgcttat acaagaactt ccagatttca cctgcggatg ggtcatcccc aaacgaagcg  27300
atagttttac caacagccat agcaccctca gttgcagcac cagctactgg acccaagact  27360
acctctgcgg gggtagtccc tcgacggtaa cccgtcagca tgtcgtagat catagaagcc  27420
tggagtggca tctgttgcat cactacgtcc atcatccgtt gttctggact acgggtatcc  27480
tctcggctag acccaccgaa cttagccatc tgacggagtt catcctggat gtaacccaga  27540
ctcatcatca gaccaagagt gaaggctaca cctgcggcac ccataccagc gttggtccaa  27600
gaaccagcga agtgtgggct cagtcgtcta cggaacatcg gtaggatgat gttaccatag  27660
gctgctgggt aacccttcaa gagggagaac atctgaacgt ttccgttgct catccacata  27720
ggcttatcag cgaaggtggg gtctaggact acctgatcta caaaccgacg catggccaaa  27780
gtcttgacgt tgttagccat caggacttca gatggagtag ccggggagat caacttgagg  27840
gcatcctgct ggctaccgat gttaaccccc atttcccgaa gctgagcaac cttcagagca  27900
ccattggcag aactgaaagg gagacctgcg gctagatcca tcaggttgtt ctgatagacc  27960
cgcttagcag tctctgttgc aaatattcgg ttaacatggg ttaggatgga caagccgttg  28020
atgaggaact gaccacggat cgccttttgg atggtagagt taaacacctc agcaccaacc  28080
cgatcagcca tcagagaagt agcagaagcc agggtgtggt tcatatcact cataaaccga  28140
ccggtctcag actttggaac cccactgtag atcctgcggg ctgcttgcct tactacctca  28200
cccatagttg ggagtacagc cccaagggta ggcataaccc ccgccttagc gaagggtagg  28260
ctgaactcgg tcagggtcga gaaaccggcg agtggaagtc ttgagagcac gagggcaccc  28320
gacgtaacag ccgctagctt cttaaggtta gggtctttga tacgaccgtg cataccatta  28380
taggcatcca ccaggtcata catccgatcc acctcttcct tggtaacccg tttaccagcc  28440
cgttgagcct cagctacagc agaagcgatc ttagcgttag ccttctctcc gttgatacca  28500
aacctttcgg taaaggcaat ccggtgggaa gccccttcga agtagtctcg gatttcctgg  28560
agacgcttct taggagtatc attaagagaa tacttattga ggatctcctg aggtacggag  28620
ccaaaggccc ggctttcttc cagttgacca tacttaggta ctgcatcgct ttgggcgaac  28680
```

```
cgtccacgta gggtatctgg gtcaccctgg atacgatagc gagggtctac ttcccaagcc  28740
ccggtctgct ggttctgagt aaccagtcgg ttaacctcag gggcagtgtt accacgagta  28800
tcatccgaga cttctgccag ccagttggct acagcatctt cagcagcttg tcggctctgg  28860
aagtacggag tgatatcgtt caggaactct ggggattgaa ccttctcagg ggacagccca  28920
aagggcatat agttggggat agtaccaacg gacattccac cacggttaac agcctcattc  28980
cttacgtcat ccatcaaagc acggagacgg gtagcttctg ggtattgac acctgcggat  29040
gtatctgaga taatcctgtc gatctctttc gaagacttac cctcgaagat gttatcgagt  29100
tcagagttcc acttacctgc ctggagttcc tgatcctcaa agatagtctt accagaggct  29160
cgcttaccac tcatatcagc cctgaaggtc tcagagaact cacgggcgat aggagaagcc  29220
ttagcaagtg gctccaggag ggacgtagct tcgtttccta gggcatccca ggctttcttg  29280
accgtacccc taggctcaag ctcagaagcc ttaggagggg ccgcagggtc gttaggatca  29340
actacggcag acccagctga gtcctgatta cgtcccaggg tgtccaatcc cgaggataca  29400
gcaccaccgg cagtacccat agctgtacca gtgaaggcag ccgtcaggag gttatccatg  29460
aactgctctg ggtttgtac ctgccctact gcatcatacg cgatagtgtc ctggagcgcc  29520
tgctgggcac cagaggtaac accttcagcc acaccagaga ctacagcgtg tttaccagct  29580
tgggttacag cctcaatggc ggtctgctta ggtagacccg attggaccaa catctggtaa  29640
gcgccatctt taccgatgtg cttgaggagt ggggcagcga taacaccagc acccgcagtg  29700
tctagtaccg agaggccagc accaccgagg actgcggtcc atgggttgct ttgatcgggg  29760
tctagttcct tcatctggtt actcagggca cctacgttga tacccatgga actcaggaag  29820
gaaccaatga gcgctccacc catacgacct ggggccccaa agacagagcc agccttagca  29880
cctgcggcac caccagcaag tacaggggcc atcgaaggga gagcctctac aatgttattc  29940
ttaaggaacg acccgatgga tgggatatct tggatatcag cgaaagaccg aacatcaggg  30000
gttccgtact gtgacgcttc ctgagcattc tcctcggcca tctgtgtgcc gtagtctttc  30060
aggtagtcac tgccagtcag ttcaccaagg gtagcaatag taccaccgat gttagactgc  30120
atggtatcaa ccccacgacc aatcgcagag ctaatagaat tagggtcagc cggagttact  30180
agggcactca ggtctggggc aggctcaggg gtagtagggg ctacttcctg ggtgcctct  30240
tcgataacct ctggctcatt caaggaagcc aattcagcgg ctacgtcgag gcccttgacc  30300
tcagccagtt ccgcatcaat agcggccttc agttctggag aaagagccat aagtcacctt  30360
ctagttgctg gaaagagaat aggctcttaa gatgtatctt aggatactaa ccttcttagt  30420
aagtaagtca aaaggaagaa ggaatcttaa gagcctatag gtctattata ctacattttg  30480
gatactttgt caagtacctt ttatcgggtt ggggcaggat agtccaaatc agcaccaaac  30540
caattacccg taggttgcag cttagcagcc tcccgctgga taatacccac tgggttagcc  30600
cccggattag cccgaagttc atttcggaca gtctgggcaa tagcctgttg ggcagtctta  30660
ctcagcttct taccacccag agcctgagaa ccgttgactt cactcaggat accaagggcg  30720
tccttagtag taacagcttc acctcgggct gccttagctg ccgcttgacg tgcctgagcg  30780
ctgatcttag cagttttgag gcgtacagca gaactaagct gggcattctc ttgagacata  30840
tcctggccac gtcgagtagt ttcagcctgt agctgggccc gttggttagc caggtcttgg  30900
ccacgtcggg tcaactccag attagcccta tctacagcag cctggttgac ccacttatca  30960
aggacgccct cagtcttacg cttggtttgc tcaagggtcc cttccttaac tttcaggttg  31020
ccctccccaa ggcgtacatc agcagcatcc ttagccacct tacgctccag atccttttcc  31080
```

```
ttgatctgac gatcagcagc tgcggcagcc atcttctgct ggttgatccc agcctgtagg  31140
ttacgatcca gttgacgctc ataggaagca gcgaacatat ccccggcttt accagtcttg  31200
tctagggccg aagccagaag accagtacca atgagagcgt aagatacata acgagacagg  31260
tcatcattat ccatagtcct catctgggtc aactcttcgt tcacccggtt cttaagctct  31320
tggggtttaa gctctacacc ttctctctgg gcatcagcct caactacagc ttgggccatt  31380
tcaggacgac ttacagcacc agtacgaaga ccctcggctg caccctgttg gatgacctgg  31440
cgattagcct cctcctcatc tgctacagca gcaccagcct cggaagccac ctctggggtg  31500
atctcaggct cgatagaggg ttggttaggg gttaccccat aggacaacag accggccccc  31560
gtagggcctc ctgtggcgtt ctgggctgca cgttggccta caccctgggc ccattggtta  31620
gcctcttgag caacctcggg acccatgttc tcaaccgctt ggctagcctg agccatttct  31680
tctgcacgag tacgctctgc atccccgagt tctcctgggg ttacagcggc ttgtacacct  31740
acagagatag gaccaccgag gatacctgcg atacgaccca aggcaccgcg accagtagct  31800
tcagccgcag gtgcaacctc ttgggctgca cgggaccaac gctctgggtt ctccagggct  31860
gcctgagcag cacgacggac acgatcagga atacctgagc cctctacagc cagcggcagt  31920
ttgttccttg cgattcgcgc catgtccagt tcattctgag cagcccggag gatgctaggg  31980
cgaattgggg acccttcata agccatgctg gccataggat taacctccaa atagtttact  32040
taggattcca gactttggct gctgtccgaa accgagttct tctgcgctag gaaggattcc  32100
cactcccgct cccatacctg ctgcaacttc cgctgcgcct cgttcgcttg ctcctctagc  32160
cccctcgaca gaaaagcttg gtactgtttc tgaagaaggc tcacttcctt gcccgaggag  32220
agccgcgagt gctgctccgc ccattgcgcc aaaagggttt gattgtccac tagactctcc  32280
cgattgcatt gtcccaaggt gggtggggcg gtaggaacct tgacggctca actgtacccg  32340
ctcctgccca ccacctatat tctgtcctat agcgaacagc ttctgaggaa gggaggccat  32400
tagaacagaa ggcccccgac cctaccacca gcattcatac caacagaagc acccgctggg  32460
ccaccgaaga gagcacccaa ggaagcacca ccgagagcac ccagggcaga cccgaggcca  32520
ccaccaccgc caccacccga agaagtagtg acattggttc cccccatatc gccggagata  32580
agctccttat aggcgaggag gtcgttgagg ctgacgttat tctcataggc ccacttctgt  32640
agagccccgt tgatttcctg ctgctcctgg ttctgaagca tgctaccagc atctacctgc  32700
atggcattac cagagccgag gcccttagca atagccgaca ggttacccag ggtattcaac  32760
ctattctggt tgtaagcctg ctggtcttgg aaagccaact gggaagcgtt attctgttga  32820
ttctgaagca gcctagcggt agcaataccc tcggctacac ccgctcggga actaccatac  32880
tgaccagcgt tggttgctcc tgcccgcagg tctggacgta ccgtagtgtc gaagtcccat  32940
tgcatctgtt cgttggctgc accaatggca ttcgccaagc cagttttgtt gggatcgtaa  33000
ggaccaaggt aatcagccag agagctaaca cctgagctac ccaggagaga ctgaagggca  33060
cccccgagac cacccagccc ttcgattcca ctaagctgga gagcattttg gtcagccacc  33120
gggtcaaagt tcggatcgcc cccgtaattg gggtcaaagc ccccgttatg tagccaatca  33180
ctggcacccg agagtagttc attatagtta ccttgctgat agggtgtgga cactgaggtg  33240
gtcttttgct tcttactacc acccttgtaa gcccgagaat ctagagcatc ctctacacca  33300
aaccccatca ggcgttttac gttaaattgg aggaagttca tctggagtta cctcacgata  33360
gaaggatacg gagtcttcgg tgtacccgag tttctctagg gtaggcttcc agccccgacg  33420
```

```
accttcgcat tggataaacc gacagttaac tcgttgggcg aactgtccga ggaagtcgtc  33480
tacctccgag taatctaccg ggtttcatt cccaggcatc tttccactcc agaagaagtg  33540
taggatgttg cccaaggggg cctgggatac ttggatgact cccgcgtacc cactctcttc  33600
ctggtagaag acataggcct cataattaac cagggaatgc accaagtgct caaagtccca  33660
gaacttaccc aagtcagtcc tgttaaaagc acgggctagg gctggaacta cggtcgggag  33720
ggagtctata ttctcacgag taatcaaatg aatcatggag tcaccaccag gggaatgtg  33780
aatgtacccc cgaagactgc tccttgggga attccttgga ttagaacacg gccattagct  33840
gtgatcttaa acattgcttg gttaaccaca ccagtctgaa tagtagccct gttgagaaca  33900
tcaaagactt gatccaacgg aggtgcgtta gggtcagacg gaggtggata agtaatagtg  33960
ctctgcgctg gtatgatgct ggagtaagcc gggataaaca actcagcagg aggccaatac  34020
gcctggggaa gatccaggac agtagctcca ttagtgtagt taccaccaga catgagcatg  34080
gttatccaca cttcatcctt agcagtgttc atcctatagg cacaggtacc catcggctga  34140
tggttgttct gtggggtaaa taggataaaa tcccccggca ggtccttggg tttagtacct  34200
gcgagtctcc attggttatc caagtcgtaa tgatagatgc cggatactgg acctaccact  34260
ccgggggcaa aatactttac agtccctggc ttgagcttct tagggggctc catagagacc  34320
ccccagtagc cgtcagctag gtcattaaga gtctgtccaa ccctaacgaa ttcttcatta  34380
aggaagggca gcagttcctc ctcttcctgt ggtggaatcg aagggctgta cttttgactc  34440
atcgcatacc tgccttcggg gccatttcaa tagtgtatcc gttgaagtac cagtcaccct  34500
ctgaggagaa gtcgaacttc aaggctatgt accggcccac atgtttagtg tcaatcttat  34560
agtcctggcc aatccggtat gggtaggggc ccttccaccg aataccagaa ccttgtacct  34620
gagcattacc aacccagatg ttgcaggtgc cgttacccgt gatatgcggg atgatagcac  34680
tcacagtctt catcattcgg tcatccccaa gatagatatc ggatctctca agggtactaa  34740
cgaagttctg cccagagaat gtagagttat taccgaagag gaacaacttc ttatcctgga  34800
aagacgagaa gatcatactg gacttttctg ggttataaga gccttcaccc cagaccgaag  34860
tatcggtatc ccaggggttg ggtcgtcat cccagaggtt agacacctta ggatcgatga  34920
tcccgtaggc tccactgaga acgttgggaa ggtctcggat actccaagtg ttttccttcc  34980
agttccagat gatagccctg tcgcagtgct tacctggctt agacctagtg gaagagtagc  35040
atacccacat ttcagtattc acgtggtctg caattacgaa ggtccgttga tagttgtcag  35100
ggttaatatc cgagaagaag aacttacgga cctgagcatc aataacagac tgcttctgca  35160
caccgttgtg gacatatacg tcaccgtggc ctactacaaa gtggttacca tcgaactcta  35220
ttgcacagtt gggtccgagg atacctacgt cgttaaacag ctgctggaac tggaagatga  35280
acaatccacc gatataccgc atggagtata cagagtcttc cttgtagatg atgaaagagt  35340
cacgaagctt cacaccatcc acgatagcac cattggtatc agccaaggtg ttctgaccag  35400
catctttagt ggggtccgtt gggtcccaag atgcaggtac accaccagca tcagccgagg  35460
tactccacca gaccatctgt ggcatttcta cagagttact tgtagcgttt aagccaacca  35520
ggaagttctt aaaagactta agcctcttaa aagtagtatt cgctgggaag ttagggagca  35580
ccctaaaggt tgattctgac ggtggaagat gatgaggagg gttaacccca tcgttagcaa  35640
agattacccc gttgaacgat cctacagacc atctgttagt tatactagca gcgtaaggtc  35700
ctggggatac atcgatgatt gtagtcccgt cggctagata caaccgttgt tcagaacaca  35760
ggagccaata ggggatgtta ttccggatga aaggaaacat atccaagatt ggggcctggg  35820
```

ctgtatcaaa gataggcgta tggcccagag ccttctgagc cttgccgttc ttaaaccgga 35880
cgttgttccc gaaggaccat ttctccagtg gcaggtcagc gggggcgata tcggtcacaa 35940
tccccgtagg gttcttgacc tcttgtctct ctagggccat tgtatacctc agttcttaat 36000
gatgaagaac acagaacaga acggtgggat attacccaac ggcatgttga tctttactgc 36060
atggttgtga gtctgacctt gaccagcagg gccagtctca aggttggtat tggctgcgtt 36120
accagagcca cccgtcagag caccagagtc acccgcagaa ccggtgaggg tagtagcccc 36180
tcgggatctc caagtgtggg tgtgcgatgg gatttgggct agggtaaggg cagtcccttc 36240
agtgaaccca tcccatacga tgttagcgct accacctcta gtccctacag cctgggaaga 36300
accatcgata ccccaaggga atgcaccaat caggttaggg acgggaaccc cgttagaggt 36360
agtacctacc ccattgcaca acttccaacc tgctgggatc tgagctagtg acccagccca 36420
catgataacc atcccaggtt taacatactg ggttgtatca gcgactgcgt ttagctgggc 36480
tgccgttaca gtgacagcct gagaaatatt ggggaaggtg ttcttaatag cactcttaat 36540
gagacgcagg tggtcatccc caaaggattt cagatcagag ccggtagggt tcgtaggcac 36600
caactggtta atgtaagttg cgacctcaag acccattctt ggcctccttt atctcttctt 36660
tcatttcttt tcgggtgaca taccgctccc caaagattgc catagaaatc tggagatcgc 36720
tcaccgcttg ggtgagcttc tccgtggcct ggatgtttct ttcaagcaga gcctgattaa 36780
cattctgacc gacaaccgag gaacctaccg tcactaccga ggatacgacc agggcactga 36840
cgatgctgcc caggttatca gttagaagtt gcatcctccg tcttctcctt aaggttgtct 36900
tccaggactt ttacgaactc gtcgtcaacc ttagagttag tcttctccgc cagagcctta 36960
gcaccagtca cgatggactt agcgattacc ttggttggga agagggtagc cagaaggttg 37020
attgcgaggg tttttagaaa gataggcatc tgaatctcct taacgttcaa tgtctttgat 37080
cgccagtcga gtgctagcga agtcagcggc attctcctcg ttctggagtt ccataacagc 37140
ccgttcgagt ttctgacccc agaactggga ccgagcttca tccatggtgt acagataaat 37200
ctgctcaagg acaccataga gataaatctg cggatacttc gtcagagccc aagtcgttgg 37260
gttagcgagg cttagctctg ggagtacagt ccagtagttc acaatgaacg gggcaccgtc 37320
aggaacaacg gggaatactc gccagaagtt acccaaccga gtgtagtagg ttacaccctg 37380
aggttggtag ttgtagttaa cataatgggt gaaggtatcc tgggtgatgt actgaagagt 37440
acgtccaccg ataagggagt cacccgtgat agatcgtaga gcaacaaagt gctcaggtat 37500
ctcaatgcca ccaccgaagg ccattaggat ttcgaagtgt tcgttctccc tcacccgtag 37560
caatcggtta agacggtcag tggtattacc aatgaacaac atcagaagtt cttgggtaag 37620
atcctgacgg tcagaccact ggatagcggc gatagcgaga tcagttacgt tgttgatcgt 37680
agccattcat tacacccgtg cctcagaggt ccgcatccga tagttatctc ggtcattaag 37740
ccaacgggta aatcttgcgg catggtctgg gtcacaaccg atcaggttaa gatcgatggg 37800
accaccttca gacatggggc gattccgtag ggcctctaca acaaccaggg ggatacttgc 37860
taccttgcgc atattatcct ttcggttact gttgacaccc gagtggcgct cttcggcgtt 37920
agcggacagg attgactcaa catcttgagt atcctttcgg ataaagagcc caaggtcttc 37980
gtcaattgca taagtcgatt ggatactcat gatgtacctc ctaaggggaa acaaagggcc 38040
ccgaagggcc ccgttgggtt agacctgggc tacaacgtcg cggatcagag caccggactt 38100
ctcgttgttt acacgcaggg tgtactcaac cagcagttgg cgcttctcgc tgtcaccggt 38160

```
cttagccagt tcatgctgga agaacggacg caggtagcag agggcgtgca tcttcggatc  38220
aaagatgaac atggtgtttt cgtggaacca gcggttggca cgaatggtgt acttaccgaa  38280
gtcactctcg tagacgtcca cggtctgcgc aatgcggttg tccgaggcat ccagggtgat  38340
ctcagttgca cgacccttca tgttcttgct gatggccttc ttgatcgagc tcgaagtctg  38400
gatcgagtta gcctgaccac cgttgcgcca gatggcctca gaggcattca ggagcatgtc  38460
ttcggtcaga agacggaggt caccagcggt accagtgtcg gaaccatcac cagttggcag  38520
ggtaccgtta gcacctaccg aaccgttggt cttgtagtag gcaaagatgt ttgccatctg  38580
acccggagta gtggtgttac gctggatctt agcctgaggg gcaccgacca tggcgtattc  38640
catgtccagc ttcagttcct tcgacttctt agccagctga tacgccagtt cgttcttacg  38700
accagccttc ttgaccttat ctgcggtacc ggtgacttgc agggtctcgt ccgagatttg  38760
gcagtagttg ttcaacatgg tggtgaagct accagccttg atggttgcat cctcaccttc  38820
cactcgggtg ttcttacccg gctggcggag ttcatcagtc tgccactcgt gggtgatagc  38880
ggtagctacg cccttgccga tagcagtcat gaacggggtg tcatagggtg cgatgttgta  38940
gatgatatcg ataaggtctt cgcgcttacc gttgatctct acagtcgaga cggcattagt  39000
tggagttgcc ataagttacg tttccttcta ttagaaaata tcgagagagg agaagagagc  39060
agcagcggct tcaaccgact ggtctttcct cagattagcg cgggcagctt taacccgctt  39120
agaaccctct gaggcttccg acctacgagc agcaggttta actgcggcag gtagttcagt  39180
ctcctccttc ttctctaggg cagccttgcg acggacctga gattcagccc acttacgtgc  39240
tgcatcgagt acagccagtt ggcgggcatc agatatccct cggatctcat cctcggagta  39300
tccaatcgat ttgccgtaag acacgatctt gtcaccccaa gactcatccg tagtcatttc  39360
cgggataagt ttcttggcta gctctgtctg acgcttaacg taggcagagt ggacaatctc  39420
ggctcgcttc tcttgcatag ccttaatgtc gttacgacgt ttgataagag cctgggctcg  39480
gtctcgggct tccagggctt ccagtcgaag ggtttgatac ttctctgggt cctgggcctt  39540
aagctgctcc cagtttacat tgtcatactg attagcacca gcaatagcgg taacagcata  39600
ctgctcaagc tcggccagta gattagagcg ttcagcatca agctcttcga atttagctgc  39660
atactgatcc tctagttcag cttgtcgagt tacaaactct tcattgcgaa ggtagccact  39720
cttaagctct tcgaagttaa cctcgtagac ttcatcccca atcgggatct caaagagttt  39780
atcctcagga tcttcctcgg actcaacctc ggggtcttcc tcagaacctt cttctggttc  39840
ctcctcggac tcaacctctt cggtgtcctc tggagtacct tcatctacta cctcttcctc  39900
ctcttcttcc cctacgactt taccatctac ggtttcatca ccgggggcca ggaggtcatc  39960
accgagcaaa tctccgaagg cttccgctgc ctcgaattca tccatgcctt gattctcaag  40020
gtccattact tatactcctt tagagtgatc gaatccagga tagcctgaat acgaagttgt  40080
acgcggttga gggcatgtag ttcgtggtag atggcctccc tggactctga atccttaggt  40140
gccgtggact tccactctcc ctcgatctct tcttggacaa tacggaaaag ctcaggaaga  40200
acgttctcac gtaccatctg ttgtgccgca tcagtcagca ctagactata gccaaaacgt  40260
tctcccaaga ttatttcctc actgccttcg agggcttctt agtctcaggt accttaccgt  40320
ctccgatata agcagcccga gcctgagttg cctcaagatg atactccgct tcgttacgag  40380
cccgttccca agtgaaacga tcacgctcaa gttgtagttc cgcttcctta agggccattt  40440
ctctctgctg aaggacagcc tcttgcttct tcagttcgat ctcagccagt ctgatctgag  40500
cctctacctg cttcatctgg gcctccgctt gcttagccat agcgtccgat tgggcacgtt  40560
```

```
gggcatcagc ttgggctttg atatcttcag gcttaggttg tgcttccttc tgctctctga  40620
tggccttagc ccgttgagct tcaggagaat ccgggttagt ccagaagcga tccgggtctt  40680
tgtacccagc gttctctgtg acttccttaa ggatgttgta aagattctgc tcagagacaa  40740
ggaccccgag acctccaccc ccgactacag cctgggccat ttcccagata cgcatcaggt  40800
ggagcatctg ctggtctttg ttcatgttgc caataccaac ggtaaccgtc aggtcggatc  40860
tctctcgcca gttggcaggg ttaatagcaa cccacttgcc tcgtagctgg aagacctctt  40920
cctgattctg gtacttgatg gcatggtcat gcagaagttg gaacaaacgc ttaacaccag  40980
tctctgcaaa catccgggca atcaggtcaa tctgttgctc agcagcagtc atcaactggt  41040
ttacactcat agccgcttgg ttagagtgca gggtgttttg gtctagacct cgggtacggt  41100
cagtgatacc tgtccgctta cctctgtctg cctctagtcg atccagcatc ccatagactt  41160
ccccagacaa ctgaggggtc tccaggggca tgatggaatt catggcctta actcgaacaa  41220
taccagctgc ctcgttggtc agcaagtctt cgaggttcac ctgaccgtcc aagaccacag  41280
atcggccctg gttagtacgg tagatgttat ccatgatgtt ccgcatgaga accgaacgga  41340
tctcttgaat gtctcggatc ttatcgtaga cactcatccc gtggaactta tgggcaattc  41400
gataggcatt caggtcagcg aagggacggc aatcccaagg ctcgttgctg ataatgtagt  41460
caccaacgta caggatacgg cgcaactcag agataccatc cccatctacg tcaagaaggg  41520
tgtagcactc agaggcccat acctcacggt tggcttcagc atcatcccca gagttgtact  41580
ggagttggcc agtcatatcg aagttatcac gtaccaacct ttctggctga ctatcagaga  41640
attcatactc atcgtatgga agctcatcta gtacatcctc gggaacaccc aagagccgca  41700
ggtcacttac ggtatacttc tcacggtgac agaggaagcg tgcatcatca atacaggtag  41760
ccaaccgatc aaccaggaag ttctcaggct tgatacaggt gactttaatc tctcgcttct  41820
tcttgtcctt gcgaatttta atactgtagg ttccatcctc gtccacactc tgtgctagaa  41880
tctcagtgtc tggatcagcc aggatatccg ctaccatttc ctcagagaga ccagagaatc  41940
gttcgaaggt agggttcagg acctcttcta catagacctt tacaacaccg gtcttcatca  42000
tcagagtgtc ttggaaccag tcgaacatta ccttgaaccc ctcgttctta cgcatgaaga  42060
ggtagttcac atactcagtc tcttgctctg cctgttcaac atcttcggca gtctgaggtt  42120
catacttaac tacttgaccg cctgacgtga ataccttcat aagagaaggc ataatccagt  42180
ctacagtctc ttgaacgtcc ctagatacaa tcgcggactt cccagggcgc tcgttaccga  42240
agggctctcc gaagtaatac ttcagggcct cagaacgctg cttggaaagt tccgaagagt  42300
tgaaatcaag ggcgtcgtta acaagttggt ctagatgacg aagtacctgt tcatcatcca  42360
taggcttaat cttgcgacga cgcttagcca ttagacaata ctcccaaacc aatcaggggt  42420
caactttgca gtatcactcc tgtagtatcc actgtttcgt acagcaccag gacgtgcatg  42480
ccgggaagcc atcaacaggg cataccgggt agcggagatc atatcgtcgt ttctgtcgat  42540
aatctttccg tcctttcggt ggtacatttt catttctttt aggaagttcg tacacgtatt  42600
aaacaccttc agatcaccat tctccatacg ggtcaacatc cagttaacgc cgaactctac  42660
agagttaccc ccgtgtttac catcaggacc tggggggttg ctgaagggtt cataaacaac  42720
attgaggttg tggtcatcct tcaggaggtc tacgaagcga cgacctgagg tagctccatc  42780
atgcttaaac gcatcgtggg ggactacaac agggatctgg tgaccaccct tgaggtagat  42840
agcatcagcg tgcatgccga gggtttcgcc agattcactt cgttcatcat acaggtaata  42900
```

```
cttgtccttc tctgcatccc aggctacaca ggcgatagcg ttagggtggt caaaccctag  42960
gtcgatacct ataatcctgt ggaagtggtc cgggatatca aaaggctcac atacgaactt  43020
ctcttccaga atggggaaga ctacaccaga tccgagcata ggaacaccct cggccctcat  43080
cctgcgttct gctggagagt ataccgagag tagctgctct ttaacttctg gactgaggtg  43140
tggggcgtct tcccagcttg catggacaag gaactgacca ggtttaagat cctggaggaa  43200
gtccttgacg atctccgtca gaccatgctc tggggtaaac gtcagatata caataccccc  43260
agtagtagcc gttcgggtta cacactgggt ataaatatcc ttggggcatt cctcatcgag  43320
ccagatgacg tcgatggcag tacccatgaa tttgtcctgg gacatttcgt aggacttgaa  43380
gataagggac gagaggcccc cggaggcatg cttaacaact actgcttgca cacatccggg  43440
tttaccttcc ctacgaatcg tctctacgat atcttccttg ggatcatcc ccgttccaaa  43500
agcctcaggg ttcttccagt cacctagtag ttcggactga agaatatccc gagtggtatc  43560
cgtggagatc cccgccgccc agcagttcac tggacgatca tactttctac cagtccacca  43620
ctcagggtag cgaccggtga ggtggcaggc catgataaag gccccggtgt aggttttacc  43680
acagcggtta ccagtcatag ccagcaactg ggcgcagttc gaggaagctg cgataaactt  43740
ctcttgccac ccataaggag tgtactggtt catgcggaaa tacttctgcc gctccgccaa  43800
ctccctgact agattccgta gccgctcttg ggtatccatt agaccacctt gtcacctact  43860
gttgatgcac gccacagggc ccgttggagg tcccttacgc gcactggagt ttgtttagcc  43920
cagagactat cttctgcctc ccatgcagcc tcgtcaaacc ttccggattt cagaagattc  43980
cacgtcttgg ggaacttctt cgtccacgct gtacccagct ggaagttgac gctaacgagg  44040
gcatcgaata gctctggagt gcaaaaaggc agctgagata cttgcccttg ggctgcatca  44100
taggctgcct tactatcttt ctctagccaa gtctctgctc gtgctagggt aatcggtccg  44160
tcttccccag ggagttgcaa gtggccataa ccaccagtta tcttcccgag ggagtctttg  44220
taccacttta gtaccaaccc ctctcttcgc ttgattagat caaggtactt aagaggctgg  44280
gaaagaaatg actttagcca actctggctc ttcgtcgaga attcgtcgaa cttcactgat  44340
tagatcctct gcggacatat cttccacatt cttagtagta agctccagtt tctgcttagc  44400
tccgaagcct ccacgatcca ggatatcctg ggccgccttg aggcgaatcc cacctttctc  44460
ttctgggttg ctagcgatct ctacaaccac acgaagcgcc atggggacgt gactcccgat  44520
gcgctcagag ataaaggcgt tgatgtattc ggcatgcttt cgatggtatg cagctacgtt  44580
gcgttgcgca tgattaggag agaacccagc ggctatatat gcttgggttt tgttcatacc  44640
atctgccaga gcctcacaat agaggtctag cttttcttta gcagaaagag gagcagcccc  44700
aatcgagaca accttttcgt ctgacataca ctgctccgat ctctctaaat ggtcaccccg  44760
gtaggactcg aacctacgac ctcctgtgtc caagacaggc actctaacca actgagctac  44820
gaggagttaa tggtggtcga aggaaggaat tgaacctcta gcctaaggcg tccgggttac  44880
aaccggatgg tagtagccat ctacctctac aacgaccttt gttggcgacc catgtcggat  44940
tcgaaccgac ggcttctccc tagacagggg agcactctaa ccgctgagtt aatgggccat  45000
aatggctggg acggtagggc tcgaacctac gacctgagag ttaacagctc cctgctctac  45060
caactgagct acatcccaat gaattctaaa ggttaatttc tcaaccttat aatactatta  45120
tatcacactt tttctatttt gtcaagccct tttttcatct tttttatttt tagtcgcaag  45180
acccggattt gttagggttt ttgctggaat ggggaagggg ttcttaagac tatcttaaga  45240
taaccttaag gtaactaacc ttcttagtaa gtaagtcaaa aggaagaagg aatcttaaga  45300
```

gcctataggt ctattatact acattttgga tac 45333

<210> SEQ ID NO 4
<211> LENGTH: 44884
<212> TYPE: DNA
<213> ORGANISM: Bacteriophage P1797

<400> SEQUENCE: 4
ctaaccttct tagtaagtaa gtcaaaagga agaaggaatc ttaagagcct ataggtctat 60
tatactacat tttcgatacc ttgtcaagta ctttttgata tttctttgat aatcacatga 120
tttacccgac gaacggtatg atagggttct atagatatac cctaagacta cccttcgtag 180
gttgctggta aggggtaagt ggcatagggc tcccttgatc caggttctat aggtatacct 240
tagggctacc tctgttctct atgccctggt ctattgcccc tttatccagt aatataccaa 300
cagttatcga agggtgcctt tgatccaggg cctataaccg gggatacccc caaaagtcta 360
ttttatcctc cggtgtatct ggggaatatc cccccaggag tcccccagat aaagtggggg 420
tggcctatcc ccaggggtat agcccctagc cctccctag gataccatga gactaacccc 480
aagatcaacc cctagggata ccgttcatcg ggtggaccca agggtattca taagaaaaat 540
cttagggtat tcaggggtg gatcgggggg aatatccatt gataacccct tgatccccta 600
ttgacttccg ttgataccct atgttaatca aagactgtct atatccgggg gtttgctggg 660
ggactgatag tccataggct gtatgaaaaa ccagtagaca accccgtaaa gaatatggcg 720
taatggcgcc gccttgaggg aaaccgatag gcaacggggg aaaccccagg ggcttgacaa 780
accccgcgga accgggtcta atggccccca cgttctacct aggccaccat ccccccttgcc 840 gcagtgctat ccgggggctg ccaaccaggg aagagcgccc aagtcgccca agtgtaaagc 900
cggcaggtat cgggggttga caagggatcg gtgaagcggt atagttcgcc ccacgtcaac 960
ggcataacgt gcatgactcc ctcgggatta gcgtagcctt gacaagcaag actgatggcc 1020
actcagcaaa agagcctatg ccagagaact ggacgaacta acccccgtca gagggttgac 1080
aaggcaagcc caagcctcta acatgggcac ccatcaggtg acggccacct ggggaaagtg 1140
taccttcgac ggtccttgga ctgaacaagg gagaaacccg aaagctgagg gaataacgca 1200
cactccgaaa gagcgtaggt cctggccttg taccatagaa ggtccgactg gtagcctgtc 1260
ccagcgcaat caattgacag accccgtggt tcaagcgcga cggggagtat gatgggttag 1320
tgtcgaaggc ttagcgcaga gggcgaagct tggtagatac ggcgaaggta ggggcgagtg 1380
gatacgaaga cccccgagga taaccgagga cagaccataa cgacgacact aacgcggaaa 1440
ggggccggct acgccaatgc caaggtttgc cgataaaccc ctttgtcgta tcgggatgtg 1500
tgtcccggct gatgattcct aaaggatgaa acgaccatga ctcaggctct tgacaaaaag 1560
ctgcgtcgca aggccaaccg caaggccaag gctttgggtt acaaccttgg gaatctgggg 1620
aaggcccaac agcgtagtga gcagaagttt gggattattg caagttgtaa caagatcctc 1680
gacgacaaga ccacttcgtt gcaagaaaag gcaggggcgc gtaaacgcaa ggctcttatg 1740
agtaccgact ggcgtaaccg tgaggttact aaccttcgga actggtataa gccgagcaag 1800
tgcggtaact ctgccgtcat cactgtcgaa gtaaacaact gaggtaatta caatgagcga 1860
ctacaagcgc atcaacggga tcatcaagac cattgccaac cggggtgctg ccctggacaa 1920
gctggttcaa accactggca tggatatcct caagcacatc gacgagcatg gcgaggtgtc 1980
cttggcctgc aagctgttca acgcgatgcc tcaaggctcc cgccggctgg ccctggccca 2040

-continued

```
ctggttcatc gacaacggca agatcgaggc caataccgac aaggaaaagg ccaaggaatt   2100
cccgttcgtc ttcgccaagg acaaggccac tcgtctggag cgtgccgcag agaaaccctg   2160
gttcaagtac aagaaagagc gtgacgtggc cgacgagttc tccctcgatc aagccatcgc   2220
cgccttcaag gccaagatcc agcgtgccat cgacaagggc cagctccagg cagcggacga   2280
gcgtatcgcc gtgatccagc gactggaagt caaggacgaa gcgaaggcag cgtaacgccg   2340
ggtgcgccag gggtgtgtac tatgacgcgc ccctggtcta tccctagagt gcatggtagg   2400
tccgtgcatt gtagcgatag accatcagga ggtttccgtg ggttactgta tctttgggca   2460
ggttcattcc atccaaggcc aggattatgt ttctggtttc tgcgatgcaa gggtaggttt   2520
cgacgctggt attgtgtacc gttggacatt caaggacggt aaatttgcct gcggtgtcta   2580
ctccctggat ggtatccgtc tgaacatctg cgggtggatc aaatgaagtc accctacgaa   2640
gcggcccatg aacgtgccca aatgattaac cgtctcaaga aactcactag gatgatccgg   2700
gtgcatcccg atccccggtg gattgttgag cgtcaggaac tcataaggaa actaagcaag   2760
tgacaatcgc tatcattgta tccagcattg gtatcgccta cttcttcttt cgtgattgga   2820
aagaggaaat gggtatctaa ccccaactga tgaggccaag gtgattcctg gccgaaaccc   2880
ccaccggacc tatggtcgca ggctggggcg tcttgggaaa tcaactaagg aaaccatccc   2940
gtgaagcgca acgactaccg aaaggtgaat cggaacatgc aagccatcga ggccatcgac   3000
cgcaagattg ccaaggctgt ccgtgagttg actaactccg gaggaaacca cgttggtaaa   3060
accctggagc tgaatcggct gcgggctaag cgtgcatcgc tggccaaggt aagggcacgg   3120
tgagtacatg gaagtctatt gtatgtgccg ccatacgctc acgttccaat gggttgctgc   3180
tggtaacgtg ggtggttctc ttcgtcctgt cctcgatctt ggacagcatc cctttttgcat   3240
cgtgaggtag tcccatggat atcaaggtgt ggccccgcaa cggcgtaacc ctcagttctc   3300
tggttaagtc ccaaaccttt ctcatcaatg gggatgtgta catggtctgc gaactccgaa   3360
gcatcaagat gaagagtgaa tctgacgagg ttcccgttct caatctcaag actggcaacg   3420
tcatttacat gcctccgttg agcctggtat acccagtaac tgccgagctg aattgctacg   3480
aggtgtaaca tgaaactcca atacaacatg attaccagta agatcaaggt tgtgatgtgg   3540
aatgaccttg agccgggttg cctgtacatc ttcgcagagg atgacgggaa gaagaacccc   3600
aaagtcttcc agtacctgga gcttaatgat gaattcttca tctgcgaaat cttcggcgga   3660
cctgagggcg atgtattctt cagcagcgat gttgactgcg ggttcttccc ggtgactgtc   3720
aagtacgcag agatcgaagt ccatcggttc ggcctaccgg actgagggtg tgtactatga   3780
cgcccgccca atacatctac ctctggttgg tatccaaggt tgtcatccgt cgataccagc   3840
ctaaccccaa actgtacccc aactggtccg ttactcatat ccgtgtgtcg atcttcggca   3900
aacgtgcagg tatcgtctat gaaatccact gaaccccaag tctattggct ggctagcgcc   3960
gatggtgaat tccacctcaa ggtcatcaac ttcggccagt tcatcaccga aaccctttac   4020
gaactcggca ttccggtgga ccacaaggtt catcgggtcc actgaggtgc aaccatgtca   4080
aacaccacct tcactgtagc agcaacccgc ccccggaacg accttcacat cagtaagcgg   4140
gcggatgggg tttatgtgaa ccctaaaaac tctggcgata ttgtcttcct caaggaaggt   4200
aataaggttg tcgtcctcag ccagagcggg ttcagcatcc tcgaagccca gaccatgccc   4260
aacatcgggg aactctgccc ggctaaggag gtccatgtat ccgccagggt atgggggccg   4320
tatgaagaat aaacccatga tcggccagat aatggcccag gagcgccgca tgaagcgtcg   4380
tgtagaaaag cgggggttca acatgagcct ccaggaaagc ccccaggagc cccgtggtga   4440
```

```
gcttggtttc accctggctg ccgtaggtat ggagtccagc cgatcggctt acctgcgtca   4500
cgccagggag gctatgatcc aatccgggga gccttgcccc cattgcatgc cagtcttcgg   4560
tcccaaagag ggtcgttgct gcaactgcgc gagggactgg tgatggatct cggtaatctt   4620
tggtgtctct tgggtgtcca tcggtacaag atacttgatg gtggacccta cgagattcgt   4680
cacaagggtc ggctagtgga actctgccac tattacgacc tgaggtgtga tcgctgcggt   4740
gacgtacatc ggaaggtggt ccgcagcaaa tgatgacata cctcctgata atcccagcga   4800
tcctgatcta tatggcttta tctttgctcg tggctggcat cgccgggttg gcggcaaatt   4860
gcgatgagca tggaaggatg agccagaagg atcaggacat ttcaatcatc ctcggtatcc   4920
tgtggccagt gtcactacct tggatgtgct tctcggttgt tatctggaaa cctttggcta   4980
ccaccatccg tgcggccaaa cgactaatca aaggagatta ctaatgcacc gcagagactt   5040
tccctcctgc tgtaccgcaa aaatctacat cggcatggga ccctcgggta ccgctgacca   5100
ttacgccggc ctcgcatcca acgggttcag cccccgtggt ttcgccaagg aactgatcgg   5160
cgccatccgt cgtgaatcca acgagggcca cggtacgatg gtcttcacgg tgaacagcga   5220
gcaggtggta gcagatacca tcctccgccg catgggcagc cactacaacc cctgggcatc   5280
cagcgacaac cactcgacca aggtccgggt ccacgtcatc aacgtgaagt ctgcggcaga   5340
tatcctcatc aaccatgggg ttctccgtcg tcacctcggt ggcttgcagg actaccccgg   5400
taccgtcgag cactcggagt acctcgacaa gctctgtaaa ggtctgtaac atctaggcct   5460
tgacattctg ctggaagtgt ggtataataa ccttaaggtg ccgggggttg ctttatatcc   5520
ctaaggtacc taaggttcta ccttctatct tcttcatctt aagaaagagg taagaacaat   5580
ggtcctcaag ctctacactc gggtaatgct cctggctatc cccgcatggg taagcgtaag   5640
gttttctacg agcgtctctg ctccaacggt gaattgaccc tgaacggcaa cctcaaggcc   5700
accaaggtgt cggcaccaac caaaggcaag caacagcgcc gtggcacctt ctaagtaact   5760
tagaggtcgc tagtaatacc cctagtattc ctgtcctggg ggtattgctg gctaactcaa   5820
ccaaggagaa aacaaatggc ccgtatcaag tatgccttcg gtatgaaacc caagaagggc   5880
gagggtaaag ccctcaaggt aatgacctct tcctcctgct tcggtacaat ggaaggtccg   5940
gtaacccacg gctataagct cgacggttgg accttcatct gctcccgccg aagcaagaag   6000
ttcatcgatg tgctcaacaa gtgtacccaa ggtgaactca agaccatcac catcggcggc   6060
aaggccttca aaatcccgaa ggtccacttc tggtcttacg aaagcaaggc caaggattcc   6120
cccttcgaga agtattctaa cgggacggaa atgatttccc ccacccatca cggaaaagaa   6180
ggggtctgcg gtatctactt caaccccaag gtacacaccc tggattcctg gtaccccatc   6240
atgaaattcc tcttcaagat gatctccagc ggactcgact accaaggtcg tgaagaggag   6300
gttcacctga agcttgctga gaagtatggc ttctggaagt cctacctcgc aatgtccttc   6360
cacggactga tagccaatgg ctacaccggg tacccactct ccaactacat gttcagtagt   6420
gattgggatg atctcaagaa gggagatatc cacatccaat ccgctgacga gtctatccga   6480
ttcggtcgtt ggatgcccaa ccgggatgcc ccaggtggac gtgagtgggt aaggaataca   6540
ccctggcggt ctgaattcct gaagattcag ttggacaagg tggaggtagt taccatagca   6600
cctcagccaa ccatcttcgg aaagaaagat ccctacatga ccgtagatag cgagatggga   6660
ggtttcatcc gcctttatcc tcatacctgt gaaaaatacg gagtggtcat gctggggatc   6720
atgggtgagg ttggctgggg gagcggcata aaggatatct tactggccct cgaagacttc   6780
```

```
atcgagaaaa acttctgaca accaaggaga aatcaaatgg gaatgtatgc agcccataac   6840
gtgtactatg atgtcgaggg tgctgagatt ggtcactgct gcgtaaaata cgtggctgaa   6900
tataccaact gcttcggtgc attctgcgac gaaacgggac ctttccggga tgtagtgtgg   6960
gagaccgggg ttggacacct cctggtgtct acccacgaga acactgctgg taagttggtg   7020
gagttcttga acagtgatct ggtcaacagg atcaccgacg gtggaatcct ctcagcttcc   7080
caggactggc caaccaagtg gtggacagga tctgacgggg ctacccaaaa cctctccaat   7140
cctgaccact tcagcccccc tggccgccga caggctgtgt acgttcgggt ggacctcaag   7200
aagaacgcat cggcaatcat ctgtgccctc cgaatgggag atcgcttgtg ggtgtaggt    7260
gattccatgc gtcgcatcac ccaggaaaat cgtgataaga tcctggtctg caatgcagag   7320
atcctcaccc tcgcggcttg tgcccaggta ggtagcactg ctcattgcga cagctacccg   7380
gccatgttcc cggtgactgc tggtgaatac cgggagggat gcgagagcca cggctgggag   7440
gtggatgaca gctacataag cgaggtcatg gatggtatcg taggtggata caagaatatc   7500
acctacttcg atattaagag catccatgag cggactcgcg aagagttcaa ggacaagctc   7560
aagcatcacg acgctgagtt gtggcagggg tataccaagg atgatgacct gatcgaatgc   7620
gacggtctcg aaggtgtacc taatgaccga atcctttcca tcatggcccc aatcaccatt   7680
gacgtcggtg acccaggtcg ggaaaggtcc gaggtcgtac ccaccagcca atacagcatc   7740
cccgaaatcc tcgaaaaact ggagaacatg caatgaacaa cgcaatcccc ctgatcggtg   7800
cagatcccga agttttcgtc ggctacgacc gtaaccccca gagcgtcatc ggcttcatcg   7860
gcggcaccaa ggaagagccc ttggctgtag ccggtggtgc tgtccaggaa gacaacgttc   7920
ttctggagta caacatcgac ccggccagta ccaaggaaga gttcgtggag cgtatcgtct   7980
ccgttcgact cctgggtgcc cagatgctcc accccttcgg catgaacatc atcgagaacc   8040
tgtcctctca cctgtacgac gaggaactcc tccgcagctt cggtccccag gcttacgtct   8100
tcggttgcga gccggactac aactgctgga ctcgtcgtca gaacgtgatg ccgaaggatg   8160
cccctccgac cctgcgtact gccggcggcc acgtccatat cggcttcagc cacatcgagc   8220
gagtcaccaa ggctaccacc agagaagtca tgcagatgtg tgactacctc ctgggcctgg   8280
cctctgtcat cctcgatggt gacacccagc gtaagaagct gtacggcaag gctggcgcaa   8340
tgcgctataa gccctacggc ggcgagtacc gtagcctatc gaacttctgg atcttctctg   8400
tcgatctgac cgagtgggtc tatgaaatgg cagtgcaagc ctacacctcc aagcacctcc   8460
tggaggagta caagtcgatc gtatccggtg atgaagtcca gcggatcatc aacgagaacg   8520
acggcgctgc ggcagttgcg gccctccaag ccctgggggt gaagtatgaa tgacctgaat   8580
aatcgccatc ggttggccgg ggacttcaac atgtactact cctccaccta tgccttcttc   8640
cgggttgacg gtgagcctcg ggtagtgtac gtggacgata ccgagtccat tggtgacgac   8700
cgtcaattcg acgggtttcg tctcctgggt aatgtgtatc gccccgacgg cagtaactac   8760
tacggtgggg ttgtctacag cgaggtagaa agcgtgcggc cctccagtgg gtactatgac   8820
gtctttggcc gtggggttcg tgatacttat gtatccttcc tcgtgaacaa tcggactcag   8880
cgtaagggta tggaccccag gaacatcctg ctgaaccatg cccaacaggc catcactgga   8940
gaaatgatga tccgaatctt cacccaggcc gaggaaatga tctctgcccc atcccaccgg   9000
gacttcttca tcaaggatgg ggtagttcac tggaaggggg tgaaggttgg tcagatggta   9060
gatggccgac tgtccgcaga tgaacaattc aagaaccagg aggacttgct atgtcagtta   9120
ttggcacaca gatagggttc cgtaagaacc agatcattgc cccggaacat cacgaggaac   9180
```

```
tgcctgcggt tgcttccttc gggttcgaag tcgaactgga aggcctcaac aactggccgg   9240
aagtggacgg gtgggatctg aagggtgacg gctctctgcg ggatggtatg gagtatgtct   9300
tctccggtcc cgcctctggc cagaaggcaa tcactcgggt tgaatccttt gtgagtgcga   9360
tggaggaaac tcctccggcc cccaccttcc gttgctccac ccacctgcac atggatatgc   9420
gtgacgtaga gtggcctgtt tatgaacgaa cggtcctgac ctacatggca ttcgaggatg   9480
ttttcttcga tcactgccaa ccgtatcgtc gggatagtaa cttctgcatc ccgttcttca   9540
gcaacgactg gctggcccag accttcggtc gccgtatcct ggccccggaa ggtgaccgag   9600
agaaagtctt gggtcttacc tcctggccaa agtattcggc cttgaacctc caggtaaccc   9660
acaacttcgg gtccatcgag ttccgtggtg cccatgctct cactactcgg caggaaatgg   9720
taggcctgat gcagcgtatg ttgtgtctca aggccttcgc catggctcac gcagaaaccc   9780
cgctggaaga gttccttaag gtactctccg aggtgaatct ccgtgatgta ttcttcctgg   9840
gggtatctcc ggactatgaa atgtctccgg gtggtcgtga aatggggatc gccagtgcta   9900
ctctcgcggt agcaaccatg ggctttgttc gctccggggt agatcccctg gaagatgaac   9960
agaaccgtca gcgtcgtctc cgggagcagg aacgtgagcg tcagagggct ttggatcgta  10020
ggctgctctt tgctcgcgct attacctcac gactactaga tggtgcagca gagcggtaca  10080
acttggcaat ggtgccaggt acccaggttc gactggatac ggcgattact gcggtaactt  10140
ctctgcgtcg tattggtcac caagtgcgtg tacgagacct tctggaggac caagaggctc  10200
ttcaagatgc cttcgtactg ctcatggata acccgcagca ccttcagcgc cataccggcg  10260
taacaatcga accagatatg tactaaggag aaatacaatg tgtggattgg taggcttctg  10320
ttccacaact aacgcgagtg ataacgaaat cgctcttctc aaatccctcc tggccgtgga  10380
tattatccgt ggtgctcacg ccaccggttt ggccaagatc gacccggtta agaacgaggt  10440
aggaattcac aagcgggcag tagatgccta cgacttcctg gctgatcctg aaaccaagga  10500
gttcctggac aagggtcggg ctcgcatcta catgggtcac aaccgttacg ccacgatggg  10560
cgacaagacg gaccatggga atgcccaccc cttccaggta gaccacatca ccatggtaca  10620
taacggcacc gtagatacct ggggcctgca cctgctggat ggcaatgata agtacaacgt  10680
ggattcgaac atgctgtgcg ctaccattgc caaccacgga gccaagaaga ccttcgaaga  10740
gaagttctcc ggtgctgctg cggtaatctg gtgggactcc aaggaacgta ccctgaactt  10800
catccgcaac gatgagcgtc cgttgttcat ggcggtgacc accactggta ccatcgtgtg  10860
ggcatccgag cctggtatgc tcaaggtttt cctggagcgt cccaacgcta agatccgcct  10920
tcgttctccc atcgctgaac tgaaggctga agtcctggta actatcccgt tcacggaggc  10980
cggagtgcga aagggtgcag aaccccagac cactccggtc acgtttctgg acctcccaat  11040
tcccgaaagc gaaaggcaaa cagcggcatg gtggagtcgc tacgtcggtg tctcggacta  11100
tgatgactac agccgaagcc aaggcagcca agcgggaacg aaaggcagcc aagcgggctc  11160
gtcgtatgga acgtctggcg atgcgtacgc aaggaacacc ctccggatca acaacaacct  11220
cgacgcagca ggtagcacct tcaagcaccg gcaactcgtc accttcgatg ttgtcaagat  11280
cgaggcctac gcaaacggca gcgagtacgg aactgtcact ggaatcgagc gtgaagaaaa  11340
ccttctcatc gaagctcatg gcatcaacgt cgccaaggtc cacggataca ccgtcctccg  11400
agggagtatc tccaatgcct acttcatcgg ccaagaccgt gatctcaagg ttactgtcga  11460
ggatctggcg gtaagctgcc tggacccaaa gcatcggccg actcctgggg agactacccc  11520
```

```
agtgttgagg attggaacga tctcatcgga gacgaaatcc cattctaaac ccagggttca  11580
agtcggcggc acctcgggga ataccccctcc ggccaacatc agctacccct tgaaggttca  11640
gggacacacg ttcaacaacg ttcatgtctt tcgggacttc gtatcccagg ggtgtgcatc  11700
ttgcggtaag atccctaccg cgtatgacca gcgtaatcgt catctgacgg tgtacgaggg  11760
tgccaagttc actggtagcc tggatgagtg cgagttcatc tgtggtgagt gtgtaatcga  11820
aaataaatag gaggtcaaaa tgacccaagt aacgatgaag cgtcaagtag tgatccagat  11880
ggagaccgac gcaacccgta agtatccctt ctcccgtgac accctggaca agatccagtc  11940
gattcgtcga gtcaaggagc aggaactcaa tgatgccaac ccggacgagg aattcctggt  12000
accggccccg gtagtcattg cggaagctat cgaccgactc ttcgaagact acttcgagta  12060
aggtagtgcg ttagtaatag tccctggccg acccatgccg gttcctaaga tgcgtacatg  12120
ggatctaact taggattcca ggggctattg ctggcttcac taccctcaac agaaacagga  12180
gatttgccat gttctatatc tataaaggtg cccgcccctc tgctggtgct gtcgctcttc  12240
gtaacgccat gggtgctcga atccttcgct ccgaggggtc tacctatcgg ggtcgttcgg  12300
gtactgcggt aatcaactgg ggaaccgttg gtgcagaggc acgacgccta cagggtatcg  12360
ccccggtctt cctcaacgac ccggctatgg ttgctcgctg caccaacaag ctggatttct  12420
tccgccactt cgaggccaac gccccccatc tgatcccccg ctggacggat tcctgggcta  12480
atgtccaccc gatcctgaat tcctgcggtc gaatgtacgc tcgtacggac ctcaatggtc  12540
atagcggcag ggtatccac ctggtgtgca gcatcaacga cgcagaagtc caggccatcg  12600
atgcccttcg tcgccagggg aactacccgg tacacatctg ggtcataccc cacatcccgg  12660
aggtcgtcga gaacgcccaa ttgttcaccc agggcatcgt cggtaagcgt accgagttcc  12720
gagtccacat gatccgtggg gaggtagccc tgctccaggt caagctccga cgtgttgcca  12780
atgaaatggt gaccaacgaa ggacaaagta tcgttcgtaa cgtagctggc ggctgggtct  12840
atggcgtcaa cgatgcaatg ggacgggatg gcgctgagca ggctatgtcg gcagcagcag  12900
aagctatcca agttgcaggc ctggacttcg gcgctgtgga tattatctac cagcacgcta  12960
ctagccgggc gtttgtcctg gaaatcaaca ccgcgccggg cctggatgca gaaggcagcg  13020
ccctggaggc ctacgtcaag ggcttcaata aaatcttcga ggagactatc taatggctgt  13080
tcgtgttttc gtttatggta ctctcctgtc tggtttgtac aaccactacc ttctggaagg  13140
ggccgagttt gtcggcaatg ctgtatcctg cgagcggggt ctgatgtact ccgctggcgg  13200
cttccctatc ctctccttcg cctcccgtgc tgatctcatc gtaggtgaaa tctggcaact  13260
ccccgaaggc gagaaggggg aggaaatgct ggagaacctg gatgccctgg agggttatcc  13320
gggttggtat gatcgtaccc tcaaggattt ccgaatcaat ggggaacgaa tcaaggccct  13380
ggtgtaccat caggatagcc acatggcgat ggatatcgtc aaggatggcg actggaaggc  13440
acacctggca aaacgacaag gagcagtatg atggatgaaa tgaccgtaga caaagcagta  13500
gaagtctacc gcgatactcc gaacaccttc ggacaccaag agctacatgc ccagaagatg  13560
ctcctcaagg agatcctggg ccttgtcgcc tcccaacgac acctccaaga ctccatcgag  13620
gtctccaaga ttccggaggc ctcggatagc cccgagacca gctacggcgg gtactgtgac  13680
gagtctgttg gtattcgctt catgtgggag cgactgaaga agatcgagga ccgcctccgt  13740
gaactggaga aggtctacgg tactttcgta acaactcctt acaagaccct gccgggcaac  13800
gtcaacgctg tacctagctt ggtgctcaag agccagatgg aggaataagt gaagcagatt  13860
atcggtgata cggcctgtcc gggttgccga gctaaaggtg ggataaaac aggtaatcac  13920
```

```
ctcatcttgt tcgtagacaa agagaaaggt acccgcttcg gtagttgtaa ccgttgcggc  13980
cactatgaag tcctcgaaga agggttcaag gttcctgaac gaagggagaa gtccgaagag  14040
gatatcatcc atgaagtcaa cgaagtcctt gagtatccaa ttaaagccct cgatactcgg  14100
aagatcagca aatcaatcgc tgaacgatac ggggtacgtg ttggtctatc acaagaaaac  14160
ggtgaggacg ttatcgagca ttactatcca cgcacccgcg atggggagta ccgagcgttt  14220
aacgtccgaa tcctagaccc taaggctttc tactatcgtg gtagccccaa gggtggtgtt  14280
gaccccttcg gttataacac ccttcggcat aaggatatgg gccacctgcg gttagtcatc  14340
tgcgaggatg aactgtcggc aatgtcagtg gctcagatca tggagtcgaa gctgcccgag  14400
aagtggaagc acctacgtca agcagccatt agctggtcct caggtgttgg ttctgctgga  14460
cgggatatcg cattcctaaa ggaatctggt gtactcgaac ggttcaacga ggtcatctat  14520
tgccacgatg ctgatgacga ggggcgtaag tcagtagaaa aggtacgtgc cctgtacccc  14580
gagtgtaagt tcgtagagct tcccctgaag gatgctaacg acatgcttat gcgtaatcgg  14640
ggggatgagg tctaccagat gatccgattc ggcagcaagg ttaagtcccc ggactgttcc  14700
gtaactgtcg atgaggtata cgctgaggcg ctagaacccc ctaagtgggg taagagctat  14760
ccctgggaag gtctaaccaa ccttacctat ggtcagcgtg atggtgagat catcggggta  14820
ggtggaggta ctggtatcgg taagaccctg ttggcccacg agattgctgc ctggaattgc  14880
attgagcacg gggagaacgt agggacattc ctgttggaag agcaggtagc catgacactg  14940
aagaatatcg cggggaaggt agctaacgta cccttccacc gaccggatat cgagtgggat  15000
gagcaagcct ttaaagacgc tgcgggtaaa ctccgtggca agctcttcat gtggaagaac  15060
aagggtcaga acgattggga tcatatcaag gaatgtattc gcttctgggc agtagccatg  15120
gatgtgaaga ctatcctgct ggataacatg accgccatga ccaaccacct tagtccttcc  15180
gaaatgaaca cggagatcgc ccgtatctgt acagagcttg caggtatggc cgatgagctg  15240
ggtcttcgga tcttcatctt ctcccacctt aacccgccca agggtaatcg tacccacgag  15300
gaaggcgctg aagtaaagga aagccagttc accggctccc gagctatgca gcgttggtgt  15360
cagcttatga tcggcttcga gcggaacaag caggctgacg gggaagagaa gcacgagagc  15420
agaatccgtg taatcaagga caggaactac ggtaatactg gactagtgtt taccaagtat  15480
aacccagaga cgggtcgctt ggttgaacgt gagggcagtt acgacgaggt acctgctgac  15540
gatgacaccc caatttgatt acgttatcta tgacctagag gggacggcc tcttcaatac  15600
ggtcacaagg ctttggtgcg ctgttgttgt agacattccg actggggtag tccggggatt  15660
ccggcccgag gaaatggatg tgttctatag gatcatcgcc catgcaaagt tcgtggtcgg  15720
gcataacatc ctagactacg acaaccgggt ccttgagaaa cttcatggga ttatcatacc  15780
ccccgaccga agctatgata ccttggttgc atcgaggttg acttggccag ataggcccca  15840
gggtcattcc ctgggagcct ggggtaagtt cctgaagtgt cacaagggtg acttcaacga  15900
cttctccaag ttctcagagg aaatgtttga gtattgcctt caggatggag tggtcagtca  15960
cgcactgttc aactacctcc tccgggtact cggcatgact tggcaagagc ttgttgaatg  16020
gaggactgta gattggctaa aaagcgagtg aggaactaca agcgtgagag agaactggct  16080
attcgacgcg gcgaaacggg cgtgggctct aagtcaggag atgctcagcg gcaccgagcc  16140
cgccgaaagg tggaaaagcg tcttggcagg aagctcggaa ccgacgaggt tgtcgatcat  16200
atcaaacgtg ttaaagatgg tggcggtaac ggggattcta atcttcgcgt ccgtggccgt  16260
```

```
tcttctaacg ctgctgatgg tggtcgggtg ggcgatcgta aggccaaagg cattcgcaag  16320
aaaaagtaaa tgaagagggg ccttcgggcc cccgaggact cattatgttc aatcgaaagc  16380
taagcatcag taaaatcctc agttcctttg acaacgagat caatctactg aagaccttta  16440
tcaaagagtc ttcggatgaa tctgaacgga tctacaacga gatcagcttc ctgaaggcgg  16500
agcgtaccca ggtcatgcag gacaacctga aggcccagaa ggtactggct aacctggaag  16560
aactgctggg aggtaagagt gaagaagtat cgagttaatg tggggttcca ggacaccaag  16620
gtgttcaacg cagacttcta ccgcatcgag ttggatatca tccggttctt cgcgggagat  16680
tctgatgcca accccatgac cgtccgagcc aatgagatcg gtgctgtccg tggatgggtt  16740
tctgtggagg agattaacga tggcgagtaa gaaggaaagc ctggaggatc aggcacggaa  16800
ggagattgcc ctggagaagg agttctctgg tagctggggt ggccccgaga tcgatgctga  16860
tgacttcccc ttgggtagtg cctgtggcct agatcccgag gtatgcgagt catgcagctg  16920
agccagtgcg taccctggct gtgggctact gatcgatgcg ggtatggggt ccttaccttc  16980
aagaggaaac tcaggaaagc ccaccgggtt gcctactgta tggccaacag tctacaaatt  17040
gaggacatcg acggggttat catcagacat aaatgtgata acccatggtg tgtaaatgta  17100
gatcacctcg aacctggaac tcatcaggat aacgaggatg ataagaccaa aagaggtagg  17160
cgacctatgg gagagaaggt tggctcagca aaactgaata gggctcaagt agagtccatc  17220
cggaaggagt atgtaaaaag ctcaaagact ttcggttcgg ttgccctggg taagaaatac  17280
ggggtacatt cctcaacgat cagatacatc atagcaggag atatctggtg agtatcctag  17340
cgcaagtcct tgtcatcttc tggagtgcat tcttccaggt attcctcctg ggattgaact  17400
ctaagctgct ccgggatgac aagatcaagg ctgggttcgt agtgtcttgg tgtatcacgc  17460
tggctcagtt tgcttacatc aaggcggtag cctcctccca cttggatatc ggatggttta  17520
tcttcgtgtc cgggtgggga ggtgcccttg ggattacctc tgctcaatac ttctacaagt  17580
ggtacgacag ggtattccac aagaaggctt gacaaatcca gaaaagtgtg gtataataac  17640
cttaaggtgt ccggggttgc tttacccta taggagatac aaatgagtga ccatgtaagc  17700
tattccaaac atgtccgtgg caagtacctg tgtaatatgg cctctgccct ccataagagc  17760
atggagatac aaaggactaa catccggaag ttcctcagca gtccccagat tactctccgg  17820
gagaagcgtc gggtattcct gagcctcccc gctggattcc tgggggtgag ctacttctca  17880
ggctcccacc tgaatctgag ttcctactcg cctaaacgca atagccgggt acgggagaag  17940
gatcttagcc tgtacgacga cttctacatc gacaggaata cccagctaga tccgcgagac  18000
ctcttgttta cctcccaaga agagaagaaa tgggagtttc aatacctgaa ggagaagcgg  18060
ggtgatgggt tcgagctatc cgatgaagaa ctgagcgacg ttaaggatat ccagcgcaag  18120
atcgacctgt cctggtacct ggtagacctg gcctgtgaac gtgggtgttc ctacttcatt  18180
ttcgactggt gattacatga gcaagatcaa gagtatcctc atggagcggg tagatgactt  18240
cctgctcaag caagttgctg tggccttcct ggagcagcaa tggaagctgg accgcagtgg  18300
taccgtggac tacctctcct acctggaggg tgtatcccac gaagctgtgg agacagttgt  18360
agagaatctg gcggagcgtc ttaaggggga ttaagtggat tggagaaagt cactgttcgt  18420
tgagcacaag gtagctgata tcatcagccg ccagagtaaa cgtggagtct acttccagac  18480
tcagcgggcc aagtggctga tccatgtgct tagcgaacga atcctcaaga ttgaccttga  18540
ggctgtcccc cagatgccca tgatgatcgt aagggctggg gccttcagca agccattcct  18600
aaagagtggt aagccgaacc aaaggctcca gtccctgtgg caacgtcttg ggcacttcga  18660
```

```
ggtatctgga cccttctctg caatcgagta tgtacccttc gaccttggta agactgccaa  18720
gttcaaggac tggatgctgg atcaggggtg gatacctgac caatggaaca tcaaggatat  18780
tactgtcggc actgatggca agaagctacg tggatctgac cttaatgaat ccttgaataa  18840
gtacattgag gatctccgac agagcaagtc tggacgactc cgaatgaagc tccaggggat  18900
catccctggg aaaactacca ttggggaagt caagagaaag ctcgaaaagc aacgtaaggt  18960
cctaacgact ccgaagatga ctgaagagtc gatggatacc gtccagggag acctgggaaa  19020
gctggtgatg cagcgaatgg tttgggccca ccgtcggtcc ctcttgcagg ggctggtaga  19080
tcaggtgagg cctgatggac gcctagaggg gagtgctaac ccctgtgcaa cacctacggg  19140
ccgtatgagg caccgtgtag tagtcaatat ccccgctgct cgttctcctt tcggacctga  19200
aatccgtggg ttgttccagg ggacacctga ggctggtgaa tggaaatgga ctgtcctccg  19260
ccgtgatctt ggggagaacg aaagggttag gcccttcact aacatcgtgg aggaactcaa  19320
gaagggtaag tggaagactg taggaaagta ccgggtatac gtcccagcga accaattagt  19380
attcgtgggc tacgatggtg ctggtctaga gcttcggatg cttgcatcct acatcaacaa  19440
cccagagtac accaaagagg tggtcgaggg tgatgtacac acggccaacc agatagccgc  19500
agggcttccc acacgggatg atgctaagac gttcatctac gccttcatct acggtgctgg  19560
ggatgccaag atcgggacta tcattggtgg cacaagggcg gacggggcta agctccgggc  19620
ccagttcctt gaagctaacc cagaccttgc tgcactgatt gagagggtta agcaggaagc  19680
cgagaggggt tatctcgaag ggctagacgg acgaaagcta accatgcgac gttctgagtc  19740
tggcgacgtg atgatccaca aggcattgaa caccctcctg caagcagcag gtgctattgt  19800
catgaaatgg gcaatggtac tcctggatga gcgagtccgc aggttaaacc tgagggcttg  19860
gaaagtcttg gatatccacg acgaaggcca gtgggaatgc cacccagagg atctcaaggc  19920
gctacgtgag cagatggaag tctgcgttcg ggatgctggg gaactcctcg ggttaactg  19980
tcctttggct agtgattcta ttgcagggag atcatggaaa gacactcatt aaagcataaa  20040
gtgggtgcta ttagcgaagc gagagcgaag cttatgtacc taaagagggg ttgggaggtg  20100
tactccccgg atatgcctca aagcagatgc gacttcattg tagatagtgg aaaaggtctt  20160
tttaaagttc aagtaaagac cgcctcttgg tgcaagactg gtaagtttaa tcactgccag  20220
ataaggcttg taaataggaa tggaaacccc tacgagaggg aagactttga tctacttgtt  20280
gtagtagatg ctgactgcat atacgaaata ccccatgatg acatcctcgg gaggacttca  20340
ctctatttca aaagtgataa cccaaacccg aggaagttaa aaagggatta caacccagag  20400
ggttgggttg taacacactg atacatctgg gggttgactt tcagcccccct ctgtggtata  20460
ataccttctt ccctacgaga ggtttaagat atgtctaaga aagtttccca acgattcacc  20520
ttcccggtag cgaagctgat cttcccctac atcgtaactc cggacaccga gtacggtgaa  20580
gtctaccaag taaccatctg cattccgacc aaggaagagg cagacaagct ggtccaacag  20640
atggaatcca aagatgcccg tctgaagggt accatcaaat accaagagcg tgatggcgag  20700
tacctgttca aggtaaagca gaagaagcac gtggattgga tgcaagacgg tgagcgcaag  20760
tctgctgtaa tgaagccggt ggttctgacc tcggacaaca agccgtatga tggccccaac  20820
ccgtggggtg gctctactgg tgaagttggc atcctgatcg agacccaaaa gggcccacga  20880
ggcaagggta ctatgacggc cctgcgactg cgcggtgtac gactccacga gattgtatcc  20940
ggtggtgacg gtgaggacga tccgctgttc ggtggtgcct tcaccgagga agagccagag  21000
```

```
gacgtattcg acgaggtatt cgatgacgaa gacgctccta tctaaggggt tggaggatca  21060
tgagtcgggg gtatgccggt caggctgccc ctactgctta attgaattcg agagagtgtg  21120
gggtgtaagg gtggtcagtt ctacagctgc atctaataat aaagtagagg tcgatcctaa  21180
tggaatcaag ccgggtgagc cgggcgctaa acttgatagc ggcaaggtgg atgttggaat  21240
catcttcgaa gcgttcccga gggctctata tgcagtggca caagttgcta acttcggagc  21300
cagaaagtat agtcgcgggg gttggaggtc tgtcgagaac ggagtccagc gatatgatgc  21360
tgccttcggt agacacctcc ttgagcgaca caagggtgaa gctttggacc cccaaagtaa  21420
tctaccccac cggtatcacg aagtatggaa cgccctagcg tccctggaac tcgtcattca  21480
gcaagaggag gaatccaatg gaacttctgt tggacccaag ggctaagact gttcctagca  21540
actactctgt gatgggcatt gatgtagacc tggggcttcc cccaggctac agcctaacgg  21600
aggaagctat ggacaaagcc aagcgtcaag agagcgagta ttacgactgg aaggggtatg  21660
aagcactggc caatccagtg gtagagcacc cagagtaccg agccaagggt gaagcctttg  21720
ccctccgtgt cttctgggaa gagaagctca aagaatccca ggtcgtagaa gaggtagcgt  21780
gatgatagct ggtatcgatg gtgacgttct taggtatgag ctaggccacg tggctatgtc  21840
gaaggaacac atcttcgata tccaggtgga gaagccatgg cctgaggaag aggtccataa  21900
gctcgtcgat gataaagtcg aacaaattat caaaagggta aatgcagatg agtgtgaaat  21960
ctaccttact ggccaaggaa attttaggct ggagcttgcg aaaatcaagc aatataaggg  22020
tactcgaatc ggtcttgaaa agcctcatca ctgggaaacc gtgtcagcca gacttaagga  22080
caagtgggga gcaatcactt tccacggtat cgaggctgat gactggctcg ggattcgagg  22140
cactgaagag ggagctaact ttacagcgtg ttctagagac aaggatatcc gccaagtccc  22200
aggatgctac cattacagtt ggccctgtgg agattcccag ccggagttgg gaccgtttca  22260
agttgatggt cttggaaggg tctccgcttc ttggagaatg tatggcgtta agaagccgca  22320
gaaatcatgg aagcttgagg gcaacggtac ggcattcctc tacgggcaac tccttgttgg  22380
tgactccgtg gataacatac caggcctccc agggacggga ccaaagacag cggcagattt  22440
gcttggggag ctttctagtg agagagatct cttcgcagct tgcgcttacg cctaccaaca  22500
gaagtacgga gataattgga aagagtacct tctggagaat tttcgtctcc tctacctcat  22560
tcgggaccgc tcttggcttg atattcagca gtccggtaac gagtatcact gctcactgaa  22620
gaaacattgg gagattccct atgacgatga agaaatattc tattgatgaa gcacagagga  22680
tctgtgaagg tctctttgag atcctcgaag gtcttggctt cactgactac aaggtcgctg  22740
gtggtttcct tcgggatgca gacaacgggg ttgcacctaa ggatatcgac ctctatgtcc  22800
gtaggccata cgtggaggac cctactgata ctcgccgtag ccggttcggc ccacggttga  22860
tcccatgtga tgatgatacc ctagaggtag aggtcactcg gttctacaac aagctgggcc  22920
acaagaaggt ccggtgtagg actggagata agcctgatgg gtatcctgcg ggggtttgatg  22980
tgtgggaatc tattggtgtt gacctacccg tcaacctagt cgtgactact cactcccacc  23040
cagcagagtt cgatgtagga ctatgtgaga tcgcatgttg gcctttaaat cggctgggct  23100
tgaggtctca aatctaccgc acaaagtctt atgagtttga taaggaagag aagtgtatta  23160
ctcttaaccg agtcctagac cctcttctgg atcactctca gcccctaact gacaaccaag  23220
ttgaaaaggt tgtctcccat atccaacgta tcaaactgaa gtatccggag ttccgggtgt  23280
gcctagggga ttggatctgg cttctgattc ggtctaactc tatcctcact gagagtacac  23340
tgtcggttgt ccgtaagctt caagaaggag ggctcattgg caaagcaggg gagattcttc  23400
```

```
agaaccaaac tgaagtcatt gattgggacg aagtacgaca gcgaaaccga gaagatcgtc  23460
cacgagacga tgccttggat gcagttcaag ccggagccgg tgccatacgt catcaagcac  23520
aagtacaagc cggacttcaa ggtatcgaca ttacaaccct gtggatcgac gaagaaccta  23580
ttggtcgagg tcaaggggta cttccaggaa gcttcagagg catctaagta catctgggtg  23640
agggaagctc tccccccaga tactgaactt gtgtttatct tcgagcgccc taatacagct  23700
tgccattggc tttccaagcg taaagatggc acaaagcaat ccatggcgga atgggccgag  23760
cgtaacggct tccgctggtt tactctagag actttcaagg agtccttccc taatgagtaa  23820
gaagtataat gaagacactc tcgtcattgc ggacacccaa gttcgatccg aggtcaacat  23880
cgatcacctc gggaaccttg gggagtggat cgcacgtaac cgccccaagc gaattgttca  23940
tattggggac cattgggaca tgcccagtct gtcaagctac gaccgtggta ccgctaagat  24000
cgaaggccgt cgagtcctcg ctgacataca agctggtaat gatgcgatgc gagttctgct  24060
ggatcctctt cgccgcctac agcaacacca agcgggttgt aagaagcgta tctaccgacc  24120
agaaatgcac ttcttcatcg gaaaccacga ggagcgtatc aagcggtatg aaaactctaa  24180
ccctgctctc caaggtttta ttgggtacga tcattttgat ctgtccgatt ggattgtcca  24240
tgatttcctc gacgtgggtg ttatcgaagg tgtcgccttc gcccactact tctacaatcc  24300
caacagtggt cggccatacg gcgggagtgc cgagcatcgc ctcaataaga tcaagcgcag  24360
cttcgtccaa ggccatgagc agggattcaa gtaccacatc gaggcagtag gcaagaagcg  24420
aatccacgga ttggtagtcg gtagcttcta tacccacgat gaatcctaca agggtcctca  24480
gggtaacgac cattggcgag gcgtagccct cctccggaac cacaaggatg gagagtatga  24540
cctcaagctg atgagtgtgg aggagttcct gtgagtaagt tcttgccaga cctgtactat  24600
attaagtctg agcatgactt cggtcaacgg gggttggcgt ttaagacgcc gatctccgca  24660
gaactctggc tggatatgaa gtttgggaaa gggggtgctg aggaggggct taggcgaggg  24720
atgtattcca tcgaagtcct ggagatcctc tacatcccca gcgttcacct tccggatatc  24780
ttggggtaat ctatgaaaga ccgagtagga cgtaaactag aggtggggga caacgtagtc  24840
ttcctgatcc acaggaacac atcctcccac ctagccattg gtaccgtcga tgggtttacc  24900
cccaagatga ttcggatcaa atgcccgacc atgagttgga ctattgacgc tgagtatgtt  24960
ctcaggagca gtgacaaggt ggtgtactat gacaaaggct gaactggaga aagcacttga  25020
agaggcggag agcaatcttg cgaaggtcca agcggaactg gagcttgctt ctgataaagt  25080
ccgagagatt acggaagaat atctcttcct tagctcaatg ttggatatcg tagatcaaag  25140
gtcgaacgtc ttctataaag actggagggg ttatgcgtca agatcaagaa gttaagggtg  25200
gattcccttg gacctacatt gcggtggcag ccttgtttgc cctgctggtt tatgtaggat  25260
atagctgact gatgttactc ctgaccattg gagagatatc cagactcctc gttgaagtgt  25320
tatcttgggc aggttcctta tgaagtatcg agtgaagcaa gtggggaagt tcttcttccc  25380
tcagtataag caatggtttc gttggaggaa tttcgagcag agaaaacagg ggatggggat  25440
ccactgtgtc agctcgtatc tagagtccct tcctgtagtc ttcgagaacc tacaggatag  25500
ctgttgcttc atccgggacc acatggacag gatatccgaa gatactccta tctaccaccc  25560
cgtcgagtaa ccaaaaaaag gccccaaggg tgttatccca aggggcctta tctttagctc  25620
cggagagcgt tcagtagtgt attgaactta tccacgagtg cctcgtgagt atccgtatag  25680
gaagccacgg ggatctcaga tatcttatcc tggatggaag ccgcaatggc ttcatatagg  25740
```

```
ccactcactt cgctagcctt gggtttccag ttacctggtt tagcctcgct agccttagca  25800
cctacctcca gaagcttagg cttcccctca atatcctccc acttcactgg ctcaaaatct  25860
ttcgggccaa tgacttgtcg aagggtccca tcttcattac gtacagcaat agccttcgat  25920
tgaataacga atacactgtt gccgtcgttg tcagcgatat aacctgccat aatctaactc  25980
ctattaaact gccgatttga aggtacccac ggtaccaccg aaaggataca ctcggacagt  26040
gcattcccca aattgaccat cagtttccgt ctgattaccc ttagcatacc aagccttgtc  26100
cggagataca gcgaacttga tcttagctgt agacccttgg ataaagtgga agtgacaacc  26160
tggggttaca tctggaccaa gagtcacggt gatatccgtg gtcccttgag acatgaagaa  26220
ccaaccagac tgctgcttag tcagggtaat gttctgagta agctgctggg tgttgacgac  26280
attaccacca aggtgagtag tcacgaggcg gggatccagg tagttctgtt ggagagaacc  26340
aatgttcttc acaggaccac gcatgtcatc aaactgctcg ataatgtaat ccccgatggt  26400
accaccgttt tggtcatccg ggccaatcac gtgcttaata gccacgtaaa cacccaggtg  26460
ttcccgacga gggtctactc ggaattcact accgaatgca gtaccgcaag gtgcctcaat  26520
catggtctca gagaatagac caatcacgtg gccagggtca cggttaccac ccgaggtttc  26580
cccaggagcg cccacgaggg tgttgaccag gacagatggg ataacggcct ctgatggatt  26640
ctccgggaag gaggctgtaa cgttctctac taccagggct gcgttctcct taactgcata  26700
atagtcaggg aggaactctg tagcggtaac gatgttagta tttacccgac cggcatccga  26760
ggtaatctca atgagatcac catcggaatt acgtcggaag acttttggca catcaaccac  26820
gtaggcacgg ccaccaggac cagcggcatc agtttctaca taagttgcca tattacttct  26880
ccttaaagat ccagagcatc ttccatcgct tccataccgg caacgaaagg acgtgctgga  26940
gtttgcttat acaagaactt ccagatttca cctgcggatg ggtcatcccc aaacgaagcg  27000
atagttttac caacagccat agcaccctca gttgcagcac cagctactgg acccaatagt  27060
acctctgcgg gggtagtccc tcgacggtaa cccgtcagca tgtcgtagat catagaagcc  27120
tggagtggca tctgttgcat cactacgtcc atcatccgtt gttctggact acgggtatcc  27180
tctcggctag acccaccgaa cttagccagt tgacgaagct catcctggag ataccccaga  27240
ctcatcatca gaccaagagt gaaggctaca cctgcggcac ccataccagc gttggtccag  27300
gaaccagcga agtgtgggct cattcgtcta cggaacatcg gtaggatgat gttaccatag  27360
gctgctgggt aacccttcaa gagggagaac atctgaacgt ttccgttgct catccacata  27420
ggcttatcag cgaaggtggg atcgaggact acctgatcta caaaccgacg catggccaaa  27480
gtcttgacgt tgttagccat caggacttca gatggggtag ccggggagat caacttgagg  27540
gcatcctgct ggctaccgat gttaaccccc atttcccgaa gctgagcaac cttcagagca  27600
ccattggcag aactgaaggg gagacctgcg gctagatcca tcaggttgtt ctgatagacc  27660
ctcttggcag tctctgttgc aaagattcgg ttaacatggg ttaggatgga caagccgtta  27720
atgaggaact gaccacggat cgtcttttgg atagtagagt taaacacctc agcaccaacc  27780
cgatcagcca tcagagaggt agcagaggcc agggtgtggt tcatatcact cataaaccga  27840
ccggtctcag actttggaac cccactgtag atcctacggg ctgcttgtct tactacttca  27900
cccatggttg ggagtacagc cccaagggta ggcataaccc ccgccttagc gaagggtagg  27960
ctgaactcag ttagggtaga gaaccctgcg aggggtagtc gggagagcac gagggcacct  28020
gacgtaacag ccgccagctt cttaaggttg ggtctttga tacgaccgtg cataccattg  28080
taggcatcca ctaggtcata catccgatcc acttcttcct tggtaacccg cttaccagcc  28140
```

cgttgagcct cagctacagc agaagcaatc ttagcgttag ccttctctcc gttgatacca 28200
aaccgttcgg taaaggcaat ccggtgggaa gccccctcga agtaatctcg gatttcctgg 28260
agacgcttct taggagtatc attaagagaa tacttattga ggatctcttg ggaacggag 28320
ccaaaggccc gactctcttc cagctgacca tacttaggta ccgcatcact ttgggcaaac 28380
cgtccacgta gagtatctgg atcaccctgg atacggtaac gtgggtctac ttcccaagcc 28440
ccggtctgct ggttctgagt aaccaatcga ttaacctcag gggcagtgtt accacgagta 28500
tcatccgaga cttcagccag ccagttagct acagcatctt cagcagcttg tcggttctgg 28560
aagtaaggag tgatatcgtt caggaactct ggggattgaa ccttctcagg ggacagccca 28620
aagggcatat agttggggat agtcccaaca gacatgccac cacggttaac agcctcattc 28680
cttacgtcat ccatcaaaga acgtagacgg gtagcctcag gggtgttgac accagcggat 28740
gtatcagcga taatcctatc gatctctttg gaagacttac cctcaaagat gctatctagt 28800
tcagagttcc acttacctgc ctgtagttcc tggtcctcaa agatagtctt accagaggcc 28860
cgcttaccac tcatatcagc acggaaggtc tcagagaact cacgagcgat aggggaggcc 28920
ttagcgagtg gctctaggag cgacgtagct tcgtttccta gggcatccca agccttcttg 28980
accgtacccc taggttcaaa ctcagaagcc ttaggaggtg cctcaggggc gttaggatca 29040
accacggcag atccagcgga gtcctgatga cgacccaggg tgtccatccc cgaggataca 29100
gcaccaccgg cagtacccat agcggtacca gtgaatgcag cagtcaggag gttatccatg 29160
aactgctcag ggtttgtac ctgccctact gcatcatacg cgatagtgtc ctggaggacc 29220
tgctgggcac cagaggtaac accttcagcc acaccagaga ctacagcgtg tttaccagct 29280
tgggttacag cctcaatggc ggtctgctta ggtagtcccg attggaccaa catctggtaa 29340
gcgccatctt taccgatgtg cttgaggagt ggggcagcga taacaacagc acccgcagtg 29400
tctagtaccg agaggccagc accaccgagg actgcggtcc atgggttgct ttgatcgggg 29460
tctagttcct tcatctggtt actcagggca cctacgttga tacccatgga actcaggaag 29520
gaaccaatga gcgctccacc catacgacct ggggccccaa agacagagcc agccttagca 29580
cctgcggcac caccagcaag tacaggggcc atcgaaggga gagcctctac aatgttattc 29640
tttaggaacg aaccgatgga tgggatatct tggatatcag cgaaagaccg aacatcgggg 29700
gttccgtact gtgacgcttc ctgagcattc tcctcggcca tctgtgtgcc gtagtctttc 29760
aggtagtcac tgccagtcag ttcaccaagg gtagcaatag taccaccgat gttagactgc 29820
atggtatcaa ccccacgacc aatcgcagag ctaatagaat tagggtcagc cggagttact 29880
agggcactca ggtctggggc aggctcaggg gtagtaggga ctacttcctg ggtgcctct 29940
tcgataacct ctggctcatt caaggaagcc aattcagcgg ctacgtcgag gcccttgacc 30000
tcagccagtt ccgcatcaat agcggccttc agttctggag aaagagccat aagtcacctt 30060
ctagttgctg gaaagagaat aggctcttaa gatgtatctt aggatactaa ccttcttagt 30120
aagtaagtca aaaggaagaa ggaatcttaa gagcctatag gtctattata ctacatttca 30180
aaccaattac ccgtaggttg aagcttagca gcctcccgct ggataatacc cactgggtta 30240
gccccaggat tagcccgaag ttcatttcgg acagtctggg caatagcatg ttggcagtc 30300
ttactcagct tcttaccacc cagagcctga gaaccgttga cttcactcag gataccaagg 30360
gcgtccttag tagtaacagc ttcacctcgg gctgccttag ctgccgcttg acgtgcctga 30420
gcgctgatct tagcagtttt gaggcgtaca gcagaactaa gctgggcatt ctcttgagac 30480

```
atatcctggc cacgtcgagt agtttcagcc tgtagctggg cccgttggtt agccaggtct  30540
tggccacgtc gggtcaactc cagattagcc ctatctacag cagcctggtt gacccactta  30600
tcaaggacgc cctcagtctt acgcttggtt tgctcaagga tcccttcctt aactttcagg  30660
ttgccctccc caaggagtac atcagcagca tccttagcca ccttacgctc cagatccttt  30720
tccttgatct gacgatcagc agctgcggca gccatcttct gctggttgat cccagcctgt  30780
aggttacgat ccagttgacg ctcataggaa gcagcgaaca tatccccggc tttaccagtc  30840
ttgtctaggg ccgaagccag aagaccagta ccaatgagag cgtaagatac ataacgagac  30900
aggtcatcat tatccatagt cctcatctgg gtcaactctt cgttcacccg gttcttaagc  30960
tcttggggtt taagctctac accttctcgc tgggcatcag cctcaactac agcttgggcc  31020
atttcaggac gacttacagc accagtacga agaccctcgg ctgcaccctg ttggatgacc  31080
tggcgattag cctcctcctc atctgctaca gcagcaccag cctcggaagc cacctctggg  31140
gtgatctcag gctcgataga gggttggtta ggggttaccc cataggacaa cagaccggcc  31200
cccgtagggc ctcctgtggc gttctgggct gcacgttggc ctacaccctg ggcccattgg  31260
tttgcctctt gagcaacctc gggacccatg ttctcaaccg cttgactagc ctgagccatt  31320
tcttcagcac gagtacgctc tgcatccccg agttctcctg ggttacagc ggcttgtaca  31380
cctacagaga taggaccacc gaggatacct gcgatacgac ccaaggcacc gcgaccagta  31440
gcttcagccg caggtgcaac ctcttgggct gcacgggacc aacgctctgg gttctccagg  31500
gctgcctgag cagcacgacg gacacgatca ggaatacctg agccctctac agccagcggc  31560
agtttgttcc ttgcgattcg cgccatatcc agttcattct gagcagcccg gaggatgcta  31620
gggcgaattg gggacccttc ataagccatg ctggccatag gattaacctc caaatagttt  31680
acttaggatt ccagactttg gctgctgtcc gaaaccgagt tcttctgcgc taggaaggat  31740
tcccactccc gctcccatgc ctgctgcaac ttccgctgcg cctcgttcgc ttgctcctct  31800
agccccctcg acagaaaagc ttggtactgt ttctgaagaa ggctcacttc cttgcccgag  31860
gagagccgcg agtgctgctc cgcccattgc gccaaaaggg tttgattgtc cactagactc  31920
tcccgattgc attgtcccaa ggtgggtggg gcggtaggaa ccttgacggc tcaactgtac  31980
ccgctcctgc ccaccaccta tattctgtcc tatagcgaac agcttctgag gaagggaggc  32040
cattagaaca gaaggccccc taccctacca cctgcgttca taccaacaga agcacccgct  32100
gggccaccga agagagcacc caaggaagca ccaccgagag cacccagggc agacccgagg  32160
ccaccaccac cgccaccacc cgaagaagta gtgacattgg ttccccccat atcgccggag  32220
ataagctcct tataggcgag gaggtcgttg aggctgacgt tattctcata ggcccacttc  32280
tgtagagccc cgttgatttc ctgctgctcc tggttctgaa gcatgctacc agcatctacc  32340
tgcatggcat taccagagcc gaggccctta gcaatagccg acaggttacc cagggtattc  32400
aacctattct ggttgtaagc ctgctggtct tggaaagcca actgggaagc gttattctgt  32460
tgattctgaa gcagcctagc ggtagcaata ccctcggcta cacccgctcg ggaactgcca  32520
tactggccag cattagtcgc tcctgcacgc aggtctgggc gtaccgtagt gtcgaagtcc  32580
cattgcatct gctcgttggc tgcaccaatg gcgttcgcca agccagtttt attgggatcg  32640
taaggaccaa ggtaatcagc cagagagcta acacctgagc tacccaggag agactgaagg  32700
gcacccccga gaccacccag cccttcgatg ccactaagct ggagagcatt ttggtcagcc  32760
accgggtcaa agttcggatc gcccccgtaa ttggggtcaa agccccccgtt atgtagccaa  32820
tcactggcac ccgagagtag ttcattatag ttaccttgct gatagggtgt agagacagag  32880
```

```
gtggtctttt gcttcttact accacccttg taagcccgag aatctagggc atcctctaca  32940
tcgaacccca tcagacgctt tacgttaaat tggaggaagt tcatctggag ttacctcacg  33000
atagaaggaa acggagtctt cggtgtaccc gagtttctca agggtaggct tccagccccg  33060
acgaccttca cattggataa accgacagtt aactcgttgg gcgaactgtc cgaggaagtc  33120
gtctacctcc gagtaatcta ccggggtttc attcccaggc atcttaccac tccagaagaa  33180
gtgaaggatg ttgcccaagg gggcctggga tacttggatg actcccgcgt acccactctc  33240
ttcctggtag aagacatagg cctcataatt aaccagggaa tgcaccaagt gctcaaagtc  33300
ccagaactta cccaagtcag tcctgttaaa agcacgggct agggctggaa ctacggtcgg  33360
gagggagtct atattctcac gagtaatcaa atgaatcatg gagtcaccac caggggggaat  33420
gtgaatgtac ccccgaagac tgctccttgg ggaattcctt ggattagaac acggccatta  33480
gctgtgatct taaacattgc ttggttaacc acaccagtct gaatagtagc cctgttgaga  33540
acatcaaaga cttgatccaa cggaggtgcg ttagggtcag acggaggtgg ataagtaata  33600
gtgctctgcg ctgggatgat gctggaatag gccgggataa acaactcagc aggaggccaa  33660
tacgcctggg gaagatccag gacagtagct ccattagtgt agttaccacc agacatgagc  33720
atggttatcc atacttcatc cttagcagtg ttcatcctat aggcacaggt acccatcggc  33780
tgatggttgt tctgtggggt aaataggata aaaccccccg gcaggtcctt gggtttagta  33840
cctgcgagtc tccattggtt atccaagtcg taatgataga tgccggatac tggacctacc  33900
actccggggg caaaatactt tacagtccct ggcttgagct tcttaggggg ctccatagag  33960
acccccccagt agccgtcagc taggtcattc agagtctgtc caaccctaac gaattcttca  34020
ttaaggaagg gcagcagttc ctcctcttcc tgtggtggaa tcgaagggct gtacttttga  34080
ctcatcgcat acctgccttc ggggccattt caatagtgta tccgttgaag taccaatctc  34140
cctccgaaga gaagtcgaac ttcaaggcta tataccggcc cacatgttta gtgtcaatct  34200
tatagtcctg gccaatccgg tatgggtagg ggcccttcca ccgaatacca gaaccttgta  34260
cctgagcatt accaacccag atgttgcagg tgccgttacc cgtgatatgc gggatgatag  34320
cactcacagt cttcatcatt cggtcatccc caagatagat atcggatctc tcaagggtac  34380
tgacgaagtt ctgcccagag aatgtagagt tattaccgaa gaggaacaac ttcttatcct  34440
ggaaagacga gaagatcata ctggactttg ctgggttata agagccttca ccccagaccg  34500
aagtatcggt atcccagggg ttggggtcgt catcccagag gttagacacc ttaggatcga  34560
tgatcccgta ggctccactg agaacgttgg gaaggtctcg gatactccaa gtgttttcct  34620
tccagttcca gatgatagcc ctgtcgcagt gcttacctgg ctcagaccta gtggaagagt  34680
agcataccca catttcagta ttcacgtggt ctgcaagtac gaatgtccgt tgatagttgt  34740
cagggttaat atccgagaag aagaacttac ggacctgggc atcaataaca gactgcttct  34800
gaacaccatt gtggacatat acatcaccgt gacctactac aaagtggtta ccatcgaact  34860
ctactgcaca gttgggccca aggataccta cgtcgttaaa cagctgctgg aactggaaga  34920
tgaacaatcc accgatatac cgcatggagt atacagagtc ttccttgtag atgatgaaag  34980
agtcacgaag cttcacacca tccacgatag caccattggt atcagccaag gtgttctgac  35040
cagcatcttt agtggggtcc gttgggtccc aagatgcagg tacaccacca gcatcagccg  35100
aggtactcca ccagaccatc tgtggcattt ctacagagtt acttgtagcg tttaagccaa  35160
ccaggaagtt cttaaaagac ttaagcctct taaaagtagt attcgctggg aagttaggaa  35220
```

gtaccctaaa ggttgattct gacggtggaa gatgatgagg ggggttaacc ccatcgttag 35280
caaagattac cccgttgaac gaccctacag accacctgtt agttatacta gcagcgtaag 35340
gtcctgggga tacatcgatg attgtagtcc cgtcggctag atacaacctt tgttcagaac 35400
acaggagcca ataggggatg ttattccgga tgaaaggaaa catatccaag attggggcct 35460
gggctgtatc aaagataggc gtatggccca gagccttctg agccttgccg ttcttaaacc 35520
ggacgttgtt cccgaaggac catttctcca gtggcaggtc agcgggggcg atatcggtca 35580
caatccccgt agggttcttg acctcttgtc tctctagggc cattgtatac ctcagttctt 35640
aatgatgaag aacacagaac agaacggtgg gatattaccc aacggcatgt tgatctttac 35700
tgcatggttg tgagtctgac cttgaccagc agggccagtc tcaaggttgg tattggctgc 35760
gttaccagag ccacccgtca gagcacccga gtcacccgca gaaccaacca atgcagcagc 35820
acctctggtt ctccaagtgt gggtgtgtga tgggatctgg gctagggtaa gagcagtacc 35880
ttcagtgaat ccatcccata caatgttagc gctaccacct ctagtcccta cagcctggga 35940
agaaccatcg ataccccaag ggaatgcacc aatcaggtta gggacgggaa tcccgttaga 36000
ggtagtacct accccattgc acaacttcca acctgctggg atctgagcta gtgacccagc 36060
ccacatgata accatcccag gtttaacata ctgggttgta tcagcgactg cgtttagctg 36120
ggctgccgtt acagtgacag cctgagaaat attggggaag gtgttcttaa tagcactctt 36180
aatgagacgc aggtggtcat ccccaaagga tttcagatca gagccggtag ggttcgtagg 36240
caccaactgg ttaatgtaag ttgcgacctc aagacccatt cttggcctcc tttatctctt 36300
ctttcatttc ttttcgggtg acataccgct ccccaaagat tgccatagaa atctggagat 36360
cgctcaccgc ttgggtgagc ttctccgtgg cctggatgtt tctttcaagc agagcctgat 36420
taacattctg accgacaacc gaggaaccta ccgtcactac cgaggatacg accagggcac 36480
tgacgatgct gcccaggtta tcagttagaa gttgcatcct ccgtcttctc cttaaggttg 36540
tcttccagga cttttacgaa ctcgtcgtca accttagagt tagtcttctc cgccagagcc 36600
ttagcaccag tcacgatgga cttagcgatt accttggttg ggaagagggt agccagaagg 36660
ttgattgcga gggtttttag aaagataggc atctgaatct ccttaacgtt caatgtcttt 36720
gatcgccagt cgagtgctag cgaagtcagc ggcattctcc tcgttctgga gttccataac 36780
agcccgttcg agtttctgac cccagaactg ggaccgagct tcatccatgg tgtacagata 36840
aatctgctca aggacaccat agagataaat ctgcggatac ttcgtcagag cccaagtcgt 36900
tgggttagcg aggcttagct ctgggagtac agtccagtag ttcacaatga acggggcacc 36960
gtcaggaaca acggggaata ctcgccagaa gttacccaac cgagtgtagt aggttacacc 37020
ctgaggttgg tagttgtagt taacataatg ggtgaaggta tcctgggtga tgtactgaag 37080
agtacgtcca ccgataaggg agtcacccgt gatagatcgt agagcaacaa agtgctcagg 37140
tatctcaatg ccaccaccga aggccattag ggtttcgaag tgttcgttct ccctcacccg 37200
tagcaatcgg ttaagacggt cagtggtatt accaatgaac aacatcagaa gttcttgggt 37260
aagatcctga cggtcagacc actggatagc ggcaatagcg agatcagtta cgttgttgat 37320
cgtagccatt cattacaccc gtgcctcaga ggtccgcatc cgatagttat ctcggtcatt 37380
aagccaacgg gtaaatcgtg cggcatggtc tgggtcacaa ccgatcaggt taagatcgat 37440
gggaccacct tcagacatgg ggcgattccg tagggcctct acaacaacca gggggatact 37500
tgctaccttg cgcatattat ccttgcggtt gctattgaca cccgagtggc gctcttcggc 37560
gttagcggac aggattgact caacatcttg agtatccttt cggataaaga gcccaaggtc 37620

```
ttcgtcaatt gcataagtcg attggatact catgatgtac ctcctaaggg gaaacaaagg  37680
gccccgaagg gccccgttgg gttagacctg ggctacaacg tcgcggatca gagcaccgga  37740
cttctcgttg tttacacgca gggtgtactc aaccagcagt tggcgcttct cgctgtcacc  37800
ggtcttagcc agttcatgct ggaagaacgg acgcaggtag cagagggcgt gcatcttcgg  37860
atcaaagatg aacatggtgt tttcgtggaa ccagcggttg gcacgaatgg tgtacttacc  37920
gaagtcactc tcgtagacgt ccacggtctg cgcaatgcgg ttgtccgagg catccagggt  37980
gatctcagtt gcacgaccct tcatgttctt gctgatggcc ttcttgatcg agctcgaagt  38040
ctggatcgag ttagcctgac caccgttgcg ccagatggcc tcagaggcat tcaggagcat  38100
gtcttcggtc agaagacgga ggtcaccagc ggtaccagtg tcggaaccat caccagttgg  38160
cagggtaccg ttagcaccta ccgaaccgtt ggtcttgtag taggcaaaga tgtttgccat  38220
ctgacccgga gtagtggtgt tacgctggat cttagcctga ggggcaccga ccatggcgta  38280
ttccatgtcc agcttcagtt ccttcgactt cttagccagc tgatacgcca gttcgttctt  38340
acgaccagcc ttcttgacct tatctgcggt accggtgact tgcagggtct cgtccgagat  38400
ttggcagtag ttgttcaaca tggtggtgaa gctaccagcc ttgatggttg catcctcacc  38460
ttccactcgg gtgttcttac ccggctggcg gagttcatca gtctgccact cgtgggtgat  38520
agcggtagct acgcccttgc cgatagcagt catgaacggg gtgtcatagg gtgcgatgtt  38580
gtagatgata tcgataaggt cttcgcgctt accgttgatc tctacagtgg agacggcatt  38640
agttggagtt gccatataat gtacttcctt ctattagaaa atgtcgagag aggagaagag  38700
agcagcagcg gcttcaaccg actggtcttt cctcagatta gcgcgggcag ctttaacccg  38760
cttagaaccc tctgaggctt ccgccctacg agcagcaggc ttaactgcgg caggtagttc  38820
agtctcctcc ttcttctcta gggcagcctt gcgacggacc tgagattcag cccacttacg  38880
tgctgcatcg agtacagcca gttggcgggc atcagatatc cctcggatct catcctcgga  38940
gtatccaatc gatttgccgt aggacacaat cttgtcaccc caagactcat ccgtggtcat  39000
ttccgggata agtttcttgg ctagctctgt ctgacgctta acgtaggcag agtggacaat  39060
ctcggctcgc ttctcttgca tagccttaat gtcgttacga cgtttgataa gagcctgggc  39120
tcggtctcgg gcttccaggg cttccagtcg aagggtttga tacttctctg ggtcctgggc  39180
cttaagctgc tcccagttta cattgtcata ctgattagca ccagcaatag cggtaacagc  39240
atactgctca agctcggcca gtagattaga gcgttcagca tcaagctctt cgaatttagc  39300
tgcatactga tcctctagtt cagcttgtcg agttacaaac tcttcattgc gaaggtagcc  39360
actcttaagc tcttcgaagt taacctcgta gacttcatcc ccaatcggga tctcaaagag  39420
tttatcctca ggatcttcct cggactcaac ctcgggatct tcctcagaac cctcttcttc  39480
ctcctcggac tcaacctctt cggtgtcctc tggagtacct tcgtctacta cctcttcctc  39540
ctcttcttcc cctacgactt taccatccac ggtttcatca ccgggggcca ggaggtcatc  39600
acctagcaaa tctccgaagg cttccgctgc ctcgaattca tccatgcctt gattctcaag  39660
gtccattact tatactcctt tagagtgatc gaatccagga tagcctgaat acgaagttgt  39720
acgcggttga gggcatgtag ttcgtggtag atggcctccc tggactctga atccttaggt  39780
gccgtggact tccactctcc ctcgatctct tcttggacaa tacggaaaag ctcaggaaga  39840
acgttctcac gtaccatctg ttgtgccgca tcagtcagca ctagactata gccaaaacgt  39900
tctcccaaga ttaattcctc actgccttag atggcttctt agtctcaggt accttaccgt  39960
```

-continued

```
ctccgatata agcagcccga gcctgagtag cctcaagatg atactccgct tcgttacgag  40020
cccgttccca agtgaaacga tcacgctcaa gttgtagttc cgcttcctta agggccattt  40080
ctctctgctg aaggacagcc tcttgcttct tcagttcgat ctcagccagt cggatctgag  40140
cctctacctg cttcatctgg gcctccgctt gcttagccat agcgtccgat tgggcacgtt  40200
gggcatcagc ttgggctttg atatcttcag gcttaggttg tgcttccttc tgctctctaa  40260
tggccttagc ccgttgagct tcaggagaat ccgggttagt ccagaagcga tccgggtctt  40320
tgtacccagc gttctctgtg acttccttaa ggatgttgta aagattctgc tcagagacaa  40380
ggaccccgag acctccaccc ccgactacag cctgggccat ttcccagata cgcatcaggt  40440
ggagcatctg ctggtctttg ttcatgttgc caataccaac ggtaaccgtc aggtcggatc  40500
tctctcgcca gttggcaggg ttaatagcaa cccacttgcc tcgtagctgg aagacctctt  40560
cctgattctg gtacttgatg gcatggtcat gcagaagttg gaacaaacgc ttaacaccag  40620
tctctgcaaa catccgggca atcaggtcaa tctgttgctc agcagcagtc atcaactggt  40680
ttacactcat agccgcttgg ttagagtgca gggtgttttg gtctagacct cgggtacggt  40740
cagtgatacc tgtccgctta cctctgtctg cctctagtcg atccagcatc ccatagactt  40800
ccccagacaa ctgaggggtc tccagaggca tgatagagtt catggcctta acccgaacga  40860
tacccgctgc ctcgttggtc agcaagtctt cgaggttaac ctggccatcc aggactacag  40920
agcgcccttg gttggtccgg tagatgttat ccatgatgtt ccgcatgagt accgaacgga  40980
tctcttgaat gtctcggatc ttatcgtaga cactcatccc gtggaactta tgggcaattc  41040
gataggcatt caggtcagcg aagggacggc aatcccaagg ctcgttgctg atgatgtagt  41100
cgcccacgta caggatacgg cgcaactcag agataccatc cccatctacg tccagaaggg  41160
tgtagcactc agaggcccat acctcacggt tggcttcagc gtcatcccca gagttatact  41220
ggagttggcc agtcatatcg aagttatcac gtaccaacct ttctggctga ctatcagaga  41280
actcatactc atcgtatgga agctcatcta gtacatcctc gggaacaccc aagagccgaa  41340
ggtcacttac ggtatacttc tcacggtgac agaggaagcg tgcatcatca atgcaggtag  41400
ccaaccgatc aaccaggaag ttctcaggct tgatacaggt gactttaatc tctcgcttct  41460
tcttgtcctt gcgaatttta atactgtagg ttccatcctc gtccacactc tgtgctagaa  41520
tctcagtgtc tggatcagcc aggatatccg ctaccatttc ctcagagaga ccagagaatc  41580
gttcgaaggt agggttcagg acctcttcta catagacctt tacaacaccg gtcttcatca  41640
tcagagtgtc ttggaaccag tcgaacatta ccttgaaccc ctcgttctta cgcatgaaga  41700
ggtagttcac atactcagtc tcttgctctg cctgttcaac atcttcggca gtctgaggtt  41760
catacttaac tacttgaccg cctgacgtga ataccttcat aagagaaggc ataatccagt  41820
ctacagtctc ttgaacgtcc ctagatacaa tcgcggactt cccagggcgc tcgttaccga  41880
agggctctcc gaagtaatac ttcagggcct cagaacgctg cttggaaagt tccgaagagt  41940
tgaaatcaag ggcgtcgtta acaagttggt ctagatgacg aagtacctgt tcatcatcca  42000
taggcttaat cttgcgacga cgcttagcca ttagacaata ctcccaaacc aatcaggggt  42060
caactttgca gtatcactcc tgtagtatcc actgtttcgt acagcaccag gacgtgcatg  42120
ccgggaagcc atcaacaggg cataccgggt agcggagatc atatcgtcgt ttctgtcgat  42180
aatctttccg tcctttcggt ggtacatttt catttctttt aggaagttcg tacacgtatt  42240
aaacaccttc agatcaccat tctccatacg ggtcaacatc cagttaacgc cgaactctac  42300
agagttaccc ccgtgtttac catcaggacc tggtgggttg ctgaagggct catacactac  42360
```

```
attgaggttg tggtcatctt taagaaggtc tacgaatcta cgaccagagg ttgctccatc  42420
gtgcttaaag gcatcgtggg ggacaactac cgggatctgg tgaccaccct tcaagtagat  42480
agcatcagcg tgcatcccaa gggtctcacc actctcactc ctctcatcat agaggtaata  42540
cttgtctttc tcagggtccc aagcaacaca ggcgatagcg ttagggtggt caaacccgag  42600
gtcgataccg atgatcctgt ggaagtggtc agggatctgg aaaggctcac atacaaactt  42660
ctcttccaga atggggaaga ctacaccaga tccgagcata ggaacaccct cggccctcat  42720
cctgcgttct gctggagagt ataccgagag tagctgctct ttaacttctg gactgaggtg  42780
tggagcgtct tcccagcttg catggacaag gaactgacca ggtttaagat cctggaggaa  42840
gtccttgacg atctccgtca gaccatgctc tggggtaaac gtcagatata caataccccc  42900
agtagtagcc gttcgggtta cacactgggt ataaatatcc ttggggcatt cctcatcgag  42960
ccagatgacg tcgatggcag tacccatgaa tttgtcctgg gacatttcgt aggacttgaa  43020
gataagggac gagaggcccc cggaggcatg cttaacaact actgcttgca cacatccggg  43080
tttaccttcc ctacgaatcg tctctacgat atcttccttg ggatcatcc ccgttccaaa  43140
agcctcaggg ttcttccagt cacctagtag ttcggactga agaatatccc gagtggtatc  43200
cgtggagatc cccgccgccc agcagttcac tggacgatca tactttctac cagtccacca  43260
ctcagggtag cgaccggtga ggtggcaggc catgataaag gccccggtgt aggttttacc  43320
acagcggtta ccagtcatag ccagcaactg ggcgcagttc gaggaagctg cgataaactt  43380
ctcttgccac ccataaggag tatactggtt catgcggaaa tacttctgcc gctccgccaa  43440
ctccctgact agattccgta gccgctcttg ggtatccatt agaccacctt gtcacctact  43500
gttgatgcac gccacagggc tcgttggaag tcccttacgc gtaccggagt ttgtttggcc  43560
cagaggctat cctctgcctc ccatgcagct tcatcaaacc ttccggattt cagaagattc  43620
cacgtcttgg ggaacttctt cgtccacgct gtacccagct ggaaattgac gctaacgagg  43680
gcatcgaata gctctggagt gcaaaaaggc agctgagata cttgcccttg ggctgcatca  43740
taggctgcct tactatcgtt ctctagccaa gtctctgctc gggccagggt aatcggtccg  43800
tcctcaccag ggagttgcaa gtgtccataa cccccggtca ttttcccaag ggagtctttg  43860
taccacttta gaaccaatcc ctcccttcgc ttgattagat caaggtactt aagaggctgg  43920
gaaagaaatg actttagcca actctggctc ttcgtcgaga attcgtcgaa cttcactgat  43980
tagatcctct gcggacatat cttccacatt cttagtagta agctccagtt tctgcttagc  44040
tccgaagcct ccacggtcca ggatatcctg ggctgccttg aggcgaatcc cacctttctc  44100
ttctgggttg ctagcaatct ctacaaccac acgaagcgcc atggggacat gactcccgat  44160
gcgctcagag ataaaggcgt tgatatattc ggcatgcttt cgatggtatg cagcaacgtt  44220
gcgttgagcg tgattaggag agaacccagc ggctatatac gcttgggttt tattcatacc  44280
atctgccaga gcctcacaat agaggtctag cttttcttta gcagaaagag gagcagcccc  44340
aatcgagaca atcttttcgt ctgacataca ctgctccgat ctctctaaat ggtcaccccg  44400
gtaggactcg aacctacgac ctcctgtgtc caagacaggc actctaacca actgagctac  44460
gaggagttaa tggcgaccca tgtcggattc gaaccgacgg cttctcccta gacaggggag  44520
cactctaacc gctgagttaa tgggccataa tggttgggac ggtagggctc gaacctacga  44580
cctgagagtt atcggctccc tgctctacca actgagctac atcccaatta attctaaagc  44640
acccttaagg ttaatttctc aaccttataa tactattata tcacactttt tctattttgt  44700
```

```
caagcccctt ttcatctttt tttattttta gtcgcaagac ccggatttgt taggggtttt  44760

gctggaattg gaaaggggtt cttaagacta tcttaagata accttaaggt aactaacctt  44820

cttagtaagt aagtcaaaag gaagaaggaa tcttaagagc ctataggtct attatactac  44880

attt                                                               44884
```

<210> SEQ ID NO 5
<211> LENGTH: 45010
<212> TYPE: DNA
<213> ORGANISM: Bacteriophage P1800

<400> SEQUENCE: 5

```
cccctagccc ctccctagga taccatggga ttagtccggg ggtcaacccc ttgagatacc     60

gttcatcggg tggaccctag ggtattcata agaaaaatct tagggtattc agggggtgga    120

tcggggggaa tatccattga taaccccttg atcccctatt gacttccgtt gataccctat    180

gttaatcaaa gactgtctat atccgggggt ttgctggggg actgatagtc cataggctgt    240

atgaaaaacc agtagacaac cccgtaaaga atatggcgta atggcgccgc cttgagggaa    300

accgataggc aacgggggaa accccagggg cttgacaaac cccgcggaac cgggtctaat    360

ggcccccacg ttctacctag gccaccatcc cccttgccgc agtgctatcc gggggctgcc    420

aaccagggaa gagcgcccaa gtcgcccaag tgtaaagccg gcaggtatcg gggttgaca     480

agggatcggt gaagcggtat agttcgcccc acgtcaacgg cataacgtgc atgactccct    540

cgggattagc gtagccttga caagcaagac tgatggccac tcagcaaaag agcctatgcc    600

agagaactgg acgaactaac cccgtcaga gggttgacaa ggcaagccca agcctctaac     660

atgggcaccc atcaggtgac ggccacctgg ggaaagtgta ccttcgacgg tccttggact    720

gaacaaggga gaaacccgaa agctgaggga ataacgcaca ctccgaaaga gcgtaggtcc    780

tggccttgta ccatagaagg tccgactggt agcctgtccc agcgcaatca attgacagac    840

cccgtggttc aagcgcgacg gggagtatga tgggttagtg tcgaaggctt agcgcagagg    900

gcgaagcttg gtagatacgg cgaaggtagg ggcgagtgga tacgaagacc cccgaggata    960

accgaggaca gaccataacg acgacactaa cgcggaaagg ggccggctac gccaatgcca   1020

aggtttgccg ataaacccct ttgtcgtatc gggatgtgtg tcccggctga tgattcctaa   1080

aggatgaaac gaccatgact caggctcttg acaaaaagct gcgtcgcaag gccaaccgca   1140

aggccaaggc tttgggttac aaccttggga atctggggaa ggcccaacag cgtagtgagc   1200

agaagtttgg gattattgca agttgtaaca agatcctcga cgacaagacc acttcgttgc   1260

aagaaaaggc aggggcgcgt aaacgcaagg ctcttatgag taccgactgg cgtaaccgtg   1320

aggttactaa ccttcggaac tggtataagc cgagcaagtg cggtaactct gccgtcatca   1380

ctgtcgaagt aaacaactga ggtaattaca atgagcgact acaagcgcat caacgggatc   1440

atcaagacca ttgccaaccg gggtgctgcc ctggacaagc tggttcaaac cactggcatg   1500

gatatcctca agcacatcga cgagcatggc gaggtgtcct tggcctgcaa gctgttcaac   1560

gcgatgcctc aaggctcccg ccggctggcc ctggcccact ggttcatcga caacggcaag   1620

atcgaggcca ataccgacaa ggaaaaggcc aaggaattcc cgttcgtctt cgccaaggac   1680

aaggccactc gtctggagcg tgccgcagag aaaccctggt tcaagtacaa gaaagagcgt   1740

gacgtggccg acgagttctc cctcgatcaa gccatcgccg ccttcaaggc caagatccag   1800

cgtgccatcg acaagggcca gctccaggca gcggacgagc gtatcgccgt gatccagcga   1860

ctggaagtca aggacgaagc gaaggcagcg taacgccggg tgcgccaggg gtgtgtacta   1920
```

```
tgacgcgccc ctggtctatc cctagagtgc atggtaggtc cgtgcattgt agcgatagac   1980
catcaggagg tttccgtggg ttactgtatc tttgggcagg ttcattccat ccaaggccag   2040
gattatgttt ctggtttctg cgatgcaagg gtaggtttcg acgctggtat tgtgtaccgt   2100
tggacattca aggacggtaa atttgcctgc ggtgtctact ccctggatgg tatccgtctg   2160
aacatctgcg ggtggatcaa atgaagtcac cctacgaagc ggcccatgaa cgtgcccaaa   2220
tgattaaccg tctcaagaaa ctcactagga tgatccgggt gcatcccgat ccccggtgga   2280
ttgttgagcg tcaggaactc ataaggaaac taagcaagtg acaatcgcta tcattgtatc   2340
cagcattggt atcgcctact tcttctttcg tgattggaaa gaggaaatgg gtatctaacc   2400
ccaactgatg aggccaaggt gattcctggc cgaaaccccc accggaccta tggtcgcagg   2460
ctggggcgtc ttgggaaatc aactaaggaa accatcccgt gaagcgcaac gactaccgaa   2520
aggtgaatcg gaacatgcaa gccatcgagg ccatcgaccg caagattgcc aaggctgtcc   2580
gtgagttgac taactccgga ggaaaccacg ttggtaaaac cctggagctg aatcggctgc   2640
gggctaagcg tgcatcgctg gccaaggtaa gggcacggtg agtacatgga agtctattgt   2700
atgtgccgcc atacgctcac gttccaatgg gttgctgctg gtaacgtggg tggttctctt   2760
cgtcctgtcc tcgatcttgg acagcatccc ttttgcatcg tgaggtagtc ccatggatat   2820
caaggtgtgg ccccgcaacg gcgtaaccct cagttctctg gttaagtccc aaacctttct   2880
catcaatggg gatgtgtaca tggtctgcga actccgaagc atcaagatga agagtgaatc   2940
tgacgaggtt cccgttctca atctcaagac tggcaacgtc atttacatgc ctccgttgag   3000
cctggtatac ccagtaactg ccgagctgaa ttgctacgag gtgtaacatg aaactccaat   3060
acaacatgat taccagtaag atcaaggttg tgatgtggaa tgaccttgag ccgggttgcc   3120
tgtacatctt cgcagaggat gacgggaaga agaaccccaa agtcttccag tacctggagc   3180
ttaatgatga attcttcatc tgcgaaatct tcggcggacc tgagggcgat gtattcttca   3240
gcagcgatgt tgactgcggg ttcttcccgg tgactgtcaa gtacgcagag atcgaagtcc   3300
atcggttcgg cctaccggac tgagggtgtg tactatgacg cccgcccaat acatctacct   3360
ctggttggta tccaaggttg tcatccgtcg ataccagcct aaccccaaac tgtaccccaa   3420
ctggtccgtt actcatatcc gtgtgtcgat cttcggcaaa cgtgcaggta tcgtctatga   3480
aatccactga accccaagtc tattggctgg ctagcgccga tggtgaattc cacctcaagg   3540
tcatcaactt cggccagttc atcaccgaaa ccctttacga actcggcatt ccggtggacc   3600
acaaggttca tcgggtccac tgaggtgcaa ccatgtcaaa caccaccttc actgtagcag   3660
caacccgccc ccggaacgac cttcacatca gtaagcgggc ggatggggtt tatgtgaacc   3720
ctaaaaactc tggcgatatt gtcttcctca aggaaggtaa taaggttgtc gtcctcagcc   3780
agagcgggtt cagcatcctc gaagcccaga ccatgcccaa catcggggaa ctctgcccgg   3840
ctaaggaggt ccatgtatcc gccagggtat gggggccgta tgaagaataa acccatgatc   3900
ggccagataa tggcccagga gcgccgcatg aagcgtcgtg tagaaaagcg gggggttcaac   3960
atgagcctcc aggaaagccc ccaggagccc cgtggtgagc ttggtttcac cctggctgcc   4020
gtaggtatgg agtccagccg atcggcttac ctgcgtcacg ccagggaggc tatgatccaa   4080
tccggggagc cttgccccca ttgcatgcca gtcttcggtc ccaaagaggg tcgttgctgc   4140
aactgcgcga gggactggtg atggatctcg gtaatctttg gtgtctcttg ggtgtccatc   4200
ggtacaagat acttgatggt ggaccctacg agattcgtca caagggtcgg ctagtggaac   4260
```

```
tctgccacta ttacgacctg aggtgtgatc gctgcggtga cgtacatcgg aaggtggtcc   4320
gcagcaaatg atgacatacc tcctgataat cccagcgatc ctgatctata tggctttatc   4380
tttgctcgtg gctggcatcg ccgggttggc ggcaaattgc gatgagcatg gaaggatgag   4440
ccagaaggat caggacattt caatcatcct cggtatcctg tggccagtgt cactaccttg   4500
gatgtgcttc tcggttgtta tctggaaacc tttggctacc accatccgtg cggccaaacg   4560
actaatcaaa ggagattact aatgcaccgc agagactttc cctcctgctg taccgcaaaa   4620
atctacatcg gcatgggacc ctcgggtacc gctgaccatt acgccggcct cgcatccaac   4680
gggttcagcc cccgtggttt cgccaaggaa ctgatcggcg ccatccgtcg tgaatccaac   4740
gagggccacg gtacgatggt cttcacggtg aacagcgagc aggtggtagc agataccatc   4800
ctccgccgca tgggcagcca ctacaacccc tgggcatcca gcgacaacca ctcgaccaag   4860
gtccgggtcc acgtcatcaa cgtgaagtct gcggcagata tcctcatcaa ccatggggtt   4920
ctccgtcgtc acctcggtgg cttgcaggac taccccggta ccgtcgagca ctcggagtac   4980
ctcgacaagc tctgtaaagg tctgtaacat ctaggccttg acattctgct ggaagtgtgg   5040
tataataacc ttaaggtgcc gggggttgct ttatatccct aaggtaccta aggttctacc   5100
ttctatcttc ttcatcttaa gaaagaggta agaacaatgg tcctcaagct ctacactcgg   5160
gtaatgctcc tggctatccc cgcatgggta agcgtaaggt tttctacgag cgtctctgct   5220
ccaacggtga attgaccctg aacggcaacc tcaaggccac caaggtgtcg gcaccaacca   5280
aaggcaagca acagcgccgt ggcaccttct aagtaactta gaggtcgcta gtaatacccc   5340
tagtattcct gtcctggggg tattgctggc taactcaacc aaggagaaaa caaatggccc   5400
gtatcaagta tgccttcggt atgaaaccca agaagggcga gggtaaagcc ctcaaggtaa   5460
tgacctcttc ctcctgcttc ggtacaatgg aaggtccggt aacccacggc tataagctcg   5520
acggttggac cttcatctgc tcccgccgaa gcaagaagtt catcgatgtg ctcaacaagt   5580
gtacccaagg tgaactcaag accatcacca tcggcggcaa ggccttcaaa atcccgaagg   5640
tccacttctg gtcttacgaa agcaaggcca aggattcccc cttcgagaag tattctaacg   5700
ggacggaaat gatttccccc acccatcacg gaaaagaagg ggtctgcggt atctacttca   5760
accccaaggt acacaccctg gattcctggt accccatcat gaaattcctc ttcaagatga   5820
tctccagcgg actcgactac caaggtcgtg aagaggaggt tcacctgaag cttgctgaga   5880
agtatggctt ctggaagtcc tacctcgcaa tgtccttcca cggactgata gccaatggct   5940
acaccgggta cccactctcc aactacatgt tcagtagtga ttgggatgat ctcaagaagg   6000
gagatatcca catccaatcc gctgacgagt ctatccgatt cggtcgttgg atgcccaacc   6060
gggatgcccc aggtggacgt gagtgggtaa ggaatacacc ctggcggtct gaattcctga   6120
agattcagtt ggacaaggtg gaggtagtta ccatagcacc tcagccaacc atcttcggaa   6180
agaaagatcc ctacatgacc gtagatagcg agatgggagg tttcatccgc ctttatcctc   6240
atacctgtga aaaatacgga gtggtcatgc tggggatcat gggtgaggtt ggctggggga   6300
gcggcataaa ggatatctta ctggccctcg aagacttcat cgagaaaaac ttctgacaac   6360
caaggagaaa tcaaatggga atgtatgcag cccataacgt gtactatgat gtcgagggtg   6420
ctgagattgg tcactgctgc gtaaaatacg tggctgaata taccaactgc ttcggtgcat   6480
tctgcgacga aacgggacct ttccgggatg tagtgtggga gaccggggtt ggacacctcc   6540
tggtgtctac ccacgagaac actgctggta agttggtgga gttcttgaac agtgatctgg   6600
tcaacaggat caccgacggt ggaatcctct cagcttccca ggactggcca accaagtggt   6660
```

```
ggacaggatc tgacggggct acccaaaacc tctccaatcc tgaccacttc agcccccctg   6720
gccgccgaca ggctgtgtac gttcgggtgg acctcaagaa gaacgcatcg gcaatcatct   6780
gtgccctccg aatgggagat cgcttgtggg gtgtaggtga ttccatgcgt cgcatcaccc   6840
aggaaaatcg tgataagatc ctggtctgca atgcagagat cctcaccctc gcggcttgtg   6900
cccaggtagg tagcactgct cattgcgaca gctacccggc catgttcccg gtgactgctg   6960
gtgaataccg ggagggatgc gagagccacg gctgggaggt ggatgacagc tacataagcg   7020
aggtcatgga tggtatcgta ggtggataca agaatatcac ctacttcgat attaagagca   7080
tccatgagcg gactcgcgaa gagttcaagg acaagctcaa gcatcacgac gctgagttgt   7140
ggcaggggta taccaaggat gatgacctga tcgaatgcga cggtctcgaa ggtgtaccta   7200
atgaccgaat cctttccatc atggccccaa tcaccattga cgtcggtgac ccaggtcggg   7260
aaaggtccga ggtcgtaccc accagccaat acagcatccc cgaaatcctc gaaaaactgg   7320
agaacatgca atgaacaacg caatcccccct gatcggtgca gatcccgaag ttttcgtcgg   7380
ctacgaccgt aacccccaga gcgtcatcgg cttcatcggc ggcaccaagg aagagccctt   7440
ggctgtagcc ggtggtgctg tccaggaaga caacgttctt ctggagtaca acatcgaccc   7500
ggccagtacc aaggaagagt tcgtggagcg tatcgtctcc gttcgactcc tgggtgccca   7560
gatgctccac cccttcggca tgaacatcat cgagaacctg tcctctcacc tgtacgacga   7620
ggaactcctc cgcagcttcg gtccccaggc ttacgtcttc ggttgcgagc cggactacaa   7680
ctgctggact cgtcgtcaga acgtgatgcc gaaggatgcc cctccgaccc tgcgtactgc   7740
cggcggccac gtccatatcg gcttcagcca catcgagcga gtcaccaagg ctaccaccag   7800
agaagtcatg cagatgtgtg actacctcct gggcctggcc tctgtcatcc tcgatggtga   7860
cacccagcgt aagaagctgt acggcaaggc tggcgcaatg cgctataagc cctacggcgg   7920
cgagtaccgt agcctatcga acttctggat cttctctgtc gatctgaccg agtgggtcta   7980
tgaaatggca gtgcaagcct acacctccaa gcacctcctg gaggagtaca agtcgatcgt   8040
atccggtgat gaagtccagc ggatcatcaa cgagaacgac ggcgctgcgg cagttgcggc   8100
cctccaagcc ctgggggtga agtatgaatg acctgaataa tcgccatcgg ttggccgggg   8160
acttcaacat gtactactcc tccacctatg ccttcttccg ggttgacggt gagcctcggg   8220
tagtgtacgt ggacgatacc gagtccattg gtgacgaccg tcaattcgac gggtttcgtc   8280
tcctgggtaa tgtgtatcgc cccgacggca gtaactacta cggtggggtt gtctacagcg   8340
aggtagaaag cgtgcggccc tccagtgggt actatgacgt ctttggccgt ggggttcgtg   8400
atacttatgt atccttcctc gtgaacaatc ggactcagcg taagggtatg gaccccagga   8460
acatcctgct gaaccatgcc caacaggcca tcactggaga aatgatgatc cgaatcttca   8520
cccaggccga ggaaatgatc tctgccccat cccaccggga cttcttcatc aaggatgggg   8580
tagttcactg gaagggggtg aaggtcggcc agatggtgga tgggcggctg tccgcagatg   8640
aacaattcaa gaaccaggag gacttgctat gtcagttatt ggcacacaga tagggttcca   8700
taagaaccag atcatcgccc cggaacacca cgaggaactt cctgcggttg cttccttcgg   8760
gttcgaagtc gaactggaag gcctcaacaa ctggccagaa gtggatgggt gggatctgaa   8820
gggtgacggc tctctgcggg ggggtatgga gtatgtcttc tccggtcccg cctctggcca   8880
gagggcaatc actcgggttg aatcctttgt gagtgcgatg gaggaaactc ctccggcccc   8940
caccttccgt tgctccaccc acctgcacat ggatatgcgt gacgtagagt ggcctgttta   9000
```

```
tgaacgaacg gtcctgacct acatggcatt cgaggatgtt ttcttcgatc actgccaacc   9060
gtatcgtcgg gatagtaact tctgcatccc gttcttcagc aacgactggc tggcccagac   9120
cttcggtcgc cgtatcctgg ccccggaagg tgaccgagag aaagtcttgg gtcttacctc   9180
ctggccaaag tattcggcct tgaacctcca ggtaacccac aacttcgggt ccatcgagtt   9240
ccgtggtgcc catgctctca ctactcggca ggaaatggta ggcctgatgc agcgtatgtt   9300
gtgtctcaag gccttcgcca tggctcacgc agaaaccccg ctggaagagt tccttaaggt   9360
actctccgag gtgaatctcc gtgatgtatt cttcctgggg gtatctccgg actatgaaat   9420
gtctccgggt ggtcgtgaaa tggggatcgc cagtgctact ctcgcggtag caaccatggg   9480
ctttgttcgc tccggggtag atcccctgga agatgaacag aaccgtcagc gtcgtctccg   9540
ggagcaggaa cgtgagcgtc agagggcttt ggatcgtagg ctgctctttg ctcgcgctat   9600
tacctcacga ctactagatg gtgcagcaga gcggtacaac ttggcaatgg tgccaggtac   9660
ccaggttcga ctggatacgg cgattactgc ggtaacttct ctgcgtcgta ttggtcacca   9720
agtgcgtgta cgagaccttc tggaggacca agaggctctt caagatgcct tcgtactgct   9780
catggataac ccgcagcacc ttcagcgcca taccggcgta acaatcgaac cagatatgta   9840
ctaaggagaa atacaatgtg tggattggta ggcttctgtt ccacaactaa cgcgagtgat   9900
aacgaaatcg ctcttctcaa atccctcctg gccgtggata ttatccgtgg tgctcacgcc   9960
accggtttgg ccaagatcga cccggttaag aacgaggtag gaattcacaa gcgggcagta  10020
gatgcctacg acttcctggc tgatcctgaa accaaggagt tcctggacaa gggtcgggct  10080
cgcatctaca tgggtcacaa ccgttacgcc acgatgggcg acaagacgga ccatgggaat  10140
gcccacccct tccaggtaga ccacatcacc atggtacata acggcaccgt agatacctgg  10200
ggcctgcacc tgctggatgg caatgataag tacaacgtgg attcgaacat gctgtgcgct  10260
accattgcca accacggagc caagaagacc ttcgaagaga agttctccgg tgctgctgcg  10320
gtaatctggt gggactccaa ggaacgtacc ctgaacttca tccgcaacga tgagcgtccg  10380
ttgttcatgg cggtgaccac cactggtacc atcgtgtggg catccgagcc tggtatgctc  10440
aaggttttcc tggagcgtcc caacgctaag atccgccttc gttctcccat cgctgaactg  10500
aaggctgaag tcctggtaac tatcccgttc acggaggccg gagtgcgaaa gggtgcagaa  10560
ccccagacca ctccggtcac gtttctggac ctcccaattc ccgaaagcga aaggcaaaca  10620
gcggcatggt ggagtcgcta cgtcggtgtc tcggactatg atgactacag ccgaagccaa  10680
ggcagccaag cgggaacgaa aggcagccaa gcgggctcgt cgtatggaac gtctggcgat  10740
gcgtacgcaa ggaacaccct ccggatcaac aacaacctcg acgcagcagg tagcaccttc  10800
aagcaccggc aactcgtcac cttcgatgtt gtcaagatcg aggcctacgc aaacggcagc  10860
gagtacggaa ctgtcactgg aatcgagcgt gaagaaaacc ttctcatcga agctcatggc  10920
atcaacgtcg ccaaggtcca cggatacacc gtcctccgag ggagtatctc caatgcctac  10980
ttcatcggcc aagaccgtga tctcaaggtt actgtcgagg atctggcggt aagctgcctg  11040
gacccaaagc atcggccgac tcctggggag actaccccag tgttgaggat tggaacgatc  11100
tcatcggaga cgaaatccca ttctaaaccc agggttcaag tcggcggcac ctcggggaat  11160
acccctccgg ccaacatcag ctaccccttg aaggttcagg gacacacgtt caacaacgtt  11220
catgtctttc gggacttcgt atcccagggg tgtgcatctt gcggtaagat ccctaccgcg  11280
tatgaccagc gtaatcgtca tctgacggtg tacgagggtg ccaagttcac tggtagcctg  11340
gatgagtgcg agttcatctg tggtgagtgt gtaatcgaaa ataaatagga ggtcaaaatg  11400
```

```
acccaagtaa cgatgaagcg tcaagtagtg atccagatgg agaccgacgc aacccgtaag  11460
tatcccttct cccgtgacac cctggacaag atccagtcga ttcgtcgagt caaggagcag  11520
gaactcaatg atgccaaccc ggacgaggaa ttcctggtac cggccccggt agtcattgcg  11580
gaagctatcg accgactctt cgaagactac ttcgagtaag gtagtgcgtt agtaatagtc  11640
cctggccgac ccatgccggt tcctaagatg cgtacatggg atctaactta ggattccagg  11700
ggctattgct ggcttcacta ccctcaacag aaacaggaga tttgccatgt tctatatcta  11760
taaaggtgcc cgcccctctg ctggtgctgt cgctcttcgt aacgccatgg gtgctcgaat  11820
ccttcgctcc gaggggtcta cctatcgggg tcgttcgggt actgcggtaa tcaactgggg  11880
aaccgttggt gcagaggcac gacgcctaca gggtatcgcc ccggtcttcc tcaacgaccc  11940
ggctatggtt gctcgctgca ccaacaagct ggatttcttc cgccacttcg aggccaacgc  12000
cccccatctg atcccccgct ggacggattc ctgggctaat gtccacccga tcctgaattc  12060
ctgcggtcga atgtacgctc gtacggacct caatggtcat agcggcaggg gtatccacct  12120
ggtgtgcagc atcaacgacg cagaagtcca ggccatcgat gcccttcgtc gccaggggaa  12180
ctacccggta cacatctggg gtcataccca catcccggag gtcgtcgaga acgcccaatt  12240
gttcacccag ggcatcgtcg gtaagcgtac cgagttccga gtccacatga tccgtgggga  12300
ggtagccctg ctccaggtca agctccgacg tgttgccaat gaaatggtga ccaacgaagg  12360
acaaagtatc gttcgtaacg tagctggcgg ctgggtctat ggcgtcaacg atgcaatggg  12420
acgggatggc gctgagcagg ctatgtcggc agcagcagaa gctatccaag ttgcaggcct  12480
ggacttcggc gctgtggata ttatctacca gcacgctact agccgggcgt ttgtcctgga  12540
aatcaacacc gcgccgggcc tggatgcaga aggcagcgcc ctggaggcct acgtcaaggg  12600
cttcaataaa atcttcgagg agactatcta atggctgttc gtgttttcgt ttatggtact  12660
ctcctgtctg gtttgtacaa ccactacctt ctggaagggg ccgagtttgt cggcaatgct  12720
gtatcctgcg agcggggtct gatgtactcc gctggcggct tccctatcct ctccttcgcc  12780
tcccgtgctg atctcatcgt aggtgaaatc tggcaactcc ccgaaggcga gaagggggag  12840
gaaatgctgg agaacctgga tgccctggag ggttatccgg gttggtatga tcgtaccctc  12900
aaggatttcc gaatcaatgg ggaacgaatc aaggccctgg tgtaccatca ggatagccac  12960
atggcgatgg atatcgtcaa ggatggcgac tggaaggcac acctggcaaa acgacaagga  13020
gcagtataat gaacgaaatg accgtagaca aagcagtaga agtctaccgc gatactccga  13080
atacattcgg acaccaagag ctacatgccc agaagatgct tctcaaggag atcctgggcc  13140
ttgtagcttc ccagcgacac ctccaagact ctatcgaggt ctccaagatt ccggaggcct  13200
cggatagtcc cgagaccagc tacggtgggt actgtgacga atccattggc attcgcttca  13260
tgtgggagcg actgaagaaa atcgaggatc gtcttcggga actggaggag gtctacggta  13320
ccttcgtaac aactccttat aaaaccctac cgggcaacgt gaatgctgta ccaagcctgg  13380
ttctcaagag tcaactggag gggtaagtga agaagatcat cggtgatacg gcttgtccgg  13440
gttgccgagc taaaggtggg gataaaacag gaaatcacct catcttgttc gttgatacag  13500
aaaagggtac tcggttcgga agttgtaacc gttgtggtca ctacgaagtc ctcgaagagg  13560
gtttcaaggt gccagagcgt aaggagaaat ccgaggagga tatcatccat gaagtcaacg  13620
aagtccttga gtatccaatt aaagccctcg atactcgaaa gatcagcaaa tcaatcgctg  13680
aacggtacgg ggtacgtgtt ggtctatcac aagagaatgg tgaggacgtt atcgagcatt  13740
```

actatccacg cactcgcgaa ggggagtacc gagcgttcaa cgtccgaatc ctagaaccta 13800
aggctttcta ctaccgtgga agccccaagg gcggtgtaga ccccttcggg tataacaccc 13860
ttcggcataa ggatatggga cacctgcggt tagtcatctg cgaagatgaa ctgtcggcta 13920
tgtctgtggc ccagatcatg gagtcgaaac tcccggagaa gtggaagcat cttcgtcagg 13980
catccattag ctggtcctcg ggtgttggtt ctgctggacg ggacattgcg ttccttaagg 14040
agtctggtgt acttgagcgg ttcaacgagg tcatctattg ccacgatgcg gacgacgaag 14100
gccgtaaatc agtagaaaag gtacgtgccc tgtaccccga gtgtaagttt gtcgagctcc 14160
cgctgaagga tgctaacgac atgctcatgc gtaatcgggg ggatgaggtt taccagatga 14220
tacgtttcgg cagcaaggtc aagtctccgg actgttccgt tactgtcgat gaggtatacg 14280
ctgaggctct ggaacccccc aagtggggca agagttaccc gtgggaaggt ttaaccaacc 14340
taacctatgg tcagcgggat ggtgaaatca tcggggtagg cggtggtact ggtatcggta 14400
agaccctgtt ggcccacgag attgctgcct ggaattgcat tgagcacggg gagaacgtag 14460
ggacattcct gttggaagag caggtagcca tgacccttaa gaatatcgcg gggaaggttg 14520
ccaacgtgcc cttccaccga ccggatatcg agtgggatga gcaagccttt aaagatgctg 14580
ctggtaaact ccgtggcaaa ctcttcatgt ggaagaacaa gggtcagaac gattgggatc 14640
atatcaagga gtgtattcgc ttctgggctg tagccatgga tgtgaagact atccttctgg 14700
ataacatgac cgccatgacc aaccacctta gtccttctga aatgaacacg gagatagccc 14760
gtatctgtac agaactcgca gggatggccg acgagctagg actgcggatc ttcatcttct 14820
cccaccttaa cccacccaag ggtaaccgta cccacgagga gggcgctgaa gtaaaggaaa 14880
gccagttcac tggttcccga gctatgcagc ggtggtgtca gcttatgatc ggcttcgagc 14940
ggaacaagca ggctgacggg gaagagaagc acgagagtcg aatccgtgta atcaaggaca 15000
ggaactacgg taacactggc ctagtgttca ccaagtataa ccctgagacg ggtcgcttgg 15060
ttgagcgcga gggcagttac gacgaggtac ctgctgacga tgacacccca atttgattac 15120
gttatctatg acctagaggg ggacggcctc ttcaatacgg tcacaaggct ttggtgcgct 15180
gttgttgtag acattccgac tggggtagtc cggggattcc ggcccgagga aatggatgtg 15240
ttctatagga tcatcgccca tgcaaagttc gtggtcgggc ataacatcct agactacgac 15300
aaccgggtcc ttgagaaact tcatgggatt atcataccca ccgaccgaag ctatgatacc 15360
ttggttgcat cgaggttgac ttggccagat aggccccagg gtcattccct gggagcctgg 15420
ggtaagttcc tgaagtgtca caagggtgac ttcaacgact tctccaagtt ctcagaggaa 15480
atgtttgagt attgccttca ggatggagtg gtcagtcacg cactgttcaa ctacctcctc 15540
cgggtactcg gcatgacttg gcaagagctt gttgaatgga ggactgtaga ttggctaaaa 15600
agcgagtgag gaactacaag cgtgagagag aactggctat tcgacgcggc gaaacgggcg 15660
tgggctctaa gtcaggagat gctcagcggc accgagcccg ccgaaaggtg gaaaagcgtc 15720
ttggcaggaa gctcggaacc gacgaggttg tcgatcatat caaacgtgtt aaagatggtg 15780
gcggtaacgg ggattctaat cttcgcgtcc gtggccgttc ttctaacgct gctgatggtg 15840
gtcgggtggg cgatcgtaag gccaaaggca ttcgcaagaa aaagtaaatg aagaggggcc 15900
ttcgggcccc cgaggactca ttatgttcaa tcgaaagcta agcatcagta aaatcctcag 15960
ttcctttgac aacgagatca atctactgaa gacctttatc aaagagtctt cggatgaatc 16020
tgaacggatc tacaacgaga tcagcttcct gaaggcggag cgtacccagg tcatgcagga 16080
caacctgaag gcccagaagg tactggctaa cctggaagaa ctgctgggag gtaagagtga 16140

```
agaagtatcg agttaatgtg gggttccagg acaccaaggt gttcaacgca gacttctacc  16200
gcatcgagtt ggatatcatc cggttcttcg cgggagattc tgatgccaac cccatgaccg  16260
tccgagccaa tgagatcggt gctgtccgtg gatgggtttc tgtggaggag attaacgatg  16320
gcgagtaaga aggaaagcct ggaggatcag gcacggaagg agattgccct ggagaaggag  16380
ttctctggta gctggggtgg ccccgagatc gatgctgatg acttcccctt gggtagtgcc  16440
tgtggcctag atcccgaggt atgcgagtca tgcagctgag ccagtgcgta ccctggctgt  16500
gggctactga tcgatgcggg tatggggtcc ttaccttcaa gaggaaactc aggaaagccc  16560
accgggttgc ctactgtatg gccaacagtc tacaaattga ggacatcgac ggggttatca  16620
tcagacataa atgtgataac ccatggtgtg taaatgtaga tcacctcgaa cctggaactc  16680
atcaggataa cgaggatgat aagaccaaaa gaggtaggcg acctatggga gagaaggttg  16740
gctcagcaaa actgaatagg gctcaagtag agtccatccg gaaggagtat gtaaaaagct  16800
caaagacttt cggttcggtt gccctgggta agaaatacgg ggtacattcc tcaacgatca  16860
gatacatcat agcaggagat atctggtgag tatcctagcg caagtccttg tcatcttctg  16920
gagtgcattc ttccaggtat tcctcctggg attgaactct aagctgctcc gggatgacaa  16980
gatcaaggct gggttcgtag tgtcttggtg tatcacgctg gctcagtttg cttacatcaa  17040
ggcggtagcc tcctcccact tggatatcgg atggtttatc ttcgtgtccg ggtggggagg  17100
tgcccttggg attacctctg ctcaatactt ctacaagtgg tacgacaggg ttttccacag  17160
atagtcttga caaatccagc aaagtgtgat ataataacct taaggtgccg gggttgcctt  17220
taccccctata ggagatacaa atgagtgacc atgtaagcta ctccaaacat gtccgtggta  17280
agtacctgtg taatatggct tctgccctac ataagagcat ggaggtacaa aggactaaca  17340
tccggaagtt cctcagcagt ccccacatta ccctacggga gaagcgtcgg gtgttcctga  17400
gcctgccaga gggattcctg ggggtgagct acttcacagg ctctcatctt aacctgagtt  17460
cctactcgga tcgtcgaaac gcccggattc gtgacaagga tatgagcctc tacgatgact  17520
tctacgtgga caggggcgcc cagctggacc ctcgggatgt cctgcttacc tcccaagagg  17580
agaagaagtg gggggtttcaa ttccttaaga agaggcgggg tggtgtcttc aacctgtccg  17640
acgaagagtt gagcgatgcc aaggatatcc agcgcaagct tgacctgtcc tggtacctgg  17700
tggaccttgc ctgtgagcgt gggtgttcct acttcatttt cgactggtga taacatgagc  17760
aagatcaaga gtgttctcat ggagcgggta gatgacttcc tgctcaagca agttgctgta  17820
gcgttcttgg aacagcaatg gcgactggac cgaagcggaa ccgtggacta cctctcctac  17880
ctggagggta tctccgacga ggcagtggag gtagtcatag agaatctggc ggagcgtctt  17940
aagggggatt aagtggattg gagaaagtca ctgttcgttg agcacaaggt agctgatatc  18000
atcagtcgcc agagtaaacg tggagtccac ttcaagactc agcgggccaa gtggctgatc  18060
catgtgctta ccgaacgaat cctcaagatt gaccttgagg ccgtcccccca gatgccgatg  18120
atgatcgtaa aggctggggc cttcagcaag ccattcctaa agagtggtaa gccgaaccaa  18180
aggctccagt ccttatggca acgtcttggg cacttcgagg tatctggacc attcactgca  18240
atcgagtaca taccccttcga ccttggtaag actgccaagt tcaaggattg gatgctggat  18300
cagggatggg ttcctgacca atggaacatc aaggatatta ctgtcggcac tgatggcaag  18360
aagctacgtg gatccgacct taatgaatcc ttgaacaagt acattgaaga cctccgacag  18420
agtaaatctg gacgactccg aatgaagctc cagggtatca tccctggtaa gactacaatc  18480
```

ggagaggtca agagaaagct agaaaggcaa cgaaaggtac taacgactcc taagatgact 18540
gaagagtcga tggataccgt ccagggagac ctgggaaagc tggtgatgca gcgaatggtt 18600
tgggcccacc gtcggtccct cttgcagggg ctggtagatc aggtgaggcc cgatggacgc 18660
ctagagggga gtgctaaccc ctgtgcaaca cctacgggcc gtatgaggca ccgtgtagta 18720
gttaatatcc ccgctgctcg ttctcccttt ggaccagaaa tccgagggtt gttccagggg 18780
acacctgatg ccggtgaatg gaaatggact gtcctccgcc gagacattgg agagaacgaa 18840
agggttaggc ccttcactaa catcgtggag gaactcaaga aaggtaagtg gaagcctgta 18900
ggaaagcaca agatatacgt cccagcgaat caaatgatct tcgtgggcta tgatggtgct 18960
ggactagagc ttcggatgct tgcatcctac atcaataacc cagagtacac caaagaggtg 19020
gtcgagggtg atgtacacac ggccaaccag atagccgcag ggctcccaac ccgtgacgat 19080
gctaagacct tcatctgtga gatatggatg acttggggga aacccctcga ttaaaactgg 19140
gtgaactcag ggaacccttt aatatgggaa tcctgagcca agacacttga catttcccgt 19200
agaatgtgtt atactgatat tttatgggag gtgtttatga agtacccaaa tggatggttt 19260
aagattaaga actgtagaaa gtgctcctcg gagttccagc ctactgcccc tagccaccac 19320
tactgctcag acgagtgcaa ggagtggggt aggatcaatg cctactacac cagagtctat 19380
ggactcacgt atgatgaagt aagggctatg gctgatgaac gagaccacaa gtgtgatatc 19440
tgcggggaga agggattcct gatggactcc tctaagcaca ttgcattctt agtcgttgac 19500
cactgccatg caactggtaa ggttcgtgga ctcttgtgtc acaactgtaa cagagcattg 19560
ggactgatga aagattctcc agagcttctt cggaaggctg ctgagtatct tcaagtgtaa 19620
ggtgcagaga ctattatgta ggacccaagc gggttcgaag cgcccagccc ctggaagaca 19680
gggtgatgat atagtccgat ccccagggga aaccttgggg cagccgagag gcgggccagt 19740
agtagcgaca ctggttgaac ttttgatgcg ttcatctacg gtgctgggga tgccaagatc 19800
gggactatca ttggaggcac cagggcagac ggggctaggc tccgggccca gttccttgag 19860
gctaaccctg atcttgctgc attgattgag agggttaagc aggaagccga gagaggttat 19920
ctcgaagggc tagacggacg gaagctaacc atgcgacgtt ctgagtctgg cgacgtgatg 19980
atccataagg cattgaacac cctcctacaa gcggcaggtg caattgtcat gaagtgggcc 20040
atggtgctcc tagatgaacg ggtccggagg ttgaaccttc gggcttggaa agtcctggat 20100
atccatgacg aaggtcagtg ggaatgccac ccagaggatc tcattgcgct acgtggacag 20160
atggaaatct gtgtccggga tgctggagtt ctccttgggg ttaactgtcc tttggctagt 20220
gattccatcg ctggtcgctc gtggtatgac acacactgat acatctgggg gttgactttc 20280
agccccccttt gtggtataat accttcttcc ctacgagagg tttaagatat gtctaagaaa 20340
gtatcccaac gattcacctt cccggtagcg aagctgatct tcccctacat cgtaactccg 20400
gacaccgagt acggtgaagt ctaccaagta accatctgca ttccgaccaa ggaagaggcc 20460
gacaatctgg tacagcagat ggagtccaag gatgcccgac tgaagggtac catcaagtac 20520
caagagcgtg acggagagta cctgttcaag gtcaagcaga agaagcacgt ggattggatg 20580
caagacggtg agcgcaaatc tgccgtgatg aagccggtgg ttctgacctc ggacaacaag 20640
ccgtatgatg gccccaatcc gtggggtggc tctactggtg aagttggcat cctgatcgag 20700
acccaaaagg gcccacgagg caagggtact atgacggccc tgcggctgcg cggtgtacga 20760
ctccacgaga tcgtatccgg tggtgacggt gaggacgatc cgctgttcgg tggtgccttc 20820
accgaggaag agcccgagga tgtattcgac gaggtgttcg atgacgaaga cgctcctatc 20880

```
taaggggttg gggatcacg aggcgggggt atgcccacgg ggctgcccct actgcttaat 20940
cgaattcgaa agagtgtggg gtgtaagggt ggtcagttct acagctgcat ctaataataa 21000
agtagaggtc gatcctaatg gaatcaagcc gggtgagccg ggcgctaaac ttgatagcgg 21060
caaggtggat gttggaatca tcttcgaagc gttcccgagg gctctatatg cagtggcaca 21120
agttgctaac ttcggagcca gcaagtatag tcgcgggggt tggaggtctg tcgagaacgg 21180
agtccagcga tatgatgctg ccttcgggag acacctcctt gagcgacaca agggtgaggc 21240
tttggacccc caaagtaaac taccccaccg ataccacgaa gtgtggaacg ctctagcatc 21300
cctggaacta gtcattcagc aagaggagga ctccaatgga acttctgttg gatccaaggg 21360
ctaagactgt tcctagcaac tactctgtaa aaggcgttga tgtagacctg gggcttcccc 21420
caggctacag cctaacggag gaagctatgg acaaggccaa gcgtcaagag agtgaatatt 21480
acgactggaa gggctacgaa gcactggtta atccggtggt agagcaccca gagtatcgag 21540
ccaagggtga agcctttgcc ctccgtgtat tctgggaaga gaagctcaaa gagtctcagg 21600
tcgtagaaga ggtaacgtaa tgattgctgg tatcgatggt gacgttctta ggtatgagct 21660
aggccacgtg gctatgtcga aggaacacat cttcgatatc caggtggaga agccatggcc 21720
tgaggaagaa gtccacaagc tcgtcgatga taaagtcgaa caaattatca aaagggtgaa 21780
tgcagatgag tgtgaaatct accttactgg ccaaggaaat tttaggctgg agcttgcgaa 21840
aatcaagcaa tataagggta ctcgaatcgg tcttgaaaag cctcatcact gggaaaccgt 21900
gtcagccaga cttaaggaca agtggggagc aatcactttc cacggtatcg aggctgatga 21960
ctggctcggg attcgaggga ctgaagaggg agataacttt acagcgtgtt ctagagacaa 22020
ggatatccgc caagtcccag gatgctacca ttacagttgg ccctgtggag attcccagcc 22080
ggagttggga ccgtttcaag ttgatggtct tggaagagtc tccgcttctt ggagaatgta 22140
tggcgttaaa aagccgcaga aatcatggaa gcttgagggc aacggtacgg cattcctcta 22200
cgggcaactc cttgttggtg actctgtgga taacatacca ggcctcccag ggacgggacc 22260
aaagacagcg gcagatttgc ttggggagct ttctagtgag agagatctct tcgcagcttg 22320
cgcttacgcc taccaacaga agtacggaga taattggaaa gagtaccttc tggagaattt 22380
tcgtctcctc tacctcattc gggaccgctc ttggcttgat attcagcagt ccggtaacga 22440
gtatcactgc tcactgaaga aacattggga gattccctat gacgatgaag aaatattcta 22500
ttgaggaagc acagaaaatc tgtgaaggcc tctttgagat ccttgagggt cttaacttta 22560
ctgactacaa ggtcgctggt ggtttccttc gggatgcaga caacggggtt gcacccaagg 22620
atatcgacct gtatgtccgt aggccctatg tggaggaccc cactgatact cggcgtagtc 22680
gctttggccc acggttgatc ccctgtgatg acgataccct agaggtagag gtcactcggt 22740
tctacaataa gctgggccac aagaaagtcc ggtgtaggac tggggataag cctgatgggt 22800
atcctgcggg gtttgatgtg tgggaatcca ttggtgttga cctacccgtc aaccttgtcg 22860
tgagtactca ctcccatcca gcagagttcg atgtaggact gtgtgagatt gcatgctggc 22920
ccataagtat ccgtggactg aaatctcaaa tctaccgttc aagggcttat gagtttgata 22980
aagaagagaa gtgcattact cttaaccgag tcctagaccc tcttctggat cattctcaac 23040
ccctaactga caatcaagtt gaaaaggttg tctctcatat ccaacgtatc aaactgaagt 23100
atccggagtt ccgggtgtgc ctgggggatt ggatctggct tctggttcgg gctaattcta 23160
tcctgactga agggacactc tcggttatct ggaagcttca agaaggaggg ctcattggca 23220
```

```
aagcagggga gattcttcag acccaaactg aagtcattga ttgggacgaa gtacgacagc  23280
gaaaccgaga agatcgtcca cgagacgatg ccctggatgc agttcaagcc agacccggtg  23340
agctacgtca tacagcacaa gtacaagccc gacttcaagg tatcgacctc acaaccttgt  23400
ggatcgacga agcacctgct ggtcgaggtc aaggggtact tccaggaagc ctcggaggca  23460
tctaagtaca tctgggtgag ggaggctctc cccccagata ctgaacttgt gtttatcttc  23520
gagcgtccta acacagcttg ccattggctt agtaagcgta aagatggcac aaagcaatcc  23580
atggcggaat gggccgaacg taatggcttc cgctggttta ctctagagac tttcaaggag  23640
tccttcccta atgagtaaga agtataatga agacactctc gtcattgcgg acacccaagt  23700
tcgatccgag gtcaacatcg atcacctcgg gaaccttggg gagtggatcg cacgtaaccg  23760
ccccaagcga attgttcata ttggggacca ttgggacatg cccagtctgt caagctacga  23820
ccgtggtacc gctaagatcg aaggccgccg agtcctcgct gacatacaag ctggtaatga  23880
tgcgatgcga gttctgctcg accctcttcg ccgcctacag caacaccaag cgggttgtaa  23940
gaagcgtatc taccgaccag aaatgcactt cttcatcgga aaccacgagg agcgtatcaa  24000
gcggtatgaa aattctaacc ctgctctcca aggttttatt gggtacgatc attttgatct  24060
gtccgattgg attgtccatg atttcctcga cgtgggtgtt atcgaaggtg tcgccttcgc  24120
ccactacttc tacaatccca acagtggtcg gccatacggc gggagtgccg agcatcgcct  24180
caataagatc aagcgcagct tcgtccaagg ccacgaacag ggattcaagt accacatcga  24240
ggcagtaggc aagaagcgaa tccacgggct tgtagtcggt agcttctaca ctcacgatga  24300
gtcctacaaa gggccccagg gtaacgacca ctggcgaggt gtagccctcc tccggaacca  24360
caaggacgga gagtatgacc tcaagctgat gagtgtggag gagttcctgt gagtaagttc  24420
ttgccagacc tgtactacat taagtctgag catgacttcg gtcaacgggg gttggcgttt  24480
aagacgccga tctccgcaga actctggctg gatatgaagt ttgggaaagg tggtgctgag  24540
gatgggctta gacgagggat gtattccatc gaagtcctgg agatcctcta catccccagc  24600
gttcaccttc cggatatctt ggggtaatct atgaaagatc gagtgggacg taagctagag  24660
gtaggggaca gtgtagtctt cctggtccac aggaacacct cctcccatct agccattggc  24720
accgtcgatg ggtttacccc caagatgatt cggatcaaat gcccgaccat gagttggact  24780
attgacgctg agtatgttct aagaagcagt gacaaggtgg tgtactatga caaaggctga  24840
actggagaaa gcacttgaag agacgcaaag cgctcttgcg aaggctgagg cgaaggcctt  24900
ttcctttgaa gaactggctg aagaagctaa aagacagatt gaattcctcg aagggatgct  24960
agacctagta gaccttaggg cttctgtatt ctacggagat tggagggggtt atgcagaaag  25020
atcaaaaggg taagggtgga ttcccttgga cctacattgc ggtagcagcc ttgtttgccc  25080
tgctggttta tgtaggatat agctgactga tgttactcct gaccctggga gaaatatcca  25140
gactcctcat cgatgtatta tcttgggcag gttcactgta ggtatccatc gagtaaccaa  25200
aaaaaaggcc ccaagggtat catcccaagg ggccttatct ttagctccgt agagcgttca  25260
gcagtgtgtt gaacttatca acgagtgcct cgtgagtatc cgtataggaa gccacgggga  25320
tctcaactac cttacccttg acgtaagccg caatggctgc atctaggcca ctcacttcgc  25380
tagccttggg tttccagtta cctggtttag cctcgctagc cttagcacct acctccagaa  25440
gctcaggctt cccctcaata tcctcccatt tcactggctc aaagtctttc gggccaatga  25500
cttgtcgaag ggtcccatct tcattacgta cagcaatagc cttcgattga ataacgaata  25560
cactgttgcc gtcgttgtca gcgatataac ctgccataat ctaactccta attaaactgc  25620
```

cgatttgaag gtacccacgg taccaccgaa aggatacact cggacagtgc attccccaaa 25680
ttgaccatca gtctccgtct gattaccctt agcataccaa gccttgtccg gagatacagc 25740
gaacttgatc ttagctgtag acccttggat aaagtggaag tgacaacctg ggttacatc 25800 cggaccaaga gtaacggtaa tatccgtagt cccctgggac atgaagaacc aaccagactg 25860
ctgcttagta agggtaatgt tctgggtgag ttgctgggtg ttgacaacgt taccaccgag 25920
gtgagtagtc accagtcggg gatccaggta gttctgttga agagaaccaa tgttcttcac 25980
aggaccacgc atgtcgtcaa actgctcgat aatgtaatcc ccgatggtac caccgttttg 26040
gtcatccggg ccaatcacgt gcttaatagc cacgtaaaca cccaggtgtt cccgtcgagg 26100
gtctactcgg aattcactac cgaatgcagt accgcaaggt gcctcaatca tggtctcaga 26160
gaacagacca atcacgtggc cagggtcacg gttaccaccc gaggtttctc caggagcacc 26220
cacgagggta ttgaccagga cagaggggat aacggcctct gagggattct ccgggaagga 26280
ggctgtaacg ttctctacta ccagggctgc gttctcctta actgcataat agtcagggag 26340
gaactctgta gcggtaacga tgttagtatt tacccgaccg gcatccgagg taatctcaat 26400
gagatcacca tcggcattac gtcggaagac ttttggaaca tcaaccacgt aggcacggcc 26460
accaggacca gcggcatcag tttctacata agttgccata ttacttctcc ttaaagatcc 26520
agagcatctt ccatcgcttc cataccggca acgaaaggac gtgctggagt ttgcttatac 26580
aagaacttcc agatttcacc tgcggatggg tcatccccaa acgaagcgat agttttacca 26640
acagccatag caccctcagt tgcagcacca gctactggac ccaagactac ctctgcgggg 26700
gtagtccctc gacggtaacc cgtcagcatg tcgtagatca tagaagcctg gagtggcatc 26760
tgttgcatca ctacgtccat catccgttgt tctggactac gggtatcctc tcggctagac 26820
ccaccgaact tagccatctg acggagttca tcctggatgt aacccagact catcatcaga 26880
ccaagagtga aggctacacc tgcggcaccc ataccagcgt tggtccaaga accagcgaag 26940
tgtgggctca gtcgtctacg gaacatcggt aggatgatgt taccataggc tgctgggtaa 27000
cccttcaaga gggagaacat ctgaacgttt ccgttgctca tccacatagg cttatcagcg 27060
aaggtggggt ctaggactac ctgatccaca aaccgacgca tagccagagt cttgacgttg 27120
ttagccatca ggacttcaga tggagtggct ggggatacca gcttaagagc atcctgctga 27180
ctaccgatgt taactcccat ttcccgaagc tgagcaacct tcagagcacc attggcagaa 27240
ctgaagggga gccctgcggc tagatccatc aggttattct gatagacccg cttggcagtc 27300
tctgttgcaa atacccggtt aacatgggtt aggatggaca agccgttgat gaggaactga 27360
ccacggataa ccttttggat ggtagagtta aacacctcag cgccaacacg gtcagccatc 27420
agagaggtag cagaggccag ggtatggttc atatcactca taaaccgacc ggtctcagac 27480
tttggaaccc cactgtagat cctgcgggct gcttgcctta ctacctcacc catggttgga 27540
agtacagccc caagggtagg cataacccca gccttagcga agggtatgct gaactcggtt 27600
agggtcgaga agccggcgag gggaagtctg gagagcacga gggcacccga cgtaacagcc 27660
gctagcttct taaggttagg atctttgata cgaccgtgca taccattata ggcatccact 27720
aggtcataca tccgatccac ttcttccttg gtaacccgct taccagcccg ttgagcctca 27780
gctacagcag atgcaatctt agcgttagcc ttctccccgt tgataccaaa cctttcggta 27840
aaggcaatcc ggtgggaagc cccttctaag tagtcccgaa tctcttggag acgcttctta 27900
ggagtatcgt tcagggaata cttgttgagg atctcttggg gtacagaacc aaaggcccga 27960

```
ctctcttcca attgaccata cttaggtact gcatcactct gggcgaaccg tccccgaagg  28020
gtatcaggat ctccctggat acgataccgt ggatctactt cccaagcacc cgtagtctga  28080
ttctgagtaa ctaggcgggt aacctctggg gcagtattac ctcgggtatc atccgaagtc  28140
tctgccagcc agttagctac agcgtcctca gcagcttgtc ggttctggaa gtacggagta  28200
atgtcgttca ggaactctgg agattgaacc ttctcagggg atagaccaaa tggcatatag  28260
ttggggatag taccaacaga catgccacca cggttaacag cctcattcct tacgtcatcc  28320
agcaaagaac gcagacgggt agcctcaggg gtgttgacac cagcggatgt atcagcgata  28380
atcctatcga tctctttgga agacttaccc tcaaagatgc tatcaagttc ggatttccac  28440
ttacctgcct ggagttcctg gtcctcaaag atagtcttac cagaggctcg cttaccactc  28500
atgtcagccc taaagatctc agagaactca cgggctatcg gggaggcctt agcaagtggc  28560
tccaggaggg ccgtagcttc gtttccaagg gcatcccagg ctttcttaat ggtaccccta  28620
ggctcaagct cagaagcctt aggaggggcc gcaggggcgt taggatcaac tacggcagac  28680
ccagctgagt cctgattacg tcccagggtg tccaaaccag aggatacagc accaccggca  28740
gtacccatag cggtaccagt gaatgcagca gtcaggaggt tatccatgaa ctgctcaggg  28800
gattgggtct gcccaacggc atcatacgcg attgtgtcct ggagggcctg ctgggtacca  28860
gaggtaacac cttcagccac accagagact gctgcatgct taccagcctg ggttacagcc  28920
tcaatggcgg tctgcctagg tagtcccgat tggaccaaca tctggtaagc gccatcttta  28980
ccgatgtgct tgaggagtgg ggcagcgata acaacagcac ccgcagtgtc tagtaccgag  29040
aggccagcac caccgaggac tgaggtccat gggttgcttt gatcggggtc tagttccttc  29100
atctggttac tcagggcacc tacgttgata cccatggaac tcaggaagga accaatgagc  29160
gctccaccca tacgacctgg gcccccaaag acagagccag ccttagcacc tgcggcacca  29220
ccagcaagta caggggccat cgaagggaga gcctctacga tgttattctt taggaacgaa  29280
ccgatggatg ggatatcttg gatatcagcg aaagaccgaa catcaggggt tccgtactgt  29340
gacgcttcct gagcattctc ctcggccatc tgtgtgccgt agtctttcag gtagtcactg  29400
ccagtcagtt caccaatggt agcaatagta ccacctatgt tagactgcat ggtatcaacc  29460
ccacgaccaa tcgcagagct aatagaatta gggtcagccg gagttactag ggcactcagg  29520
tctggggcag gctcaggggt agcaggggct acttcctggg gtgcctcttc gataacctct  29580
ggctcattca aggaagccaa ttcagcggct acgtcgaggc ccttgacctc agccagttcc  29640
gcatcaatag cggccttcag ttctggagaa agagccataa gtcaccttct agttgctgga  29700
aagagaatag gctcttaaga tgtatcttag gatactaacc ttcttagtaa gtaagtcaaa  29760
aggaagaagg aatcttaaga gcctataggt ctattatatt acattttgga tactttgtca  29820
agtacctttt atcgggttgg ggcaggatag tccaaatcag caccaaacca gttacccgta  29880
ggttgcagct tagcagcctc ccgctggata atacccactg ggttagcccc cggattagcc  29940
cgaagttcat ttcggacagt ctgggcaata gcctgttggg cagtcttact caacttctta  30000
ccacccagag cctgagaacc attgacttca ctcaggatac caagggcgtc cttagtagta  30060
acagcttcac ctcgggctgc cttagctgct gcctgtcgag cctgagcgct gattttagca  30120
gtcttcagac gtacagcaga actgagctgg gcattctctt gagacatatc ctggccacga  30180
cgggctgttt cagcctgtag ctgggcccgt tggttagcca tatcctgacc tcgctgggtt  30240
agggcaaggt tggctcggcc ccgagcagcc tcctcagtcc accgatccag aagaccagtg  30300
ttcttacgag aggtttcctc aagggttccc ttcttgacct ccaggtttcc ttccccgaga  30360
```

```
cgtacatcag cagcatcctt agccacctta cgctccagat ccttttcctt gatctgacga  30420
tcagcagctg cggcagccat cttctgctgg ttgatcccag cctgtaggtt acgatccaac  30480
tgacgctcgt aggaagcagc gaacatatcc ccagctttac cagtcttgtc tagggccgaa  30540
gccagaagac cagtaccaat gagagcgtaa gatacataac gagacaggtc atcattatcc  30600
atagtcctca tctgggtcaa ctcttcgttc acccggttct taagctcttg ggtttaagc   30660
tctacaccct ctctctgggc atcagcttca actacagcct gggccatttc aggacgactt  30720
acagcaccag tacgaagacc ctcggctgca ccctgttgga tgacctgacg attagcctcc  30780
tcctcatctg ctacagcagc accagccgca gaggccacct ctggggtgat ctcaggctcg  30840
atagagggtt ggttgggggt taccccatag gacaggagtt cagcccccgt agggccccct  30900
gtggcgttct gggctgcacg ttggcctaca ccctgggccc attggtttgc ctcttgagca  30960
acctcaggcc ccatattctc cacagcctga ctagcctgag ctatttcttc agcacgagta  31020
cgctctgcat ccccaagttc tcctggggtt acagccgctt ggatgccaac agatactgga  31080
ccaccgagga tacctgcgat acgacccagg gctccacgac cagtagcttc agccgcaggg  31140
accacctctt gggcagcccg agaccaacgg tcagggttct ctagggcagc ctgagcagcc  31200
cgtcggacac gatcagggat tcctgagccc tctacagcca gcggcagttt gttccttgcg  31260
attcgcgcca tgtccagttc attctgagca gcccggagga tgctagggcg aattggggac  31320
ccttcataag acatgctggc cataggatta acctccaaat agtttactta ggattccaga  31380
ctttggctgc tgtccgaaac cgagttcttc tgcgctagga aggattccca ctcccgctcc  31440
catacctgct gcaacttccg ctgcgcctcg ttcgcttgct cctctagccc cctcgacaga  31500
aaagcttggt actgtttctg aagaaggctc acttcctttc ccgaggagag ccgcgagtgc  31560
tgctccgccc attgcgccaa aagggtttga ttgtccacta gactctcccg attgcattgt  31620
cccaaggtgg gtgggtcggt aggagccttg acgactcaac tgaacccgct cctgcccacc  31680
acctatattc tgtcctatag cgaacagttt ctgagggagg gaagccatta gaagagaagg  31740
ccccctaccc taccacctgc gttcatacca acagaagcac cagctggacc accgaagaga  31800
gcacccaagg aagcaccacc gagagcaccc agggcagacc cgaggccacc accaccgcca  31860
ccacccgaag aagtagtgac attggttccc cccatatcgc cggagataag ctccttatag  31920
gcgaggaggt cgttgaggct gacgttattc tcataggccc acttctgtag agccccgttg  31980
atttcctgct gctcctggtt ctgaagcatg ctaccagcat ctacctgcat ggcattacca  32040
gagccgaggc ccttagcaat agccgacagg ttacccaggg tgttcaacct attctggttg  32100
taagcctgct ggtcttggaa agccaactgg gaggcgttat tctgttgatt ctggagcaac  32160
ctagcggtag caataccttc tgctacaccc gctcgggaac tcccatactg accagcatta  32220
gtggcccctg ctcgcaggtc tggacgtacc gtagtgtcga agtcccattg catctgctcg  32280
ttggctgcac caatggcgtt cgccaagcca gttttgttgg gatcgtaagg accaaggtaa  32340
tcagccagag agctaacacc tgagctaccc aggagagact gaagggcacc cccgagacca  32400
cccagccctt cgatgccacc aagctggaga gcattttggt cagccaccgg gtcaaagttc  32460
ggatcgcccc cgtaattggg gtcaaagccc ccgttatgta gccaatcact ggcacccgag  32520
agtagttcat tatagttacc ttgctgatag ggtgtagaga cagaggtggt cttttgcttc  32580
ttactaccac ccttgtaagc ccgagaatct agggcatcct ctacatcgaa ccccatcaga  32640
cgctttacat taaattggag gaagttcatc tggagttacc tcacgataga aggatacgga  32700
```

```
gtcttcggta tacccgagtt tctctagggt aggcttccag ccccgacgac cttcacattg  32760
gataaaccga cagttaactc gttgggcgaa ctgtccgagg aagtcgtcta cctccgagta  32820
atctaccggg gtttcattcc caggcatctt accactccag aagaagtgaa ggatgttacc  32880
caggggtgct tgggacactt gaattacacc agcgtagcca ctctcttctt ggtagaagac  32940
ataggcctcg tagttaacca aggagtgaac caagtgttcg aagtcccaaa acttaccgag  33000
gtccgtcctg ttgaaggctc gggccagagc agggactacg gtaggaagca gatcgatatt  33060
ctcacgagta atcaaatgaa tcatggagtc accaccaggg ggaatgtgaa tgtacccccg  33120
aagactgctc cttggggaat tccttggatt agaacacggc cattagctgt gatcttaaac  33180
attgcttggt taaccacccc agtctgaata gtagccctgt tgagaacatc aaagacttga  33240
tccaacggag gtgcgttagg gtcagacgga ggtggataag taatagtgct ctgcgctggg  33300
atgatgctgg aataggccgg gataaacaac tcagcaggag gccaatacgc ctggggaaga  33360
tccaggacag tagctccatt agtgtagtta ccaccagaca tgagcatggt tatccatact  33420
tcatccttag cagtgttcat cctataggca caggtaccca tcggctgatg gttgttctgt  33480
ggggtaaata ggataaaatc cccggcaggt tccttgggtt tagtacctgc gagtctccat  33540
tggttatcca agtcgtaatg atagatgccg gatactggac ctaccactcc gggggcaaaa  33600
tactttacag tccctggctt gagcttctta gggggctcca tagagacccc ccagtagccg  33660
tcagctaggt cattaagagt ctgtccaacc ctaacgaatt cttcattaag gaagggcagc  33720
agttcctcct cttcctgtgg tggaatcgaa gggctgtact tttgactcat cgcatacctg  33780
ccttcggggc catttcaata gtgtatccgt tgaagtacca atccccctcc gaagagaagt  33840
cgaacttcaa ggctatatac cggcccacat gtttagtgtc aatcttatag tcctgaccaa  33900
tccggtatgg gtaagggcct ttccatcgaa taccagaacc ttgtacctga gcgttaccca  33960
cccagatgtt acaagtaccg ttaccagtaa tgtgtggaat gatggcactc actgtcttca  34020
tcattcgatc atccccgaga tagatatcgg atctctcaag ggtactgacg aagttctgtc  34080
cagagaatgt agagttatta ccaaagagga acaacttctt atcctggaaa gacgagaaga  34140
tcatactgga ctttgctggg ttataagagc cttcacccca gaccgaagta tcggtatccc  34200
aggggttggg gtcgtcatcc cagaggttag acaccttagg atcgatgatc ccgtaggctc  34260
cactgagaac gttgggaagg tctcggatac tccaagtgtt ttccttccag ttccagatga  34320
tagccctgtc gcagtgctta cctggctcag acctagtgga agagtagcat acccacattt  34380
cagtattcac gtggtctgca agtacgaatg tccgttgata gttgtcaggg ttaatatccg  34440
agaagaagaa cttacggacc tgggcatcaa taacagactg cttctgcaca ccgttgtgga  34500
catatacatc accgtgacct actacaaagt ggttaccatc gaactctact gcacagttgg  34560
gcccaaggat acctacgtcg ttaaacagct gctggaattg gaagatgaac aatccaccga  34620
tataccgcat ggagtataca gagtcttcct tgtagatgat gaaggagtca cgaagcttaa  34680
caccatctac gatggcacca ttggtatcag ccaaggtgtt ctgaccagca tccttagtag  34740
gatctgttgg gtcccaagat gcaggaatac cccagcatc agccgaggta ctccaccaga  34800
ccatctgtgg catttctaca gagttctggg ttacgttcaa ggcaatcata aagttcttga  34860
acgacttcat tcgtttagcg aacgtgttag ccggccagtt aggcatggga ataaacccac  34920
tattctgggg catcaacacg taagggtagt tgcttgggtt gttagcgaag atgacaccgt  34980
tgaatgaacc ggaggaccat ctactggtta cacttgcaga gtgtccacct ggggatacat  35040
ccacaatggt agtaccatcc gccaagtaca tacgctgttc gccacacagg agccaatagg  35100
```

```
gaatattatt ccggatgaaa gggaacatat ccaagattgg ggcctgggct gtatcaaaga  35160
taggcgtatg gcccagagcc ttctgagcct tgccgttctt aaaccggacg ttgttcccga  35220
aggaccattt ctccagtggc aggtcagcgg gggcgatatc ggtcacaatc cccgtagggt  35280
tcttgacctc ttgtctctct agggccattg tatacctcag ttcttaatga tgaagaacac  35340
agaacagaac ggtgggatat tacccaacgg aatgttgatc tttactgcat ggttgtgagt  35400
ctgaccttga ccagcagggc cagtctcaag gttggtattg gctgcgttac cagagcctcc  35460
cgtcagagca cccgagtcac ccgcagaacc ggtgagggta gtagcacccc tagttctcca  35520
agtgtgggtg tgtgatggga tttgggctag ggtaagggca gtaccttcag tgaacccatc  35580
ccatacaatg ttagcgctac cgcctctagt ccctacagcc tgggaagaac catcgatacc  35640
ccaagggaat gcaccaatca ggttagggac gggaatcccg ttagaggtag tacctacccc  35700
attgcacaac ttccaacctg ctgggatctg agctagtgac ccagcccaca tgataaccat  35760
cccaggttta acatactggg ttgtatcagc gactgcgttt agctgggctg ccgttacagt  35820
gacagcctga gaaatattgg ggaaggtgtt cttaatagca ctcttaatga gacgcaggtg  35880
gtcatcccca aaggatttca gatcagagcc ggtagggttc gtaggcacca actggttaat  35940
gtaagttgcg acctcaagac ccattcttgg cctcctttat ctcttctttc atttcttttc  36000
gggtgacata ccgctcccca aagattgcca tagaaatctg gagatcgctc accgcttggg  36060
tgagcttctc cgtggcctgg atgtttcttt caagcagagc ctgattaaca ttctgaccga  36120
caaccgagga acctaccgtc actaccgagg atacgaccag ggcactgacg atgctgccca  36180
ggttatcagt tagaagttgc atcctccgtc ttctccttaa ggttgtcttc caggactttt  36240
acgaactcgt cgtcaacctt agagttagtc ttctccgcca gagccttagc accagtcacg  36300
atggacttag cgattacctt ggttgggaag agggtagcca gaaggttgat tgcgagggtt  36360
tttagaaaga taggcatctg aatctcctta acgttcaatg tctttgatcg ccagtcgagt  36420
gctagcgaag tcagcggcat tctcctcgtt ctggagttcc ataacagccc gttcgagttt  36480
ctgaccccag aactgggacc gagcttcatc catggtgtac agataaatct gctcaaggac  36540
accatagaga taaatctgcg gatacttcgt cagagcccaa gtcgttgggt tagcgaggct  36600
tagctctggg agtacagtcc agtagttcac aatgaacggg gcaccgtcag gaacaacggg  36660
gaatactcgc cagaagttac ccaaccgagt gtagtaggtt acaccctgag gttggtagtt  36720
gtagttaaca taatgggtga aggtatcctg ggtgatgtac tgaagagtac gtccaccgat  36780
aagggagtca cccgtgatag atcgtagagc aacaaagtgc tcaggtatct caatgccacc  36840
accgaaggcc attagggttt cgaagtgttc gttctccctc acccgtagca atcggttaag  36900
acggtcagtg gtattaccaa tgaacaacat cagaagttct tgggtaagat cctgacggtc  36960
agaccactgg atagcggcaa tagcgagatc agttacgttg ttgatcgtag ccattcatta  37020
cacccgtgcc tcagaggtcc gcatccgata gttatctcgg tcattaagcc aacgggtaaa  37080
tcgtgcggca tggtctgggt cacaaccgat caggttaaga tcgatgggac caccttcaga  37140
catggggcga ttccgtaggg cctctacaac aaccaggggg atacttgcta ccttgcgcat  37200
attatccttg cggttgctat tgacacccga gtggcgctct tcggcgttag cggacaggat  37260
tgactcaaca tcttgagtat cctttcggat aaagagccca aggtcttcgt caattgcata  37320
agtcgattgg atactcatga tgtacctcct aaggggaaac aaagggcccc gaagggcccc  37380
gttgggttag acctgggcta caacgtcgcg gatcagagca ccggacttct cgttgtttac  37440
```

```
acgcagggtg tactcaacca gcagttggcg cttctcgctg tcaccggtct tagccagttc  37500
atgctggaag aacggacgca ggtagcagag ggcgtgcatc ttcggatcaa agatgaacat  37560
ggtgttttcg tggaaccagc ggttggcacg aatggtgtac ttaccgaagt cactctcgta  37620
gacgtccacg gtctgcgcaa tgcggttgtc cgaggcatcc agggtgatct cagttgcacg  37680
acccttcatg ttcttgctga tggccttctt gatcgagctc gaagtctgga tcgagttagc  37740
ctgaccaccg ttgcgccaga tggcctcaga ggcattcagg agcatgtctt cggtcagaag  37800
acggaggtca ccagcggtac cagtgtcgga accatcacca gttggcaggg taccgttagc  37860
acctaccgaa ccgttggtct tgtagtaggc aaagatgttt gccatctgac ccggagtagt  37920
ggtgttacgc tggatcttag cctgaggggc accgaccatg gcgtattcca tgtccagctt  37980
cagttccttc gacttcttag ccagctgata cgccagttcg ttcttacgac cagccttctt  38040
gaccttatct gcggtaccgg tgacttgcag ggtctcgtcc gagatttggc agtagttgtt  38100
caacatggtg gtgaagctac cagccttgat ggttgcatcc tcaccttcca ctcgggtgtt  38160
cttacccggc tggcggagtt catcagtctg ccactcgtgg gtgatagcgg tagctacgcc  38220
cttgccgata gcagtcatga acggggtgtc atagggtgcg atgttgtaga tgatatcgat  38280
aaggtcttcg cgcttaccgt tgatctctac agtggagacg gcattagttg gagttgccat  38340
ataatgtact tccttctatt agaaaatgtc gagagaggag aagagagcag cagcggcttc  38400
aaccgactgg tctttcctca gattagcgcg ggcagcttta acccgcttag aaccctctga  38460
ggcttccgcc ctacgagcag caggcttaac tgcggcaggt agttcagtct cctccttctt  38520
ctctagggca gccttgcgac ggacctgaga ttcagcccac ttacgtgctg catcgagtac  38580
agccagttgg cgggcatcag atatccctcg gatctcatcc tcggagtatc caatcgattt  38640
gccgtaggac acaatcttgt caccccaaga ctcatccgtg gtcatttccg ggataagttt  38700
cttggctagc tctgtctgac gcttaacgta ggcagagtgg acaatctcgg ctcgcttctc  38760
ttgcatagcc ttaatgtcgt tacgacgttt gataagagcc tgggctcggt ctcgggcttc  38820
cagggcttcc agtcgaaggg tttgatactt ctctgggtcc tgggccttaa gctgctccca  38880
gtttacattg tcatactgat tagcaccagc aatagcggta acagcatact gctcaagctc  38940
ggccagtaga ttagagcgtt cagcatcaag ctcttcgaat ttagctgcat actgatcctc  39000
tagttcagct tgtcgagtta caaactcttc attgcgaagg tagccactct taagctcttc  39060
gaagttaacc tcgtagactt catccccaat cgggatctca aagagtttat cctcaggatc  39120
ttcctcggac tcaacctcgg gatcttcctc agaaccctct tcttcctcct cggactcaac  39180
ctcttcggtg tcctctggag taccttcgtc tactacctct tcctcctctt cttcccctac  39240
gactttacca tccacggttt catcaccggg ggccaggagg tcatcaccta gcaaatctcc  39300
gaaggcttcc gctgcctcga attcatccat gccttgattc tcaaggtcca ttacttatac  39360
tcctttagag tgatcgaatc caggatagcc tgaatacgaa gttgtacgcg gttgagggca  39420
tgtagttcgt ggtagatggc ctccctggac tctgaatcct taggtgccgt ggacttccac  39480
tctccctcga tctcttcttg gacaatacgg aaaagctcag gaagaacgtt ctcacgtacc  39540
atctgttgtg ccgcatcagt cagcactaga ctatagccaa aacgttctcc caagattaat  39600
tcctcactgc cttagatggc ttcttagtct caggtacctt accgtctccg atataagcag  39660
cccgagcctg agtagcctca agatgatact ccgcttcgtt acgagcccgt tcccaagtga  39720
aacgatcacg ctcaagttgt agttccgctt ccttaagggc catttctctc tgctgaagga  39780
cagcctcttg cttcttcagt tcgatctcag ccagtcggat ctgagcctct acctgcttca  39840
```

```
tctgggcctc cgcttgctta gccaaggcgt ccgattgggc acgttgggca tcagcttggg  39900
ctttgatatc ttcaggctta ggttgtgctt ccttctgctc tctgatggcc ttagcccgtt  39960
gagcttcagg agaatccggg ttagtccaga agcgatccgg gtctttgtac ccagcgttct  40020
ctgtgacttc cttaaggatg ttgtaaagat tctgctcaga gacaaggacc ccgagacctc  40080
cacccccgac tacagcctgg gccatttccc agatacgcat caggtggagc atctgctggt  40140
ctttgttcat gttgccaata ccaacggtaa ccgtcaggtc ggatctctct cgccagttgg  40200
cagggttaat agcaacccac ttgcctcgta gctggaagac ctcttcctga ttctggtact  40260
tgatggcatg gtcatgcaga agttggaaca aacgcttaac accagtctct gcaaacatcc  40320
gggcaatcag gtcaatctgt tgctcagcag cagtcatcaa ctggtttaca ctcatagccg  40380
cttggttaga gtgcagggtg ttttggtcta gacctcgggt acggtcagtg atacctgtcc  40440
gcttacctct gtctgcctct agtcgatcca gcatcccata gacttcccca gacaactgag  40500
gggtctccag aggcatgata gagttcatgg ccttaacccg aacgataccc gctgcctcgt  40560
tggtcagcaa gtcttcgagg ttaacctggc catccaggac tacagatcgc ccttggttgg  40620
tccggtagat attgtccatg atgttgcgca tgagcaccga gcggatctct tgaatgtctc  40680
ggatcttatc gtagacactc atcccgtgga acttatgggc aattcgatag gcattcaggt  40740
cagcgaaggg acggcaatcc caaggctcgt tgctgatgat gtagtcgccc acgtacagga  40800
tacggcgcaa ctcagagata ccatccccat ctacgtccag aagggtgtag cactcggagg  40860
cccatacctc acggttggct tcagcatcat ccccagagtt gtactggagt tggccagtca  40920
tatcgaagtt atcacgtacc aacctttctg gctgactatc agagaattca tactcatcgt  40980
atggaagctc atctagtaca tcctcgggaa cacccaagag ccgcaggtca cttacggtat  41040
acttctcacg gtgacagagg aagcgtgcat cgtcaatgca ggtagccaac cgatcaacca  41100
ggaagttctc tggcttaata caggtgacct taatctctcg cttcttcttg tccttgcgaa  41160
ttttaatact gtaggttcca tcctcgtcca cactctgtgc tagaatctcg gtgtctggat  41220
cagccaggat atccgctacc atttcctcag agagaccaga gaatcgttcg aaggtagggt  41280
tcaggacctc ttctacatag acctttacaa caccggtctt catcatcaga gtgtcttgga  41340
accagtcgaa cattaccttg aacccctcgt tcttacgcat gaagaggtag ttcacatact  41400
cagtctcttg ctctgcctgt tcaacatctt cggcagtctg aggttcatac ttaactactt  41460
gaccgcctga cgtgaatacc ttcataagag aaggcataat ccagtctaca gtctcttgaa  41520
cgtccctaga tacaatcgcg gacttcccag ggcgctcgtt accgaagggc tctccgaagt  41580
aatacttcag ggcctcagaa cgctgcttgg aaagttccga agagttgaaa tcaagggcgt  41640
cgttaacaag ttggtctaga tgacgaagta cctgttcatc atccataggc ttaatcttgc  41700
gacgacgctt agccattaga caatactccc aaaccaatca ggggtcaact ttgcagtatc  41760
actcctgtag tatccactgt ttcgtacagc accaggacgt gcatgccggg aagccatcaa  41820
cagggcatac cgggtagcgg agatcatatc gtcgtttctg tcgataatct ttccgtcctt  41880
tcggtggtac attttcattt cttttaggaa gttcgtacac gtattaaaca ccttcagatc  41940
accattctcc atacgggtca acatccagtt aacaccgaat tctacagagt tacctccgtg  42000
tttaccatca ggacccggtg ggttgctgaa gggctcatac actacattga ggttgtggtc  42060
atctttaaga aggtctacga atctacgacc agaggttgct ccatcatgct taaaggcatc  42120
atggggaaca actaccggga tctggtgacc acccttcagg tagatagcat cagcgtgcat  42180
```

```
cccaagggtc tcaccactct cactcctctc atcatagagg taatacttgt ctttctcggg  42240
atcccaagca acacaggcga tagcgttagg gtggtcaaac ccgaggtcga taccgatgat  42300
cctatggaag tgatcgggga tctggaaagg ctcacataca aacttctctt ccagaatggg  42360
gaagactaca ccagatccga gcataggaac accctcggcc ctcatcctgc gttctgctgg  42420
agagtatacc gagagtagct gctctttaac ttctggactg aggtgtgggg cgtcttccca  42480
gcttgcatgg acaaggaact gaccaggttt aagatcctgg aggaagtcct tgacgatctc  42540
cgtcagacca tgctctgggg taaacgtcag atatacaata cccccagtag tagccgttcg  42600
ggttacacac tgggtataaa tatccttggg gcattcctca tcgagccaga tgacgtcgat  42660
ggcagtaccc atgaatttgt cctgggacat ttcgtaggac ttgaagataa gggacgagag  42720
gcccccggag gcatgcttaa caactactgc ttgcacacat ccgggtttac cttccctacg  42780
aatcgtctct acgatatctt ccttggggat catccccgtt ccaaaagcct cagggttctt  42840
ccagtcacct agtagttcgg actgaagaat atcccgagtg gtatccgtgg agatccccgc  42900
cgcccagcag ttcactggac gatcatactt tctaccagtc caccactcag ggtagcgacc  42960
ggtgaggtgg caggccatga taaaggcccc ggtgtaggtt ttaccacagc ggttaccagt  43020
catagccagc aactgggcgc agttcgagga agctgcgata aacttctctt gccacccata  43080
aggagtgtac tggttcatgc ggaaatactt ctgccgctcc gccaactccc tgactagatt  43140
ccgtagccgc tcttgggtat ccattagacc accttgtcac ctactgttga tgcacgccac  43200
agggcccgtt ggaggtccct tacgcgcact ggagtttgtt tagcccagag gctatcttct  43260
gcctcccatg cagcctcgtc aaaccttccg gatttcagaa gattccacgt cttggggaac  43320
ttcttcgtcc acgctgtacc cagctggaaa ttgacgctaa cgagggcatc gaatagctct  43380
ggagtgcaaa aaggcagctg agatacttgc ccttgggctg catcataggc tgccttacta  43440
tctttctcta gccaagtctc tgctcgtgct agggtaatcg gtccgtcttc cccagggagt  43500
tgcaagtggc cataaccacc agttactttc ccgagggagt ctttgtacca ctttagtacc  43560
aacccttctc ttcgcttgat taaatcaagg tacttaagcg gttgggaaag aaatgacttt  43620
agccaactct ggctcttcgt cgagaattcg tcgaacttca ctgattagat cctctgcgga  43680
catatcttcc acattcttag tagtaagctc cagtttctgc ttagctccga agcctccacg  43740
atccaggata tcctgggccg ccttgaggcg aatcccacct ttctcttctg ggttgctagc  43800
gatctctaca accacacgaa gcgccatggg gacgtgactc ccgatgcgct cagagataaa  43860
ggcgttgatg tattcggcat gctttcgatg gtatgcagct acgttgcgtt gcgcatgatt  43920
aggagagaac ccagcggcta tatatgcttg ggttttgttc ataccatctg ccagagcctc  43980
acaatagagg tctagctttt ctttagcaga aagaggagca gccccaatcg agacaacctt  44040
ttcgtctgac atacactgct ccgatctctc taaatggtca ccccggtagg actcgaacct  44100
acgacctcct gtgtccaaga caggcactct aaccaactga gctacgagga gttaatggcg  44160
acccatgtcg gattcgaacc gacggcttct ccctagacag gggagcactc taaccgctga  44220
gttaatgggc cataatggtt gggacggtag ggctcgaacc tacgacctga gagttatcgg  44280
ctccctgctc taccaactga gctacatccc aattaattct aaagcaccct taaggttaat  44340
ttctcaacct tataatgcta ttatatcaca ctttttctat tttgtcaagc ccttttcat  44400
cttttttta tttttagtcg caagacccgg atttgttagg ggttttgctg gaatgggaaa  44460
ggggttctta agactatctt aagataacct taaggtaact aaccttctta gtaagtaagt  44520
caaaaggaag aaggaatctt aagagcctat aggtctatta tactacattt tcgatacctt  44580
```

```
gtcaagtact ttttgatatt tctttgataa tcacatgatt tacccgacga acggtatgat  44640

agggttctat agatataccc taagactacc cttcgtaggt tgctggtaag gggtaagtgg  44700

catagggctc ccttgatcca ggttctatag gtataccttta gggctacctc tgttctctat  44760

gccctggtct attgcccctt tatccagtaa tataccaaca gttatcgaag ggtgcctttg  44820

atccagggcc tataaccggg ggatacccca aaagtctatt ttatcctccg gtgtatctgg  44880

ggaatatccc cccaggagtc ccccagataa agtgggggtg gcctatcccc aggggtatag  44940

cccctagccc ctccctagga taccatggga ttagtccggg ggtcaacccc ttgagatacc  45000

gttcatcggg                                                         45010
```

<210> SEQ ID NO 6
<211> LENGTH: 66505
<212> TYPE: DNA
<213> ORGANISM: Bacteriophage P1902

<400> SEQUENCE: 6

```
tcgccagggc atcgttgaat ttctggatgt tggactcgcc ctggaccctg gactggagtt     60

ccgcagtcgt cagctcagtg acttttccca tggccgggcc gatcttcgcc agggtgctta    120

gatagtctcg cgagacgcca agggcatcgg cgtaggcgga aatttcatcc ggcttcaact    180

tggccatttt cgtggccaga tcggtgatga tgtcgttgag cggccgtatg cccttttgga    240

agctcccgac atcaacgccg gccatacgca gaattcgcgc ttccgggccg actcgtccga    300

tatcgcgata agcgcgccgg aaagtgtccg ccagattttt ggtcatttcc gcgccctgct    360

cgcggctgat ggttccaccg gactggcgaa cgaattttct ctggtactct tccaagcgtg    420

ccggggcgat gccgatgtcc atcgcctgga tgcgctgttg attgtactgg tccctggtgt    480

tcatgaacgc cttgacgccg gccgcgacca gggccacgcc agtggcgcct attgccagtt    540

gcgcgttcat tccgcgaatt gcgctcgtca cagaatcaat ctgcggaacg actcggccga    600

gttcggtggc cgcgccgtct gcgaagtggc gcaaatcctg aaggccactc gtcgatgcgc    660

tgttcacgcg cctgatctgg ttctggaggc gctccagatt gcgctcggct ctggcagtat    720

cggcctcata ccgaagtatg aattcatcca aatcactaga catgaatcac tccggcttgt    780

tggcgagtcc ttcggcgatc ttcattgctg gaccaatgag cttggacgcc tcggccagaa    840

atgcgatggc catctgcgat ccgacttgtt cccaatagtc cggccggtcg gcgtgcgtgg    900

ccgggtcgat gccattgtgc ttgagaacag agttgaaaac cagttccacg ttcttccagt    960

ggccgaggtg gttgttgatg actgccgcgg tggtcagcgg aatgccggcg tcatcgtcgc   1020

caagcagcac tttcgcatag cccaggattt ccatggtgaa agagcggcgg aagtcggaat   1080

cttggctgac agcgaattcg acgaaacggc gctggaggtc ccagccatcc aatgccgacc   1140

acgcctcgat ttgtacgcga gtttgacggc catcgggaag attgatttca agcatgatac   1200

atcctcagaa gtagctggtc acgcgattat atagcgattt tgcggccgaa gatatcgaat   1260

cgccgatggc gcccaaatcc agcaaattag catcagaaag agattgaatc tgtaccccat   1320

aagtcggact atcttgaggg aacgcaggat cgaattcatt caatactgga ggctcaacct   1380

gctcgaattc catattgatc tcagccgcgt tcaacatgtc tggagactga tctacatcga   1440

gcgtcatgat ggccagttta tcggccaata tcgacttaga agtgatagcg aaagtcgagg   1500

tgttatcatt gaaagcgttc atgatacttt caacggtgga caggtccgga cagatagcat   1560

tgatgcggag tcgcaccggt tggatgatct ttccattctt cacatcaatg tccagagctt   1620
```

```
cggtgtacac ttgagcttcc gtctggtctt tcgtcgccag aggtttcgac actacggaag   1680

ccggcgagta aatttccact ttcttgactt gaagactctt ccagacagga agtttggtaa   1740

catcatcgcg tatggtgaga gtaggcgtgt tgagaataga cttgaggaaa gagttcaatt   1800

ggcacctcag aacaagtctg cggcgttctg gacgccgttc actgcgtagt cgaacagatc   1860

gccggccgag ccaaccacgt cttcagctag ggccagccct cggtcgatca tagaagagtc   1920

ccctgcattt ctgaacatta taggcttggg attctggacg agaacttggg agaatgtcag   1980

ccgcgcagga gtcgccgata tcagatccgg agtctgattg agcgcttcgc tggtacacat   2040

catccgttcg aataccatgc cgcgagtgat gactttgtac agcgtgtcgc gatccaggag   2100

caattgattg atctgatcga cgacatcaat tgaagggcaa aatacttcga tgatgatttc   2160

catagggtgg atcgttctgg aatccatctt ggtcgtacca tcttccagca tgtggcgttg   2220

ccctacagaa gaaaaccggg tgttgacccg gcttatcctc aaatccgcag caactagctg   2280

gtttgtgttt tggtccacaa tcgaaaaaga tcgcgaactt aggaggctgg tgaaaatccc   2340

taacatcaga ccacctccag taccgattgg ataacgttag aaatggcttg acgcgcagtc   2400

tgggcgccaa gatagctacc gaaaacaaag gtgtacgtgt tgcctttgcg ccgtccggtg   2460

ttctgtatgg tgtcgatggc cggacccttg aggatggttc cattggacag aacggtgcgg   2520

ccgccatcag gaagagtggc cacgagagtc gtcatgtccg ggatgattcc cggaagaaat   2580

ctgaatgatc cctttttgga attgagaagg atgcgaaggt taatatcatc ctcgctccct   2640

gcgatgacgg atacagatac ttccagagga gcagccttgt caaaggcgaa taggccgccg   2700

tcataaagca tctcatatcc gaacggctcc agctctttgg aggatatcgg actctcatca   2760

tcagcgaact tcgacaagga aaaccccatc gggaacgatg aggcggaaac tattacaatt   2820

cctgtgccga agccgctgac gttgatcatg tcgagtcctt acttgctggt ggttttgcga   2880

gaggtggcct tggcgggagc cggggcttcc tcttcagcgg ccggcgaggc tgtttcctcg   2940

gctttttcta ctggggcggt ggtcggggct tcctcggcgc ctttctcgtc gccttggccc   3000

gctgcaggag cttcctgggc gccttccggg gccgattcgg ccgcaggagc gtcggtcgat   3060

gccggagccg ggatggttcc gccgttgtcg acattggaat cgacgtttac cgggggaacg   3120

ggaagaccgg ccggcgagga gtcgcccttg tcggtgttct tttcgcggtc caggccttcc   3180

agatcttcga cagacgggtt aaacgagggc agcgggtcca ggggcggcgg atttttgccg   3240

tccaggaaca gttgggtgcc gttggcgtat tggatgcgga tggtactcat ttcaaactcc   3300

tgtggtaaca ggcccgtgga tggtgatgac tttcgcatcg acgccgaaga cttccccggt   3360

tatgtcgatg tcaagctgct cgatgccggt cacatccggt gaggataaaa ttgcatccgc   3420

gatggatttg cgagcgtcat catagctttt ctgcggcgag aagatgtatt cgaaataccc   3480

cacaccggag ttcacatcga aaatgttttc gccggtgcgc atgagcatcg ccgcccgaac   3540

gtcctgggcg cacgcttcga catccctgag gataaccatg tttccattgt cgtccaaaag   3600

gatatcgttg ttcgtcccgg ttctgatcgt tgatgtgctc attctttcct cgtggcaagc   3660

gcctgatact cggcgaattc ggcgccgtcc agatagaaca ggttaatgcc gtcgccgaac   3720

aatgtccaat cggcgtcgcg gtcgaagacg aaattgccat agtcaggtcg gtactgatgg   3780

ctgtactgga gaagaggaat cccgccgaag cagcggaccc catggcaaac gatcacgccg   3840

tcgcggctga tatcggcatt catcatgtcc atgttctggt acaggcgaat cttccaatag   3900

ctgctaccgg cgttaaatga gatcgcttga ttggggactg ctgtcagcgg aattttcttc   3960

atcagctagt accggctttg atcacttttt caaatcggaa ccgatacggc ttggtcttca   4020
```

```
gacggccgac gcttgccacc gcgttgatca gaacgccgtc gattggggtg ccgttggtgc   4080
aggtgatttt gctgccgtcc ggcatcgcca cgaccaggcc gacgacatca cgagcgcccg   4140
acttgtcctt tccggtgcgg ttggcatcca gcaggactgc caggttgcgc tcgccctcgg   4200
tattcggaat gacgttgacg actacttcca ggatgttcgc ccggttccaa actaccatgt   4260
caccgttgag accgacgccg gtatcggcag cggtgaacgg cgggctgtcg atgggatcgg   4320
catcgtcggc gaactcggtg acggtgaatc cgttcgggaa agttctgctt gccgtgaact   4380
ggcagatcga gccgaacgca gaaatgttga tcattgttta ttcctcactc catttatgga   4440
aggtcgcggc ggatcgagtc cgccgcaaac cattagatca tcacatccga cccttcgacg   4500
aagcggatgg catcgccctt cgaatagatc agcgtgtagt tggccttcca ctcggtcaag   4560
ccagtgttgc tgttggtata gctggagaag gtgatgttga tccagtaacc cagggtttgg   4620
acttgacgcc aggcgcggcg atcaccggtg acttgggtga tgtactgctg ctggacggcg   4680
ctgatttcct tgccgtaggt gaacgtgccg ttggcggtcg ccttgtccag aaccggctgc   4740
agcaccgcca gggtcatcgc ctcgccagtg ctgctcgccg gaaccgcatt gacgttcagg   4800
aacaagtcca ggagcgcttg agcgatagcc gacttcagcc agatttcgtt ggcatagacg   4860
ttcatgtcca cagcatcggt cggaccgccg cacagaatgc ctcgctggta gaacgcgagt   4920
tgctggccat tggcctgggt gacgccgatg tagttgcccc ggctcttgtc gacggtgttc   4980
gcaacggtat cgtcggaaac ggtgatgttg cggccaggga attggtagta catgtagttt   5040
tgcgaagcgc ccggctcatc gtagttggtg gcggccagaa tctcgctggg gcactgctcc   5100
acgaagtcgt tggcagcagt cgccgacagc acgttcaggg cggtcccggc gttgccattc   5160
accaaggtga aaagagtgcc gaggttcgcc agggaagtag cgaccgtgta gatgaactgg   5220
ttgttctgag ccgcgttcca ggccgacacg gccttgatct ggtcattgtc gagcggcgca   5280
ccggcgaaca ggaacgaacc gaagttgttg ctgacattgg tgctcttggc aacggccgcg   5340
tcgggaagat cggcagcctg gccggcgacg ttgacgacgt tggaggtgga ccagccgagg   5400
gcagtggaca tgtcctgggg gtcggcagat ttcgccacgg ccagaacgcc ggtgccaatg   5460
gtggcgccga ccaaggtgaa ctggttggtg ttctgattcc aggtaacggt agcctgggcc   5520
agctgcgggt cagcgttctt gcggatttcg gtctggatga tcgacgccac gttgtccata   5580
gaagtcgcgg cggacgtatc gatggcggtg atgttctgtt cggccgcgcc gaccatgatg   5640
gtcagaaccc ctgctgagaa gccggcgaaa tcggcgatgg tcttcggcag attgtcacca   5700
actaccatcg gcgcgatggc ggtatttacc cagcgagcga agctgatgct ggacggcgaa   5760
ttcacgcttt tgctgatgaa cttgaagtat gccgcagcgc gctggtactc ttccgactgc   5820
gcgccgaagt aagacatgac tgcgttggcg ttgtcgaact cgatgacgat tccgggcggg   5880
atgacgttgt tggtcgtcat tacgcgcaga atcagctttc ggcctgcgac cggagcgcct   5940
gcgcctacgc ccgaaatgat ccggatataa cggctctgac tgatcactgg atgatctcct   6000
ggttatgtta ctctgctgct aatcgattga agcatgtgcg ccgtatcgac cagcggtctg   6060
ttgaatccct ttctcctgac cgtagatgct gagttagcca cccatggccc ggtccttatg   6120
cttctggcta tgtatccttc caacgccagg ccgatctggg caagagcttg atctggagtg   6180
atctgtcctc tggccagcct catggctatc cggttctgga ttgcggcgcg atctgcggaa   6240
aacaagttcc aagcatatcg cataaacggt ctagccggga tggtaattct gtgaggctta   6300
gttacctcgg tttctcccgg aaagtcgttt ctgacgaacc gaacgccaac aaaccggccc   6360
```

```
cgaacaatgg cgtccctaat atacctggtc ccgcccggat ggtcgatagt tccgccgtac   6420
tcattgagac gtgcgattct cgcgacttgt attccgaccg acccacctgc cttgtcagga   6480
tatcgagccg tggaatacca tccagctgaa acagacctgc cgcgcatggc tcttaacatc   6540
tggaggtgcg cggcgattag ctctgaatcg cgcctcagac tcatatgcct atcaataccc   6600
catcggccga atatgctgcg ttttcgtaca ggcgaatata ttggttgtaa gtgacaacca   6660
tgtcaaaact tgggtggaat tcgaactggt gattgtcgtt ctcgaatgcc tcgttggaaa   6720
tttgagacac gcgaagaatg aggaagtcca gttcctttac gcgctcaatt gtggatcgag   6780
cttggaaata agctctcaca tagttggcga tatcagaagc cgtaaccacg tgagtgattt   6840
caggattctg ccaatgaagg gaactgatct ggaaagtcgt ctctacatgc tgtcgagtta   6900
tttccacata tttgcgggcc gtgttgtcca ggtaccaatc ggtggcaggc cagccgcgag   6960
gaatgtcaaa cagcttctgg aaaaagatgg tcggcctggt tgacgttccc tgttgggtcg   7020
gctgagcttt ctggacgact tcaaaatccg ggaactgcaa agcctcttta gcagatgcca   7080
tcgccgcatt cagctcgaca accattttcg ctatcagttc gccgtcaaac atacaccacc   7140
tagaaagtcg gtttcccgtc atcggtgaac ttggccgcac cgatatccac ggccaggcaa   7200
actccccagc cgtcctgata aaaccaggag ccttgagact ccagctgaaa aactcttccg   7260
gtccagagga actggtcacc ggcaacatcg cgatccaagt caaccatctc aaagttggcg   7320
aagatcataa cataattccg ttggaactct agattaaact ggacatactg atcgcgtcgg   7380
actcgctgga cagatgctgc caggtcgaaa ggctccccga acatggaaac gtactgggct   7440
tgatcattct tcactcgctg ctcaaacttg cgatatctca caatttgagt gccgatgacc   7500
ccgaaggcca tgcgcaggag attcgcccca gggatcacca gaacgtccct ccaaccttcc   7560
ggaatcctcg acgctctgga aggccgccga tgtagaatcc acccacagac ttgacgctga   7620
ggagcgccca cagctcttgg ccgtaaggcg tcccggacag ccaccactgc caaccattct   7680
tggccggggg cgcgagcttg gccacgctaa cttcgccgac agtggcgctg gtgatgaaac   7740
cgccttgggt cccacctgct gttacgccac ctccagccgc gccctgaact tgcatcgtgg   7800
acagcgacag gaggtgggcg gtcagaagat acagacaggc ttccagggct ttaccattga   7860
gaatccggta tggcgaatcg cgatcagaaa tgaattcgca cgcaatgtcg aagtacatct   7920
gcaggcgcac gtccggataa gcggctggat cagcaaactc cggaaacagc gtgcgaaact   7980
tatgttcgtc gaaaatcacc ataccgaaac cctcggttaa atccggaact cttgttcctg   8040
ggaagcgctg gctgtggtca ccttgatttt ctgctgcagg cgagtagcat ccagaggctg   8100
gaatccatcg cgctccatgg tgcgagtctc tttggaaatc cgctggtggt cactggtgat   8160
gtcggtcttc acgactcgca gataaccctt ctccatgtga cgcatgaaaa tcttattggc   8220
ctgaagcagc tcgaaatccg aatcgctcac ggcagtacaa tcgccctgtg gggtccagat   8280
cggacgtccg gcctcgtcgg aaatcatgtc gccgaagccg gaagtttcgg atgcgatgcc   8340
tgcgcggccg cgaatcagaa tctttcgctg gaggcgagga ttggacggat cagaggtgtc   8400
atacgcattg taagacaccg attgagtcat ggaggaaacg atataaacag tcattggcgt   8460
agtcctagta attatgccct aaccggcccc tacaaccgag ttagagtcag agtgaacaaa   8520
ggccggaagc ccggcctttg gtgaataggc atctgttaga tgccgaggta gcgcaccaca   8580
gcccacggac gcttgcacag cgcaccggcg gtgccgttgg agaagtcttc cacgtacgac   8640
ttcgcccgct tttcgacacc cagggtgatg aacttgctct gtaccagctg gctgaacacg   8700
ctgccgccat cggtgctgcc atcgacggcc gcgttcacgt cttcgacgaa gagcaccaga   8760
```

```
gcatcttccg gctcttggtt tttcatctgg acgccggaca attccggagc cgacacgatc   8820
cgcattttcg gataggtctg ttcgatccag tccgaaaccg aaatgccgta gggcgtggtg   8880
accgacaggt agtccacctt gctggtagcc agggccaggg tgatcttttc cgccttcgga   8940
tcgatctgat cttggctctg aatacgcagc tggcgaacgg cctcgcggat gtcgccgatg   9000
atgcctgccc agtcggcagt ggaccagccc tggctcggcg gggtctggaa tgccggcagg   9060
ttgggatcgt tcaggaaacc ataggtgcga ttgcccaggc cgctctgcca gccgtagaag   9120
ccgatggcgt tgcggaagat ttccagaccg atggccgcct gttggcgctt ggtttcggcg   9180
ctgttcagac ggatggccga ggcgcgaccc tcttccaggg tgcccaccat catgcccagc   9240
tcgccacgaa cgatggtgcg acgttcgaag ttggggttcc agctggtcag cgggatgttg   9300
gtgtggtcgc cgtattccac cgcagtgccg gccggctcca cgatgccctg gacgatttct   9360
tgatcttccc aggagccaac ggtatcgatg ccgatgattt cgtcgatctt ccgtgcagcg   9420
gtcatgacct tcacgaagcc cggcaaccag gtctgcagga actggatggg agtcgggatg   9480
gacggcgtgg tcaccggggc ggtgaagttg ctgtccatgg ccgagccgga gcggaacgcg   9540
ccggccttcg ccaaggcctt gatctggtcc tggacgacgg cgtgatcgaa taccaggccg   9600
atgcggcgca gagacgccac ggcgtcattg gtgatgtttt tcaggtcgaa aggtttcgca   9660
ttgcggcctg cgaggcgcga atgggtcttg ctgatctggc tcatgacgcc tccttactgc   9720
gtgagctgga cgatggtaac gccagcaacc agattccccg ccgactgggc cggcagactg   9780
atggcgttaa cgatgcgtgc gttgggaatc tggaccaagc cggtcggcat ggagccggcc   9840
ttgaagccaa ccagggcgcc ggccggcagg ccaagcgcgt tgtcggcggt aggcaggttg   9900
tttggtacat aggcgaccag gtcaccatag tccaggtcca gggcggttgc ggcgccgttg   9960
aaaatttcga cgaccaggcc ggtggccatg tcgaagaact cgccttcggc gccatcgggc  10020
agatcatagc tgggagccag ggagtctccg gccgaaccga acagcgcata gtgcttcgga  10080
tgaccgagga caccaaagaa gttggcgccg ccgatcacga cttcagaagc gcgagccgcg  10140
atggtcttcg gctgaccttc gccgagggcg ctgacgtcac cggcgtaacc gaaagcgcga  10200
ctgatgcggt tggggccggt ggcggtggca gccggattta cggcagacag agacatgatt  10260
cgacccggcc gcgcccgctt cgggccgtcc tcgatcagat cgcccggaaa accaggagtg  10320
tactggcggt aaacttgttt ctggaacatg agttactccc ccttcaggta gctgtccagc  10380
tcggcgcact gcggagcaga accggccgaa tcctgggctt tcgattgacg gctggccgcg  10440
ccgcgcgagg cttcgacgcc tttcaggtac atgtcgagcg ccagagcttc ctggcccttc  10500
gcacagctga tgttcagctt tttcacgccg taaacagcga cttcagccga gtccatagct  10560
cggtgatcga acgcaccaac cacggagcta agacgcttgt agaggcgatc tttagcagca  10620
atgtcgcgat agagaccgcg aattgcagca tcttgcgcgt tcttctgtgc catttcagga  10680
agttcctcgc tgttatcctt gctctcacca ccatcgtcgc tggcggtttg cgagccgctg  10740
aggctgctct gctcctccaa gccctcgacg acatcttgac cttcgccatg ctcttcgtct  10800
gccccttcgg ctaccgtgcc ctccagtcga gccagaatgg ctttgacctg agagatcagt  10860
tcggcgactt cgccttcacc ggacatttcg gatgcggcgc tttcttgatg ctccggctcg  10920
acggcggcca cggccggatc gacaacggga ggctcctctt cctgctcttc gtcatccttc  10980
tgagcacctt ccagagtcgg atgctcggtc aggtgctcgc tgtcggttgg ttcggccgga  11040
gctgcgcctt cctgatgctc cggctcctgc tcttcttcgc ccaggaactt ctggacagac  11100
```

```
gcagatagct tcggccacag ggcgcgcaac tcttcgaccg ccgagtcagc agcttgccct  11160
acgcgctgga caggggggctt ccgcttggct ttcttgagac tcatttcatt accctcatcg  11220
gatggtctga aatcaaaact gagatggtca aaacacagac catccaatac tctggccccc  11280
ggcacacgac cctcttttac cagggcgatg tggttgccgc gcatcttgtc ctggacgact  11340
tcataaggcg tcccgttcca gatgccgggt tgctcagtgt agcggcaact atagcctagg  11400
gacaggtctt ctttgcccct ttccagctga ttctgcatgt tgcgggaata gatgcggata  11460
tcgccgcgtg cccatggggc ttcgtagtaa gcgttggatg tgatgatgcc ctccacccct  11520
ttgtcttcgg gggccacgct atcgtcatca tcgtcgaatc ccgacagcat ctcatgctcg  11580
tcgatcaacg ggagattctt cagagattcg atgtactccg gatcgctgac ggcagactcc  11640
gggcgatata cgttgacaat ccgcgtcgga tcgcccggaa gaccgagttg accagcagaa  11700
tattggaaaa cgccataaga gctgatcggg cagccctcta tggtcatata tccattttcg  11760
tcaatttttc ttttcgactt tgccatcgtt aattcgaaga gtcgtggact atggctgtat  11820
tatatacgca gtacatctaa gggtaaataa gcggaacaat aattagatgt agccgtgact  11880
gttaacttac attataattt gtattatgat ctaattacca gtttcctcag ccgcgaaaat  11940
tcggtaattt ggtctcggaa acttgacggg atttgtctaa gcctactgcc gcgaggcttt  12000
caactcctaa actaattcaa attaccaatt taccgattaa aaattgaatt tcaatacgtc  12060
tagagcatat agattgacgt tatattataa cgttacttat agatgaattc tattggaacg  12120
ttacttctaa tttcccaggc tatatacttt tgaagcatgc ggctaaatcg gaaattagga  12180
actggctctg ttaaagcctc gcggcagtag gatttccaaa ttactgctat tttccgtaaa  12240
cggtaacttg cggctatccg gactagaatt tttagtcaga atccagattt ttctcagcat  12300
tatcggccaa aagccatcaa gatggcgacg ccgatgattg ccaaatcgat ggcggcaaac  12360
ttcaggctga agaatccgcc gtgaatattg gccctgatta catcgaccac gagtcggcgc  12420
cggcacgtct tgcggttcat ttcacgagcc tcgacagagc gtccaccagg gcgcgaagat  12480
cggcgacgag ctcaggcgaa caatctttcg ccgtcttccc tttctcactg cgctggatgg  12540
aataagcgat ggccgcagcc tgctttgggt ctttaccggc ttcgatttcc cgcttgatgt  12600
tttcagaacg agcctcattg gaagtgccat gaactaacgg catatagcgc tcctatcgat  12660
gtcaaatgac tggtatcttt ctgcatctac agttaatcgc ccatcctggc ggcccctggt  12720
ctgctttcgg accctcccaa agtctggggt cattcagctt gaacctcttc ccatctttct  12780
ccaggtgggt gtggcgagga gtcttgccgg cagaagagtg tagccactcg aactcctcga  12840
ctccattttc cgccattctc tcatcgctca gagaactgta aagcttgctt gtttgatctc  12900
ttgcgatgag ttcgattcga tcttcagaaa acttcccgac tttgcgaagt gcgttagtta  12960
tgccggaagt tccttgctct tccggattcg gggaagtcag agacagcatt actgatgtgt  13020
aaatcttctc gtggacttcc tcttggatct tggtgatgag agtatgattg taagtggttg  13080
cggcctccag ggtgttcctg acgctctcat tatacgcagc tcgtggctga tcgacgccgg  13140
ccaccgacaa gctgtgaagg gtcgcggcgg tagcggcttc ttcggtccgg ttgacgaact  13200
ccggggcgat cttggccgcg aaaccttcaa aaatgcggct ccatcgctgc tgtaggcttc  13260
gaagggtcat cttgaacagg acgttaacgg attcgtctct ggcgaagaaa cgttcggccg  13320
caggctggga cagcgccttc tcaatctcgt ttcgatagtc ggagatcatg agcttggaca  13380
tatccttcat ctgctttcga taccaggcct cgattcctgc cgatggaatt atgggcttcc  13440
ctcttccgac tggaagaggt gcccggcgct cgcgcttttt ggaggccttg aatgccatca  13500
```

```
ctcgcccccg aacggtttgg tggtgtcgcc gttcgccagc cagcgacgga aagcgggcag  13560

gtcaacttca tggatggagc cgagaccatc ccagcccgga cggaagcagg acagatatcc  13620

agacttcgca tcgttgatgt tgttgaagcc gagcatacac ttgtgctcgt caaactgacc  13680

ttccttgttc acttggttga cgacgaagac ccgtttggat cccagattcg gaccgacgaa  13740

gcaatcgact tcatccccat cagcgccttt cgttcccttg atgaacccgt agtgatgttt  13800

catctgaact cgccaactcc catccttgcc ttgtcgaatg cttccgcgcg gattttcgat  13860

caaggtggtt attccattca ccttgattct ctggagttcc gaatgatcac gaggcccgac  13920

gatgcggttg gacgaaaaca ccgaaggctc cataccagac acgccaggtt tggatgtgcg  13980

ctttaagcca ggcgcatcat tgtgctctat gtctacgccg tccggcgcct taatgtcgtc  14040

caggtcttgg agcttcgaca aaagatcgac caacaagttc cgcagctcgg ccttggggtc  14100

cggcctcgac ggcggttcag cggcctcgct ggccccttcc tcggccgctt tcgcgagagg  14160

cttagtcccg cgtggagcgg cgggaaccgg gccgcctgcg ccctctacgg cgcccgcctg  14220

ggcttcggct cgctcggctt cgcctttcgc cttggccgac tgtgcaccgg ccttctcgaa  14280

ttcggccagg ttttccggag acatgcccgg ttcggtttcc gcctgatcgt cggtgagtcg  14340

gttgtagccg gaacgcggat cgtcacgcag acgctcgcga acttcatccg gagacacaac  14400

gccagagttg atgtagattt catcggtcgc ggctttctta ttgttcaatt cggcttgttg  14460

ctggctggac gtggagtcca caggattcca gacgatttcc agctgcacat cgatttcttc  14520

cgacttcgcc agaagcaaat agtggcgttc aagaagtggg tcgaatatgt gctcttgaat  14580

ggactccagt tcttcgtgat aagaaatcgt ttcgtgctca ccagtggcat tgaatccttt  14640

tggagaagtg ccgaggagct tcgtggctgg agtcttggcg atggccgcga ccagctgata  14700

ttggttcatg atgatgctgt cgaagtcggc caggttcgtg tcgaactgct ccatgtcttc  14760

gtcaattccc agaactttca cgccgtggtt atcacggttg gcgatccaga acgccaggcg  14820

agcgttgaag gcctcttcgt tcgcgatggc cttctccacg tcaacgtgga tggtgctggt  14880

tcgcttcgac atggcaagca gcggggcttc gttcgccgtc cgttccgctg catacacgcg  14940

ctcatagatt ctctgggtga gcgggatacc gccgaagatg tatgtaggct tcaggatatc  15000

tggcggctgc ggtccacgaa ccaccactag gtggctgcgg tgatattttt taccgctgat  15060

aatccagaaa tccggctcat agaaatgttc ggaagacgga tctgccgtcg agccagcagt  15120

gagctgcggc attgcccagt atggatcgat ctgggagatt cccttgtagg agccgggcgt  15180

gattccatcc ggattgaacg gcttttcgta gtagtccgga tcgtcagact ccacaacgaa  15240

cagcgcgata cgaacgccga aaacgttctt gaatctgttg agttcgacaa ggttgtcttt  15300

gacgcgaaac tccatgtcgc gccgggcgat cagcgcgctt tgttcatcgg atagcttcct  15360

gccgtccgat ttgagttccc atccgttccg tgctgcgtct tccccagaca tggaacaagc  15420

tttgtccacc aaccagtgtt gggaaatgat tgcgcaagct tggtatccga tgaacccttg  15480

ggaattgtac cagtcctgca acatagtcgg gacgacatag ggattctggc cgcccgcagc  15540

agccttcgcg gccggagttg gtccatcacc atacgcacta tccattgcta cagataggcc  15600

cggctccagg aaatctttca cgctacgaat taccggggct ttctccggct cgacgttcca  15660

gccgcgaatc cttcccagct tgatcattgg gtcgagcgga tcgtgttgag ggatttttgc  15720

gactttctcc ggcgccgatt cagaacaggc agcattatcc tttttgcgcc cgaatatcca  15780

ggaaagttta aacattgtag ttccacgtgg ttgttggctg tgtgcgctta ttatagggga  15840
```

-continued

```
aacatcaaac gttcaaaaga gattcaaaca tatacatcag attaacagtt gcaactaatc  15900
agttatgaga aaataattct ttacgggaac ttttcggcag attagactct aattatcaac  15960
caatggagat taaacatgaa tactcttttg ccaatcgtac atatcgtgtt gaaagacggc  16020
gaagttctgg gcgtattcga ttgcgacaaa tcggcaagat tgtttcgcga catgaaaggc  16080
ggcgtgctgg attcctgggt agtggaatcg cagaacagct cgcgttcacg cctcgtcacg  16140
aaagaaagct atgaagtcgg cgatcacgtc atatacctgg acgagcacgg agaagggcac  16200
ggcaaggttc tggcggttga gccgcgaggc gagcgcgctg tcggcggacg ggagctgtac  16260
aacctgtacc aaatcagcag cgacgatccg tccgtggaga tttggatgct cgacgcagac  16320
atcatcggca tttatcccga cgaaaagcgc tttactcctg gcgagcagat ggaatagact  16380
ctgctcatca actaaagagg gtgacgaaat ggcgagtatc accgtatgga ttgctactgc  16440
tttcctttgc actggagacg gctgcgtcca gatgccggac catactagca gacggttcga  16500
cagtaaggct cagtgcgaag acgtcatgct aagagcgatt gataagatgt gggagcggca  16560
ccaattggtc gtccaggccg tttgcacgcc ttatttcctg agcagcactg agactcccgg  16620
attctacagt ccgccgcccc agccgccgac tggtctgaac cgtatgtggg acaattggat  16680
tcgcggcggc ggtctgccat cctatgagcc aggaagaggg tggagcgaat gaagccgcgc  16740
cgtccggaag ttcgggtgag cctggaaacc gccctctgga tgtcgacatc cgctgcactc  16800
ctcgcggcga ttatcgccgg cgcggttttc ccgccttcga cgattcaatg tccggaagaa  16860
agaccgcctg cgaccgagcg ttttcaccat ccggaaaaca gcaagttctt tcctcacata  16920
caaaagggat agtgagtatg aagtatgtag tcctgaagct gacggtccgt ggcatgtcgc  16980
gtgaagttcc tgtgatcttc cccgacctca tcagtcatgt gaacatggcc gcgagtgcaa  17040
ttgtggccct cgatgctgag tgcgaaggct tcaagaaggc cggcgacaaa gttgatatca  17100
ccgcagtatc ggcaggattc ctgtcttcga tggatatcga tgcgaaatgc gacggccagt  17160
cggactcttt gggcggtctg aagtcgagag aatcagagga tgatgagctc atccgaatga  17220
tcgactatac ccatggttac gtcggttaag gcacgctgcc tttcctgcga cagacgcgcc  17280
gtcctggacg aacgaaaact gaagtcgaag cgcccgccaa tttgcagatg gtgtggagga  17340
tcgacctggc gaatagtcag ggaagtcacc tgttatagtt cgtgtagacc ctatccacac  17400
agggctggct cggtcggatg cattctagac cgatcaggct caacaataat cgtcgagctt  17460
cctggagtct cagacgattt tcctttctga ggtgaacatg gctactaagg ccgatttgga  17520
gttggaagtt caacagcttc gacgagtatt aaaatctcgc gagcacgaaa ttgaagagtt  17580
gcacggacga ctggagcgcc atcgcgacat tattcgtcgc gtccggctct acctttggag  17640
tcgcctgctg atccatcgcc ggacggccga aaccctggaa gtcggcgaca gcatcgccaa  17700
gaccatcgcc gcgaaaagac acaaggccgc gaacgacgtt ctaggcatca ttcagcattt  17760
gaacgactac tgcgaaagtt atgttgagta cgactacaac gacggcgctg agcatgggtt  17820
caagatcaat agcgacattt attgattgtc ttcgacccga cgaacggtag tgagaaatcg  17880
ctaccgtttt tccatttctg gcgtatagtc aactcatcga aacgaacttt ccaaacagga  17940
gaatcgacat gaacgcagca gagaatctgt tcaccggctt cgaagacctg ggtgatgact  18000
tcgctaccgt agagatcaac aacgaagcgc cgaagaccct ggaagacgtg tccatgggtg  18060
cccgcccgaa ctcccggaag gaagtgaagc tgtatcgcga caagtgcacc aaatgcgcag  18120
gcaccggcct gtaccgtggc ccttcgtctt atggtcgcgc ctgctttgcc tgcggcggcg  18180
tcggatacaa agagtacaaa accagcccgg agcagcgcgc caagagccgt gctaaggcgg  18240
```

cagaaaagcg catcgagaaa atctgtagcg ctgcgcaaga gcgcgacctc aaaattaagg 18300
ccttcgaagc cgcgcacccg gacatcatcg agtggtggac tggaaattcc ttcagcttcg 18360
ctcagagcct tcaggagtcg ttgtataaat acggctcctt gacagaaaat cagatcgctg 18420
ctgcgaagcg cgccatcgaa aacctcgcca agtatcgcga gaaagtggcc gcgcaggaag 18480
ctgctgcgcc gactctggac atttccggca tcgaaaaggc gtttgagaag gcgaaagcat 18540
ctggaatcaa gcgcccgaaa atccgcctgg ctggcgaagg cgaggagccg ctcatcgttg 18600
tggtgaaaga ggctagcgct cacagccgga acgccggtag cttgtacgtc ttgggcgaca 18660
tctacctcgg ccggatcacc aatggcaaat tcatcaagag tcgcgactgc accgacactg 18720
agcacgacga cgttctgaag atgttcgaaa agccgatgga atcggcagtc gcctacggtc 18780
ggaagactgg tcagtgctcc tgctgcggtc gcgagttgac caaccacgca tccatcgaaa 18840
tgggcattgg cccgatctgc gccggaaagt tcttcggatg atttacatga ccatcaaagc 18900
catggcctgg ttcgcccttc tatgggcggc cggcttggcc ctaataaccg taacaattca 18960
cttctgctac tgaggattat tcatgagcac cgtccctgat ccgatgaagg acaagatcac 19020
gctgcacggc ctgggtttca tccaggtcca gcttccggca ggacgcctcc atgtgtggca 19080
tccggaattg ccgcgccggc gttgcttcca acactcgtcc atccacgatc atcgattcga 19140
tttcgagtct ctggtgctgg ttggatcgat ggagaacatc aattatcagg tggatcgctc 19200
ggctcgcctt ggcgcgctga cccatgaagg gtatgagcac tcttctgctc gccaggcttg 19260
cggcggtcgc ggatgggact ctataggttc tgtgtccctg cgtccggtgt ccagccttat 19320
cgtgtccgct gggcagtcct attcgatcca gccttatgtt ccacacaaga cgaatccgct 19380
cggtgacggc cgcgtggcca ctctcatgcg gaaaggcagc gttcacatat ggcctgctac 19440
ttcctatgtg acgctgggcg tcgatcctga aaccgacttc gaccgctacc agtggtcggt 19500
gccgacgctc tgggaagtcg tcaccgatgt actcggtggc gcagagttcc aaatcccctc 19560
catcccgtaa ccgaaggaat ctgaaaatga aaaagttctg tatcgacatc accaatggtc 19620
tggccggctt catcatctgg ggcggcgcaa tcgtcctggc cgcttctgtc tttctcatcg 19680
gcccgctggc cctcctgctg accggcgcct gggttgtgtg tacgtctgtc gtgttcgccc 19740
tctggttcgc cgtcgccggc atctacgaag agtcgcaaaa gcagaccgag tatctgaaat 19800
ccctggtgtc gctccaggcg cgtgaacgcg gcatcggcta cggcccagga gacgccggtt 19860
gcagcgccag cgctccggcc gttcccgtag agcccaagct cagccatccc aaactgaagc 19920
cgggcgcaca gctcgcggcc gctgtcttgt tcttcgccgc tctcattctc ctgctggtag 19980
caggcgattg gatctggaat ttcttccagt ccatgccgaa atagtggaag aaagtgcttt 20040
acttccattc tgaatgaagg cagaataact ccattgaaac gcgaaaccct tcagacaaaa 20100
aggaaccgac catgaccgac cagaacgaat tcaccccgga agccatcgag aaggcgaaag 20160
accgcatccg caaactgacc gccatggctg ccgactcctc cagcccgcac gaagcggcca 20220
tcgcagccga gcgcgtgaag aagctgaagg acaaatatga ccttcacgac ttcgaagcga 20280
ccggcgagat tcgcgaagag ttcgatgagc aaattgccac tcgttactat tccgcaatcc 20340
cgaactggat gaaatttttc tcggtggccg tggcgacgta caatgattgc atcatggatt 20400
tcgccggtgg catcaacaac catcgggcat cggctaaggc atccagaagc gcccgcgacg 20460
gaagcactac caagcgctgg ggtcatgccg tacgctttaa aggctacaag tcggacgttg 20520
agctggcggt gaacatgttc aactccctgg tcgaggccgt tgatcgtctg tgccgggagt 20580

```
atcagaaggc tcaagggtac gaacggttca acgtaaaggt tgccgcgcaa ttcaagctgg  20640
ccgcgaccca ggaaatcagc tatcgccttc agtccatcac caggaagcgt atggagctgg  20700
tgtcttcggc cggaacgtct ctggttgtgg tgaaggaagc tgcggttcac gaacatttcg  20760
gcgatcctgg ctacaagaag tccaatgtta ctaagctcat gcgtctggac gatagcgacg  20820
gtcggcgcgc cttcaatgcc gggaccaatg ccgggcgcaa catggaaatc gttcggtcgg  20880
tggaggattg atcatgagct tccctagcga caaagcgatg ctgcgaatcg tccaatccat  20940
cctcgcgatt ctcatcggga tcgcttgggc ctgcgccgac tatggagtcg tggctgctga  21000
acttactcca tcgctgcagg cccatcccgc gaggccaggg cacagcgaag tctcggcccg  21060
cgaccctagg tcggtcgagg ccgaaaaagc gcgggaagag gccttagaat atgtcctgtc  21120
gctgcgcccg gaagttatcg aggcgaaagc ccgcttcgcg gccgaggcgg cgcagcacgg  21180
aatgtctacc gagaaatacg ctgagatgca gcgcctgtca acgctgatgt ccggcatatt  21240
tgtgccgttt gcgttccttg cgttcatctt catcatgctg ctcatgctgt aataggcctg  21300
agcagcgaac aaccaccaac caaaagagaa tcatcatgaa gaaagaaccg attcgactca  21360
gctccatggc ctcggcccgt gccatcgatg cggaattcgc attccggatg gacgagttca  21420
tggcgcgcgt cgctaaagag cacgaagcgc tcgccgcccg actgaatgcc gagcatctgg  21480
tgctctggga cgaaatccgc actgtcgccg gcctgagcgc aaccgacttc ccgaacatcg  21540
ctatggcaca cgacactgcc gatgggaagc tctatgtcat ggatgccgac gagttggagc  21600
gcgtccgcca agcctgtccc tgcccggact gcgaagctgc tcgcgccgaa agcatgccgt  21660
cgcaagccag tggaggtatt cactgatgcc gatcaagcta tcttccgtcc atgtacggat  21720
caccgggcct gatggcaggg ttttgtccga aggccgcgca gaattttccg gaacggcatt  21780
ctggttggcc gcgcaacgcg aaatgaagtt caaacacctc gtcggaactt ccttcgaagg  21840
cgccctgacc tacctggccg acaacggcta caacgtaaca ttcagcaaag gtgaaaagca  21900
atgatcgaaa gacatgtagt tgatgcggaa accgtcgagc ggattcatgc tcttcgcatt  21960
cggttcaacg tcctggacga aaccctgcaa cgggccgttg acatggccat gcttagccac  22020
cagaaggctc tgcaagacct gcggacctat gaggcccagc tctgggacgc gctcaacgcc  22080
cgttacggtc tgtccgtcga aaagacctat gacctgcggt tcgaaggcga agaagccgtg  22140
ctggtcgagg ttccgccagg cgatggccaa ggtgatgact tcatcgtcga gtcggaagcc  22200
gaagcgctcg cggccggtca ggaagctctg ggcgtcggcg aggccgttgc gtcgacactc  22260
agcgccagga accacaccga gtaagacccg aagcccggag cgatccgggc ttttctatgt  22320
ttagaagtcg aagaagcctt tgggcttccg gatcggcaga atggccgaca taataaccga  22380
atcagcgatg ttcggcgact tgatcttgcg tttctcgcgc atatccttct tggactcgac  22440
tttgaaccgg ccgttcatgt ccaggtcttt gcgcggcgac gaaagttcga tacacagctg  22500
attcagtttg tccgggtgaa tcgtttcaga gttaatcgaa atcaattcgt cgaatggata  22560
aacctttcca tgctcaaccg cttcataagt cttccggaat cgggtcgcga cttcttccca  22620
cttctgcgcc ttgatgttgc tgaagtggtc tttgttcttg atcgtcgtgt gcggcagctt  22680
catgtaaaca tcatcaggct tatcgacagc gccgcccgcg ttgaatgggt catagatcag  22740
cttgaagtcg gggctggcat cgttcaattc ggcgaacttc gaaccgacgt gagcaccgac  22800
gccgatggag tcataagtga ccgaggcgcc tttcatcttc gccaggttgt aaacgcggct  22860
ggacgacttg agcagttcat cttccaggcc gtcccattcg tccacttcca tgatgacgtt  22920
gccgtgcatg agcgtagtgg cgttcgcatc ctcgccgtcg tccgcaacgt cgaagccgat  22980
```

gcgcttcgat ccggccggct cccagccgag tttcttgtgg gcgtcgatgg ccgcgagaat 23040
gaacttgagg ttgatgacgg atttgtcgcc tccagtcttc ggaatcccgc cataaatgtg 23100
ctcggcctgc tcccggtcgc gttcataggc ttcgtgaatc actttgagca tcgtctcgct 23160
taggaacgga ttttcgttcc agttgatcat cttgacgcag gagtctttcg gtggtttgac 23220
cacgaagttc tgatacacga aatcggtgac ttcgttaggg ttgaagatga tccagatttc 23280
agagttttct ttccggatgg tcggctcgat aacttcccac tgctcctgtg tcaggtagtg 23340
agcttcctca agccagagaa tgtcgatgcc ttcggtggac ttgatttccg acaggttacg 23400
ggcgatccca taaaacagga actctgagcc ggtaatcttg tgcttgatgg agttcttggt 23460
gaagatgaat tcgccattat actctgagtt ttcgatcttg tctttgatca atgtgtagac 23520
agattcgctg atgcggttct ggaactggcg agcacagagg aatttgagct tgtagttggc 23580
cgcgaggaaa acggctatac cgccagcgtc gtgcgacttc gaagacgccc ggccgccata 23640
gatgactttg taacgggcac gagttcgcca gaccgctcgc agtgcaggat tgagcttgaa 23700
catttaatca gtccattgtt cgcaataggc cgagtatatc gacaccgcag cagacggtcg 23760
agcacaaccg ttcgtcggtg tacagaaatt tcttcgatca gacactttac ttccagtctg 23820
actgtcggca taatctcctc atcgaaacgc gaaacccttc aaacaaaagg aagccgaaat 23880
gaccaaagat caaatcaacg acaaaatccg cgcagccaag atcgcaatca gcgaggctga 23940
aatggaaggc ctgcgcggtc aggcgatgat cgatctgaaa gctgaactgg ccaacctcaa 24000
agcccaattc aaagccgcta agtaaggata cgaaaatgac caaacaagtc cagatcgaag 24060
tcaccaatct cgatgaagct ttcgtccagc acctcctgac tggcggccat ctgttcgatg 24120
tagacgacta tgaagtcgca gaccgcatcc tgatggaagt cgatggcgag caaatggtcc 24180
agttcgagct gaatgctgaa ttgtggaatg aagaaactct gggcgttccg atggatatcg 24240
acagtgacga gttcgccgat gagctgcagg attgggtcga gtcgaaggtg aatttcgcct 24300
tcgaagagtg gctgagcgcg gacgaaggcg aagagtgatt acgatgcgcg gccaggatgg 24360
tcccggccgc gacttcttat gaggattgtg ttatgtccac catttctttc cgaagcatca 24420
agaacgccat ttatgtccct ctggaaatca tctgcgaaga gtcgggcgca tcgcagacgg 24480
tcaaggcgca tgtcgatgcg aaaagctttc gcgcattctg gcctgtggcc gataatctgg 24540
cctgggaccc agacgcctgc aagttcgcgc ctctgtatcg agcccacttc atggccaaga 24600
cagttaagga tacagaccga gcactgctcg ccttcgcggc tgggcaatac tatctgcgca 24660
ataagcaggc cgcagagtcg caagaatcgg acgccgatct gcatgcgctg gagttgtccg 24720
cattgcgagc agaactgcga aggaccaaag tcgccaaaca gcagctggtg cgcgaaaata 24780
ctcgtcttgt cgaccgcctg cagaacttcg tagcccgcga agacaaggtc gccgagcaga 24840
accgccagct tcaactcaga atccaggatt tggaggccga gctagcatcg cagaaggctc 24900
ttcgggaaga gttagacaag agcctggacg gcagcatcaa gaacgccaat tcccagcaca 24960
agacggcgtg cgacgccatg gagcagctta ccaaagccag gaaagaagcc gatttctatc 25020
gcctcggtat gcagaaagta gcggctatcg caaacgcgaa accttttgag gatcactgac 25080
cgtgcagaaa tacgccatgt cccatatccc tcgcccagga acgctccagt tcgaattcga 25140
atggctcgcc gttacccggt tcggcatcaa ggatggtgct ctggctatgt cgttcgatgg 25200
cgagcgttac tgcaacgaac acatcgactg gctctggcgg cagttcctga cttcaaaagg 25260
tttcagataa tcttaagaaa atgctttact caatgaggtg acttaggtat agtcacctca 25320

```
ttgaaacgga acaatctcgg agagaaagcg atgccggtat ttaacattga ccagtccgta  25380
actgtagaag ctgaagtaga aaagggctgt atctctcgca ttgcccatct gtgggacgaa  25440
gaggggaatg atctttcctg caaactcggc gcaatccgag ctttgaatgt caaagccgcc  25500
tgtgcttatc ttgttcgcga tcctgccgct aaggaagtga ctactgaatg cggcgtgaca  25560
atccgtcgcg gcaaagccta atccaacgcg cccgattctc cgggtaccac cgaggaacga  25620
aacaatgatc ggcaccgtac acaaagaatc cccgctcacc ttaagcaccc gcatcggctc  25680
cgcatccggc gagaaacata cctacacaat gctggtgggc gagccgctgc ggactccaat  25740
tatcattcgt gatgacggca aaacctttac tttgacatgg ccagagatca tcgacctggc  25800
gcgatcggcg ttcgctatcg atgacgcggc cgattgattt ttgtcttcca gaaattttag  25860
acaatctgtt caaaagtgct ttactcgatg aggtgactga ggtatagtta cctcatcgaa  25920
acgcgaaaca ctccaaaaag aggattgcga catgactagc tccaaatgga acatcggcag  25980
aaacgacaca atcgaagtcg aggccgtaaa cagccgcgaa gatttccgct ggaatggcaa  26040
ggttcgcgtc gtccactaca gcgccggtca aatcgtcaac atcatcgagt tctatcacca  26100
cgatctggac tgggcgatca agaatttcgg catcaagctg aaggccattt ccaagggcct  26160
ggaaatcctc cacacctgct acttcgggaa gtgtgtcaag tgatcgtcca actcgattcc  26220
caagaagaga aaatcatcgg cctgagaact ctgtccaagt atcgtcgcgc cggtggcaag  26280
ttcgcaccgg tggacggaac tcagaccggt ccctggggtc cagtcgacaa cgcgctttgg  26340
gcgaagctcg aagccgaagc cagggcagaa tacatccgca aacaggagcg caaagcatga  26400
tcaagcaaga cctgtacaag cagatcgcct tcgcggcgat tggctccggc atcaagatgt  26460
tcgtcaagct ttactgcaac gacaccatcc tggaagtcat cggcgtcgag gaatcccaca  26520
ttgatgggac gactcggctg cgttacaccg gccgcgccga tggtgtcgat gtccatttct  26580
tcgtcaatga aatcgacatg gtgatggtat gattggtcat tcgctattcg actttgaagt  26640
cgattgcaat agcaccacca atagcgccac catggaaatc gatcccggtt cattctatgt  26700
aggcttcggg tttggcgcga ctgctctgtc agtcctgatc tatgtagatg gagtttgggt  26760
gactgaacgt acaccatgga tccacgatcc aaaggaaata tcgccatgag caagcgcaaa  26820
aactatcagg gcggctgggc gcaacccggc gatgctcgca aagtccactt cttcacttcg  26880
gacggccgca gcctgtgcaa gcgctggctg tacctaggca agacttacag cgagctgccc  26940
gacctggaaa tcacctgcgc gatatgcgag aagaagcgcc agagtccttt cgagaaatac  27000
tgcgacacca ttctctaacg ttcaagcctt ccaaaaccga ggaacagtta tgaaactcta  27060
ccatgcaaaa gtcagtcctc catccttcta tcgccacaac cagaccgacg aagagcggaa  27120
agccttggag gcggaatatg tcagcaagct ccacgttctc ctggggaacc tggaaggcgt  27180
aacaatcggg aatcctggtg agcggaactg ggagccgtcc acctggagca acgacgttcc  27240
tgtgacgtgt aatgaaatcg gcctgggccg tctgaccgct tcggcctggg atctggacaa  27300
ggactatccg tacaccatca tcaacctggt cctgctctgg gacgatgtcg acccggaagc  27360
cgctctgcgg cccatgctgg agcgcctgga gctggccgcg agccgtctac agggacgctc  27420
gccaggctac atatctgagc cgcagatggt gctcggcatc gaaggctgga actcggtcac  27480
cggctcggcc atccctggtc cgaatctcca gggcgtcaac cgtctcctac tcaaggaaga  27540
ctgctgcacg gacgaactcc agtatgccct ggacgcagga tggcgccttc tcgccgtttg  27600
tccgcaggaa gcgcgccggc ccgactacat cctggggcgg ttcgatcctg tcccgccgac  27660
cggaccgcgt ggcgcggcca ggagcatcga ttaaatgacc atggtaggcc cggctggcaa  27720
```

gcgctactgg cttcggtatg aaaccaaata ctgggaatgt cttgacggac acaccctgcg 27780
cctggtcttc gtcatcaacg gtcgccgata cgaaatcaat cggcgggtga atgtcgacat 27840
cctggctagc cggcgccggc tcgaatcctt cggccgagtc ctggcaagga tggaaatcag 27900
cttgtggttc gaagtctgtg agcaagaagg gccatggcgt gggagcgtag caatcagcga 27960
taccgcgctt tggttccatt taactggaga attggtacac aagtgcttta ctcgatggcg 28020
atgatcaggc ataatctctt caccggctga gtagccggac ccgaagtcca aaaaggaatc 28080
tcgaaatgta cagaattccc tcgtccaaat tcttgttcat ctgcaacggc ctcgcccaga 28140
acacagaagt gacggttctg ctaagaaagc agaagccgga agatgtatgg gtggtggacg 28200
aagctccagt tgcgaacctg attcgcatcc atgaacgcag caatccgcgc cgtcgccgta 28260
ccatcagcat cctcgacgtg gacgccgtgt ccatccttcg caagcgttaa tccatctgcg 28320
cggctgggat cgtcctggcc gcgccttctc ataggagtgt attatggcca aaatattgat 28380
ggcctgtgag ttgctcgtcg gcgacgaaat actcactcat gttgacgtca atgatcccgt 28440
tcggcgtcgg gctatagtcc tgcgatctgg agctgcgccg caccgcaaag taagcatcga 28500
agtcgcggcg ctcatcggtg ctgactgggt ggacttcaag ctcaagctgg ccagggacta 28560
tcccaccatc tgcttacatg acatcgaccc gatccgtcct cgtggcgcga cccaatagga 28620
gaacaccatg gctaaaatag taagagtcga tgagctgaaa actggcgatg aaattctgat 28680
taagctcaga gcagattcag cagccaggaa caaggcgatt gtcctttctg tcgaatgctg 28740
gcgcgacgaa atcactctgg agcttacctg cccggccggc gactactggg aagactggcg 28800
cggtaaatat cgcgcatatg acaaagtcgt tctgttgaag cgcgactaac aacaaccagc 28860
ctctgcgact cggcagaggc tttctcattg gagggcagct tatgtccgat aaagaacaaa 28920
gtggccatta ctgggtaacg gtcagtccga ccgatctgtc tagcgcgtcg gccgcgcagc 28980
gactctgcga aacgatccat ctgaacatga cgcgaggcgt cgcggcctac atcaagttct 29040
acggctcgaa aggcgaaggc ctggtgacgc gagtcattcc gcaccagtgc gaactattcg 29100
tcaatgacga gtcgggcacg aatcggcgtc gaacggcgat gatgatcgaa tacgtccgct 29160
tcaaagttcc ggccggtatg tctctggtcg aacaccaaaa gcaaccttat tgagggcgcc 29220
atgaggaacg taaagatcga tcataaatgg gagtcgagcg aactaagctc aggcatgaac 29280
gtctggaagc cagatgatcg ctacagcggg agcgcctggg aacgctgctt catcgcaggg 29340
ttggaaggaa cggaccactt tgcgatcatc cgtcacgaca acgtggcact gacgccgttc 29400
tggccacgac tgaagatcgc ctactacctt cgaaagaaca atttcgccaa agaggagtaa 29460
caccatgctg tacatctggg aagatcaaga tatccaccac aacatcgaaa ccctggcttt 29520
cgtcggcgag tccaggtcca actacagaat catcgggttc aagctcggtg atctgttcgc 29580
cgtcgccgaa gagtctactg gccagatcgt ggtaagcccg ctgactcggc aagggatggc 29640
ggaatggctt accatggacg gccatattcc tgccgagatc atcagccacg gacccggcaa 29700
ccacaagaat ccgtatgtct gggcagattc catagttctg aaaaatctgc ctacccatcc 29760
gaacatgcgc tgcgttacca ctccattcac gggcttcgat ccggcagagc cgggcggcga 29820
caagacggcc ataggtcaag tcatcaaggg caaccgatcc gccgaaatgt tcggcgacaa 29880
tccggcgcag cagtcgcagc ggtcctttgg cggcatagcg ccgagtcttc ccgatcttcc 29940
cgatcttccg gaacctccca gggcgccgat ggctcctcca ggcctgccgg ttccgcccgc 30000
gcctcctgcg ccaaaagcgc ctccagctcc gcaggtgagc aggcagtcgg aatctctgga 30060

```
gcttcggtcc ggcgcaatcc cgtccagtcc ggcgcccgca tcggacaacg acaagcccgg  30120
cgatccgccc atcgagccta tcacgatccc gacgttctga ccatcaccct cgcccacaaa  30180
caccgcagcc cgttctgcgg tgttttcaca tccgacaacc gttcgtcggc tttgcgatca  30240
atctgatgaa ataaatgtag acacgcagca tcgacctagg cataatctct ttcaacgggg  30300
cgacaaaccg aagcccgaaa gaaatcttcc aaaacagagg atcgcaaaaa tgaccaactc  30360
catcaaaacc ttcggcgaca tccagaacgc agaaatgaaa gaactggtcg ccttctacaa  30420
cgctcacaac gccgatgcga ctgtcaagcg cttctctgac cgcaagaccg ctgagcgtcg  30480
ctgcctcgcc atcctgaacg ctctgccggc cgaggaagag gccttccagg aagaggaagc  30540
cccggccaaa gtctacaaaa cccgcacttc caagaagaag ggagaagaga aggccgagga  30600
agagaatctg aagcctgaag aagagatcac cgaagaggaa gcgctggaag aaatccggaa  30660
gatgcgcgaa gaggccaaga acgctccgga gaaagccaaa gagtccaaag acctgtcggc  30720
agccatcgcc aactcctgga aagacccgga agtttccaag aaacgcactc agcgccatgg  30780
cgtggctgtg actgtcaaag gcaagcgcgg cgagttccgg tccaccaacg cagcattcat  30840
cgagttcggc ctgccttctt cgaaacacat ccgcttccgc atgcagctga aggcggctgg  30900
caaaatgact ttcgagcacg aaggcgtcaa atacaacttc gaaatcatcg aagctggcga  30960
ataaggcgcc caaaagaaag ccccggattc tgaactagag tccggggctt tgtcgtttct  31020
gagggttagg ctacgacttc ctagaaccgc cctagaatcg tttttcgtcc cttcccgcta  31080
ccgtcgcctt agttcggtcc gattcgggcc tagaacgatg ttattttatg tctaaatggg  31140
gttggcgcgg tcttcctcgg tcagttccgg cgtcggagac gggaaatctc cctcttcgcc  31200
ttccggcaca tagccattgg cttcggccgc agcagcgacg gtggcggtct gagcctcggc  31260
ttctgatgcg tagaagtcgg ccaggccgcg accgatcctg gtcttgcccg actcgtccac  31320
gaacgtgatt tcagccagaa cgttcaattc cttgatggcc gacagacggc tggagtcctt  31380
gacggtgggg tcacgaacca tttggaggag ttcgtggagc gccgtctttg gattccacaa  31440
atcggacgtt ttggtcgcgt tcaacttggc cttgaactgc ttgcgatagt acgggttgga  31500
ctccatcgcg aagatgcggg cttgcgcggg accgtccata tgctcctcgc cccagatggc  31560
ccggaagacc cgccaggagc tgtaaccttg gacgcgcagg tcgatgtaca ggtcgaatcg  31620
cttttggttg atcgccgcga aatgcgggtc tgcgaattcc tgtggcgtga ctagatcgtc  31680
ggggctgtag aatttggtca tttggcgctg cgtccctgag ttcgattctg gagtcgtcgc  31740
ggtggctcgg ttggtggatg gggcctggtg ctctgtcgcg acactgagta tggcgcgatt  31800
gtactatggg gccagggatc gcgtctatgg gctgcttgtg ggtgggctgt aggtctgggt  31860
gggtttgatg atgaatgagt gttaggtggt gttatagggt gttatacggg cgatccgctg  31920
gtgggtgagg atcgagtcgg cggttggtgg gtgacgatgg cggtgagtgt ttgagaggag  31980
tgttaaatcg aatgttagaa atatgtccag ctgagctatt ttgtcgtgcg cccaaattcc  32040
cggttccgtt cgtcgagttt tggtccttgc cgcttagtcc gccgtggtgt tgccgcgacc  32100
catggattgg aagtccggaa gtttccggcg accctgccgc gagctggctg gaatcggaaa  32160
cttgacggga tatgtacaag cttagtgcag cgaggctttc aaataccaaa gtataccaaa  32220
ttaccaaatt actattaatt taattaattt taaagatagg taacgtccgt gatagatttt  32280
ttctattagg attgtgcaat cgattttcgc tgtagtatac ttttgcggct gcatccgaaa  32340
ccggaaagta tccgaagaaa cccttcaagc ccacgcggca ctaaggctcg accctaattc  32400
ctggtttcgg taattaccgg ctagccagcc gcggccgacc ccaaaaatcc agtcagaatc  32460
```

```
gtcgattttc cataattcat ccaatcacca cacagaatct tcgatccacc gtccacgaac  32520
tttccacact gcacggccat cgcccccaac ctaattcccg gatagcttcc gaatctcact  32580
cggccacaac ctaaatcgaa tgtacgtcgc accaaagaaa aagaccgccc gaaggcggcc  32640
tagtccaagt acactccatc actccattag aaatcctcgc ccaatattct tgcgcgctcg  32700
gctttgactt tgcggatttg aatcatggcg gcttcatcag taacctcaga atccaccttc  32760
ctcagcaaat acaccagcgc atcattgaac ggcggcaacg tcgtatgcat acccttcgac  32820
catccaggtg caaccttatc aaccggcaaa caccatccgt tcagtccgtt cttgttctga  32880
acgagtccca gcgctttcag gtgcggagtt aaatggcgag aaatcggctt cttcctggcg  32940
agaatatcga accatttcag aatttcgact gtgttgactc tccatccagg attctttgaa  33000
ttcccgcccg gcttaacctc ttcgaactcg caactgatca gcacgttgat cagatacatg  33060
tcaatcgtat cgtcacgaac tacaccacgc gcattctcca tttccgaaat agagaatttc  33120
tgcacttcgt tattggtcgc ccgaactaga tcaagatatc cctccactcc attcgcctca  33180
atccaggcgc gacattcagc catagcctgc cagaacttgc ggccgaagtc ggtgaagtca  33240
acgcggaaag tctcgttacc atcacccggc ttaacccagt tcggctttcc atcttcgtcg  33300
ggcagttgcg caacgaacat cggatagaat cgacggttcc ccgactcatc cctctggagt  33360
ccgtcgtagc cgttgccgtc catgatggtg atccattgtc ggctgatcgt ctcgcctggt  33420
tcgaacttct gatcgaaagt gtcatcggac cgcaccagga attccttaat gcgttccatg  33480
tcgccctttt tgaagccgga catttcgccg acgttcgcaa taaccgagtt gccggtgata  33540
ttgcgaagga acggcgtctg atcgtgccgg ctcaggtcga gctggactgg cgataacttt  33600
cggtcgcccg acagctcttt acagatcaag attgaaaagt aagtctttcc cgcatcctgc  33660
ccaccaatca acgccaacga gatcggcgcc gagattccag ggtagttgat gcggcagtac  33720
aagctcagcc agaaatactt gctcaccatc cggttaagct cggtgtcgaa cggtttgaac  33780
aagtcgatca gcagcgtgtc aatccgctct ttgccatccc actccggtat cttcttctca  33840
aacgtctcga tcaaagagtt gcggcgatat cgacgcgccc acacgcagca agtctcaatc  33900
gtcttcttaa tcgagggatc gtccaaggcc gcagccgcga gggcgcccat caggtcaatc  33960
ggatcgaggg tcttgttgtt gaacgccacg cctcggtggt ccaccagccg gccgcgaaac  34020
tcgtcgaagt gcggatgcgg gacggttccg tcgcctttac agaacaacgt atcatagacc  34080
gcgaggtagt tgctgtctga agtcgaactg tactttgtga tgaagtcatc gaacggtcct  34140
ttcaccagcc ggctgaccgg aagatcaaag gcctgatcga gcatcaacaa tcgcgctcgc  34200
ttcttcaaat ctggttccgc atacgcctcg gcatactttg ctgccttttg cgcgcggtac  34260
gtctcattcc tcgcaatcgc atcatcggcc gctttacttg cggcggtcat caaagggtcc  34320
attccagcat cttctatctg tgtgagatcg aactcattgg accccgattc gtcatcatca  34380
agaatgttat cgtcgtcgat aatcatgtta ggtttgccgc cttctgcttt acatgatcgg  34440
atataacact gcctctacat attgaggcga aagggacggc tattatctcc tacctaaacc  34500
ggcagagcta ataagttccg tccccatccg aaaatttccg gaccgttcgt cgactaaaac  34560
acgtcaaacg ccaagacgaa ccagcaggtt aaagcagaaa ggccgaaaaa gaagcacagg  34620
agcgacgcca gaaagttcgc tactggtatt ttccatccct tcaggccttc gaagaagatg  34680
aggaggccga gaagcaacaa gccgatggcg gtaatcagaa ttccaggatc attttgcata  34740
gttactactc ctcgccgatg tgacggcggt tgatgcgttc caattgttcg acgatatagg  34800
```

```
gcaggacgac ttcatcagtg aaggccgccc acgtccgtcg atgctctttg cggcaagtat  34860
cgtgtccgca gccgaacaca tattcgtgct cggcgccagg tatcggtccg cgaaagtatg  34920
cgccgaaagg atcgccgttg gtgtgctcgt cgccccaggg acagcggatg cggtattttc  34980
cagacatgtt ctgctggacc tggccgcctg ccgcttcgcc catcttgtat ttcgtgcaga  35040
tgtgctcggc atacttcagc catacttggt catacaccca atcgtcgcgg tttatctcca  35100
ccttcttcat ctgtggcatg atgatgcgga cgccgaaggc ctgggcaatc tcttccggcg  35160
agtagcgctt ggaatagtcg gcgctgtaca gtcgcacgag ttcgggcttg ccattttcgt  35220
cggcatactt gaacttgccg tctttcccgc gcttgttgtt gaagccgaat ggcatccgac  35280
cgtaacggct gacgtccttg actgtgttgt cgccgccttt ctttaacacc tggtccacga  35340
acgaatagag cagcgccttg aactggagca tgtgggacat cggctctttg aagaaatacc  35400
agaactgata gttgttcggc gaagtctcca caatcgcggt cggctccagt cgctcgcgga  35460
actcgtcgcg gtcgaagtcg cccttggacc ctttgccgga gccgatgtca tcgaccatca  35520
acgccaggcc gtggccgaaa gaggcttcgc cgcgccagta tcgcatctgg ccggtcttcg  35580
ggttgggcgt cttgatggac gacgagatac acgcgtaggc gttggatctg gagttgatgt  35640
atttcccttc tttccagggc acaggccacc agccggcgtt gagcttgcgg ccgttctcgt  35700
cggtttggac tgtggcctct tcagcgtagc cgaccatcac ccgttcgtcg tccggaatcc  35760
ctcggccgag ttcgcgcagg aactcttcgg cctgtgccag tcttatttcg tgaggcttca  35820
tgcaagtcgc tccgggcgcc ccttgcgtcg cggcacttcc acgaactgtc gcgcagcgct  35880
cgcctttctg gcggagttta ggccatcttc atggattcga ctccaggctt caatgatctt  35940
gtgctgtctc gccttttcga gcgccggggg aatcttcgca tcgtcgatgc cgcgcaccca  36000
catgaacatg aggaacgtcg ccaggtccag gaggttgttc tcatttccct tcagcgcatg  36060
ttcggcgaat ccgttgatca gaatatcttc gtcgcagtcg atccagccgc ctcggccttt  36120
atcgcgggag cgctgcagtt tctggcggat cgctgctgcg aacatggaca cggcgcactc  36180
gtcctgcgct tctggcttcg cctttcgaag aatgcgaatg tcgagatcgg tcatggcgat  36240
ggctccatct acttccgaag gtttctgctg ttccattaca taaactcctt acttggcact  36300
taccgctcgc acccgcagcg ggcaggatag gcctgtggtt gctggcacgg ctgaggatgc  36360
gcggccggat cgatgggtga gggcgctact gcgagcattt gccggtaaat ctcgccgatg  36420
ctgtttaccg agtcataacg cagggactgg ccgacgaatg tcatttgcgg cgtcggttcc  36480
atcggaacgg gtttccaccc atcaggcacg ctgggttgag cctggactac aggcgcggtg  36540
tagagggaac ctttcctgag cgtcaatgag tcgctgcttc ggtgcatgtc gaggatatac  36600
gcctctatct gagcctcagt ttcgcattgc gtatacagct tgccgtcgcg cttcccgccg  36660
aaatggaagg cccccatgcc accggctctt gtttctccag ctcggccagc ttcatcttca  36720
gctcatgaat ctccatttcc atgccgccag cagcgtggcg ggcagcatca ccctttgctg  36780
ctgcgtcgcg tgccatcgcc agttctttct ccagctccgc caccctggcc agggcgactt  36840
ctagctgttt tgcgttctcg tctcgctcgt acatcatctt catgcatctg tcgaagctgc  36900
cagaaggatc gcattttgat tctcgcaggc gctcgacttc ggccagggcg gcgtcgcgtt  36960
ccactttata acgacaataa ggatgaccgt gttcatcgcc gatcacgcca tcgcaatagc  37020
tcgcggccag ttcgctcccg cgcttttcgg attcggacaa ttccttttcc agctcagcga  37080
tcctggccag ggctgcgtag cgctcggatg ttactttgcg gatttcaact tgcgccaaag  37140
ctaggcggtt accagcgcaa ttccataggt tgttgtagcg attgcgcgcc tcagtcatcg  37200
```

```
aggttaatgc agtcagcagc tccccgacta tgcggtcgtg ctgggagaca agcatcatcg  37260
gctcaggatt ctgcagtcca tagtcctttt catagaccat gcgagaagcc gcgctgcgat  37320
agccgactac ctctggccgt tccacttctg ccagatcgcg tgtgcgcttt tcggattcgt  37380
cccacttctt ctccagctcc gcaatcgtct ccagagcctc ataaagtttt ttggcgtcga  37440
tcttctcgaa ctccggaata ctgggctttc ccaaatcttc catatcattc acctcaatta  37500
cagatggcga tgttgagaac tttatcgcgc ccggccgcga acttctccag gaagtccacc  37560
aggtcattca ggatggtccc cgctcgacct agcttgtggc cgatcaggag ctgcgcgact  37620
cggtgtccga cgaatttccc cgaaggaatt ttcggccatg tttcaccgat gcttttgagc  37680
actgcatcag tgtagatttt gtccgcgccg actttgtggt gatcgaggat tgtgcgatca  37740
cgaacatacc gattgatgat ccgccgcagg aactcgtctt cagtcccggc cagggcgccg  37800
cactcgcgga gttggcgcag gagacgccac cccaagttcc gctcccactt ttcagcgaac  37860
tcttccgctt cggcgaatga cgctcgcatg atgtgatcga ctggaatgat gacggcgccg  37920
ccttctttcg ttccggattc catgaccgcc cattcgccgt gctcgcgatg ctcgatgaag  37980
ccgatcagca tgcctatgaa agctccatct tccggaactc cggtcacgcg aacgactgaa  38040
tggcgcggga aggctttcga tccatagagg ctggactgtg aattgaccca tccggccatg  38100
gccaagtcgg acgcttcggc gtggatcagc tcgcgacgaa tgcgaacgga cagcgccggg  38160
tccagctcgc ggctccggcg caggaaaccg ggttttaggt tcgggtcgcg ggtcttgtcg  38220
acattgggat tcggattacc gaccgggagt tggtcgcggg aaatcttgca ttcttgcatt  38280
taatgtatcc tctgttttgg agggcagtac aggcggcggc gctagtatcg gccactttcc  38340
tgccgaagta aagttggatt aaattcgctc gctttggcga gtcagctgat agtatactct  38400
tcctgcgcag aggtaaagca taactgtacg ttataaagga acattcgatg gcggaacata  38460
tttttactca cgaaggcaca gtggtgttcg aggggcgatc ccgaacggtc aagctccggc  38520
gcggcaacca ccactgggta gacttcgata gacatcgcta tagcccacag gacggccgcg  38580
ccgcttccca ggctattaag ggtgcggtcc tggtcctttc gaccgtccgc tggctccctg  38640
gggccaaaga ggccgcagag caggcgaagg ctttcccgta taaaggaagg gtccacgcgc  38700
ttggagctgc ttggcattat gttctgctgc ggcgcacgaa gaacttctat gtcgatccgc  38760
aaggccgcaa gtatcgtcgt gatactggct ggtctgtgga cggcgtgctt aaactgagcc  38820
tcgattcaat taaacctagc gttggagaac gcaaatatgt cagcatctaa cttcaccgtc  38880
gatcagatcg aagagcgatt cggctttcga ccaaacagtc agcagatcga cgcgatcaat  38940
tccgttgtgg actggtatcg cggttggtgt gatcgagcgc accgccgcca ggtctatcga  39000
ctcgctggtt tcgccggaac tggtaagact tccatcgcga agatcatcgc cgaactttgc  39060
tgctcgatgg actggacggt cttcgtcgcg ccaaccggga aagcagcagc gcggcttcgc  39120
gagaagggtt gcaccaatgc ccggaccctc cacagcttca tctatcggcc gattggcgaa  39180
gatgaagacg gcgaaatcat gtttgccaac aaagactcgc tcgacgagaa gccgaagttg  39240
gtcgtgctcg acgaggcgtc aatgaccggt gagtgggatg aagagcgctt gttggcgcat  39300
cgaattccgg ttctggagat cggcgacttt ggccaagttc cccctgtgcg cggcgttcag  39360
gttttccacg aacatagctg cgacacagtc atgactgaaa tcgagcgtaa cgccgggaat  39420
atcgttcgag cgtcgatgtt cgtccgccag ggcaagcgcc taccctgccg cgagtatgac  39480
gacattctgg tacgggccgg attcgacatg tcggacgacg aaatgcggac gttcttggac  39540
```

```
gatgacggcg tgatcctttg cgcctacaac aatactcgtc gccgtttgaa cgccagggcg  39600
cgccgcatcc tcggctacaa gggtgtacaa ccggaaatcg gcgagaagct ggtgtgcacc  39660
gggaaccagc acgaatatgg catcatgaac ggcgagcaag caattctgct ggacttcaag  39720
ccggtccccg aaggccaaga agatgatgac gagccggatg aaatgttgtt cgccaaagtt  39780
cgcattatcg gcacgaacta tgagcgctgg gtgaagttca atcccttgag cttttcggtc  39840
gaggaagatg tgcggctgga ggcgcagaag gccattggcg gattcgactt cggctgggcg  39900
atgacgttcc acaagtcgca gggatcggaa tggaaacggg ttgccatgct ggaagaaaac  39960
ttgccgtcaa ttccttatag tcagttgatg tatactggca taactcgtgc aattgaatac  40020
ttgttgtttt tgcgtaagag ttgaaaactt cgcgaacata aataagttcc tggagtctgg  40080
actttcccga aaggaaaata tttagagaag ttcaggcgaa aggtattccc ttcttcaatt  40140
agtttagaga taatcccctc acaggccaat aagccatccc tttaaacatt cccggagtaa  40200
gaacatggaa cagaaagacc agaacgagca gacccaaggc gaagagctga ccaaggaaca  40260
agcagccgcc ctgcgcaagg ccgagaaggc cgctgagcgt caacgtaaag agcgcgagcg  40320
cgccgagaag gccgaggcca aggccaagga agccgaacag aagaaagccg agcgcgaaga  40380
gaagcgcaag gccgagcgtg agaagaagga agccgagcgc gccgagaagg cgaagggaaa  40440
ggccgccgcc aaggaagccg agcgtgctga aaaggccaag gcgaaggaag ccgagcaggc  40500
cgagaaggcg aaggccaagg aagccgagcg cgagcagaag aaggccgaga aggaagccga  40560
gcgcgccaag aaggccgaag agaagaaggc cgcgcaggaa gcccagaaag ccgcacgcga  40620
agaagagcgc aagcgcctgg ccgagcagaa gaaggcagag cgcgaagccg agaagcagcg  40680
ccgcaaggaa gagcaggaag agcgccgcgc gaaggccgaa gcccgccgcg aagacctgaa  40740
gtccaacggc tcgcgtcgcc cccgcgccac tcacttcatc ccgaccggcg acggccatgg  40800
aaccccgcag gccttctcga ctcgcggcaa ggtgtttgct tacatcaacg agcactgcac  40860
cgttggtgag ccggtcgaaa tcgaatcctt cggcgagaag gtggcccacc tgctgtacgg  40920
cacctcggtt cgcagctacc tgagcaagct ggaaatcatg ggctgggtcg atctggttgc  40980
catcgcttcg aaggaagacg aagctggcca gggcgatgac gagaaggccg atgaaggcca  41040
ggagcacgac ggtgaaggtc agggcgccga cggttccgat ggtgaagaag agtaagccgc  41100
cgctcttctg agaccgaatc gtctagctct tcaagggact catgaaaatg ggtccctttt  41160
ttatcctctc aagttttgta cactcataag ggacacatca tgattcctga tcagaaagta  41220
atcatcgtag gtgccggact cgccggactg atcgccgcgc atcgctttcc tcaagcccaa  41280
atcatcgacg cggcgacgcc ggagaataag gagcgccaca acgcacttct gcgattccgc  41340
tcgccagtga ttggccaact caccggcatc ccgttccgcg aagtcactgt gcacaaagct  41400
atctacatcg acggcgagtt catttcccag ccgcgcatcg accactgcaa catgtactcc  41460
aggaaagtaa ctggcggcct gtcggaccgg tccatctgga atctggcgac tgaaaagcgt  41520
tggatcgcac cggccgacta ctatgagcag ctggtggcta agcttgcgaa tcgtatcact  41580
tggagccgtc ctttcgacgc ctctttcttc cagtatcttc gccggcaaga tgaccacgtg  41640
aatatcatca gcaccgcgcc gttccgcgcc aatctggctg cggcagggct ggacctggga  41700
atcgacccgt cattcggtga aggaacctcc atcatcgtga gtcgatacaa gctttccatc  41760
ccctgtgatg tcttccagac cgtgtatttc cctggtccta aagtgggaac gtttcgagcg  41820
tccatcaccg gtgatactct gatcgtcgaa tccatcacta aggggatagt ggagacttta  41880
gatggtaaaa tcgaaaccat cgaatgggac agcgactggg acatggatta cgtttgcgcg  41940
```

```
gccttcggca tcaggaaaag gcatctcatc gaggacggcg agccgaccat ccagaccaaa  42000
ggcaaaatcg ttccgctcgg ccgcgacgag cgcgaatcca tgatctggaa tctcacccat  42060
gaagccggca tcttctcgct cggccggttc gctacctggc gcaacgtcct tctggacgat  42120
ctggtttctg acatggacgt catcgagcgc ctgatgactt cttcgtctta tcagaaggcc  42180
aagaaaatgt tcgtgaagta atttacaaaa gtgctttact tctggatcag gtgggcgtaa  42240
cattccctca tcgaaacgcg aaacccttca accaaaagga atcgacaaat ggcccgcgaa  42300
gtaaccttct ccaccgacaa gaaccacacc aagacctacg ccaccaaggc caatctcgaa  42360
cgcgccatcg ccaaggccga ttggctcggt gaaggcgccc gctacttcgt ccatatgacc  42420
gaggatggcc gcctgactcc tgtgttcctt ctgaatagtc ttcctgcagg gaccggtgcc  42480
gtgtggtgcg ctcagcacgg ctggaacgtg gtaggttaat ggccgtcgat cctcgcgaag  42540
cagcgctcaa gcgggcgctg ctagctttct tcagggacac cgatgccctt ggcggcggga  42600
gtctcacaat aacggcccga atcgtcgggc cagagggcga caggaagttt cgcgccagtt  42660
atttcctgaa tggcgagaag ttaagcctgt ccgatataat cgctaaagtg gaggctgaag  42720
atgggccgga tcgttaatat caaagcagtc atttcgcgca ccaccgagcg cgattccatg  42780
gggtcgccgt acatccatga gtcttaccgc actttctctt tctccgcttc caccgcactg  42840
gtcgcggcca tcgactgggt gaaaggccag tgcccggaaa tcgttgacat gctcatctat  42900
gagccggaaa ccgtagctgc tcagcaggag cgctattaat gtacgcacca gatcatcctg  42960
aagaggttcc catgtctttc ctcgaaatgc aaatcgaccc gccgcaaacg cgacagacag  43020
cgccgtcttt cgtgctggta ggcgtcctgt acctgattgg cgatgggcgc ctggacgata  43080
agcctttcac ttcgttcaac ctgtcgttcg gcagtcgaga agaggccgag cgcgcccgcg  43140
ataagattcg tgagcactac ctcgaccgtc gagatatccg cgccgaaatc atccgctgct  43200
actgaggtca tcatgtcgat tgaacttgtg taccgaacct ctgatggagc cgtcttctca  43260
tccgtccatg aggctgaaga gtatgaggcg cgtctggagg cctgcgaact gctcaaggaa  43320
gagatagagc agtatggcct taacagggag caagcccaag gcctggccct ggctctcacc  43380
gaaaaattcc acttcacgcc aattccggaa gatttctgat gaagatttct ctgattagtt  43440
acacccagaa cgcctgggaa ttgctcttgg gaacgaagtc cacccgcatg cgcggccaag  43500
acccggcgac catgaccgag gccgaaaagc tcgaccactg gaagtacatg ctggacacca  43560
tccgctcgcc gttcgagttc gtggacttca ttttccagat cgagggtgtc agcaagaact  43620
tcacccatca actcgttcgg actcgtaccg gggcttacca gcaggaaacc agtcgcgctc  43680
tggaaatcag cgccgtcgtt cagccggaag ccttccgctg ggaattcgac gaaccggcta  43740
cggtaaatgg cgagcctgac ccgacctacc atgtccgcga agagctgaac cgcctgtggc  43800
acgacgccat tgccgacgcg caaaccagct accagaagct tctggaggcc ggcgcgtcgc  43860
tccaggacgc tcgtgccatc atcccttcca acatggaaac gaagatcgcg gccaagttca  43920
atctgcggac tctcagcgac atggcgaagg ttcgcctgtg cgttcggacc cagggtgaat  43980
atcaggaagt attccgcgaa atgcgccggc tggttctgga agtctatcct atgttcgaca  44040
gcctgctcca gccgcactgc gtcgccaccg gctcctgcgc cttcccgcgc tatgggtcga  44100
aggtgatgaa tgaagaggaa atccagcaga aatcctatga ccggttcatg gccgctctgg  44160
agacaaagcc aggtcagatt cctgtgattg atgttccgtt ggaacctatc taccagtgca  44220
agttctatcg cccctggatg gatcgctcgg ccgagcagga agaactgcgc cgcgatttct  44280
```

```
ggggatcgga aaaacaagag gccaaccctg tggccgtcaa tgggaagtcc atgtaacatg  44340
aagatcattg tcgagaaagt tggcgacatc gcacaagtcg aagtgaccaa cggcagcgaa  44400
tccattcgca tcacgatgaa cgtgcaatcg ttcgatttca tccagaatgg cgaagttttc  44460
cgcctcactt ctgatgggac attcatcgat aaaaccgtca cccagaaagc aaccagtaag  44520
gaaatctgaa tatggaacgc aaaccaaaga atggcatcat catcttcgac ctggacggct  44580
gcgtattcga cgatagccac cgcaagagct tcgccttgga acggcaatgg gacgagtatc  44640
attctcgtct cgacaaggac actctcaacc cgcacgctgt aggtcgcatc aggaatgcca  44700
tcgacgccga cctcatgatt ttcttcgtca ccggccgaac cgacaaccac tttttccaga  44760
ccagggccaa gctccaccgc gaactcggca tcgccgaaca tcgcgagtat gaactcatca  44820
tgcggccgta tggtaacacc gagccggcgc ctcagttcaa gcgggcagtc gcgctcgaca  44880
tcctgaagaa aatcgaaggc gtcaccaaga tcgtcgcggc gttcgatgat cgccaggaca  44940
tcatcgatgc ctacaatagc ctggggatcg actcctacat cctgaacctg gaaggttgcg  45000
atgcgccgtt cttcgccgtc gcggccgata gcgaccccga tagcgcgccc aacgacatgg  45060
caggcgagcc gttcccggcc gccccgaact ccgcccctac cctcgacgag gcgtttgcga  45120
aagccccgtc tccgctcgct gaaacggctc agtccgaaga cccgaccgaa gacgtcgcgc  45180
cgttcgccat ggaatccgtc tggcctggcg aagatgacgc tcatcccgat gatttcgcgg  45240
aagatgttct caacaatctg tacgccgcag cagaagtctt ccgcgcccgc cagagcacct  45300
atggtcgcaa tgatctgatg tacggaaaga tcatggaaat cctcttcccg aacggcctgg  45360
tggcgaagac cgccgatgat catcgactcg ccctgttcgt gatgcatatg gtgggtaaac  45420
tcactcgcct ggcgaatagc gggttcaagg atgccgattc ggccttggac tcgatcaact  45480
attcggcgtt tgttcacgcc accatgcgct ccggccgcat cacgccgaaa gacggacaga  45540
aggcgtaaat cttcagccgt cgcggtatac tcctcaggcc ggtcgcgaaa gcagccggcc  45600
tttcgacata agagggaaca aacatgatat tcgctgtatg ggatactgag accacaggac  45660
tcccgttcca ccagagggtg agtctgagaa agcagccgag aatcatcgaa ttcgcaggcg  45720
tgataactga tggcgaaaag attttggatg aagtagagtt catctgcaat cctggaatcg  45780
tcatcgagga aatcatcacc aagatcaccg ggttgaagaa cgaagacctg atcaagcacc  45840
catctttcct cgatcagcgc cagaaagttc gcgacttctt ttccagagcc gacgcgaata  45900
ttgcccacaa cctaccattc gataagttca tgctgacctg cgatctggct cgcggcaagt  45960
tcggcctgga cgaagtcaat ttcccatcac tcgatatctg tactgtggaa gagtcggcgc  46020
cgttgttcgg ccaccgcatg cggttgcaac atctttatga gcactactgc ggcccatatg  46080
tacagaaaca ccgggcactg gacgacgtgc ggctgctcca cgaagtctgt aagcgcatgg  46140
gagtatatcg ggcatatcaa gcaatggagg ccgcataatg tctttccctc agcttcgcgt  46200
tcgctctggc tactcctacg gcgccgcata tggccgattc ccggagatca tcgagcgcgc  46260
caaagagatc gaatccccat tcgtcgccat cgtcgatgat ggaacatggg gtcacgtccg  46320
ttgggagcag gccgctatca aagcagaact gcctcgcgga ttcggcatgg aaataccgat  46380
caaatgcgcc gacgatggcg agaaagagct gaagctcaaa gcctgggtgc tcgccaagga  46440
caccaagaag ttctaccgct tgacttccaa gtcggtccag aatcaaggat tgactccgca  46500
agaattccag gaagctgacg gcgtcatcaa attcgctggc gaggcctatg cccatctgga  46560
tctggccgga atcgactaca ttgacatcaa tcccgcgtcg atggtcgccg cgcacggcgc  46620
tatggagacg gccagggcat tcggaaagcc ggtggtaatt acctcttaca acgacatgcc  46680
```

```
gtccatcgac catgctgatt tcgcgtcggc ctggaaggtg cgggaatcgg tcggccttcg  46740
ccacatcgcc accgaagagg agctgtggag ccgtttacgc cacatcatga ctcgcgaaga  46800
gttcgacgcc gccgccgcca atactcgtgc ggtagtcgaa caattggcgg atgtgaaact  46860
ggcgaaggcg cctatgatcc acctggatgg ggatatcgtc gcgctggctc gcgaggggca  46920
agcctaccgt ctcagtcgcg gccacatcaa ggaatggacc caggagtatg aggatcgatt  46980
ccaagaagag atcaagcaga ttcagctgaa agatttcgac agctacttcc tggtcgtggc  47040
agatctggtc gcgttcgcca agaagcatat gctggtcggc ccagctcgcg gctcttcggc  47100
cggctctttg gtctgctatc tccttggcat taccgaggtt gacccgctcc ctcatcgcct  47160
tctcttccag cgctttatcg acatttcccg gtccgatctt cccgatatag atatcgactt  47220
cgccgatacc catcgctatc tagtgttcga atatctccag cagaagtatg gcacttggaa  47280
cgtggtgaag ttgggtaaca ttaacacgct caaggccgca tcggttatcg ctcacgtcgg  47340
aaagcgcttc ggcatcccct tccacgatac cgacaacatc aaaaactcga tcatcgaata  47400
tacatcggcg gacgaacgat atggaaaagg attggaggat actttcgaaa aaactcagcc  47460
cggccgcgac ttccgcgaaa agtatgagat cgcgtccgcc tgcatgggcg acctcgaaat  47520
tcacccatcc cactctggcg tccacgcggc aggcatcctg gtctgcaacg atgaagtcat  47580
caacttctgt acggtaactt ctgaaggtgt cgcgcagctc gacaagcccg attcggaata  47640
tctgaatctt ctcaaaattg atgcgctcgg ccttcgaact ctgggagtca tccaggacgc  47700
gaactgcgtg accgcgcaag agttgtacga cttgcctttg aacgacaagg cggttctgga  47760
cgtcctcaat gaagacaaaa tgtccggcat cttccagttc gaagggcagg ccgttcgctc  47820
ggtagcgaac gcgatcaaca tcaccgcgtt cgagaacatc gaccacatca cggcgctcgc  47880
ccgtccgggt ccgttgtctt ctggtatggc aaccaagtat atcgagcgcg tggccggccg  47940
cgagcctgtg acctatacca ttccgcaggt cgagcaatat ctgtcaggga cgtacggagt  48000
cttcctgtat caggaacaga tcatgtccat cgtcaaggac atcggccagt tcgactggga  48060
acaaacgtcg gcaatccgga aggccatgtc tgcgcgaaag ggcgaagagt tcttcaacaa  48120
gcgccgggaa ttgttcatcg agggcgccaa gaccataggc gtcgccccgg acgatgctca  48180
tcgtgtatgg caggaaatgg tgacattcgg cgcctgggga ttcaaccgct cccactcggt  48240
cagctacgct gtggtgacgt actggacctg ctacatgaag cggtatcatc gcctggaata  48300
cgcggccgcg tgtcttcggg cggcgaaaga cgaccagcaa actgtgtcaa tccttcgcga  48360
attggccaag gaaggcgtag aatatacggc cctggacccg gagcattccg aacttaactg  48420
ggtagtggcg gacggacgcc tgatcggcgg catcatgaac gccaaaggct tcggcccggc  48480
gaaggcagag aagttcctgc gccttcgtga tgacgtcaag gccgcgagga tcgccctggc  48540
caattgcccg atatcggcac aggatgttga ggacaaggct gctgatgtag cagcgctgga  48600
agcccagatt ctttcggcga aaatcagcca agacaaagaa ctggaaaaac tgttgaaggc  48660
cgatctgaag gagttaaagg ccgatcttag ggagctgaaa gctcaatata aagagctggc  48720
cggaacccac ctgaagacgc ttcaggattg ggagaaagtc gccgcgagtc tgtcgaattc  48780
tgaagttcaa ttcgcagatt tgaacgaagc tcacacgctc tggggtcatg cttatgacaa  48840
tccggagctg gttggagtaa cttccggaaa ccccatccag aacattcggg atatccgcga  48900
tggagacgat ggcctggtca ttgtcaagat ggtgaaaaaa gttctgtctg atgagaacga  48960
accgattcgc cagaagaaga gggcagatca agggaaaaac ccggtgtaca agggccagtc  49020
```

```
gcagtttctc gacatcatgt gtgttgacga ctcggttgat cagccgatac gtttcagaat  49080
taggcctgaa aaatatctgc aatacggaaa gcagattgct gaaggaacgc cgacaggctc  49140
ttggttcctc atcaaaggct ggaagctcag cggaatcgat atgttcatcg tgaaggccgt  49200
caagaggatt ttgaccgaac gcgaaaaagc aaagctggca gcgcaagcag agaaagtttc  49260
caaagagggc gaaggcgatg aatgatcgcg aaacgaaagc ggcgaatgcg tttaagcaac  49320
gctcactcgg ccgaatcctg atcgactttc tggagacgcg gcggtctggt atgtccgatt  49380
cgatttgcct gaatcgtcga ggcgtccagt tctgggtcga gttcaaggcg ttggaggagt  49440
ggccgaaacg cgcctccacc tgcccaatgg ccagatgttt cgagcctggg caaatccctt  49500
tccttcggga acggatcggc tggggcggcc gtggcttcgt cctggccaag atcgggaccg  49560
attggctgct gctgaatccc atgctcgatt tgttcgagct taacagccgc gacttggtgg  49620
aagttgcgag ctatgcagaa ggactggata acattgttca gttcctcgcc gatttggaga  49680
acaaatgaaa gccaaaacat atcccgtcaa gggcatgaag accgaggcca tgcagcacca  49740
gttcaatgcc ctggccgcgt ccctgaacaa acggaatttc gcatacctga tggagcaggg  49800
caccgggaag acttggacga ctttggccga tgccgttcgc ctcttcctac aggggcgcgt  49860
ggacgcgctg ctcatcgtcg cccccaaagg cgtccacacc aactggattc tgcgcgagat  49920
tcccacccac gtcgcgatca agactttgag cgtggattgg cgcggccgac cgacttccaa  49980
aaaggccaga gcgcgcttgg atcgtctgta tgccgagacg ttcgcagatg aaaaagttct  50040
tcgcgtcttc gccataaacg ttgacgcaat caaccaccag gctggctatg atgaggtcga  50100
gcgattcctt gatacattca aagtttgcgc aattgtggac gagtcaacga ggatcaaaaa  50160
cccacaagcc aagcgtgcga aaaagatcgt aaagctggga gaaaaggccg tggcccgtcg  50220
catcctttcg ggaactcctc tgacgcgggc gccgaccgat ttgttcatgc agttccaatt  50280
tttgcgcaat ggcattcttg gaacgaaatc ctatcgggcg tttgtggccg aattttccgt  50340
tttggttccc agtgacgatc ctcgaatgat cgctatcatg cgcaagctgg aaggtaagca  50400
gacgatgccg ccgcaactgg tcgaaaaaga cgagtgtggg cgcccggtat tccggaacct  50460
ggacaagctt cggtccctga tcgagccgca cagtttccgg gttacgaaga aggaagcact  50520
cccattcctg ccggacaaag tgtacaagcg catatacttc gaaatgtcgc cggagcagcg  50580
aaaggtttac cagcgcgtgg aagaagacta ccacttcgtt ctcaagaacg aagacttcat  50640
gctggacgta tctttcgatg ctgcggcagc gcgttcgaag ctcaagcaag ttgcatccgg  50700
ctatatcaac gtctatggcg agccggtgat cctgccgccc gaagacaacc cgcgattcgc  50760
cgtgttcact gatcttctgg agggtctact ggaggaagac ccggagcgtt ccatcatcat  50820
ctgggcaatg cgcattcagg aaatcgacca gatcaaggca tatctggagg cgcatgggat  50880
ttcgtttggc acctactacg gcgagaccaa agaggccgag cgggaaaaat tgatcgacga  50940
tttccaggcc aagcgcgtcc aggtattcct gggcaacccg gccgcagcag ggatcgggat  51000
cacgctcaca gccgcagacg tggccatcta ctacacgacc gacgaagaca acgagctgcg  51060
gatgcagtcc gaagaccgaa atcaccgaat cggcaccgtc aactctgttc tgtacttcga  51120
cctgatatgt ttggattcca tcgacgagaa aatccaggtc agcttggagt ggaaacgcaa  51180
cctggcaagt tatgtcgttg atggcgtgtt tgaggctgac gttagcactc gcgacgaaat  51240
ttaatatgta aatcagtagc cgtatcaagg aagatgcggc ataatatcta ctcaatactt  51300
ggttcaagta agggaacatc actaagttgg aggcggacat gaaagagcaa gagcttgaaa  51360
tcccggaata cttgaaagag aacgcgccgg gcgaaatcga ctattttggc gtcatggatg  51420
```

```
aaatggcggt tgaagccacc gacatcggcc atcgactgct gaacttggtg gacaaggctt  51480
cgcagctgga cggcgaaatc ctcgatcttc aaaaggcgct ggccgaaaag gaagaggagc  51540
tgaagaccct caagcgtaac accattccgg agctgttgga ggagcttggt cagaagacca  51600
ctactctggc ggacggtcgc acggtaaaag tagagccgaa ggccatcatt tccgtcaagg  51660
aagagaacaa atcgaagttc tggaagtggc tggaagacac cgacaacgac ggcatcatca  51720
agaccaaggt tctggccgaa ttcggtcgcg gcgaaatgga agatgcgaag aaggcggccg  51780
aggctatcat tgaagccggc tatgacgcta ctatcaaccg cgatgtccac taccagaccc  51840
ttcaggcgtt cgggcgcgag tgtctggaga agggcgaaga gctgccagat ttcatcggcg  51900
tgcacgaata caaagaggcc aaaatcacga aaccgaaggt gaaaaagagc aaatcctaat  51960
atgtaatttg ctttacttag ctgcaacttc cgttattata gacccacagt tagcgataac  52020
tgaaattcga caaacaagga gcctaacatg gctggtaaga aaaccgaaac ttccgaagca  52080
accgaagaaa ccaaggccgt agcagttgcc accggtggcg gcgccgtcgc gactaccgaa  52140
gttcccgact tcatggattt gggatcgtat gacggcgcag gcttcgaagg cgccgatgcc  52200
gagtcctatg ccatcccctt catccaggtt ttgcagaaga tgtctcccca ggtcgatgaa  52260
gatgacccga agtacatcga aggcgcgaag gccggcatgt tcctgaacac cgtcaccagc  52320
aagatttacg acggcaagac cggcctgctg atcattccgg ccgcgtaccg ccgcgagttc  52380
atccgctggg ccggtcgcga ggccgagggc ggtttcaagg gcgccatcag cgtcgaagac  52440
ttcaaggaaa tgatgaaaga cccgaccaag gtgaaggaag tcgaagggcg cctgtacgcg  52500
ccgaacgaag atggttcggt cagcgacaag aagtctgact acttcgccga cacccgtggt  52560
cattacgtca tcgtcatcga tccggacacc ggcgatttcg gccaggctct gatctccctg  52620
tcgtcttcgc agatcaaggc ctcgaagaag ctcatgaccg cgctgtccca gaaaaaggtt  52680
cagactccgc agggcctgcg caccccgccg actttcgcca acctggtacg catgaccacc  52740
gtcggcatgt cgaacgacaa ggggagctgg tccggcgtcc agttcgaact ggaaggcctg  52800
gtgaagaacc cggatcactt caaggctgcg gccgaccttt acaagtcatt cgtcggcggc  52860
gaggtgaaag tggactacag caagcaggaa cagcctcgca gtgacgccgg tggcgtcggc  52920
gatgcgaccg aagccgaaga gttctaaaaa tcaccggccg gagaaaggcg ctgtaatggc  52980
gcctttcttc taaggagtcg aaaatggact ggaaggacat aggtagtaag atcggcgcgg  53040
ctgccccggc tctggggtcg ctcctgggtg ggcctgcagg cgccgccgtg ggctctatcg  53100
tcgcgacggc gctggggtcg aaggccgacc cagcctcggt cgcgagcgct ctagacgcga  53160
atccggaagc tctagcgcgc ctcgccgaac tccagagcgc cgagcgcgtt cgtctccagg  53220
agcttgcgat tcaagccgaa caaaaccgtc ttcagtctga gcagaaccag ctccaggccg  53280
agcttagcca gttcgcagca gaggctgccg acagggattc ggcgaggaga cttgccgcgc  53340
agcagaacga tttcgttcgc ccggcgatta ccttcgctct tctgacaggc tccattctca  53400
ttatcatcgc aatcttcacc ttcggccgcg aggctctgat ggacccgaca tcctcggtcg  53460
ccatcggcac catcatcggc tattggttcg ccgagctgaa gtcggtcatg gccttctact  53520
tcggcaccac caaggatgga tcgcgccaga gcacggcgtc catcatcaac gcagtcaaat  53580
cccaaatcca aaaggaatcg aaagaatgaa tgtcgaacag atcatcatcg aacaaatcat  53640
gagtcgcgaa cttcacgacc tggttgttaa atggggttcc gaccggaacc tgatcaaagg  53700
atcttcggcc aaggatcaat tcctgaagtt ggtcgaagag ttcgcagaag tttgcgaagc  53760
```

```
ctgggtttat aacaaaccag tcgaggtgaa agacggcatc ggcgacgtaa tggtggttgc  53820
cacgatcatg gccgcgcaac tcggtgaaaa tctgttcgat catctatcgg tcttcagcga  53880
gactgtcgaa gttcatccca cctacggcga ctatttgcag cacctcggac atctggccgg  53940
cgcgctggca cgcggaaatc atggattagc catcaagagc ctggtcttgg ccgtcatgac  54000
tctgttcgat gtgacggaag agtacgacac taccatgctc gcctgctacg ctgcggccta  54060
cgacaccatc aaggatcgca aaggcgtcat gtacgacggc gtgttcatca aggagtcgga  54120
cgagcgctat gcgtcgatca tggccgaact gaaccacgcc aacgaaacca tctgagccgg  54180
cttaccgcca tttagcccgg ttcgccgggc ttcttgtctg gagaactgta tgaaacccat  54240
gctcgcatcg aattttgacc agaagctgct ggaaggccaa ctgccgatgt atttctcacc  54300
gaagatcgat ggatttcgct gcttcatatt cgaaggcgag gcgctgactc gtcaactcaa  54360
gcgtcagacc aatcagtcga tctacgaata cctcagcgat aaactgttca acggcctgga  54420
cggcgagctg gtctgcggcg acatcagcga cccgaaagtt ttccagaagt cgtctggcga  54480
tcttcgccgc cacagcggtg agccggactg gtctttccat gtgttcgatg atttcaccga  54540
tcctcgcgca ccgaccaaag agcgcctagc cattgcggct gagcgcgtga acttcctgcg  54600
caactgcatc ggctgtgaga ggattcacct ggtcgagcag gagctggtga cttccatcga  54660
acagttcagc gaagtcgagc gccgccacac gatgctggga ttcgaaggtt ccatgggcaa  54720
gcgcgccgat ggactgtaca agttcggtcg ctcgacggcc aaggaagggc attgcgtgaa  54780
agtcaagcgc tacgactacg atgaagctga gatcatcgac gtggaagagt tgatgcacaa  54840
caacaatgaa gctttcatca atgaacttgg taacacggcc cgctccagtc atgcggaaaa  54900
cctgtcgccg tccggaatgg tcggcgcgtt cgtctgccgc aacgaacgtc tgtggcctgg  54960
cgtcaccttc aacgtgtcgg cctccagcct gacccacgac gagaaacagc gccgctggaa  55020
tgacagggca tacctcaagg gccaggtcat ccgattcaag cacttctccc atggcgccaa  55080
ggacaagccg agacacgccg tcttcgattg ctggctggac ggatggggcg gaagccactg  55140
attctagcgg acactagatc gagataaacc cggacgcctt gtcctacagg cgatccgggt  55200
tttctcgttt taatgtcgac aaattaggcc ttagaccgga ccaggccgcc agagttcctt  55260
ggccagaaag aaggcgattt aatatcgcgg tgcgtatcgt taaacagtta agcgcgagca  55320
ttttcgacga gttataatag cgcccgaacc ttccgattaa cacagcgcat ccccaagcca  55380
ttatcggggt gaggagaaga ccgcagacag aggactaaac atgaaacgca aagagcatcg  55440
caagcgcttt cggccaagaa tcagccccag actccgggaa gagttaatat ccgttctgac  55500
caagatcata ggcgagacag tcaaggacaa ggtggtaaga gcgctgttaa tcggcgttct  55560
gagttcacta gggaactatg tggattcggt cactcaggaa gagtccgccg cgccggttga  55620
agtcaagatg gttgaagagg caaagccaga aagcaaaaag gccgctgaat aagcggcctt  55680
ttctttgggt ggaatatcag gagccttgat tgatcgcggc gatggtcttc atatagcggt  55740
tgatccggag ctggccgtgg ttcgcatcgt tcggcgcggc gccattgatg gttttaacga  55800
ccatggagaa gttgttggac tccgccatgg ggatgcagcg attgcgccag aagaaccagg  55860
cagaagacat cgacgcgccg gccggagttt ccagaagctc cggcttctcc agaacgtcca  55920
tgccggagtc ttcggcgaac agtgaatagt tcgacttccc ggtcagctgg atcaggccgc  55980
gcccgcgata cttccaaccg tcaccatcct gctcacagcc attacccata cgatccgcgt  56040
acacgttgtt ggcgatggca accgggttac gggccaggcg gttcgccaga gcattcggga  56100
catacgggcg gactcgcggg tctactgcgt accggcgcgg ccaggtgttg gccaaccctt  56160
```

```
gggcgctgta gttgagattc tccaccagac ttaccagtcc gccggactcg acgccgatgt  56220
tggcgaggta ggccgcgatg gctcgcggtg actcgatgtg gaacttgtcc atggccgcct  56280
gtacatcatc cagccacttg atcgcccgat ccgtggtgca cccggttccg gtgatcagaa  56340
catccttcgt gattttcatc aatactcctg atttttgaac attgttttca gagccatggg  56400
aagtcgcggc cgatccccgc tattccaatc gcgaatctgc tgcctccagt gaacaagggc  56460
tgctatcagc ccaggcccgt ccgtggtttc gatacccagc cgcctctgct cgtcgtgacg  56520
atctatgggc catcgggtat cgcgaaggat agcccgcttt tccctgtctc gtatagcgtc  56580
ctgcaaggcc tgctcccgcg tcgagtctac tggggcgata gggccgtgcg ccccggacag  56640
gatcgcagcg tgaatggccc ttccgtgggc ctccacgtcg tgcggattgg cggtgaaagg  56700
aacttctcca atcccctcga aagtaaccat ggcgtggatg tttaccgcgt ccagccaacg  56760
tgggtttctg atccgcgtcc atttcatgtt acgttacccg ctggaatagg gatgccgagt  56820
cgccgttggt ggagtctcgg ttatacacat accccatgca gcgccaggtg cccgtcggac  56880
gggcgctgct gcgataggtc gaatcgcagg acgaatagaa cagcttggaa ctgtccatga  56940
tcgttccggg ggcaatggac gctgccggcg cggatgtgtc caatacggca aggatcgcgt  57000
aggaaccgac gccgccaaga cctacctgaa ccagcgcctg gttgatgtag ttgttgtagt  57060
tgccggagtg gatgatggga tatgctacgc cgcccattgt gccgccaccg atctttacca  57120
cgttgtccgc atccaggccg aagttgacct gatatttctg cggcgaatgg aacgtgatgg  57180
cggctgcggt attggtgacg ctgttgtttt ccacaaccaa cgcaccgacc tgtccggttg  57240
atgcgattcc ggacgcccca taactgaata ttgtagggga tgacgtcgta ttgcgagctg  57300
ccaaagtcgc cttggtgtct gggttgaagt ttcccgacct ccagatggtc tgcccgttcc  57360
agttcggcgc ggcagcgtgg gatgaccaca ggctcatgag gttgttggag tcggcaatct  57420
cgaacgcgac ggcacctaga gaatagccgc cccatttcag cttgttgtcc gtgtccaggc  57480
cgaacagaac gcctcgtgcc ccgttacgaa caaacgaaat tacagcagca cgattcccgg  57540
tcggcgtcga agcctcatag ttgaagaacg acatggccgc gtcgccataa cttgtcatgg  57600
cggctatccc tacgtccttc gcggcgctgt ttaccatcct ggtgtattgg ctatcgttga  57660
atgcgtccaa cgtaagctta gtgttcggat tgaagttcca cggaccccag aactcgacat  57720
tcccccaaat cgggcgcgca gccattgtgt tgatatgggt tcggatgttg gattcgtcgg  57780
tgatcacata ggagttattg ccgagcgacc agccggcccg cttgagctgt ccatccttgt  57840
ccatgcccag ataccatccg gtctgggagt tgtcgaaata gatcgcggca ggctcaccgc  57900
cccctttcc gaagatttga atggcagcat tgccatagga tgccgtcgtg gagccggaac  57960
cccaggtgtt catgttgccg gtgttgccgt tggtattccg aatcccggtt gggccggcga  58020
tttggttcgt ggcattcacc gtcaacttgg tggaaggatc gaagttccca gaatcccaag  58080
gggtgtattg accggcgaag agcggacggt tgttgaatat gacgttcgtg gacgcccagt  58140
cccatcgcat gacctgtgaa cgataggaac cgtccggatt ggtggtattg actgcgatca  58200
ccgcgttgtt gttcgcgtcc acgccttgtg caaaggtgaa tttccaaccg ggctgatcgg  58260
cggtggtgtt ctgccaaagg gggccagagt tcgcgatgta cgcgaggttt ttcgccacat  58320
cgagtcgcgg ctggaagaaa gtcacggaat ttcggttgaa caggatgtcc tgggtaggcc  58380
cagcagaccc ctgccgcgaa tagaaagcca gcgatccgtc tgcttcagat atcagccgat  58440
agtcaaaatc tttggcgcga ttgctgttga agtggaaatc gatgaaaggc cgagcatcgg  58500
```

```
acagctccag attggcgaac cacggcgttg tatcttggat agcgacgttc ggcttgttga  58560
cgacatccgt ccaatccact tcggtgagct tttgggacgc gacatagtct ttaacttgct  58620
tccaactcgg cgcctggtag tcctgatcgg cgttgccgac ttgtatgcgc ggcgcgcctg  58680
ccagaatcct ccagcggtcg cctgctgcgt cgaagacaag ctcagcgatg agtccttggc  58740
caagttcgcc gccagtgaga gggaagttgg ccgcgccgac gatggctttg gcgccgagtc  58800
cggagacgtt gatggtagta gcgccggtgt tcatggtgtt gaacttgacc cgaagaatca  58860
tgccatccac caggccgcct tggagctgcg gaactagcgt caacgtgtaa gcgttcgccg  58920
atccggccgc gactccatag gtgacccgac cttgttgaag ggccatgacg tttaccgcat  58980
acatccagtt ggtccacgct ccggcattaa gcccgcgcac agcgacgttc ccgacgcgat  59040
cagtgtagcg ttggacgcag aacgtattgg ctccggacac ccaagatttc gcctccaaca  59100
tgccagcagc ggcaccagcg gaagccggat atacgggggc attctgagaa gcgataacca  59160
ctgaatcaga gaagaactcc cacgtcccat ttaacaggtc gttgaagttg cggccggtcg  59220
tgatgacttc tccgccagaa gataggcctg ggcctccggc cggcatcggg atgttggagc  59280
gcatcgccga ccatgcgggt tgttcttccc aagtcgtgct gctgagaggg tcgctcgcat  59340
tggcattcac catggaacga taacgccgca ttatgccgtc atttccgacg cgcacgactt  59400
ctgcattctg ttcgtagccg ccaggcatgc cctgaaacca cggcggcgcc atttgtcgct  59460
gccacgcctg tgcgttctgg gtcgcgatga agaagagttg gttttgaatt ttccgctcga  59520
ccgctttggc ctgcgggttg ttcgacgcca ggctgatttc gtagtccggc gtatagccgt  59580
cgcgaaggtt tgcgaagcca gtggaggagg tttgtggaat cgggtcttta tcgccctgag  59640
cggcaaacgg actggggatc agttcgggtg tgatcacgtc attactcctg aatgactttg  59700
acatcgcaac cggcgcaagt cggcataata ccaactgccc ggtcattcat gaggttgatc  59760
aattgcggcg acagattaag cgccggacca accctgtatt ctagcttgaa cgccccactg  59820
gtgggtaggc cgatgtatgc ggggtctgac agagtaaacg tatcctgagt cccattcccg  59880
actgcgaatc tggccggttc tgctgcagtc ccgcctttcc agtctccagt ccaatacgct  59940
tctactccgg tcggaagggg ctgtgtgaac ttgactgttc cggtctgggc gttctgcaaa  60000
acataatcgg tcatggttac gggcgccccg gtagtttcca agtatccagt tggagtatca  60060
cccagttcga tctgagcgcc ccagataagc acgtcaatcg ccgcgctgga attcgaatca  60120
atccagctga agttggtttc tgccggagcg acgtaagcag cgcggaacga agagctgacg  60180
gtcttggtcg tgagaacgca acgccaccag ccattttcca gacgaatcat tcgggcgctt  60240
accacgctgc tgtccagcat ctgatcgctg atcacgttcc cggaatccag gtcgaaaacg  60300
gcatcggctc gactggggaa atcggcagcc gactgaattg caatgaaacg ggtggagccg  60360
gctttcgcga agaacgagaa cgttacagtg ctaccggacc ccagcggccc atctatcggc  60420
gcggagacgt aagcggtact cccggccggc ttagtaagct tgcacaccgt ggcggagccg  60480
tccggggccg tagcggacgc cgtttcgacc gttaccggaa gaccgctcgc ggccggatcg  60540
actcccggcc aatcggcgtc gctggcaggg gtcgatgtca gcacatggtt cgttctgggc  60600
gaactggaca acagcaccat accttcccaa tctttccgat atatggccaa gttctccaca  60660
gggccattct cgccggttga gtccatgaga tagaagtaca gaccggtcgc ctcgtcccat  60720
ggctcatcat cattgaatat gtaacgaagc atgcgattga tgtatgcaat cgagccgttc  60780
gaaatcagcg ctacatatct tagctgaagc actttcctga tttcgtccaa gttgagaatt  60840
tcggcattgc cgccaccgta gaagttgccg ccaggcgatg cgtctgccgg tggcgggact  60900
```

```
tgtgtaccgc tatagatgaa gttctggcgt agccgaccga atgcccaaga actgttcttt  60960
ggataaaggc cgaacccttt cgaaggcgtg ccgaggatga tgcaccaaac cataaggccg  61020
aacgggttgg cggtcttcaa gttgaaaacg tcgcgctccc agttggccca gaattggcgg  61080
ctgaatctgt cataccattg cgcctttctc tggatcaggc cggtgattcc aggcgcctgg  61140
ttatggagcc atttcagagc ttgttggatg tccgaattgt acgcaggcag agtcatacga  61200
aagtcacccg aacgttacca acggaaatgg tagcctggcc gaatgcgctc atgacgtatt  61260
ccgaagtgaa atctcccgga gccggagccg gcgagccagc cgcgacgcac gcgacctggc  61320
agagtttgat gtagatgccg ggaatttcgc gagcgatggc accggcgact tcgaatgccg  61380
acagactcgc gcccaccacc agcccctctt ctccttcaac tttcccctgg gcgtaattga  61440
ccactgcgtt ctgaatggct tccggagcta cagaggagga gccttgctgg acggttacgt  61500
taacatatcc atcgtgcatg attggagtgg tccacttcac gacatacttt cgaccggacg  61560
ccggatcgcg cacaggaacg ccagtcggac cgtccaccgg gacgccgttg ttcgtcgcac  61620
catagtccca tggagttccg ccgttatggg cggcccacaa cgcatcggcg actgcttgtt  61680
tatccgggtt tccggcgacg cagacccaaa cagcatacgg aagggtaaac gagactccat  61740
tcaccacttg aacggcgccg gtgttgttct cgattacgtt caccgacgtg acgtttggaa  61800
cggcgctcac atacgccttg atggccatag tcgagttgcg gccttggatg gccaatcgat  61860
taacgcgggc attcttcaac tctgcatcgc tcatttggcg gctgcccgga tcgacgcgag  61920
tggaggcgat gactttcgct ccggaccagc caattgttcc gtcgatgatg atgagattcc  61980
cgaccggcag aggaatgttg ccatactcct gcgatttgat atcgatggtc gcgacaccac  62040
cagcaggaat cgtgacatca ctcatcactg tgaagatcgc gccggccgga gtctggaccc  62100
tagacccggt ggaaatgcgg gtttggctgc ggccggtgac ttgaactcca tagccgaagg  62160
ttgacaggtc agaaccgcgc tcgatcccca tcaaggcaca gatcgcgtcc aggaacgttc  62220
cgaatgaaac gttcgggttt atggtattgg caattcgcgc ttcattccgc atgacactgg  62280
aacgggcgat ggcctcggcc gcgacaagcg atccctgcgg agtgctcgcg gccaagttga  62340
tattggcacc gagggcggca cggaactcgg cctcaacgtc gctcagaacg tcggcggtat  62400
ctgcgactat cacaccagta tcgacgatgt agttgtagtt agccattaca accccccccc  62460
gctgttaaat cagaaaaatc aaaacttgcc atgaaaatct ccttaagcaa tcatgccgcc  62520
tttcgtccgg gcatcaggcg ggttgttttc gaggtggccg tggttgttca cgttgatgcc  62580
gtttacgacc agggtgttag cgatagtcac attgccggtg aagttcgcct gcggagtatc  62640
cacagtaacg ttcgacggcg cagttatctt gatgttatcg ccgcgaatcg aaattctggt  62700
cgctccggaa gtcgattgta tgaccatagc ggccgaatct tcggaattga tggtgtatcg  62760
acggaatacg tccgggatga acaggccatg ctcgaactta tggatgcggc cggtgttcgg  62820
cttcgacatt gacaacgact ccaggaactg agacgtgtcg cggtcggccg cataaatcca  62880
gcctatgtcg ccttgctgaa tcgggaaact tatgtggaag ccgccagccc ccatggaaat  62940
tacaggaata tcaaccagct gatgcctttg gacggcgttg tgttcagtgt caacccaggt  63000
gatgagaggt tgaatcgtcg cgatattctc ggcccggtca tattgaacaa cctgagccgg  63060
tatcattact tcgaaatcta gagcatcccg ccgcgaccga gcgtcaagag cggcgatcag  63120
tcgcgtcctg tcgggagctt ttgcggatgt tagagaaata ttggacatgg gaaagcctct  63180
gattttgcag gtctagtata gccttcccag gcccggttag gaattatccc tttttgattc  63240
```

```
tgttgtgcga tgcttcggac gccaaggcct cgttcacgct cttcgccgtc atgatatcta  63300
tcatcttaaa ggcatcttga gtcgaataat actcttccaa ctcgcgcata gaggccgaac  63360
cgttcgctac caaactcgca actacagaag gtgaatgtgc cgtcttcaca cttttgatat  63420
cttcgacaaa tctggatgga atcttgactc cggtccagtc tttgagaaaa ccaaagttcc  63480
agtcgattac cacttctgac agcagtgcaa gaacttgtac gggagctatt actttcgctc  63540
ggtcaacgac ataaagattg atgttcgcag cggtcaatgg aagccagatg ccttccggat  63600
ggtcttccgg atgcgccaat acatcggtgc ccttgagcaa ttcttctggc ggcacgctct  63660
gaatttccga catcatgctg agcccatcga cagcagagaa ttgccgcgaa gtatagtgaa  63720
ctccgaacat gttgaacgat ttgatttccc tggccattat gctgctggac tccccatgac  63780
tttgatatag aacggccgat cccgacttgc caaatcgtat tccagagcgg ttattacata  63840
gttaccattg acgcttggat tcatgagaga ttcgaccgct acgcctccag ccacacgaat  63900
cgatggctca aacagacact ggaattccac gccccattca gaccaagatg gaattccaac  63960
aaacgagttg acgttggtca cctcatccgg acgaatgact ttatcgcggt ccttcacgat  64020
caatatgtca tcatcgacga acgcggccac gtccggcatg tacatgtcct gaatcgacgc  64080
caggattgcc gacgcgacag tgatagaccg gcccggattc ttcagaactt gatcgttgta  64140
actggtatcg cagatgaagt tcaatcccat ttcgttcgcg ccccactcga cgaacttgac  64200
aaacgtcgtg ttggcgggcg gcatattccg aatggtcttc gtcctgtcga tttgcctggt  64260
atagcactgg atgcggattc caatgtccgg tggcggagaa atgatatcga caatggcaac  64320
ttcgccgaca aagactctgg aaacttgctc gcgcccctgg tcagagtagc cggcttccac  64380
cgacaccttg atcatcaatt catcttccct gcccacttga cgttgccgat gcttccacgc  64440
ggtgaactgc gacagaagag actcgcgcag ctgagtggtg aggccgaaaa tttccatcgt  64500
cgcccggttc tgaatccgca acgcagcctt cataatccgg acccgaacat ccagatcttc  64560
gcggatgact tcgggtccat aaggcatgtt gaatgttact cgcagaattc tctttttcat  64620
cagtagagta tcttagttgc ggaatcgttt tgagcgtcct ggattgccgt agtcagctgg  64680
tctgcagtct gcttgctgaa tatctcgcga gcctcttccg gagaattcgc gccggtgacg  64740
ttgaccaaca tgtcgattcg accgatggtc agctcctggc cgcgctctgg agcgctcttc  64800
agaagttgct cgccgtacgt cctgagaata tccatctctc gcgatgcggc gttcaccttg  64860
gccgtggctt cggcaagctt ggctggagac aggaatacgt tgttggcttc ggtcgcggcg  64920
gccttgatct cctgttgctt gcccaggatg gcttggttgt atccgaacag caagtcagaa  64980
cggctgattt cgcggcgcat gatctggttt gggttaacgc cgatcacttg cgcgatggct  65040
ccggcagtga gttgagcctg gatgttctgc ttggtctcgc cgcgaacttg attcgggaac  65100
ttccggaatc cagaatctgc ccggtcggcc tcttgacgtc tagacatctt gaggatttcg  65160
ccgtcgctgc ggtctggcat gcggtcgatg atgcgaattt ccggtcgcac aaccctgtcg  65220
tcatatcgac gggcttcgcg gcgctcatct tccttcttgc cctggtctgg ggtttccagt  65280
cgcccgccat catagggacg aatgtccatg tcgccgcctt ccggggcgaa cgtctcgttg  65340
gcgacggtca tggccgcagc cttctgcttg cgctgagcct cttccatcag ctcgattgga  65400
gcgctcatta ccaaacccgg atatgcgcga gtccttggac cccagttctt cggatcgagt  65460
ccgccatgat agtaggtcaa ggccaaccgc atgtcgccgt ttgctcgatc taggttttcc  65520
cgcagtaggc gcgttccgcc gaggatgttc tggcgagggt catatacgtc agtgatacca  65580
tacgccttgg cgatttccgg catcagctgc atgaggcctt tcgctccggc ttcgctggtg  65640
```

```
gccctggcgt tgaatcggct ttcggtgtat atgagtttct tgatgtccag ctcaggaatg  65700
ttgtacatct tcgaagcatc tttgatgata tcgttgatgt acgatggaac ggtgaccggc  65760
tctgccttgc gctgcggcga gaacatgcga ttgcgaagag actgggcgcc gattggctcg  65820
ccgaagacct gtccggccgc gccactcttc gactgatcat agatcgcgtg cggatagacg  65880
ccggtggccc gcgaagtcgg cgcggtgctt cccataccga ccgcccgacc aatttccccc  65940
gcccaggctg cccaagcttg gcgctcgtca acggcattcg cgaacgacga taccgcgcca  66000
ctgaacatgt tgatagccac cgcaaaatca ttggtagact tcgtggtctg gtcagccagc  66060
ttctctagct ctttcatgga cttagtagcc ttgtcctggt cttcttgttt cttggctagg  66120
tcttcgctgg tttgagcgcc gggaaccttg tccttgtcga tgagccctga ttcttccatg  66180
ccgcgacgag tcccccacgc tgccaggcga ccgagcaggg cgccggggct gagtagggat  66240
aggatatcac tgccaacggt cgccttcccg agcactccat cttcccaacg ggatttggtg  66300
tccttcgcga agctttccac ttcattggga atagcctgga ctatcttgtc gatgatttcg  66360
atcagcttgg tgaacgcagg cgcgagcttt tcgccgactc ggttttccag ggtagtgaac  66420
gtctggttga gattcgccag ggcatcgttg aatttctgga tgttggactc gccctggacc  66480
ctggactgga gttccgcagt cgtca                                        66505
```

<210> SEQ ID NO 7
<211> LENGTH: 43145
<212> TYPE: DNA
<213> ORGANISM: Bacteriophage P1940

<400> SEQUENCE: 7

```
atggttccac gcgatcccga acggcggtag ccgtggcgac gacgaacagt cgcgcaagat     60
acgcggcggc cagatgaagg ccgaaggcgc acggcagggc atcgccgata cgttcttgcc    120
ttggccggtc tacgaacaaa gcccgaccga ttcgcaacaa atggtcgtaa aatggtgcgg    180
cctttatatc gaaatgaaga agccatcgct tcgcccgaag tctgccgaag ccaaaggcgg    240
cgcatcggac gaacaaatag ccttcggcca gtacgcgcag cgcgtcggct atgggtgggc    300
cgtctgctat gattgggaac aggccgttag ttaccttcgt agctatatcg aatgggggca    360
gaaatgaaca aagacgaagc cgccgcactg ttcgaacaag tcaaggcgaa ccgtgctaag    420
attgacggat gccgaaaaca ccgcttcgac attggcgacc cgccgtatcg cttcggacag    480
aagttcgtat gcgccaactg cgggggcgaa atggacgccg tacaggcgtt ccgctactgc    540
caaggctacg aagcggcggg cggcgacccg aacgaagtta taccgggctt ccgctaatgg    600
attgcctgaa atgcgaacta acacgcgcga agcttaaaac ggctggcctg ctaattgtgg    660
gctggccgtt gtcgcgtatt gctgaacacc tttcggactg ctacggcgaa cggtactacg    720
tcgaaggcga caacctgtat cgcgcgtcga agcttccgcc gtatgaaccg cacttgataa    780
ggagtaatgg caatgacgct tgacgaagcc aagaagaagg cgcgcgaaag ccgttgtttc    840
atcgtaacga agcctgattg tttcttgctg taccgcgaat gcgaaccgaa gaacgtatgc    900
gtcggaaagc gcaaggacga aaaaggcatc atcgcgctag tgaaaaaagc ttgcgcgacc    960
gcttgacgta gtttcgaaac cgtcgtagac tatgcccata gtcaacgaac aaggggcacg   1020
aaatgggcgc atacaccgta acaactgaat tcgaaatgaa cgacggtcgc attctgtcgt   1080
gcgaatacgg cgtatcgttc acccccggtt atatcagcgg cccgcccgaa cactgctacc   1140
cggacgaaag cgaagtaggc gaaccgacgt actatatcga cggcgaagaa gtcgattaca   1200
```

-continued

```
aggatttgcc gaaaggtctt gacaagatcg ccgataagtt gtacgaagcc gggccgggcg   1260
aatacggcta caaagaaagc gaaccggact acgacggccc ggacttcgaa cccgacgact   1320
attactaagg agttaccgca atgcctaccc ttgccgaact gttttggcac ttcgtaacgc   1380
tgtccagcgg cgtaactatc ggcctaatgt tggctgcatg gttgcgtatg caatcgaaag   1440
tgaccgaaga aacctacgac accgattgcg aattcgtaac cgaatatatc gccaacatgg   1500
aaagcggccc gaagatcatt cgtcgcccgc tgtcgcaatg gccgatatgg gcggacagca   1560
ttaacccggc caagacgaac ccgcccgaac ctgaaccgcc gattcgcatt gaacgaaatt   1620
ttatcggcaa aaaggattga caaccattcg gaaccgtcgt agtcttgttc gtaccaactg   1680
gcaacctaaa ggaatcgccg ccatgtacgc acttattctt atcgcttgca ctgtcgttgc   1740
tgtcgctatt cacttcgggc ttatccgtcc cgtaatgcac gccatcgaac gccagcgcga   1800
agaatcgcgg cgtcgtgcgg cgcttgaagc tggcttggcc gctgcggcgc gcttacaggc   1860
gttcaacgcc cgtaagccgt cgaatcatcg cggcgcaaag ctgaacgccg aacgcgaatg   1920
gcggtcgcag gaatgaagcg cggacacgtc atttacacgc acccggacga actgtcgaaa   1980
tgggatcgcc ggtttatcga actggcggaa caagtcgcgt catggtcgaa ggggccgcgc   2040
aagcgcatag gcgcggccat cgttcggcct gataggtcta tcgcgtcgct tggctacaac   2100
ggcccgccgc gcggcttcga cgatgaagcc ttcttgcgca tgacgcgcga agaacaacac   2160
gccgtcgtaa ttcacgccga agcgaacgcc attgcgcagg cgcacgacgg cgaagccttg   2220
gccggttaca cgctgtacgt gtcgccgctg tttccctgcg ccgtctgcgc acgcttgatc   2280
gtgtccgcag gcatccggcg tgtcgtcgcc tattgtgggc acatttcccc ggactggcgc   2340
gcgtctgccg atgaagccga agaagttttt atcgctgcgg gcgtcgaatg tctgttcagt   2400
atggattaac gaagatgacc ctagaccatt cgcaaatcga aggactgttg ttcttcgaag   2460
accccgtaac gcataacgta atcggcgcag ccaaggccgc accgctggac atggccggac   2520
acttcgtcgc attcgggccg cgcatcaccg ttgacccgca gttgaagaac ctgtttcttg   2580
ccgcgccgac gctgtatcaa acgctgtcgc aacagtacca agcgattcaa ggtcttatcg   2640
aaatcgccga aggcttgccg cagacgccgg aacttgataa gctgcaacgg tcgttcgtcg   2700
aaatgcaaaa cggcatgtta atggcgcagc ttgtcgcgca aaaaggtatc gaagaagtag   2760
cgaattcgct tgacaagctt tagaagcggt cgtagaattc ccaacatcga aacgaaacaa   2820
ggtgcccaca atgacccgca acgctaagaa ttggttaatc gccgccgctg ttgtcgcagc   2880
attgggcatc gtcggttcga tggattacgc cgacgaagtg cgcgaacagg tttcatattg   2940
cgaaaacgtg aaggcgggcg tatggcccga ctacaacggc acgtatgaaa ctgaatgcac   3000
cgccgaacgt ctgaaagaat atcaagaaat tttgcgttga ccgcttgaca cgtcgaacgg   3060
tcggcgtaga ataacccctg tcgcaatcac gcgacgctaa cttaccttcg aaggagttac   3120
acaaatggct agcaagaagt ccaccaagaa caccgccgcc gctgttgccg ctatcggcct   3180
tgccgaaatc gttgcagccg gggcaaacgg tctgtatact cgccccgaag ttcacggccc   3240
gcttgtcgaa cagggcttcg tcgaactgaa ccccgccggg ccgaacgaat ccggcgaaac   3300
tctcacccgc gccacgcaga aaggtatcga aagcatgaac accgcaaaca acaccgccgc   3360
ccccgccgct tcggccccgg tcgccccgtc gtccttcgcc atcgaagacg gcatcgccat   3420
gccgaccgct tccggtcgcg gtcgtggcgg caacgtgtac cccttcgacg ccctgaacgt   3480
cggccaatcg ttcttcgtcc cgaacaccga agacaagccg aacgccgcca agtcgctggc   3540
ttcgaccgtt tccagcgcga ccgcgcgtta cgccgaagtc gtcgaaggcc agttcaagac   3600
```

```
gaacaagaag ggcgaacagg tgcccgtgac ccgcgaaacc cgcaagttcg ttgttcgcag   3660
cgtcgaaggc ggcgcgcgcg tctggcgtac cgcctaagcg ccccggcgtg cggcctacgg   3720
gccgcgctac ggccagaacg aagccccggc actgtccggg gcttcttttt gcctttctgc   3780
tggcctacgg ccattttttc gggtactatc gggacaattc ggggcgcagt tcgccccttg   3840
cgcgtattaa ggggctacgt agtgccattg aacaacgaag cggggcagga tatgaacgaa   3900
cgtccgcaga agatcataga cgcaaaattg ccgttacctt ggcttatcgg ttcggcttgc   3960
gccgtagtct tttcaatggg cggcgtattc gtcaaactgg acgccgtagg cgcatcgctt   4020
acgaagctgg aagcgaagac cgacacgcgc gacgaacgaa tttcaacgct tgcgcaatcg   4080
ttgatacagc aggccggaaa gaacgatacg caggacgcgc aaattacccg caacgccgca   4140
gacattaccg acttgaaacg cgacgttgaa gacatacgca agtcgcaacg ttggatgccg   4200
aagtaatgaa aaagaaagtc gaactaatcg aagattggcg caccgcccat aagctttggt   4260
cggttcgact gtcggccatc ggtgccgccg taatgggcgt gtttaccgta tggcccgaat   4320
ccgcgttgta tctttggtcg gccatgccgt ccgaagtgcg cgcgttgatc cccgaacggt   4380
tcgtatccgg catcgcgctt ttcgtattca ccatgtccgc actgtcgcgg atcgtcaagc   4440
aaaggccgaa gaatgaacga atcgaacgaa agcccgcaga agaaacagcc gaataaaaag   4500
acgcttgcgg gcgtccttgg cgcaggtgcc gccgcaatcc tgctaggcgt agccgggcaa   4560
accggcttta ccgaacgctt cgaaggcatg gttcttcgcg gctaccttga ccctatcggc   4620
gttccgacga agtgcgcagg cgatacatac ggcgtcgaag tcggcaagcg atacaccatc   4680
gaagaatgcc gcgaatcgct ggaacagggt ttgattaaac acgccgaacc cgtgttgaag   4740
tgcgcgccga acctgcgaac gcaaggctac cccttcgcac tggccgccgc agtcgatcat   4800
aactaccatt tcggcacgtt ctgcggaact tcaatcgacg cagcgtttaa gcgcggcgac   4860
tatcgtacag gttgcgcacg cttcaacgaa aacgccgcag gccgtccgca atgggtgtac   4920
gtcaaggacg gcaagggcgg ttacaagacc cttcccggcc ttatcacgcg ggccgcagcg   4980
cgccgcgaac tttgcatgaa aggggccgga taatgtgggc tatcatcgta gcgggcgcaa   5040
agcgtttcgg cggctggatt ctggccgcat tgtcgtttct ggcaatgctg gcgacagttt   5100
ggcttacgtc ccgaaaagtc ggtaagtccg aaggacaagc cgaagcggcg gaacaacgcg   5160
cagccgaccg cgaaactatc gcagtacgcg aagttaacga agcgcgcgaa gcttccgaac   5220
gtcaaacaaa ggcggtgcaa aatgcgaacg aagttgcttc cgataatgct gttcttgacg   5280
acgacggcgt ttctaagcgg ctgcgcgacg aatggtcgcg cgactaagcc gccgcaatcc   5340
atcgccgaaa ccgtacaaac gaagcccgta gtaatcgaca cggcttgcga ttgggtgcgg   5400
gcgatttggg tttcgaagtc ggacgacata acgcccggca cggcgcgcca aatcctgaac   5460
cataatcaag ccgtcgtaaa gaactgcggg ccgcagaaac cgcccaaggt cgattcgcct   5520
taacagaacg tcggccttgc ggtatagtga aggcaaatgc gaatgacagg ccgacgccat   5580
gaccgaccaa cgtaacgaat ccgaagaaaa ggccgcatat gcggccttgc ttttgaagga   5640
acgcgacccc ttcaaggctg cgcttcaact gttccccgac aacacgaatc gcgccctatg   5700
ggtggcgaat cattggccga ttgacgccga agtaaaggcc gaacaagaac ggctaatggg   5760
cgaagacgac ggttcgtcgt tccttccgtc gaaggccgaa cttgcccgcg acatttggca   5820
acgtatgcag ggcacgaccc ttgcaaacgg cgtgaccatt ccgccgaccc ccgaagaata   5880
cgcgaagctt gcgaagcttt atgccgacgt tcgcgggttc atcgaaaagc cgcaaacgaa   5940
```

```
tgtgaacgta acgacgaacg tacagcgtgt cgtcgaagtt cccgttttcc aaagtgaaag   6000
cgaatgggaa aacgccgccg cacgtcaaca gcgggaattg ttagaaaatg cccgcactcg   6060
ccattaaagc gccagaagcg ccgccgctga ttctacagaa agcgccgcca atcgaagtcg   6120
tatttaagcc gcttcccggt tcgcagacta tcgcgctttg ttcgcacgct gcgcataccc   6180
tgtacgaagg cgcacgcggc cccggcaaaa ctttaacgca gttaatgcgc tattaccgta   6240
acgtcggcaa aggttacggt aagttctggc gcggcgttat cttcgatctt gaattcgacc   6300
atttggccgg acttgtcgcc gaatctaaaa aatggttcgg cgataatggc aagctgaaag   6360
acggggcgaa gttcttagaa tcaccgtcgc aatacaaatg ggtttggccg actggcgaag   6420
aactgttgtt tcgccacgta aaaaaggtcg ccgattacga aggcttccac ggccacgaat   6480
acccgtatat cggatggaac gaattaacga agcatcctag cggcgacctg tacgacaagt   6540
ttatgtcggt caaccgcgtt acgttcgatc cgatcaaaga cacgccgaaa gacccgaaga   6600
ccgggcgtta tttgacgcct aacggcctgc cgttgcctga aatcaagtgc gaagtattca   6660
gcacgacgaa cccaagcggc cccggtcata attgggtgaa gaagcggttt attacaattg   6720
cgccgcgcgg cactgtcgtt cgtcgcagta tccagattta taacccgaag accgaacaag   6780
aagaaacgca cgtaattacg caaattgcga tcttcggttc atacaaggaa aacccgtatc   6840
ttccggcgtc gtatattgcc gaactggaaa gcattaaaga accgaacctt cgcaaagctt   6900
ggttgtatgg cgattgggac gttaccgcag gcggcgcaat cgacgacctt tggcaatcgc   6960
atatacacgt cgtaccgcgc tttgtcgtgc cgccaagctg gcgcatcgac cgcacatacg   7020
acgacggcag ttcgcacccg tttagtgtgg gctggtgggc ggaagcggac ggcaccgaag   7080
cgactatcgt tctttccgat ggaaccgaat tcgtgttctg tccgcaaccg ggttcgttga   7140
ttcagatatt cgaatggtac ggatgcaaga aggacgaaaa gggcgaattc ttgccgaacg   7200
tcggtcttaa aatatcggcg tcggacgtag cgcaaggcat tatcgaccgc gaagtttcga   7260
tgatggcaaa cggctggatt tcgtcgcagc cttggcccgg ccctgcggat aatcgcattc   7320
gacaagttat cgacgttgaa ctagatacga ccgaaaagct tatgtcgaag aagggcgttc   7380
gctggatgga atcggacaaa tcgtcgggtt cgcgtgttat cggcctacag cttttccgcg   7440
accgactaga agcgtctgtt aaacgcgaag ggccgggggt atacttcatg tcgaattgcg   7500
ttgcaagcat tgatattttg cccacattgc cccgcgacga aaagaaaatc gacgacgtag   7560
acacaagcgc agaagatcac gtttacgaca tggtgcgtta tcgtgtattg aaaggcgcga   7620
acaaagcggc tacgaaagtc aaagtatcaa tgccaactta aaggaatcga aatcatgccg   7680
aacgtatctt ttgtgcgtcc tgaactgtcg aagttgcttc ccatgtacta ccttattcgg   7740
gacgcaatcg caggcgaacc aacggttaaa gaagcgcgga cgaagtatct tccgatgccg   7800
aacgcttccg accaatcgaa ggaaaacaag gcgcgttatg atgcgtatat cgcgcgggcc   7860
gtgttctaca acgtagcccg tcgaaccctg ttcggtctta tcggacaggt gtttatgcgc   7920
gatccggtcg taaaggttcc ggcgctgctg aacccgcttg tcgcaaacgc gaccggatcg   7980
ggcattaacc ttacgcagct ttcgaagaag gccgtatcgt tgaacttggc gtattcgcgc   8040
gccggaattt tggtcgatta cccgacgacc gaaggacagg gcggcgcgtc ggttgccgaa   8100
ctggaagcgg gcaagattcg cccgacgctg tacgtctatg cgccgaccga aattatcaat   8160
tggcggacga ttgatcgcgg cgcggaagaa gttttgtcgt tggtcgttat ctttgaaacg   8220
tggtgcgttc aagatgacgg cttcgaaatg aagaacagcg gtcaattccg cgttttgcgt   8280
ttggacgacg aaggttatta cgtccatgaa atttggcgcg aaccgaaccc gaccaaagcg   8340
```

gacggtacga agattccgcg cggcaattac caacttcacg aagtattcaa gccgaccgat 8400
gcaaacggga atcgccttga cgaaatcccg tttatgttca tgggttccga aaacaacgac 8460
gttaacccgg ataatccgaa cttctacgac cttgcgtcgc tgaacttggc gcactatcgc 8520
aacagcgcgg attatgaaga atcgtgctac gtcgtaggcc agccgacgcc cgtacttacc 8580
ggcctaacgg aagaatgggt taacaacgtt ctgaaaggaa cggtcaactt cggatcacgc 8640
ggcggcattc cgcttccgac cggggccgac gcaaagctgt tgcaggccga acctaacacc 8700
atgcttaaag aagcaatgga cacaaaagaa cgccaaatgg tcgcacttgg cgcaaagctt 8760
gtcgaacaga aagaagtaca gcgcaccgca accgaagccg aattggaagc ggcgtcggaa 8820
ggttctacgc tgtccagcgc aacgaagaac gttagcgccg cgttcgaatg ggcgttgaaa 8880
tgggcggcgc gctggatcgg cgcgggcgac gctggcgtta agttcgaact gaatacagat 8940
ttcgacattg cccgcatgac gccggacgaa cgccgccaga ttatcgaaga atggcagaag 9000
ggcgcgatta cctttaccga aatgcgtaca gggcttcgga aggctggcat tgccaccgaa 9060
gacgacgcga aggcgaaggc cgacattgcc aaggacaccg ccgaagcgat ggcccttgcc 9120
atgccggaca acgtgccggg cgacggcaac acgcccccgg ctggtaatgt gggcaacggg 9180
ggtgcgtaat catggcgcta tcggataaca agcgcctata cgacatttca acgcggcttg 9240
ccgtatatgt cgaaggcgtc aaagttcagc agtcccgcca attcaacttc gtattgcgcg 9300
atattagcga agttctgaaa aagcttcttg gtcgtgttcg ttacaagacc cttgacggtc 9360
tttcgaaggc gcaactaaat aagcttgtcg cagaactgcg cgaatcgcaa tcgaagattt 9420
acagcgcgta cacgtcgcag cttatcgaac agcttaaagc gttcatggct gcggacttgg 9480
aagtaaaccg ccgcgcatgg gttacgggct atatcgaact tgacggcgat tcgccggacg 9540
aaattatttc ggacgaagac gcaatacagt tcttaatcga agccaacgac agcggcgcaa 9600
atccgttgtt cggcatcgcg gccattactg gcggcgacga acgtatttgg tcgcaagtta 9660
cgaattcgcc gcttccggcg aacgggcttt atcttctgcc gtttatcaag acgtttacaa 9720
cgtcggcgca agcgtcaatc gaaagcatta ttcgcaaggc atgggcgaac cgctggactg 9780
ttgacgaaac cttgcgcgaa atcatcggcg aagaaggcgc acgccaaggc acgccgtcgc 9840
agcttgcgcg gatcaataat caagccgcgt cggttatcca taccgccttc gcgcatactg 9900
cggcaatcgt agcggctggc gtagcgtctg cggttttcag ttggtacatt tggttttcgg 9960
ttatggatgg caacacgacc gaaatttgcc gaagccgcaa tcgcaagcgt tatcggtttg 10020
gggccgggcc gttgccgcct gcgcacattc gttgccggtc gcatactgcc ccggcgaata 10080
cggctagtga cctaatcgac gaaacgtttt atacttggct tgcgcgtcaa ccgctggaag 10140
tgcaagacga catattaggc accgaaggcg gcgaagcttt acgcgatggc aaattgaaag 10200
cttccgatat tccgaagtat gaagccgacg aaccgctaac gcttgacgaa ttccgacgca 10260
agattaaaca gattctttcc cgctgatacg gtgtatcggc ataacctgta ggagtcctac 10320
gaaatggcac tgaaaaagcg tattaccaaa gaagaacatt cgaagcttgc cgacgcgctg 10380
aaattcgaat acgtcgaaga cggcgacggt ttccgtctgg acgttgacgg cgacgaagac 10440
accggcccgc ttcgtcgcgc gaaagatcgt gaagcgcagt tgcgccgcga tgctgaaaag 10500
cgcgccaaag aagccgaaga ccgtttggcc gaactggaag gcgacgacgc ccgtaaaaag 10560
ggcgacattg ctacgctcga aaagtcgtgg caaaagaagc ttgacgacgc gaacgccgca 10620
tcgcaagcca aaatcgacaa gcttacgtcg catacgacga aaacccttgt cgataacgtc 10680

```
gcgctgtcgg tcgcaaccaa aatcagcaac gcgccgtcga tcatccttcc ccacattcgc  10740
gcgcgcctgc aagcgaactt cgacggcgac gaaccgacga ccgttgttct tggcaaggat  10800
ggcaagcctt ccgcaatgac catcgacgaa ctgtcggcgg aatttgttgc aaacaaggat  10860
ttttctgcta tcatcacggg cagtaaggcg tccggcggtg ccggtaagcc ttcgcaaaac  10920
ggcggcggtg ccccgaagat ttccggtcaa tccgacaaac ccgccgacct ttcgaagatg  10980
aatccgcaag aacttgcggc gcatctgaaa gaagcgaagg ctactactga ataaggacgc  11040
tttatcatgg cactttccga cctcgcggtt tactccgaat acgcctattc ttcgttttcc  11100
gaagtcctgc ggcagcaaat cgacctgttc aacgctgcaa cgggcggcgc gatcatcctt  11160
caaggtgcgg cgcaccaagg cgactttagc gacgtggcgt tttcgccaa ggttgcgggc  11220
ggccttgtcc gtcgtcgtaa cgcctacggt tccggcgctg tcgccgaaaa ggtgatgaaa  11280
caccttgtcg atacttcggt gaaggttgcg gcaggtacgc cgccgattcg ccttgacccc  11340
ggccaattcc gttggattca gcagaacccg gaagtcgcgg gcgctgcgat gggccaacag  11400
cttgccgtcg atacgatggc cgacatgctg aataccggcc ttggcgcgac ctacgccgcg  11460
cttacgcagg ttgcggcggt caagtacgac gctaccggca acaccgcgcc ggacgacggc  11520
ccgacgtgga acaacctgaa caacggccaa gcgaagttcg gcgaccaatc gtcgcagatt  11580
gcggcatgga tcatgcacag cacgcccatg cacaagctgt acggcaacaa cctgaacaac  11640
tccgaacgcc tgttcaccta cggcaccgtc aacgtgattc gtgatccgtt cggcaagctg  11700
ctggtgatga ccgacagtcc gaacctgttt gcggcgggta cgccgaacgt ctatcacatt  11760
cttggccttg tgccgggtgc ggtgatgatc ggccagaaca acgacttcga cgcgatggaa  11820
gaaggcaaga ccggcgacga aaacctgatt cgggtttacc aagccgaatg gtcgtacaac  11880
gtcggtgttc gcggcttcgc atgggacaag ggcaacggcg gcaagtcgcc gaccgacgcg  11940
gccctgttca cttcgacgaa ttgggatcgt tacgccacgt ccgaaaagga tttggctggc  12000
gtcatcgtcg aagttcacta accaacgaac gaacgggcgg ggcttcggcc ccgttcgttt  12060
aacgttccca aacgaaggag ttacgaagca tgaaacctgc aaagattctg tttttcgtcg  12120
atggcccggc accgaccccc gaagatttcg ccgcagccgc cgaactgaac gcaagcgttt  12180
cgttccgcaa cgcacgcgcc gtaccgtccg aagcgcattc gctggaaatc tgcgacggcg  12240
tggcgggcgc agttccgccg atctacgccg aaaagttccc cgacgccgcc gaagctatca  12300
agaagaaggc cgccgaactg aaagaactta cttcgaaggt cggcgacagt ccggcaccga  12360
aggccaaggg cggcaagacc ggccagcaag cgccgcagca gccgcagacc ccggcccccg  12420
caactggcgg ccagcagccc gcagcgggcc agcaaggcgg cgacgcgccg tcgtggaacc  12480
cgaacccggc gcagtaaggc cgggcgcagc gtagggcgcg gcctgttcgc ctagtgtggg  12540
caggccgttt ttataggcgc aacgaaagga cagacgaaca tgcaacgcat tgtctatttt  12600
accgcaggca ttaccccgac ttcgggcgaa ctggccgata ttgccaaact taacgcagcc  12660
gccgaagccg cctacgaagt caccgtagtt aacggcgcag cgaatgcgaa gtatggcgaa  12720
acgaaccgtc ttattccgtg cgatttggtc gcgggcaccg ttccgaccat ttacaacgcg  12780
aaagaagtta tcgaccccga cgcaatcccg gcgcgcggtt tgtcggatac gcaagccgtt  12840
gtcgaaaatg gcgaagcgtt gacagttccc gttactggaa cttacaccga taccgcaacc  12900
gttaccgtcg tcgatggcgc tgtaactgcc attgcacttt cgtaaggatt cggcgtcatg  12960
gcaattacta tcgtagtcga agacggaagc ggcgtagcca acgcgaacag ttacgtaagc  13020
gtcgcggatg cgcgcgtata cgcgaccaat cggggcaccg aacttccgtc caatgacgac  13080
```

```
gaagtagccg cgatgctgat tcgtgcgacg gactacctag aagcgcagga atgccggtat  13140
caaggcaaac gcacgtcgcc gacgcaggcg cttgcgtggc cgcgtaccgg cgtattcctg  13200
aactgcgatg aagtcccgtc gaacgttatt ccgaaatcgc ttatcgccgc acaagttcaa  13260
ttggcgatgg cgattaacgc aggcttcgac ctgcaaccga acatttcgcc gcaggactac  13320
gtaacgcgcg aaaaggtcgg cccaatcgaa acggaatacg ccgacccggt agccgttggc  13380
atcatgccca cgtttaccgc agcgaacgcg cttcttgcgc cgctgttcgg cgaatgcgct  13440
tcgaacaagt ttgcacttcg gacaattcgg gtttgacgta tggcacgctt cgaccgcgcg  13500
attcaaacgg cgttgcgatt gatcgcaaag aacggcgaaa aggtgaaatg gcgcgtcatt  13560
gacgacgcag ccgcgcccga tccgtcgcag ccgtggaacc ccggcccggc aacgcccgaa  13620
gacaaggacg taactatttg cttcttgccg gttgatcggc aaacgatgga aacatttacg  13680
tttatcaaag gcaccgaagt tccgaagggt tcggtaatgg ggcttatggg aaacgtgccg  13740
tttaatccta acttgaaaga cgtagttatt cgggatggcg tagaacttcg aatcgcaaat  13800
atcgacgttc tttcgccgaa tgggcaaaag gtactttaca cggtagtttt tcaagcatga  13860
tcgaatttga ccaagcccgc gacgaaatca atacgctgtt tcttacggcg tggaacgcta  13920
acgcgggcgc ggtcgtcggc tatgttcccg aaattcgttg gcagggcgta caataccgag  13980
atttgccgga cggttcgaag ttttgggttc gcgtgtcgaa acaaaccgtt ttcgaagaac  14040
aaacaacgct ttcaacttgc gaaggaaaac cgggacaaaa acgttatacg gcgtcggggc  14100
ttgttttcgt gcaagtgttt tgcccgaaat cgaatacgca agctttcgca cttggtcaaa  14160
cgctggcgaa gattgcccgc aatgcttttc gcggaaagac tacgccgggg aagatttggt  14220
ttcgaaatgt tcgcataaac gaacttgacc ccgaagaact gtacgaacgg tttaacgtcg  14280
ttaccgaatt tgaatacgac gaattaggtt gaaggagtta cgaaaatggc cgattgcgct  14340
atcaacaaaa tcgactcgaa cattaccgga ctggcgtatg ccgaagaaga atgcttgaag  14400
caacttccgg cgtccgtcac ttggtacgga ctggaaccga acagctattc ggacttcggc  14460
ggcgaactgt ccaccgtagc ccgtgcgcct atcgacccgt cgcgccagaa caagaaaggc  14520
acgattaccg atcttgacgc atcgggcggc ttcaattcgg actttacgaa gtcgaacctt  14580
actcgcattc tgcaagggtt cttcttcgca gacgcgcgcg aactgccgtc tactgcgccg  14640
ctgaacgccg cagctatcgc aatttcggct gtcgatgctg cgacgaaaac ctataccgtt  14700
gcaagcggtg gcgcggcgtt cgctgcgaac atgcttgtca acgcaaccgg cttcgcaaac  14760
gctgcgaaca acggccttaa aaccgtcgct tcgtccaccg caacgactgt cgttgttaac  14820
gaaacgctta tcgacgaagc cgcgccgcct gctggcgtga aactggaagt cgtcgggcgt  14880
caactggccg cagccgatgc gaacatcgcc gttacttccg gcgtcgcttc gttggtcgtc  14940
accgctggcg actttacgac catgcccgaa ctgttccccg gtcgttgggt gttcatcggc  15000
ggcgacgcgg cgtcgaaccg ctttgcaaat aatgtgggct acgctcgcat taagtcggtt  15060
tcggcgaagg cgcttgtttt cgacgatacg accttcgcgg ctgcaaccga aaccggaacc  15120
ggcaagtcga ttcgtctgtt cgtcggcgtc gttatcaaga acgaaaaaga cccggccctt  15180
atcaagcgtc gttcgtacaa catcgaacgc acgttgggca acggcgaaaa cggcgttcaa  15240
tgcgaatact tggaaggtgc ggtagccaac gaatttacgt tgaacattcc gcaggccgac  15300
aagctgaacg ccgatcttac gttcatcgcg tgcgataaca cgcaccgcag cggcgacccc  15360
ggcgacgaac agaaggccgg tacgcgcatt tcggcaccgg gcgaagatgc gtacaacact  15420
```

```
tcgtcggaca tttaccgtat caagatggca gttcacgacg acacttcgtc gaatcctgcc  15480
gccctgttcg gttacgtgtc cgaagcgaac gtttcgatta acaacaacgt ttcgccgaac  15540
aaggccgtcg gtatcttggg cgcgttcgac acgacggcgg gtaacttcga agtcggcggt  15600
tcgattaccg cttactttac gaccgtcgca gcggtgaagg cggttcgtgc gaatgccgac  15660
gttggtttgt cggttatcag cgcggcgaag aacgccggtt tcatcttcga tattccgttg  15720
cttggtttgg gcggcggtcg gttgaacgtc gaaaaggacg cgccgattac cgttccgctt  15780
gaacccgcag gcgcggaaaa cgaaaacggt tatacgatgc tgtacgaagt gttttcgtac  15840
ctgccaacgg tagccatgcc cgattaagtc gggtacactt gaagggccgg acttttccgg  15900
cccttctttc atccatcgga gtaaatcaaa tgtctggact gtttaagcaa ttcaaaacga  15960
attcggcgaa ggaaaccgaa ggcgtcgaaa tcgaatttcc cgaagcgcag aacgacgacg  16020
gcaccgttcc cacgttcatc atttcgcgca tgggcaagtc gaacaaagcg tattccaagt  16080
cgctggaagc cgcgacccgc ccgtatcgcc gacaggtcga attgggcacc atgaaaaacg  16140
aagtcgccga acagcttttc atgggcgttt tcgtcgatac catcctgcgc ggctggaaga  16200
acgttcagga cgaaaagggc gaagccatcg cctattcgaa ggacgcggca atttcgcttc  16260
tgtccgaact gcccgacgtt tacgaacgtc tgcaagaaga agccaagttg tcggccaact  16320
tccgcgattc ggtgttggaa accgaatcgg gaaactgata gaagttctag cgtatctgtt  16380
cgaactaggc ccgcacgaac agaccatagc aaaacaggcg atgcggtcgg gccagccgtt  16440
acccgaccgc atcgccaacg cgccagaact tgaaccgggc ttgcagttgt atttgcaagc  16500
cttcttcgat ttggatagcg aacgaacgca cgcaatggga ttgacgccga ttccttggac  16560
aagtattgcg gcgtatgcgt cggcattcga attcgacgaa gaacagcggg aagacttgtt  16620
ttattttgtt cgtaaactgg attcggaaca tttgaagaaa ctagaagcaa agcataaggc  16680
gaataaaggc aatggcaaac gaccttctaa gtctggccgt tagtctggaa cgcaaggcta  16740
aggcaatcga cgaagcggct tctaaagcag ccgtcgatac tgcaatggct attgtgggcg  16800
acttggcgta taagacgccc gtagatactt cgcaagcttt gtcgaactgg cgcgttacgc  16860
ttgattcgcc agcaaccggg acgattgcac cgcattaccc cggcattcaa ggttcgtcgc  16920
aacgggcaag cgcagccgaa acgatcaacg cggcaaaaag cgtacttgca aacaagaagc  16980
ccggtcaagc gatttttatt acgaacaacc ttccgtatat caaacggctt aacgacggat  17040
attcagcgca agcgcctgcg ggattcgtcg aacgtgcggt attgattggc cgcaagatgc  17100
ttgcgaagtt caagattaag gattaagacg aaatggccga aaacatcgaa attaaagtac  17160
aggataaagt cgattcgtcc atttcgacca agcttaaagg catcgcttcg gatgcccgca  17220
ccgccgacag cgccgtaaag gcgttgcaat cgtcgttgaa gtcgatttcg gcttcgtccg  17280
gtctttcgcg ccttcaaagc gaacttgcac gtaccgccat tctacagcag aagcttgcca  17340
ccgaaacgca gaaaacgcaa gtcgcaatgg cgaacgttga agcggcgttg caacgtgcta  17400
tcgcagccga agccaaggcg aacgccgcga ttaaccaact ttccgccgcg caatcgaagg  17460
ccgccaccga agcgcaacgt ttggcgacgg cccaacagca aaccgccgcc gcagcggcgc  17520
aggcgcaggc cgcacaagcg aacttggccg cagcgcaaac caacagcgcg accgcatcgc  17580
agcggcttgc cacggcgcag caacagacga ccgcagcaac ggccaacgcc gccgcagcgc  17640
agacgcgcgc ggctacggcg caggtacagg gccagaccgc cgcgcagaac cttgcagcgg  17700
ccaccacgcg cgccagcacg gcccaaacgc agggggcgaa cgctgcgcag cggcttgcca  17760
ccgaacagca gcgtacagcc gtccagacgg ccaacgcggc agcggccaac gaccgggcgg  17820
```

```
cccttgcagc cctgcggctg gcccaagcgc agcagcgggc cgggcaggcg tcgcagaccg  17880
caggccagca aatcgccgga tatgtcaaag ccgccgcagg catcgcaggc gtaacgctgt  17940
cggctggcgc tattctcgca tcggcggacg catatacgac gctgcaaaac aagttgcaga  18000
acgtcaccga atcgcaatcg caagtcgtaa cgcttacgaa agaattgttc gacttggcga  18060
accgcacgcg cgcgggcgtc gaagaaaccg cgacggcgtt tacgcgcttt gatcgtgcgt  18120
tgaagttcat gggcaaatcg caagaagatt cgttgcgttt gaccgaaacc attaacaaag  18180
cccttatcgt ttccggcgca actgcgcaag aagcgtcgtc ggctttgttg cagctttcgc  18240
agggcttcaa cgccggtaag ctgcaaggcg acgaattccg cgccgtatcc gaaaatatgc  18300
cgatggttct tgacgcagta gcgaaggcgc ttaacgtgcc tatcaaccgc gttaagcaac  18360
tttcgaccga aggcaaaatc acgtccgaag ttctgtttaa cgcattccag cttatacaga  18420
agtcggtcga tgacacgttc gcaaaaacga cgcccacaat cggccaaagc cttaccgtct  18480
tgaagaatag cgcaatcgaa ttcttcggcg aattgaacaa ggcgaccggc gttacggctg  18540
cgctgtcgaa ggcgattctt tggcttgccg acaacatgaa gaccgttgcc gtcgtagtta  18600
cggcgcttgg aacggcgatg cttcttgcat tcgggccgca gattgtcgcg gctatcgttt  18660
ccgcaacgac tgccgtaaag gcattcaccg tcgcgcttgc gtcgaacccg attggcctta  18720
tcgccatcgc actggcaacc gtcattgcgt accttacgct gttccgcgac gaaattaact  18780
tgggaatcga cgacgttacc acgttgggcg atttcttccg cgcgaccttc gaaggcatcg  18840
ggcaggttat tagcgacgtg accttgattg tcggccaatt gtgggcagac atgaccgaag  18900
gcgcatccgg ggcgcttggc gaaatttcgt cgttcgttgg cgatgctgtt tccggctgga  18960
cggaagacta tacgtcgttc ttccagaccg aacgcaccgg atgggccgcc gcgctggaaa  19020
acaccgcgaa agttcttgac gcaatcgccg gattcattac cggccttgca acgtttgccg  19080
gtcgtgctat ggccgaagtc gtgattaccg ttcaaaacgg aatcgcaaac ggctataact  19140
atatcgtcgg atggattgaa cgggttacga atctggcgat tgaatcggcg aacaagcttc  19200
gcgcgatggt cggcaagtcg gcatacgaac ttgtcaactt cgaacgcatg ggccaagccg  19260
gacaaaccga attcgaatct tggggcaagc tttgggccga atcgcttgaa gacggcttta  19320
agtcccaagg cggcgcaatg caaaaggtcg tcgaaggtct tatgacgcgc gcgcaacaaa  19380
tcggcgcgaa tcgtcgcgca agcgaaaacg cttcgcttcg cggcgcaggt gcgaaccaac  19440
ttagcgcagc taccgacgac aaggcggcga aggccgcaga acgtcgcggc ttggcgttgg  19500
aaaagatcaa tacgcagctt gataacgaat tgaaccgcat gtttacgctt caaccgcaac  19560
gcgaagcgca agcgaaaatg gatcaaatcg aagaatcgtt gattcaacgt aaaatcaagc  19620
ttaccgaaga cgaacgcgct tcgatcatgg cgaagattca ggccgtccag caagcgcaaa  19680
tcgtgcaaca gaagttcgac gcgatttata acgaagctgt cggcccgcaa cgcgattaca  19740
ccgccacgct tgaagcttcg aaaaagcttc ttgaccttgg cgcgatttcg caagaacagt  19800
attcgcgcgc agtaacgaag gcaaccgaag aattcaagaa cgcgcaagac ccgatgcgcg  19860
cgtataaccg cgaccttgac caacagttgc agcttttgca gttgttgccg aagcaacgcg  19920
aaatcgaaca gcaggttatg caagtgcaaa acgacctgtt gacgaagggt attacgctta  19980
atgccgaaga acttacgcaa ctgcgcgaac ggcttacgct gttgcagcag gcgaacgcgc  20040
tttcgcagca agaagccgcg ttaatggacg caagcgttac gaagcgccaa cagtatatcg  20100
accaattgaa ggcgattaac gcgcttaaaa acaatccgca aagcggtttc acgcaaggcg  20160
```

-continued acgcggctaa cgccgtaatg aacgcgaata gcgatcttga tttcacgaat accgatacgt 20220
atttcgaagg tcaagcgcag aaatacgaag atatgtattc gcgtatcgac caactgcgcc 20280
aacaggactt gattagcgaa caaaccgccg caacgctgcg ccaacgtatt tggctggatc 20340
aacagaacca aacgttaaac gccgcgtcgg gtttcttcgg acaaatggcg caattgcaga 20400
agtccgaaaa tagcaagatg gccgccgttg gcaaggccgc agccatcgcg caagcgatga 20460
ttaacacgta tcaggctgcg accggcgcgt attcgtcgct tgcgtcgatt ccttatgtcg 20520
gcccggcgtt gggcgcggct gcggctgcgg ctgcgattgc cgcaggcttg gcgaacgttc 20580
aacaaatccg gtcgcaaaat accgggttta tgtcgggcgg ttacactggc gacattccga 20640
cgaatgccgt agcgggtgcc gtgcatggtc aagaattcgt aatgaacgca gcttcgacga 20700
accgcattgg cgttgataac ctgcaagccc tgcaaagcgg cgcggccagc gtccagcgca 20760
acggggataa tgtgggcacc ggccaagcgg ccccggctgc tgcgcccgaa gtaaatgtaa 20820
ctacgccggt aactgccgtc gtggtacaat cgaaagaagc cgccttggct gcgatgaagt 20880
ccagcgaagg caaagcattt gttatcgaaa ctatcgaaga aaacggcggc accgtcgccc 20940
gaatcgtagg ggttaaataa tgggatacgc aataggcacc gtgactaaag gtagcggcgg 21000
cgacgcttat tatcagcttt tagctattat caaaactttg gccgaagcta acggatggac 21060
tacccttcgt tatgtcaaca ccggaacaaa tcgggaatgg atcggaaaag gcgtcggtct 21120
ttccggtctt gaagaaattt ttatcggttt caaaacttac aacaacgtta gcggtgatta 21180
ttacaatttt caagccgcaa ctatgattgg ctatgtagct ggaaatagtt tcgaaacgca 21240
gccgggaatt caaatttcgg gcgtacctgc ccacaataac gcaattacct atttcattac 21300
tgcgaatccg caacgcataa ccggatgcct taaagtaggt acgccggttt acgaacattt 21360
ctatttaggg aaaatgtttc cgtatgcgcg tccgggtgaa ttcccgtcgc ctttggtttg 21420
cgctggaatg tttaacggcg cagaagcgaa acgtttttcg gatacgaacc aagttttccc 21480
gtatccgggc gaatattatt cgtcgcaatg ctatatgtgg ctgcgctatc aaactggcgt 21540
atggactaaa gtttggtcgt atccttttac gaatgcaaac acaaacaacg gtttgccact 21600
ggcagggccg caaggaacga atacgcttgt tcctgccgac gtttattacc aacttgaacc 21660
gataattatt tcgcaacttc aaactaacgc gggaagcggc aacgtttggg gggaattgga 21720
cggcgtttat ttttgttccg gcttcaacaa tgggccggaa aatgtcgttc aaatgggcgg 21780
aagttctgtc gtagatcaaa caggaatgac ggtacttcaa gctgtagacg caattatagc 21840
agttggcggg cgcgctttcg taatgtgcca gaacgttaac cgtacaactt ggcgcgattt 21900
tgtcgctttg gaaatgaaat aatggcctac tataacggaa gtgccgcgac tttcgcggat 21960
ttgaaaaccg ctatcgaaaa cgcttgcgtc gctaacggct ggacgctttc taacggcatt 22020
ctttcgaaga acggttgttt tttccaactt gtcgccacta cgccgcaact tacgttgcaa 22080
ggcggaaccg gccaaactgg ttcaaccttg aacggcggcc cgtctagctt cgtaaaagtc 22140
atgtcgccaa ctggaacgcc tatcgttttt ccagttaact acgaaatcca tgtaatgact 22200
tcgccagaag acgaagttta ttgcgtaatt aactacaatg ccgattttta ccagcaactg 22260
tcgttcggaa agtcgttgat ttccggcatt ggtggaactg gcgcatggtt taccggaagt 22320
tatgacagtc gtgtagggca aagcggaaac ggaaaccaat tcgacatgaa ttccggcagt 22380
aacatggatt ctggcggaac ccgtggtttt tggggactgg ctggcggact tttcttcgaa 22440
tcgttaagcg gggtagttta cagcggcaat tattttcatt gcggacttga cgccgtaaat 22500
tggtacaaca cgcgcggttc taatcttggc tatccgcatt gcgccgcaat cattaacgca 22560

```
ttaccaaatc aatcaaattc ggcaaccgta cttgttccgg taaaaggaat aaaaacacgc  22620
ggaagcggcg gccttactat cgtagtcaat ccgccaagcg ttcgttattg ccgaatcgac  22680
aacttggaac ccggaagttt ggtcacatac ggcccggatc aatggaaggt ttatccgttt  22740
tatcggaaag accttacgca acggcaagga tcgtcaagtt ctattcacag tggaacttac  22800
ggatacgcta tcaaatacac cggaagctaa acaatggccg gacgaattgg cgtatttacg  22860
caacctttta tttatggtga agataacccc gactattcta ccgaacttga caaatattcg  22920
gaagttgaat atttgcctgt cggcatcgac gtaatcgggc gtcgtatttt cggcccttat  22980
gcggtttggc gcgttcatgc ggcgaaccgc tggcctattg tgggcgaaga attcgaaaac  23040
tttttcaaag attactattt ccgaattcac gtatcgccgc aagaaattga tttgcaaacg  23100
attgcaagta cgcaaacgcg cgaagttgac gtatggaacg catatccgtt tacttccgcg  23160
atcatgcaag atattttggt taataatccg ataggcgttg aaataatcgg gccgaatccg  23220
tttaccttcc cgccattgtt tgaacagact tacgaaattg aagtaggaac ttccggcccg  23280
gcgaacattg atcttcaaat tttgttcgac tttgccaacg taacgaatcc gcttccggta  23340
cttgtaaccg gcacgcgcgc cgttaagttc gacattatcc ccgaaacgcc ggtaacggaa  23400
gaatggcaat ggcttaccga taatatcgta gctgttgacg gcaccgaaca gcgcatcgcg  23460
ctgcgcggcg aaatgccgcg cgtcgaagaa aatttgaaag ttattttcga cgattcgacg  23520
aagattcgga agttttatag cgatcttatg gccgcagtcg gtcggctttg gattcctgaa  23580
tttcagtacg caacgcgcac gctttcggcc agcgtaacgg gcggctttaa cctttacttc  23640
gacacgtcga agaccgacat tcgcgcaggt gaatacgttt tgattcaaac gccgttgact  23700
aatgcacttg tcgaaataga cgtattgact gtaaccggcg ctactgtaac ttcgcaattg  23760
ctatttgata ttcccgcagg atcgttaatc atgccgggtt cccccgcact gttgaatgac  23820
ggttcgggac tgtcgcgtta tgccgttaac gaagttgccg aaacgacgtt ggtttgcaag  23880
atgcttcgcc agcgtgcgca gcttgtgcgc cccggatcaa ccgtaacact tccgacgtat  23940
cttggcgttc cggtcttcga aaagcgaccg cttgccgatg aaatggtaga cgacaacgta  24000
tctaccggcc aacaatcaat cgacaatcaa accggattgc cggacattat ttcgcgttgg  24060
gactatagcc gtataggcgg cgcacgttcg tacaaagtga accgcattca acgtcccgaa  24120
gaaatggact attggaaaac gctatttgcg tatatgcgcg gtgcggcgcg taaagtttgg  24180
gtgcccacat accgaaccga tatgcgattg gttgttcaac cttcggacgg cgcttcaact  24240
ttcacaattg aaggtgtcga atatgccgaa aaagtctttc ctattgtaac gcatcgttat  24300
attgaagttg aaacggcttc cggtattcat cgaacacaag taaccggcgc agccgtcgca  24360
ggaaccggcc tttctacaat catcgttttc gatcctgcgt tgcctgttgg cgcaggctgg  24420
acggacatta aacgaatttc gtttctgttg cctatgcgaa tggccgaaga caaggtaaca  24480
tggaagcatt acggattaga aagtttactt caactttcgt tgattacggc ggaaccttaa  24540
atgtccgatt acgacgacaa agaaataagc cagcaagacg gcgcgccata cgaactttac  24600
gaatgggtcg gaacttaccg tagttattac atgactacgg atagcatacc gcacgttttc  24660
aacagtacga cgtataatcc ggtttcgggt ttgaagcgta gcacgttaaa agccggaacg  24720
cacgaagaag acaatatcga ccttacgatt attgttccga ttaccgaaca gcttgtaaaa  24780
gactacggat ttcaaacgac gccgcccgcg cttgatttga cgatttatcg tttccagcgc  24840
gacgcagcgg catacgttcc gtattggaaa gggccggttg cttcgatcat cattagcggc  24900
```

```
gaagaagcaa cgttgcggac gccaagcaag ttcggcaata tcctgcaagg caacataccg  24960
aacgtttacg ttcaaccgcc ttgcaataac gttctgttcg atgaacgttg caaggtaagt  25020
cgcgtatcta attcgctgga tactgtcgta tctgcgataa gttcggacgg cttgcaaatc  25080
agcatcccgt cgattggcgg tttccctaac ggatggtttg tcggcggtga aatcgcaatt  25140
ccggcacgca acgaacgtcg aatgatcgtt gcacaaactg gcgcaattct aacggtcaac  25200
tatggatttt cgcgtatttc tgtcggcacg tcgattcaag ttacggcggg ctgcgatcat  25260
agcttcacaa gcgcgaacgg ttgtccgaag ttcaacaacc aaataaactt cggcggttgc  25320
ccgtttgttc cgggcgaatc gaataaccca tttacgaacg gaattagcta atatgtgggt  25380
cgcaatcgtt atcgcggtaa ttgcgttgct tatggtcgcg tttatgccga aaccgaacgt  25440
cgaaaacgcg cgggcggcga agcttggcga cttccaagtt ccccggtcga aatacggcga  25500
tcctatgccc ttagtgtggg gaactgttcg ccaaaagtcg ccgattacgt tttggttcgg  25560
cgacttccgc ccggttccga ttaagaagaa agtttcttcg ggcttgttca gttcgaagaa  25620
ggttattacg ggttataaaa actacgtcgg tatcgactgc tgtttgtgcc ttgggccggg  25680
cgtcgtactt cgtaagtttt gggccggtac gtatcttgtt tggactggca ccgcttcagg  25740
tattacgaat atcgtaatca atcaacctaa cttgtttggc ggcgaagatc aacgcggcgg  25800
ccttcaaggt acgtttacat tctacgacgg tcgttacgat ccgccgcgcg attcgtattt  25860
ggcttcggtt cttgatccga acgttccggc gtacaacggt tttgcgcgtg ccttattcaa  25920
gtcgttttat atcggcacga cgactaatct tgaaatgttc agcttcgaaa tttcgcgtat  25980
gacttccggt cttcacgcga catattcgat tatgccgaac ggtcttgatt taaacccgat  26040
ggaaattgcg tatgatgcca ttacgcaaaa gttcgggcgc ttcggcaact tgccttcggt  26100
tctggacttg ccttcgttcg ttgcgtgcgc gcaaacgttg tataacgaac aaatgggcat  26160
gtctatggcc gcgcaatcgg ccattacggg caaagacctg ttagaagaaa ttatgcggca  26220
atgcgacggc ttgctgtatc aagacccggc aacttcaaag attgttgcga agttgattcg  26280
tcaagactac gacattaaca ctttgccggt tcttgacgaa tccattatta aggatttgaa  26340
gaacttttcg aaaacgactt gggatagtac gttcaatcaa tgccgcgtta cgttcaagga  26400
tcgcgcgggc gattacgacg acagcgtagc cattgcccaa gacttcgcaa atatcaacta  26460
tcaacagcgc gtcaagtcta ccgaaatttc ttcgccgggc tgtacgactg ccgaagttgc  26520
aaacaagctt gcggcgcgtc aactttcgtt gattagcgtt ccgttgtata agtgcgatat  26580
tacttgcaat cgcaaggctt cgacgcttcg tccgggcgac gtgttcgttc tgaattgggg  26640
gccgttcaac ctgcaaaaaa tggtcatgcg agtttcgaaa atcgaccttg gcgaacttac  26700
gtcgggggaa gtgaagattt cttgcgttca agaccgattc gctacggcga cacctacgtt  26760
tgcgccgcct gattcttcga attggacgcc gattaacaca agtgcaaatg ccgtgacggt  26820
gcgtaacttc tttacgccgc cgcacttctt ggcgcgcgtt tctccgaacg aagccctttc  26880
gacgttcgac agtcaaggcc ggttgtatat cttggctaag gggccgtcgt ccgcttctat  26940
ttcgttcgat gctatgttca gcggcgataa cttcgctacc gatcccacac tagccattga  27000
agcggccccg tacaatggcg gcggcacgct gtcggctgca tatgcgaata cagttgcggc  27060
agatacgcga cacgacacga caggcgtatt caaagtgcaa ggcgtatcgt cggcagacat  27120
tgcgaacttg caacaatata cgacgcttga ccaagcgcgc gacggttccg cgttgcttat  27180
ggtcaataac gaactgttcg tttatgtcgg cttcgttgac aacggcgacg gttccgttac  27240
tttcccgaac ctgtatcgcg gcgttctgga taccgcaccg gcaagccatg cggcgggcga  27300
```

```
ccgtgtttgg ttcgttggcg gtatcgacgg cttgattccg cagcttgtga acaacagtgc  27360
gaccgggtac gttaagctgt tggatacgac gacttcggac aagttgccgc tgtcgtccgc  27420
cccgaccgta tccgccgcgc agaatggccg cgcacgcctg ccgtatcagc cgcagaacct  27480
tacgcttgac ggtagccgca cccctgcccc ggccacgggc gcaacgtcga tcacggcggc  27540
atgggcacgc cgcagccgcg aagcgcaagc cctgtccgtc ttcaacgatc cagacgccgg  27600
gctagaaacc gggacgcaaa cgcgcgtgcg gtggcgcgtc ggcggtggcg gatatactac  27660
ggtcatgctt tccggcactt cgacggcgct taacgtaacc ggccttgtcg gtacgttgga  27720
agttatcgta gatacgcaaa tcacggcaag cgggctgttc agtacgaaca gcgaacgctt  27780
gaccatgacg ctatcttaaa agaacgcaag ttcgccgttc ttggctttct tcaaacgtcc  27840
gcagtcgtac agcatttcga ccgcttcgtt aatgtaccag tcgtaattta tatcgtcggg  27900
aaattcggtc ggcaagtcca ttacaggacg cgcgccgtcc gttttcccga ctttgtttcc  27960
gctggcaacg taagcgatat gcccggcttc gttcttcggg taataccagc gaacgacctt  28020
gcccaagaaa cgcccgttct tttcgccgcc gccgtgaaca ttcttcacgc atacgaagcg  28080
ccggaagtcg cggcattcct taatcgtctt ttctaccggc gttccttcga caaggaaccg  28140
aataacagcg tcggaacata ccaaagcttc ggggttcttc gacagaatcg aattaagcgc  28200
ggaaccgcgt tcacaataag cgcccttcgt cttagcgcct aatttttcat ccaagaagcg  28260
cgcttcggcg tcgccgccgt cgtccttgat tgcgacataa ctattcacgt cgcgcgaata  28320
tacggctttg tatcgcgttt cttcggtctt gtatcccgta tgcgcttccc atgctgcaat  28380
caagttgcgg acttcttcat gccgcgactt gtgatatttc gaaatgaagc cgtccgtatt  28440
gccggaaata acttcgacgc cgattccttc gattgcttcg ataagcataa gcaatacaag  28500
ctgtccggta atcgtcactt gcaacataag ttgcggcgcg tacagcgttg aatatttgtt  28560
gccaagtttg ccgaagcttc cgttaatcgt aatcttcaag ctgtcggcaa ttactttcca  28620
tttcttcgcg cccttgcggt cgccttcttt cttgcacttc gccgccatcg ccttagcgtg  28680
aattcgcgtt tcgacgatct tgttataaac cgtcaagaac gcttcgccca agtgcggcgg  28740
gaacagcttt tgattaagga ttgtgcgcgg atagaacgat tctacgtcgt tatccgctag  28800
aataatgtct tcggttgcga catgcgcggt cttcttttct gtcgaatgaa ggccgcccat  28860
tccaagtttg tacgtcgatt tgccgatagt tactttcagc ttttcaattt cggtcggcat  28920
gatgggcgaa cccaagccgt ccagatagaa tgccgcgccg cgcacgactt ctagcatttg  28980
ctgtaactgc ggcgtctgga aacaaacgaa gtccggtacg ttgtaataca acgggccgtc  29040
gtctgttagt gtgggcttct tcggatagta acccaacacc ttttcaagtt ctttattgat  29100
taccgcttcg gctacctgcg catcggattt cgaccgaagt tctacgccgt attcttccga  29160
catttcggcc cgcaacttca attcgggcgc aagttcgtta aacagaagtt ccgtattcgc  29220
aaggtcgttg cagcagtacg ggcgaacgat tgcggcatct tcgcgcgtca atacgtgcgt  29280
ttcaggaaat ggcaagtcct gcatacgttc gcaatgcagc cgaccggcgt acagcttcaa  29340
cgatgccggg cgcgcagtaa cgccgccgtt caccgggcaa acgttgaaca agtcgatatg  29400
gttgtagcgg ccaatttgta cgccgtactt cttttcgaag tcgaacggtg taaccttctt  29460
tgtaccgtag gccgggccgc ttttaatgat gaagtccgaa gcttctttaa gcttggcgca  29520
cgatgcaccg cgcgccgcaa gttctatcat gggcaagtca tacgatgcac tgttgaagcc  29580
cacaatacag aatcgccaaa gcatccaaag aagcttcgtc gggttaaagt catggtcggg  29640
```

```
tgaacgttca aacgcgacga actttccggt atcaagcgac ttaaacgcga cataccaaaa  29700
gttgatatac gtttcaacgt caaagacgaa gacgcttcca gcgggaagcg ccattagttc  29760
ttcgtccgac atgaattcga caggccgcaa agcatggcga atgcttgcgg ccaacttatc  29820
gacgacgcgg cttttcttgg caacgatgaa gccttgttcg ttcaacatat gacagcccct  29880
tagaacggta tatcgtccga atacggatca tccgaagttc ggttaatgta cgtatcttcc  29940
gactgttcag tatacgacgc ttcggttcca agatcaagcc ccataactgc gccgcgcacg  30000
ttgtcgccgt agaaaattac tttgttcgtt tcggcgtcga aatgcgcttt cttgaatgcg  30060
tgttcgacgg aaagcaaaag ctttgcactg aaccccattc gttccggcaa gccttcgata  30120
cgatacgtcg aagcttcttc tttgtgcata cgcgacaata ccgcgccatc ttcgaagaag  30180
acatggccgt tcgggctgaa cgattcgata gcacgaacgc cccggtaaaa gtcttcgggg  30240
atcggccaaa ggttcagatt cggaacgtcc agaaccgaag cataattcgg gtaacgttcg  30300
ccgtaaagct gcgacttgat aaacgaaccg tcttcgaaat agaacgtcgc cgatgactgc  30360
gaatagccga acccggtaag cgccttcgat gccttcgcaa tggccgacgc tgcggccttc  30420
ggaagcataa ggccgggcgg aaggtcgatg ccgtgccacg cttccagcag ggccgccccg  30480
ttcgtcgcta cggcgcttcc agcttgcagc aggacggcgg cataggtcgc attcggcgcg  30540
ccgtccgttg ccagccctgc gaccgcagcc aaggccgctt taacccggtc gtcgatcacg  30600
gcgcattgtg gatcgggcgg catgatgggc acttcgtcga acgctacgca cggcacaagc  30660
gcccggaata cgccagacga tacggcaagc gtgttcgctg taagttgcgt aatcgacaat  30720
tcgtcgccag ccttcgacag tgcgtcgata aactgcaacg tatgcgggca cgcggtcaag  30780
tcttcttcaa tcggcgcggc cacggtcaag acgccatcga aggccgccgc ccaattgtgg  30840
gcaatgtggc cgaactggat atttaccggc ccggccttct tttgcgcaac cgaaataaac  30900
ttcaatgctg cgataagcga agcggcgggg ttcgccgtct tcttcgctgt cgtaccttcg  30960
gcttgcttgc gggcgcggct tttgcgcttc ggcttttccg gcgttgcagg aatcggaacg  31020
tcgttttcaa tttgcgttgt catagtttca ccattcagcg gaaagaactt cgggatactt  31080
cttgttcacc caaacgcgaa gccttgcggg cgttcgaagt tcggatacac gttgcaaagc  31140
ttgatacgtc gtcggcggcg gttcttcgcg gtgccgctgt cgccaccaat cccgcgaacg  31200
tttcgccgca agtccggggt gttcaagcat cacaaattcg ttaaacattt ggaagccgca  31260
aaagtacgat actttaatca ttggcggctt tgtcaagttg ccttgtgcgt cgcgtttttc  31320
gtgaaggttg tatatcacct tttgtacgtc gaaatattcg actatcgggg catcgctgcg  31380
caacggttcg gcgacgcccg gcgttgcaaa caacttcgtt tcgaagctga attcggcacc  31440
gcagttaatg cactggcgcg cggcggcatg attgtatacg ccgcaaactt cgcaaatacg  31500
aaccggcgcg tcgccgccac ctttgccggg gcgattcgga atacgcgggt cgttgatcgg  31560
gccaagccga cgaatgttcg ccgcgaagtc gccgacaaga caattcatct tgccggtttc  31620
gggacttggg cgcgttccgc gtccgtactt ctgtacgtgt ttgcccggcg ataacgtcgg  31680
gttcaaatcg ccgatgaagt cgattgccgg atggtcgaag cccgttgtaa gtttctggcc  31740
ggatacgata ccgcgaagtt cgcccgcttt gaatgcgcgc aaacgttcgg tattaacctt  31800
gtctttcaac ttcgaatgca cgggcaacac ttccagcccg taggactgaa ttacgtttgc  31860
gacgtgttcc gtattgtcaa tgccagttgc gaagacaagc caagtcgaac ggttatacgc  31920
catttccatc atttcgcgga cggcgttaaa tactacgtcg tcatcgtctg cggctttttc  31980
aagttgcttc gaattgaatt cgccgccgat tacgccaacg cctgaaatgt caatttcggt  32040
```

```
tttcgtcggg cgcgcgataa gcggcgacaa gtaaccttcg gcgattaacc gattaaacga  32100
ttcaacgccg gtaatgtcgt aacaaatatc ggtgaagatt ccgttatcgg taatcatgcc  32160
cattttcata cgatagggcg ttgcggtgaa tccgataact ttaagatgcg ggttaatcgc  32220
gcgcaattcg gcgataatgt actgatagaa cgaatcttct ttgtccgaaa gcaaatggca  32280
ttcgtcaatc aacagcaaat cacgccatcc gaaatggcga agatgcggcg ggcgtccgtc  32340
gttctgttca agcgcctttt taatcgccgg ggctacggat tgaacgccgc cgaatacgat  32400
aggcataatc atttcgcggc tgttcaagcc tgcggaatag ataccaaggg gcgcagtcgg  32460
ccaaaccgac attagctttt cggcgttctg ttcgatcaat tctttaacgt gcgtcaacat  32520
cattattcgc tgattcggcc aaagtccgaa aatgcgacga atgaagttcg caattacaac  32580
agatttgccg gttccggtcg gcatagcgac gaccgggttt ccgacgtttc cgcgctggaa  32640
atagtcgaag attgaatatt cggcttcgtc ctgataccag cgcggtacgt agatactaga  32700
cattttgcgt tgtcgccgtg ataggtacgt aagacgggca agcttgcggt acgaagtcgc  32760
ggggaattac gccgttatgt acgtcgcaaa accattcgcc gttttcgacc ggacgggccg  32820
ccttgcagct acgacagttc ttttcaggaa tcgcgccttt gtggcaaatg tccttcgccg  32880
cgcaatacgt gcaatccttg aacgtcggat tatcggaaag acgcggcggc ggttcctgcg  32940
acagaatgat ttgttcggcc ttttcccgca tttgctggcc taaccgatga tccaacttca  33000
caagttcgac gtgtaacgaa tcgtcgttct tgttaatgtt gaagtacagt acgtaacgga  33060
atccgtatgc cgcgtcgctt ccatacgttg aagtttggca aaaatgctgc ggcttcgcaa  33120
caggcatacc ggcttcgcca agcttgttaa agcctgcgcc ggttccgttc gtcttgaatt  33180
ccagcaatac aggttcgtcg attccatagc gcgccggaag ctttgcgatg ccgtcaagcg  33240
atccaccgaa atgcccattc accgccgaca cgcggtattg tgggaattcc aagccgtccg  33300
ccttcgcgcg tgcgacgtgt tgcgtatagt acggatgttc cttcgtaatc ggtgacgaaa  33360
ggccgtcgcc ttcttcgccg ggcttcgcaa tccaatacga atcgctttcg gcgtgataca  33420
taaggccgtc gcggttttcg taccaaactt cggccccgat gccttccagc cattcgataa  33480
agcgggcttc ttcacgatgc ccacgattaa acagccgttg cttgcgtccg tccgtctgtt  33540
cgcggaacgt ccatcggaac agataccaaa gcttgcgctt gcagccgtcg ccgatcaacg  33600
acgcgccaag gtgccagcgg tggccgccgt cataggtgcg aacgcaatat tcgtctatgt  33660
cttcaaggat gcgcttagaa agcgccttcg ctacgccggg cgcgtcaagt gcgacgtttt  33720
gttttccggc gtcgggcttc gtcgctggcg cgtcgttcag cgttaattgc gcgttcggtt  33780
cgcttttctt gcttggcatc gttcttcacc tttcgccgga caagtgcggc gtaattgttc  33840
gttagatagt cggcggaaag cgtcgcaacg tctttaagtt gatccttcga taaccaactg  33900
atatggcatt cggaagcgtc tatgccaagt tgcgccgcaa gccaattgta cgccttcgac  33960
cgtgacatta agccagtttg ccaaagacgg tcgaattcgt catgcgcttt tgttcgaagc  34020
tgtcgcgtag cacggtcggc catacgacca agcggaataa acgtgccggg gtgacagccg  34080
acagcggcgc gacagtcgtt gcaaaaataa atatgcggcc aatcgccgta acggcgaccg  34140
taaatccggt cgtttgttgt tagttcgatg ttgaatgaac aacaggtatc gcattgttca  34200
ggtacgggca atgcgtcttt gattttcgac atacttacgc ttttccccat aaaagaacgc  34260
cggggccggt aaaagccccg gcgatgttac gccgctacgc tagttcgtct tagcgtgcgc  34320
cccaaggtgc ggcaccgcca gccggtgcgc cgccctgcgg ttgctgctgc cagccgcccg  34380
```

```
gctgtccgcc ctgcggggcc gcgttctgct gcggctgctg gccgccccaa gctgcgccgt  34440
tgccctgcgg ctgctgcggc tgctgttggg gctgctggcc ccatgccgcg ccgccttggg  34500
ccggttgctg ctgcgcgggc tgctgctggc cctgcggctg gccgccccat gcgccgccct  34560
gcgcgggctg ttgctgcggc tgttgaccga agccgccttg gccctgcggc tgctgtccga  34620
agcctgcggc ggcctgctgc ggctgcgccg gggctgcgcc ctgtccggcc ttgcccggtt  34680
cgttgccgtt catgtcgaac accttttaa cttcggtgta ctgcgggtcg ttcttctgcg  34740
gcccgacttc gataaggaac gggattccgt gaagctgcga cgaatcgttg atttggaaca  34800
cgccgataac gtggcagact gcggacaact ggcggtgcgc gatttcgacc gtctgttggt  34860
tcgtatggta caggttcagg cgatacgcgc cggtcgtgcc agcctgcggg ccgtcgatga  34920
tccgcaagtt aagttgcaga taaccgccgt cgttcgcctt gtttgccttc acttcggaac  34980
tttcgacgat aaccggatgc ttgccgatag gcaggcttcc gacgccttgg gtcgggtcgt  35040
attgctgcgc gttgaaaggt tgaatcagtt gcatggtatt taccttttcg aaaagtcttc  35100
gccgttggtt acggtggcaa agttaccgtt tttggctgcg ccggtaggat tcgaacctac  35160
gaataccgga atcaaaatcc ggtgccttac cgcttggcga cggcgcaaaa gcttattgca  35220
tcgctttcgt gaaaagcgcc gacaaatcgg gcggttcaag ttcgcccaag ttgcccaaac  35280
gatcacgcgc gaacacttcg ggaatttcct tcgtccgcaa cgcccgaacc ggcttcggct  35340
ggcccggtac gatagcttcg cccaagtgca acacgttgtc gaacaggtgc ggaaccttta  35400
cgttaaggtc tttgccgggg aagaacggtc gcttttgcat gatcggttcg tatacgactt  35460
cgccgccctg caagatggtt tgccgtccgt tttccatgac gccttgtttc gcaatcatta  35520
cgatatgctt ttgcggcatg taatacaagt cgttgcaaat cttcatcgtg cgttcggaca  35580
tattgccgta tgccttcatg ccgtgtttga ccttcgacag ttcttcggcc aagatgattt  35640
cggcaatgtt cgaaatactg tcaatgccca aggtatcgaa gttcgcggct tcgcgcgact  35700
tcataaacca ttcgaagaat tcggtaatca gcggcgggga atacgcttcc catgcgggca  35760
cattcgaacc gcgcatagac aacatgccgg gttcagtgac caacagcacg gggcgcggcg  35820
cggtgttgat aagcggcgtc ttgcccgaac cgggcgaacc gaatacgacg gactttacgc  35880
catagcgtcg ggccagttgc gacgccggtt taagctgcga catttgcatt ttgtttactc  35940
cgattaaagc ggcattattg acgacgccga cgctttcgct ttcccgactg tccgttatgg  36000
cactatgcga cgcgatgcgc ggcccggact ttcgatgccg tcaagaatgc cgccttgatt  36060
gtgggcaagg cggcaagtgc attacttctt cgccttcggt tccttgattt caagggtcgg  36120
cgtaccttcc gacgtaacga taacgtcgtc gatgatcttg cggaagttgt cgggcagttg  36180
cttgtattcg gtaagcgaaa gttcaggcgt ccacttaacc aaacgttcgg cgatcaattc  36240
gccagcctgt ccggtctttt cgatcttcga caacgccttt tcaatgcgcg ccttgtcggt  36300
cttgccttcg gcgttctgga tgaagccgta gcgaaccgga accttcatcg tcgctttgta  36360
gccgccgccg agttcgacgt tttcggtcgt gccggacttc gccgggtcgt gcatgaacat  36420
cacggccagc ttgcgggctt ccaattcggc ttctttggcg acttcaagcg cggccttctt  36480
cgcctgccaa tcgaccaaca gacggtcgcg ttcggcgata tattcggctt cgctgtagtt  36540
cttgacttcg cccgtttccg ggttcgttac ctgaatgata ttcggggtca tctttgcacc  36600
tttcttcgtt gggccgccgc acgttgcgcc ggtatgtgcg taatgtacga cggcccgttt  36660
cggttgtcaa gccttttgtt caagaatttt tcgttcttcg aacaagtccc gattgttcgc  36720
gtcgtgttcg gtgaacttct gcgggaaccg cttacgaagc ttggcgatgt tcacggcctg  36780
```

```
cgcttcaccg aagttcgaac caatggcgcg aagcaacagc gcatcgtacc aaaagccgtc  36840
gccgacttct tcaagcgcgt tcacgtcgtc gaatacggca ccttcggcgg tcgccgacag  36900
ggcttccagc agttcgcccg cttcggtcgc tttaccgatg atcgcatgaa cgatattgac  36960
ggcgcgcgcg ttggcttcgt cggtgccatc ggtggcgatc caatcgggca gcttggcaag  37020
cgtgccggtg ttgtcgccgg gggcgggaac gccgcagtcg cggccataga aaagcgtctt  37080
cttgatcgcg tccagcttca ccagtgcggc gacagcttcg gcgatggttt cgcggaagta  37140
gccaagcgac acgcggtcgc cgtgatagct acccgacgcg gttacgtgcg cttcttcgat  37200
atagtcgaag gtcttttcgg gttcgttcat tgcttgcacc tttcaaagtc gccgggcacc  37260
gcgccgcagc gttccgacac tgtagcgccg ggcatgttgc ctgtcaacaa aattttgtct  37320
tgcctgctag aattttgtcg ggtatagtgt cgttcatctt gcccacattg aaccgccgac  37380
atggtgaaaa catggccgaa gttaccaaac tgcgggatga aacccgcgaa ctgttgttga  37440
accgcccggc gtcgatagac gttggcacca ttgcggaagc catcggcgtt tcgaagtctt  37500
gggttaattc ctttgcgcgc ggcgacatac cgaaccccgg cgtcgtcacg attgaaaccc  37560
ttaacgcttt tttgaagaag tgcgcgaaga aggcgaatta agaatgtatc aaaacatacc  37620
tatcgaaatg cggacatatc cgcaatgggt tatgtggcgg tacgaagaca cggattcgaa  37680
gaaacctact aaggttccgt attctgcccg taccggcgca ctagccagcg ttaccgattc  37740
gaacacttgg ggaacgtttg acgaatgttt gcacgcgctt aattccggct ggtataacgg  37800
aatcgggttc gtgttgaccg acgccgaccc gtattcgttt atcgaccttg acgacacgaa  37860
aggcgatcaa acggcgcttg atcgtcaaat caaaatctac aacgaattcg acagctacgc  37920
cgaacgttcg ccgtccggtt cggggctgca tatcattgta aagggcgcgg ttcccgctgg  37980
ccggcgtcgg tcgtttattg aagtgtattc gtcgcttcgt tatatgacca tgacgggcga  38040
cgtttaccgc aatgcgccaa tcaaagaaca aaacgaactg ttgaacattc tttggggcca  38100
aatggggcaa ggttctgtcg ccgttgcgca ttacgcaagc gtcgccgaag ccaaggaaac  38160
cgacgaacag gtttataacc gtgccgtcgc cgcagccaac ggggataagt tcgccgaact  38220
gttcgcgggt aaatgggaag gcatgtacgc ttcgcagtcc gaagccgact tcgcattggt  38280
cgatattatc gcgttctata cgcagaaccg ggcgcagatt gcccgcatgt tccgactgtc  38340
cggcttgggc caacgtgaca aggcgaagcg tgacgattac gtgtcgtaca tgctgaacaa  38400
atgctttgat cgcatgttgc cgcccgtcga tattgacgga ttgaaaaaca agcttgacga  38460
agcaatagcc gcaaaagaag cccgcgaccg tgccgaagcc gcatcgttga ataccaacgt  38520
tccgcaagcg ccaatcgtcg cgccatccat ccccgaaacg tcgaaggtgt attcagtgcc  38580
gcccggactt gtcggcgaaa tcgcccaata tatctacgca caagcgcccc gcccggttcc  38640
cgaaatcgcg ttggctggcg cgcttggtct tgtcgctggc atcgtaggcc gtgcgtacaa  38700
tatcagcggc accggcctta atcagtacgt attgctgttg gccccgaccg gaacaggtaa  38760
agaagccatc gcatccggca ttgataagct aatggcgcaa gtaatccgca ccgtaccggc  38820
tgcaagcgac ttcatcggcc ccggcgaaat cgcatcggcg caagcgatca ttaagtatat  38880
gtcgaagggg ccaacgtcgt tcgtatcgtt ggtcggcgaa ttcggcatct atcttcaaca  38940
aatggcaagc ttgaacgcgc cgccgcatct tttggggctg cgccgtttca tgctggacgc  39000
ttacaacaaa tccggcgaag gtaaggttct tcgtccgtct atctattcgg acaaggacaa  39060
gaacactacc gcagttcttg cgccgtcgtt ttcgttgctt ggcgaatcaa cgcccgaaaa  39120
```

```
gttttacgaa ggtttgcacg aaggtttgat taccgaaggt cttttgccgc gctttacgat  39180
gattgaatat catggtcaag tgccgccgtt gaacaaagcc ggggcgcgcg tgcaaccgtc  39240
gttcgaactt atcgaccgcc tttcgacgct ttgcgcgcat tcgcttatgt tgaacagcca  39300
acataaagca atccatgttc aattcgccga aggcgtcgaa caagcttccg acaagttcga  39360
agaacattgc cgcaataacg taaacagtag cgaccgcgac gttaagcgcc aactttggtc  39420
gcgcgcccat atgaaggcgt taaagctggc cggtatcgta gcagtcggca ataacccata  39480
cgaccccgtt attacgtcgg acgttctgtc atgggcaacc ggcgtaatcg ttgcagacgt  39540
gcgcaacttg cttgcacgct tcgacgctgg cgaaattggc gtagacaacg acgaaacgaa  39600
acagcttgcg aaggtaattg cgacggttaa agatttcgtc gtatcgcctt ggccggaagt  39660
tgcgaagtat gcaggcgaag gcgcaagcaa cttgcattcg aaccgcattg ttccgtacag  39720
ctacgtacag cgtcggcttg ccgccgtgtc ggtcttccgt aaagatcgca tcggcgcgtc  39780
tggcgcaatc aagcgcgcat tgaagacgct atgcgaacgg ggcgacctgc aagaagtgtc  39840
gcgggctacg ctgtcgaagg actacggaac gtccgccgtc gcgtacatga tcgcgcatcc  39900
gggcgtcttc ggcctgtagc ggggccggga tagtgtgggc agaactggcc gccttcgggc  39960
ggctttttcg tgcctgaacg aaacataaat aaagcgacga acggtcgtcg taggtcttga  40020
cgaagcttcg aaactatcgt acaatcgtcg catacaagaa aggagtttca acaatgcagc  40080
atcccgacga cgtagaatat ttcgaacgtt tgcgcgccat aggattcgaa atcgcaaagg  40140
ctaacaacat tcgttgcctt gtcatagaac ctaagcgtcg cgcaggcggt gcatacggac  40200
ttgcgtattt gtctgaatgt cgaatcagca ttgaagttcg cggcaaagaa cttatgcgcg  40260
atggcggcga atgggcgaag aatcgttatc gccatgcttg caacttgcat acgttggcgc  40320
acgaattggc gcatttgcaa gaacaccaaa cgcacggcaa gaccggacac ggcccgcgct  40380
tccgtactta cgaaaccgcg ttacttgctg cggttatgca gcttgacgcg acttccccac  40440
attaaccgaa ggtgccagct atggaaatcc gcatagacaa cgtgaacgaa gttctagccg  40500
caatcggctt gaccggacag cacgaacgca agggccaagg ctggcaccgc gtttacattc  40560
acgccccgca agaaggaacc gacgtaacgt tgtaccttgg ccgcgtcatg tttcaacatg  40620
gcgtattcca atgggtgaaa tggtgcgtac cgccgaacga aggcgaattg caggattacg  40680
acgtatattg gttccgttgg gccgtataca ccgcaaccgg caagcatcta gggccgaagt  40740
cttgggcgcg gttgaaggcc aaggcgcagg aacgcgcgca ggccaagcgc gacgccgcca  40800
aggccgcacg ggacgccctg aacgccgaca gggtagccgc aggcaagaag ccccggacgc  40860
gcgcccttgc gcctgtcaat ccgcgccggg cggcgtgcat gatcgtcggc gaatggctgt  40920
ccgccgaact tggccgcgaa gttcatttgt tcgcattcta acgaaggagt attgaatatg  40980
accgcattta ttgtcgcgct ttgcgcatct ttggcgctgg cgttctggcg tctggccgct  41040
actgcattcg aagccgctta ctactgcgca aagaacggtg aacgttcgaa ggcatggcgc  41100
ttcatccttc gcggtatctt ttgcgcgttt tggctttcgc taatgattgc gcccgtcgtt  41160
cgtttcttcg atagcttcga cgtgattagc atagacgaag cgccgcctac tgttgcgccg  41220
aagcgttcga cagaccttcg cgtataatag acgacgatcc gtttaacggt gccgtataac  41280
acgcaaagcc ttgatacgcc tagctttcag ggcatttata acaagtataa agtttaacgg  41340
caaagtcacc cgatccccca gcttgtaacc taataaccgt tatcactaaa taacactact  41400
tttcagtatt atacttatta tactttttat atttctttta ttttcaatgg tttaggactt  41460
ttacagcccc ttcaatccgt ataatggccc cggaacgatg cgttacgctt gactaacccg  41520
```

-continued

```
ttatcacctg atagagttac aaacgtcata actgttaagg agtgttcgaa atgtcgtacc  41580
caatcgttca agcgtcgccg acggcgatgg aaaagaagga acaggccgaa cgcagcgcgt  41640
acccgttcgc agaactggcc gtaggtcaat cgttccttgt gccaattgcc gacgtgaccg  41700
aagtaaactt gcgcatggcc gtaagtcgcc agaacaaaaa gaaggacggc aagcgtttta  41760
ccgtcgtcaa gcatggcgac ccgcataacg tgttcgaagt cgcacgcacg gcatgaacgc  41820
gcgggccaat gtgggcaagc tgcaacgggt gtttgcgccg cattacttga cgcttcgcgc  41880
gcaatggccg caggcgttcg caatcaaacc aacacgcggc ggctatgaag ccgtcgtatt  41940
catcgaaggg gcgaccaatg tacgaaatcc agaacgggca caagatgccg aaggcgcgtc  42000
gcaaggctgg aagcgaaccg ccagcggtga agaccgcatt taacgaatac gcggacgcat  42060
acaaagctgt ttacggcgtg cgtccgctgt cgtatactta cgacgcagca acgaagttta  42120
ttcgcatcga aaacagcggc ggcgtaagct tgtcgcgttt gcgcgaaatg acgaagcaac  42180
ttcgttaccg caaaggttga cagcttcgaa gtttcatcgt agtgtgacca tgcgaaccgg  42240
gcgcttcccg gcatttcaaa ggagttaacg caatgtgcat cgtttgcgaa atcaaagccg  42300
atttgtcgaa gaccaaagcg accgccgaac aggccgccgc catcatggcg aacgttgaaa  42360
agctggcccg tgcaatgggc ggcgttatcg acgtggtaga agctgcgcac gtgcgcaagc  42420
ccgacgtgtt caagccggaa gaactggcga ccatcgccga agccgaagaa ctgttcgcgc  42480
agtccgaagc cctgcccccg ttggccgccg ccctgttggg cgcgctgttg ggcggtagcg  42540
tgaaagtcga agtcgcgcat atccagatga aggacggcga gaatcccgaa caggctatcg  42600
aacgttacat ggctgaacgt aacgccgaag gttcgacgaa acattgacca aacagccccg  42660
gctagtgtat agtcggggct tcttcgtagg ggaacgaaac agacatggcc gacgaaatag  42720
acgcaacagc cgaccgcatg gacaacgaac tatcgttgat tctggcgaac actagccgcc  42780
ttgccgcgcg ataccgaaag gttatcccgg cgaatgcttt ttctgcggcg aagaattcgc  42840
cagcgtcgtc gaagtgaccg acccgcgcag cggcgaacgt gtcgattcct gcgggcgctg  42900
tcgtgacgca aggggcataa aatgacaccg aacaaacttg cgaaggaatc cgaacattcg  42960
caacaggtcg cattgttcgc atacgtagct gtcgcgtact tgcacggctt cgacgtagcg  43020
gacgaatggt gcaagaccgg caagctaccg aagcgcgatc cgaacgcacc gccagccgtc  43080
ccggcgcttg aatggttcca cgcgatcccg aacggcggta gccgtggcga cgacgaacag  43140
tcgcg                                                              43145
```

PHAGE THERAPY

CROSS-REFERENCE TO RELATED APPLICATION

This application is the U.S. national stage application of International Patent Application No. PCT/EP2015/075949, filed Nov. 6, 2015.

The Sequence Listing for this application is labeled "Seq-List.txt" which was created on Apr. 26, 2017 and is 465 KB. The entire content of the sequence listing is incorporated herein by reference in its entirety.

The present invention relates to novel bacteriophage compositions, their manufacture and the uses thereof. The invention is particularly suited for the treatment of an infection in a mammal particularly in the respiratory system.

BACKGROUND OF THE INVENTION

Bacteriophages (or phages) are small viruses displaying the ability to infect and kill bacteria while they do not affect cells from other organisms. Initially described almost a century ago by William Twort, and independently discovered shortly thereafter by Felix d'Herelle, more than 6000 different bacteriophages have been discovered so far and described morphologically, including bacterial and archeal viruses. The vast majority of these viruses are tailed while a small proportion are polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic, pseudo-lysogenic, and chronic infection (Weinbauer, 2004; Drulis-Kawa, 2012). Lytic phages cause lysis of the host bacterial cell as a normal part of their life cycles. Lysogenic phages (also termed temperate phages) can either replicate by means of the lytic life cycle and cause lysis of the host bacterium, or they can incorporate their DNA into the host bacterial DNA and become noninfectious prophages. Whatever the type of cycle of a phage, the first step is the attachment to receptors of the bacterial cell wall before phage material may enter the bacteria. This specific process influences the spectrum of the possible phage-bacteria interactions.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infection was, however, highly controversial from the very beginning and not widely accepted by the public or medical community. Early studies were widely criticized for lack of appropriate controls and inconsistent results. The lack of reproducibility and many conflicting results obtained in the various published studies led the Council on Pharmacy and Chemistry of the American Medical Association to conclude that the evidence for the therapeutic value of lytic filtrates was for the most part contradictory, unconvincing, and recommended additional research to confirm its purported benefits.

Since the introduction of antibiotics in the 1940s, little attention was paid to this field of therapeutics, especially in the Western world. But the extensive use of antibiotics has led to the widespread emergence and spread of antibiotic-resistant bacteria around the world, causing increasingly serious problems. It has therefore become a major therapeutic challenge to overcome the limited therapeutic options remaining to treat major multi-drug resistant microbes.

Since its initial discovery in the late 19th century (Fordos 1859), the Gram-negative bacterium *Pseudomonas aeruginosa* has gained a notorious place in the list of infamous human pathogens (Williams and al, 1894, Freeman and al, 1916). The arrival of the antibiotic era largely palliated the previously fatal outcome of acute infections in healthy patients. Only a relative improvement has been achieved in the eradication of chronic infections, which develop mainly in individuals suffering from cystic fibrosis or severe burns or who are immunocompromised (Gang et al, 1999, Jones and al, 2010). Two intrinsically related factors in the fatal outcome of infection in these patients are the rapid prescription of inappropriate antibiotic treatments and the development or acquisition of multidrug-resistant strains. While the use of (an) appropriate antibiotic(s) has been reported as an essential factor in the eradication of *P. aeruginosa* infections (Kang and al, 2005, Micek and al, 2005), conversely, antibiotic abuse significantly contributes to increasing resistance by exerting a continuous selective pressure for the acquisition of such capabilities. Antibiotics alone do not account for the high prevalence of multidrug-resistant variants: *P. aeruginosa* has multiple, chromosomally encoded intrinsic mechanisms of resistance, including low permeability of the cell envelope and numerous multidrug efflux pumps. Another major factor accounting for the successful invasive behavior and persistence of this bacterium is its high adaptability, allowing rapid colonization of different environments.

Furthermore, pathogenic bacteria such as *P. aeruginosa* are able to form biofilms, which contribute to their increased resistance to antibiotics. Such biofilms may comprise more than one type of bacteria supported and surrounded by an excreted extracellular matrix, and assist bacteria to colonize various surfaces. Biofilms allow bacteria to attach to surfaces and to reach population densities which would otherwise be unsupportable, imparting increased resistance to not only antibiotics but many environmental stresses including toxins such as heavy metals, bleaches and other cleaning agents. It is known that bacteria within biofilms can be 100 to 1000 times more resistant to antibiotics than the same strain of bacteria growing in planktonic forms. Such an increased resistance means that bacteria that are apparently sensitive to antibiotics in a laboratory test may be resistant to therapy in a clinical setting. Even if some are cleared, biofilms may provide resistant reservoirs permitting rapid colonization once antibiotics are no longer present. It is therefore obvious that bio films are major factors in many human diseases. Chemical treatments are unsuited to use against bio films since this is precisely what they have evolved to counter. Physical abrasion does provide a mean to disrupt bio films. Unfortunately, many surfaces where biofilms supports bacterial pathogenesis are poorly suited to rigorous abrasion, i.e. bones, joints, implanted medical devices, etc. For example, the surfaces of wounds or burns are extremely sensitive and delicate. Even where abrasion is both suitable and in routine use, clearing of bio films is limited. Oral plaque on the surface of teeth is a biofilm and is partially cleared by regular brushing. However, bacteria are maintained on unbrushed surfaces (for example in the gaps between teeth) and can recolonize cleared surfaces both rapidly and effectively. From this, it is clear that existing approaches to clearing bio films are of limited efficacy.

The capability for quick adaptation and their ability to form bio films are the main reasons that identify *P. aeruginosa* as opportunistic pathogens. They have acquired the status of hospital pathogens, and may be isolated from clinical samples taken from the wounds, sputum, bladder, urethra, vagina, ears, eyes and respiratory tract. The emergence of resistance to the most powerful new antibiotics in such clinical *P. aeruginosa* strains, occurring even during treatment, makes the fight with *P. aeruginosa* hospital pathogens a great problem.

Therefore, there is a great need for new antibacterial agents or compositions that can be used to destroy *P. aeruginosa* strains, even when organized in bacterial biofilms, suitable for use in human or animal therapy, as well, as for decontaminating materials.

SUMMARY OF THE INVENTION

The inventors have isolated and characterized new bacteriophages presenting strong and specific lytic activity to *Pseudomonas aeruginosa* (*P. aeruginosa*) strains. These bacteriophages, especially is combinations, provide very potent antibacterial effect and can be used as active agents in pharmaceutical or veterinary preparations, particularly to treat *P. aeruginosa* bacterial infections.

An object of the invention is to provide antibacterial compositions comprising at least two bacteriophages having lytic activity against a *Pseudomonas aeruginosa* (*P. aeruginosa*) strain, said at least two bacteriophages being selected from the bacteriophages having a genome comprising a nucleotide sequence of anyone of SEQ ID NOs: 1 to 7 or a sequence having at least 90% identity thereto.

A further object of the invention relates to a bacteriophage having lytic activity to a *Pseudomonas aeruginosa* (*P. aeruginosa*) strain and having a genome comprising a nucleotide sequence selected from anyone of SEQ ID NOs: 2 to 7 or a sequence having at least 95% identity thereto.

The bacteriophages of the invention exhibit strong lytic activity to multi drug resistant strains of *P. aeruginosa*, in particular to antibiotic-resistant pathogenic strains such as cephalosporinase-, carbenicillinases-, carbapenemase- and/or extended-spectrum β-lactamases-resistant strains, and are therefore particularly suitable and advantageous to treat bacterial infections.

The invention further concerns an isolated nucleic acid molecule contained in a bacteriophage of the invention, preferably an isolated nucleic acid molecule comprising a nucleotide sequence selected from anyone of SEQ ID NOs: 2 to 7 or a sequence having at least 95% identity thereto, as well as an isolated polypeptide encoded by said nucleic acid.

Another object of the invention is a composition comprising a nucleic acid or polypeptide as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in a mammal, for modifying the microbial flora in a mammal, for decontaminating a material and/or for killing a *P. aeruginosa* bacterium or for compromising the integrity of a bacterial bio film.

The invention also relates to a bacteriophage, nucleic acid, polypeptide or composition as defined above, for use to improve a subject condition by modifying the microbial flora in said subject. The microbial flora may be modified by correcting, adapting or restoring a proper balance of microorganisms in said flora.

The invention also relates to a method for treating an infection in a mammal, comprising the administration to said mammal of at least one bacteriophage, nucleic acid, polypeptide or composition as defined above.

The invention also relates to a method for treating a surface or material suspected of being contaminated with a *P. aeruginosa* bacterium, comprising applying to said surface or material at least one bacteriophage, nucleic acid, polypeptide or composition as defined above. The surface or material may be a surface of any device, vessel or laboratory material, cloth, etc.

A further object of the invention relates to a kit comprising a composition as defined above and a means for applying the same to a subject or surface.

The invention may be used in any mammal, preferably in human beings, or to treat any material, including laboratory materials or medical devices.

DETAILED DESCRIPTION OF THE INVENTION

Figure 1:
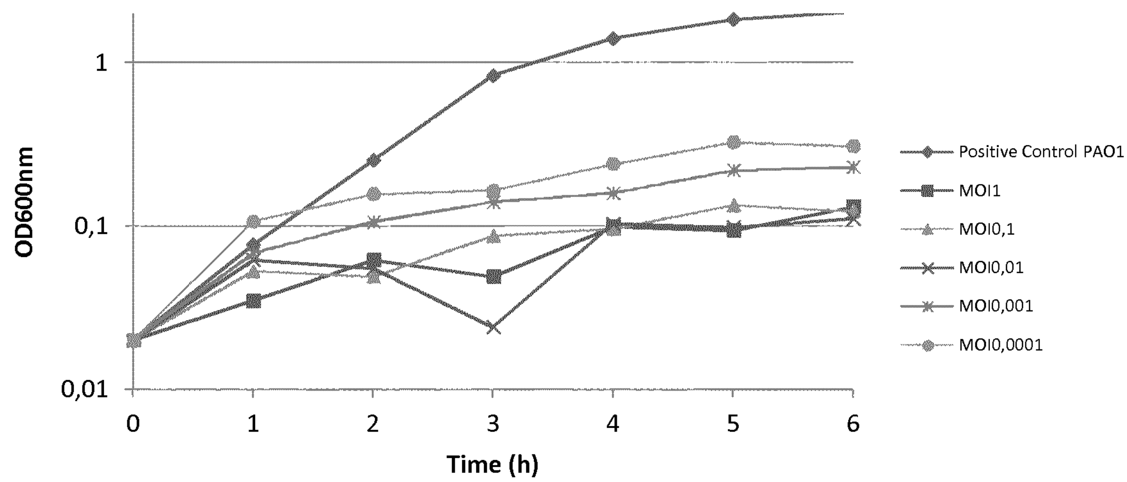
FIG. 1: Efficacy of bacteriophage 1384 on PAO1 strain.

The present invention relates to novel bacteriophages, components thereof, compositions comprising the same, their manufacture, and the uses thereof as antibacterial agents, particularly for the treatment of an infection in a mammal or for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the part and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on *P. aeruginosa* strains according to techniques known per se in the art (see also experimental section).

The term "variant" of a reference bacteriophage designates a bacteriophage having variation(s) in the genomic sequence and/or polypeptide(s) encoded thereby as compared to said reference bacteriophage, while retaining the same phenotypic characteristic as the reference bacteriophage. Variants typically comprise e.g., silent mutations, conservative mutations, minor deletions, and/or minor replications of genetic material, and retain phenotypic characteristics of the reference bacteriophage. In a preferred embodiment, variants according to the invention retain any observable characteristic or property that is dependent upon the genome of the bacteriophage of the invention, i.e. phenotypic characteristics of said bacteriophage and/or lytic activity against the *P. aeruginosa* strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The terms "ESBL *P. aeruginosa* strain" refers to cephalosporinase and/or extended-spectrum β-lactamases producing *P. aeruginosa* strains, including various forms of antibiotic resistance such as AmpC β-lactamase or Class A carbenicillin hydrolyzing β-lactamases, etc.

The term "specific" or "specificity" in relation to a bacteriophage refers to the type of host that said bacteriophage is able to infect. A bacteriophage "specific" for *P. aeruginosa* more preferably designates a bacteriophage which can infect one or several *P. aeruginosa* strains and which cannot infect non-*P. aeruginosa* bacteria under physiological conditions.

As used herein, the term "polypeptide" refers to polypeptides of any size, including small peptides of e.g., from 5 to 20 amino acids, longer polypeptides, proteins or fragments thereof.

The term "PLE" or "Productive Lytic Effect" designates the ratio between burst size and productive lytic time of a given bacteriophage. Burst size and productive lytic time are parameters defining phage-host interaction and correspond, respectively, to the mean yield of bacteriophage particles produced by infection of one bacterium by one phage, and to the time taken by a free bacteriophage to lyse a bacterial cell.

In the context of the present specification, the term "isolated bacteriophage" should be considered to mean a bacteriophage removed from its natural environment and/or separated from a component of its natural environment. The term designates, particularly, a phage that is e.g., cultivated in vitro, purified, and/or formulated with any suitable diluent or excipient. In relation to a nucleic acid or polypeptide, the term "isolated" designates e.g., a nucleic acid molecule or polypeptide which is separated from at least one component of its natural environment such as, e.g., a protein, lipid, and/or nucleic acid.

The terms "pharmaceutically or veterinary acceptable" as used herein refers to any material (e.g., carrier, excipient or diluent) that is compatible for use in a mammalian subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

The term "treatment" or "therapy" designates a curative or a prophylactic treatment of a disease. A curative treatment is defined as a treatment that results in a cure of a disease, or a treatment that alleviates, reduces, stabilizes, or eliminates the symptoms of a disease or the suffering that it causes, directly or indirectly, or that improves a subject condition or reduces progression of a disease. A prophylactic treatment comprises a treatment resulting in the prevention of a disease, and/or a treatment reducing and/or delaying the incidence of a disease or the risk of its occurrence.

The term "biofilm" as used herein designates a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial biofilm, it is understood a penetration of the biofilm by bacteriophage, an infection of bio film-associated bacteria and/or a lysis thereof and/or a partial or an entire clearing of the biofilm (i.e., by stopping colonization and/or disrupting bio films).

The term "sample", as used herein, means any sample containing cells. Examples of such samples include body fluids such as blood, plasma, saliva, or urine, as well as biopsies, organs, tissues or cell samples. The sample may be treated prior to its use.

As used herein, the term "subject" or "patient" refers to an animal, preferably a mammal, even more preferably a human, including adult and child. The term "subject" also encompasses non-human animals, in particular non-human mammals such as pets (e.g., dogs, cats), horses, cows, goats, pigs, sheep and non-human primates, among others.

The term "efficacy" of treatment or "response" to a bacteriophage therapy as used herein refers to a treatment which results in a decrease in the number of *P. aeruginosa* strains in a subject after bacteriophage treatment when compared to the number of *P. aeruginosa* strains before treatment. A "good responder" subject refers to a subject who shows or will show a clinically significant recovery when treated with a bacteriophage therapy.

The term "Cocktail" of bacteriophages designates a combination of different types of bacteriophages. The bacteriophages in a cocktail are preferably formulates together in a same vessel or packaging, although they may be used as kits of parts wherein some of the bacteriophages are formulated or packaged separately and combined when used or administered.

DESCRIPTION OF EMBODIMENTS

The present invention is related to novel bacteriophage therapies. More particularly, the present invention relates to novel bacteriophages having a high specificity against *Pseudomonas aeruginosa* strains, their manufacture, components thereof, compositions comprising the same and the uses thereof in phage therapy.

Bacteriophages:

In a first aspect, the invention discloses the isolation and characterization of novel bacteriophages that are specific for *P. aeruginosa* strains and present, either alone or in combination(s), remarkable host range spectrum of lytic activity. These bacteriophages have been selected from environmental samples, isolated, sequenced, and characterized. They are, individually and in combination(s), active against *P. aeruginosa* strains. They are remarkably effective against pathogenic *P. aeruginosa* strains, including antibiotic-resistant *P. aeruginosa* strains such as an ESBL *P. aeruginosa* strain. Furthermore, bacteriophages of the invention have a remarkable productive lytic effect ("PLE") comprised between 1 and 7. In addition, the bacteriophages of the invention are specific for *P. aeruginosa* strains, i.e., they do not cause lysis of non-*P. aeruginosa* bacteria. As will be illustrated further, the invention shows that these bacteriophages can be combined and formulated in conditions suitable for use as pharmaceutical or veterinary agents to exhibit targeted and very potent antibacterial effect against a controlled spectrum of *P. aeruginosa* strains.

More specifically, the following bacteriophages have been isolated. Their corresponding nucleic acid sequence is also indicated.

TABLE 1

| SEQ ID | Bacteriophage |
|---|---|
| SEQ ID NO: 1 | BP1384 |
| SEQ ID NO: 2 | BP1777 |
| SEQ ID NO: 3 | BP1792 |
| SEQ ID NO: 4 | BP1797 |
| SEQ ID NO: 5 | BP1800 |
| SEQ ID NO: 6 | BP1902 |
| SEQ ID NO: 7 | BP1940 |

The lytic profile of these bacteriophages has been determined on a broad number of *P. aeruginosa* strains. These bacteriophages have been selected for their potency and combination potential, as disclosed in the following table. In this table, the lytic effect of the bacteriophages on reference and pathogen-resistant strains are presented, confirming their high lytic potential.

TABLE 2

| | Phage | | | | | | |
|---|---|---|---|---|---|---|---|
| Strain | 1384 | 1777 | 1792 | 1797 | 1800 | 1902 | 1940 |
| LMG 24882 | + | + | pm | + | + | + | − |
| LMG 24886 | + | + | − | − | − | + | + |
| LMG 24887 | + | pm | + | + | + | pm | + |
| LMG 24891 | + | + | + | + | + | + | − |
| LMG 24892 | + | + | + | + | + | pm | + |
| LMG 24893 | + | pm | + | + | + | + | + |
| LMG 24896 | + | + | + | + | + | + | pm |
| LMG 24901 | pm | − | + | + | + | − | pm |
| LMG 24903 | − | pm | + | + | + | − | + |
| LMG 24904 | pm | − | + | + | + | + | − |
| LMG 24905 | − | − | pm | + | + | pm | − |
| LMG 24907 | − | − | + | + | + | − | − |
| LMG 24909 | + | + | + | + | + | + | pm |
| LMG 24913 | − | − | + | + | − | + | pm |
| LMG 24914 | − | − | + | + | + | − | + |
| LMG 24916 | − | − | + | + | + | − | + |

pm: partial lysis

As can be seen from table 2, combinations (or cocktails) of these bacteriophages may be produced that are able to kill all of the tested *P. aeruginosa* strains, thereby producing broad spectrum antibacterial compositions. As an illustrative example, a cocktail of all of the 7 bacteriophages can kill all tested bacteria.

Moreover, the specificity of the bacteriophages has been tested on many non-*P. aeruginosa* strains. More particularly, the experimental section demonstrates that the bacteriophages of the invention have no lytic effect on any bacteria selected from *Escherichia coli, Acinetobacter baumanii, Enterobacter aerogenes, Enterobacter asburiae, Enterobacter cloacae, Klebsiella pneumoniae, Proteus mirabilis, Staphylococcus aureus, Stenotrophomonas maltophila* and *Serratia marcescens*. These bacteriophages, alone or in combination(s), thus represent potent agents for treating *P. aeruginosa* infections.

A particular object of the invention thus resides in a bacteriophage having lytic activity to a *P. aeruginosa* strain and having a genome comprising a nucleotide sequence selected from anyone of SEQ ID NOs: 2 to 7 or a sequence having at least 95% identity thereto, preferably at least 96%, 97%, 98% or 99% identity thereto.

The bacteriophages of the invention may be cultured, expanded, isolated, purified, and used in e.g., phage therapy of *P. aeruginosa*-mediated disorders, as will be disclosed in more details below. Furthermore, variants of these bacteriophages retaining a phenotypic (e.g., specificity and lytic activity) of the bacteriophages can be produced and/or isolated by techniques known per se in the art.

The bacteriophages of the invention can be prepared by standard culture, isolation and purification methods. For example, *P. aeruginosa* producing bacteria are cultured, infected by a sample of a bacteriophage, and then treated to remove bacterial cells and debris. The enriched bacteriophage solution can be plated in a medium, for example agar medium, with embedded susceptible host strains of *P. aeruginosa* to obtain plaques. Then, single plaque can be picked out for subsequent bacteriophage purification and amplification. One or more cycles of selective amplification of bacteriophages of the invention may be performed, for example by mixing bacteriophages with the competent *P. aeruginosa*, followed by addition of a growth medium and incubation at selected test growing conditions. Following centrifugation, the cleared amplified supernatant is filtered through filter and subjected to another cycle of selective amplification or tested for presence of lytic activity.

The titer of phage in a suspension and the visualization of plaque morphology of bacteriophages of the invention may then be assessed by known methods, for example by plaque counting. Additionally, processing bacteriophages of the invention in various forms (liquid, lyophilized, etc.) for short-, long-, freeze- or any other kind of storage can be carried out by any suitable method as it is well-known in the art (see e.g., Clark, 1962).

The activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *P. aeruginosa* strains after a period of incubation in soft agar medium, resulting in zones of clearing on the plate known as plaques.

Nucleic Acids and Polypeptides

The invention relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from anyone of SEQ ID NOs: 2-7, or a sequence having at least 95%, 96%, 97%, 98%, 99% or more sequence identity to anyone of SEQ ID NOs: 2-7.

The nucleic acid of the invention can be in free form, or cloned in a vector, such as a plasmid, viral vector, expression cassette, cosmid, etc.

In a further aspect, the invention also relates to an isolated polypeptide encoded by a nucleic acid sequence as defined above, preferably a nucleic acid sequence selected from SEQ ID NO: 2, SEQ ID NO: 3, SEQ ID NO: 4, SEQ ID NO: 5, SEQ ID NO: 6, or SEQ ID NO: 7. The polypeptide(s) may be produced by techniques known per se in the art such as synthesis, recombinant technology, or combinations thereof. The polypeptides may be isolated or purified, and used as antibacterial agents or as reagents for in vitro analyses.

Compositions of the Invention

One aspect of the invention relates to compositions comprising at least one bacteriophage as described above, more preferably at least 2 or more and, optionally, a pharmaceutically or veterinary acceptable excipient. As described, the bacteriophages of the invention have very potent lytic activity against *P. aeruginosa* strains. Combinations of these bacteriophages may be produced to expand the host spectrum and produce highly effective antibacterial compositions.

More particularly, the invention relates to an antibacterial composition comprising at least two bacteriophages having lytic activity against a *Pseudomonas aeruginosa* (*P. aeruginosa*) strain, said at least two bacteriophages being selected from the bacteriophages having a genome comprising a nucleotide sequence of anyone of SEQ ID NOs: 1 to 7 or a sequence having at least 90% identity thereto.

In a preferred embodiment, the compositions of the invention comprise at least three, even more preferably at least four distinct bacteriophages selected from the bacteriophages having a genome comprising a nucleotide sequence of anyone of SEQ ID NOs: 1 to 7 or a sequence having at least 90% identity thereto.

Particular compositions of the invention comprise at least a bacteriophage having a genome comprising a nucleotide sequence of SEQ ID NO: 3 or 4, or a sequence having at least 90% identity thereto.

Specific examples of compositions of the invention comprise:

- a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 5 or a sequence having at least 90% identity thereto;
- a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 3 or a sequence having at least 90% identity thereto, and a bacteriophage having a genome comprising a nucleotide sequence of SEQ ID NO: 5 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;
- a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto, and a bacteriophage having a genome comprising a nucleotide sequence of SEQ ID NO: 5 or a sequence having at least 90% identity thereto.

In a preferred embodiment, the compositions of the invention comprise at least:

- a bacteriophage having a genome comprising a nucleotide sequence of SEQ ID NO: 1 or a sequence having at least 90% identity thereto;
- a bacteriophage having a genome comprising a nucleotide sequence of SEQ ID NO: 2 or a sequence having at least 90% identity thereto;
- a bacteriophage having a genome comprising a nucleotide sequence of SEQ ID NO: 3 or a sequence having at least 90% identity thereto;
- a bacteriophage having a genome comprising a nucleotide sequence of SEQ ID NO: 4 or a sequence having at least 90% identity thereto;
- a bacteriophage having a genome comprising a nucleotide sequence of SEQ ID NO: 5 or a sequence having at least 90% identity thereto;
- a bacteriophage having a genome comprising a nucleotide sequence of SEQ ID NO: 6 or a sequence having at least 90% identity thereto; and
- a bacteriophage having a genome comprising a nucleotide sequence of SEQ ID NO: 7 or a sequence having at least 90% identity thereto.

The compositions of the invention may further comprise additional antibacterial agents, particularly other bacteriophages having distinct host specificity.

Most preferred compositions of the invention are lytic against more that 85% of all bacterial strains of the LMG collection obtained from the BCCM/LMG Bacteria Collection. This collection contains a vast number of strains with a high genetic diversity among the bacterial species.

The compositions of the invention may comprise any effective amount of the selected bacteriophage(s). Preferably, they comprise between $10^{e4}$ and $10^{e12}$ PFU of each of said bacteriophages, preferably between $10^{e5}$ and $10^{e10}$. PFU. The relative amounts of each type of bacteriophage in a composition of the invention may be adjusted by a skilled artisan. Typically, When the antibacterial composition comprises several (n) distinct bacteriophages as defined above, the total relative amount % A of each bacteriophage in the composition is more preferably % $A=(100/n_i)\times V$, wherein $n_i$ represents the number of distinct types of bacteriophages and V is a variability factor comprised between 0.2 and 5. Most preferably, V is comprised between 0.3 and 3, even more preferably between 0.5 and 2, generally between 0.8 and 1.5. In a preferred typical embodiment, each type of bacteriophage is present in a composition of the invention in approximately equal relative amounts.

The antibacterial compositions of the invention may be in various forms, such as liquid, semi-liquid, solid or lyophilized formulations. The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations. Formulations for topical administration may include, band aids, dressings, patches, films, ointments, lotions, creams, gels, drops, suppositories, sprays, tampons, sanitary towels, liquids and powders. Formulations for decontamination or for medical use may also include aerosols or sprays.

The compositions of the invention may be used in the medical field, including the human or veterinary medical areas, for e.g. the treatment of an infection in a mammal or for improving a subject's condition. The compositions may be used to kill *P. aeruginosa* bacteria in an organism, for treating an infection. The composition may also be used for improving the condition of a mammal by modifying the microbial flora in said mammal. In particular, the compositions of the invention can specifically remove *P. aeruginosa* strains on the skin or mucous membranes of a mammal, thus modifying its microbial flora and restoring a proper balance.

In a particular embodiment, the invention also relates to a method for treating an infection in a mammal comprising the administration to said mammal of a composition or bacteriophage or nucleic acid or polypeptide as defined above.

The invention also relates to the use of a composition, bacteriophage, nucleic acid or polypeptide as described for the manufacture of a medicament for treating an infection in a mammal, or for restoring microbial flora in said mammal.

The compositions of the invention may be used to treat various *P. aeruginosa*-mediated infections, particularly of the respiratory system. The number of patients with pneumonia reached 2 to 3 million in USA and 3 to 4 million in Europe, in 2013. *Pseudomonas aeruginosa* is one of the major microbiological agents responsible for the pathology, especially in the young children and elderly populations, as well as, in immunocompromised, cystic fibrosis, high burn and poly-traumatized patients. Although epidemiological sources fluctuate and albeit a recent increase of gram-negative infections (including *P. aeruginosa*), estimations for 2014 indicate that at least 15% of pneumonia are caused by *P. aeruginosa* (e.g., 15.9% according to the *ECDC Annual Surveillance Report*—2013). From a conservative stand point, about 20% of these germs are resistant to several or all the antibiotics from our therapeutic arsenal (remarkably, the highest number or resistant cases is being observed in intensive care unit: See Worldwide Website: infectio-lille.com/diaporamas/DUAC/pyo-DUAC09-Cattoen.pdf). As a consequence, estimated figures indicate that at least 90 000 pneumonia cases in USA an and 120 000 in Europe are induced by antibiotic multi-resistant *P. aeruginosa* bacterial strains. The invention is thus particularly suited for treating pneumonia associated with, or caused by, *P. aeruginosa* infection. An object of the invention thus resides in a method of treating pneumonia in a subject in need thereof, comprising administering a composition of the invention to said subject. The method is particularly suited for treating pneumonia induced by antibiotic-resistant *P. aeruginosa* bacteria. The subject may be any human subject, such as children, adults or elderly people.

The compositions of the invention may be administered by any convenient route, including intravenous, oral, transdermal, subcutaneous, mucosal, intramuscular, intrapulmonary, intranasal, parenteral, rectal, vaginal and topical. In a preferred embodiment, the bacteriophages or compositions are administered by intrapulmonary or intranasal instillation. The compositions may be administered directly or indirectly, e.g., via a support. In this regard, the compositions may, for example, be applied or sprayed to the afflicted area. Compositions of the invention can also be administered by oral or parenteral routes. The dosage suitable for applying, spraying, or administrating the compositions of the present invention can be adjusted by the skilled person depending on a variety of factors including formulation, mode of administration, age, weight, sex, condition, diet of the mammal being treated at the time of administration, route of administration, and reaction sensitivity. A physician having ordinary skills in the art can readily determine and prescribe the effective amount of the composition required.

The dosing can also be adjusted by the skilled person so that a lytic activity against antibiotic-resistant *P. aeruginosa* strains is obtained. An efficient dose to obtain a lytic activity in vivo typically includes a concentration of at least $10e^4$ PFU/ml, preferably from about $10^{e2}$ to $10^{e12}$ PFU/ml, depending on the administration route.

As shown in the experimental section, the bacteriophages and compositions of the invention are able to selectively kill

*P. aeruginosa* bacteria in vitro or in vivo. The compositions can destroy mixtures of different *P. aeruginosa* bacteria, even in vivo, even at low dosage. Furthermore, the compositions of the invention are effective is killing bacteria embedded in biofilms, which is particularly important for pathogenic bacteria. Also, the compositions and bacteriophages of the invention are strictly unable to affect mammalian cells, and are therefore specific and devoid of side effects in vivo.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, etc.

Diagnostic/Predictive Tests of the Invention:

The invention also concerns a method for predicting or determining the efficacy of a bacteriophage therapy in a subject, wherein the method comprises a step of determining a lytic activity of one or more bacteriophages of the invention to a *P. aeruginosa* strain from a sample from said subject, such a lytic activity being indicative of an efficient treatment. In a preferred aspect, the method further optionally comprises a step of treating said subject by one or more bacteriophages having a lytic activity to a *P. aeruginosa* strain from a sample of said subject.

In another aspect, the invention provides a method for selecting a subject or determining whether a subject is susceptible to benefit from a bacteriophage therapy, wherein the method comprises the step of determining a lytic activity of one or more bacteriophages of the invention to a *P. aeruginosa* strain from a sample of said subject, a lytic activity of one or more bacteriophages of the invention to at least one *P. aeruginosa* strain indicating a responder subject.

Another object of the invention relates to a method for predicting the response of a subject to a bacteriophage therapy, wherein the method comprises the step of determining a lytic activity of one or more bacteriophage of the invention to a *P. aeruginosa* strain from a sample of said subject, a lytic activity of one or more bacteriophage of the invention to at least one *P. aeruginosa* strain being indicative of a good response to said therapy.

Further aspects and advantages of the invention will be disclosed in the following experimental section, which is illustrative only.

EXAMPLES

Materials and Methods

Host Range Determination.

The host ranges of bacteriophages were determined among a collection of 20 *P. aeruginosa* from the LMG collection. $10^9$ bacterial cells were mixed with melted agar and this mixture was poured on solid agar to make double layer agar plates. After solidification, isolated bacteriophage stock solutions were spotted on each plate with different bacterium strain. After allowing 20 min for the spots to be absorbed, the plates were inverted and incubated for 24 h at 37° C. before the degree of lysis was recorded (Postic, 1961; Yang, 2010).

Sequencing, Analysis and Annotation of Phage Genomes.

To isolate phage DNA, phages were propagated as described above. Phage DNA was isolated by extraction with phenol:chloroform:isoamyl alcohol (25:24:1, VAT), ethanol precipitation and resolution in water. Whole genome sequencing was done and the BLAST algorithm was used to determine the similarity to described genes in the National Center for Biotechnology Information [NCBI] database. The genomes were scanned for potential open reading frames (ORFs).

Example 1: Bacteriophage Isolation

Bacteriophages were isolated from environmental samples. Multi Drug Resistant (MDR) *P. aeruginosa* bacteria were used for isolating and enriching each virulent bacteriophage from environmental water. More particularly, environmental samples and overnight culture of bacteria in Luria Bertani (LB) were mixed and incubated at 37° C. for 24 h with shaking to enrich specific bacteriophages. At the end of incubation, drops of chloroform were added to the culture. The culture was spun down at 11,000 g for 5 minutes to remove bacterial cells and debris. The supernatant was subjected to 0.2 μm filter to remove the residual bacterial cells. The enriched phage solution was plated on LB agar medium with *P. aeruginosa* embedded. Plaques formed on the plates after 24 h incubation at 37° C. Single plaque was picked out for subsequent phage purification and amplification. The phage was then stored at 4° C. in a suspension in LB broth or physiological saline.

The titer of phage in a suspension was estimated by plaque counting (Postic, 1961). Ten-fold dilutions of a suspension were delivered on a dried lawn of the propagating strain. The plates were read after overnight incubation. The plaque-counting method also permitted visualization of plaque morphology.

7 highly active bacteriophages were selected. Their sequences were determined and are provided in the present application, in accordance with the following table:

TABLE 1

| SEQ ID | Bacteriophage |
|---|---|
| SEQ ID NO: 1 | BP1384 |
| SEQ ID NO: 2 | BP1777 |
| SEQ ID NO: 3 | BP1792 |
| SEQ ID NO: 4 | BP1797 |
| SEQ ID NO: 5 | BP1800 |
| SEQ ID NO: 6 | BP1902 |
| SEQ ID NO: 7 | BP1940 |

The activity of the bacteriophages, alone or in combination, was further tested in different models and conditions as described in the following examples.

Example 2: Bacteriophage Host Characteristics and Kinetics

One-step growth experiments were carried out according to the previous descriptions to determine first the productive lytic time, adsorption rate, and then the phage burst size. To determine the adsorption rate samples were taken at different time intervals to analyze the free phage particles in the solutions. For productive time and phage burst size determination, *P. aeruginosa* bacteria were mixed with phages solutions and phages were allowed to adsorb for 15 min. The mixture was subjected to centrifugation immediately at 5000 rpm for 10 min to remove free phage particles. The pellet was resuspended in 5 fresh LB medium and the culture was continuously incubated at 37° C. Samples were taken at 5 min intervals and phage titer was determined. These results permitted to calculate the number of phages produced per bacteria (burst size), the productive time and the productive lytic effect (PLE), as shown in table 3 below.

TABLE 3

| Phage | Productive lytic time (min) | Adsorption rate (ml−1min−1) | BURST SIZE (PFU per bacterium) | PLE (PFU per bacterium per min) |
|---|---|---|---|---|
| 1384 | 80 | 8.64E−09 | 499 | 6.24 |
| 1777 | 13 | 9.27E−08 | 55 | 4.4 |
| 1792 | 16 | 1.46E−08 | 52 | 3.3 |
| 1797 | 28 | 1.81E−08 | 31 | 1.1 |
| 1800 | 13 | 1.61E−08 | 46 | 3.5 |
| 1902 | 18 | 2.75E−08 | 54 | 2.9 |
| 1940 | 10 | 6.08E−08 | 43 | 4.3 |

These results show that all phages have potent viral production capacity and absorption rates. Most phages have a PLE below 7, which demonstrates a remarkable profile. Phage 1777 is particularly effective in this regard. In addition, the different PLE and adsorption times permit to create cocktails with selected variability.

Example 3: Composition of Bacteriophages

The following cocktail compositions are constituted, each comprising between $10^9$ and $10^{11}$ pfu of each bacteriophage:

TABLE 4

| Cocktail | Phages |
|---|---|
| I | P1797 + P1902 |
| II | P1797 + P1800 + P1384 |
| III | P1777 + P1797 + P1940 + P1384 |
| IV | P1777 + P1792 + P1797 + P1800 + P1384 |
| V | P1777 + P1792 + P1797 + P1800 + P1902 + P1384 |
| VI | P1777 + P1792 + P1797 + P1800 + P1902 + P1940 + P1384 |
| VII | P1792 + P1384 |
| VIII | P1797 + P1384 |

Example 4: Antibacterial Activity

Various strains of bacteria are incubated with a bacteriophage cocktail of the invention at $2.10^9$ bacteriophages/ml for 24 h at 37° C. Cocktails are tested on the 16 distinct *P. aeruginosa* bacteria listed in table 2. The % of bacteria species sensitive to the cocktails are listed in table 5 below:

TABLE 5

| Cocktail | % Killed *P. aeruginosa* species |
|---|---|
| I | 100% |
| II | 100% |
| III | 100% |
| IV | 100% |
| V | 100% |
| VI | 100% |
| VII | 100% |
| VIII | 100% |

Bacteria were enumerated and used to the calculation of resistance rate (number of bacteria after incubation/number of bacteria plated) with cocktail VI. Resistance rates were obtained, as shown in the following table 6:

TABLE 6

| Bacteria | Rate (bacteria/ml) |
|---|---|
| LMG 24891 | 4.90E−06 |
| LMG 24945 | 2.40E−07 |
| LMG 24970 | 2.00E−08 |
| LMG 25082 | 1.30E−07 |
| LMG 25131 | <1.00E−08 |
| LMG 25194 | 7.75E−06 |

All tested bacteria are sensitive to compositions of the invention.

Example 5: Cocktail Specificity

The cocktail specificity was confirmed by testing on ten different gram-negative and gram-positive bacteria species, including *Escherichia coli* (several strains), *Acinetobacter baumanii, Enterobacter aerogenes C, Enterobacter asburiae, Enterobacter cloacae, Klebsiella pneumoniae, Proteus mirabilis, Staphylococcus aureus, Stenotrophomonas maltophila, Serratia marcescens.*

Table 7 shows the lack of lytic activity of the cocktail containing the 7 bacteriophages.

TABLE 7

| Bacterium Species/stains | Cocktail |
|---|---|
| *Acinetobacter baumanii* | — |
| *Escherichia coli* K12 | — |
| *Escherichia coli* S176 | — |
| *Escherichia coli* ECOR5 | — |
| *Escherichia coli* ECOR54 | — |
| *Escherichia coli* ECOR60 | — |
| *Escherichia coli* SH146 | — |
| *Enterobacter aerogens* | — |
| *Enterobacter amnigeus* | — |
| *Enterobacter asburiae* | — |
| *Enterobacter cloacae* | — |
| *Klebsiella pneumoniae* | — |
| *Proteus mirabilis* | — |
| *Serratia marcescens* | — |
| *Strenophomonas maltophila* | — |
| *Staphylococcus aureus* | — |

The above table clearly shows that no lytic activity on bacteria other than *P. aeruginosa* strains occurred. The bacteriophages and cocktail of the invention are therefore highly specific to *P. aeruginosa* strains.

Example 6: Efficiency of each Bacteriophage on *P. aeruginosa* PAO1 Strain

PAO1 strain was selected because it is a commonly used laboratory strain. Bacteria were grown individually and each bacteriophage was added individually (FIG. 1-6) or in cocktail (FIG. 7) at a MOI of 1 to $10^{e-4}$, i.e. at a dilution ratio (bacteria/phage) of 1 to 10 000.

FIG. 1 shows that bacteriophage 1384 is efficient at MOIs of 1, 0.1 or 0.01.

Figure 2:
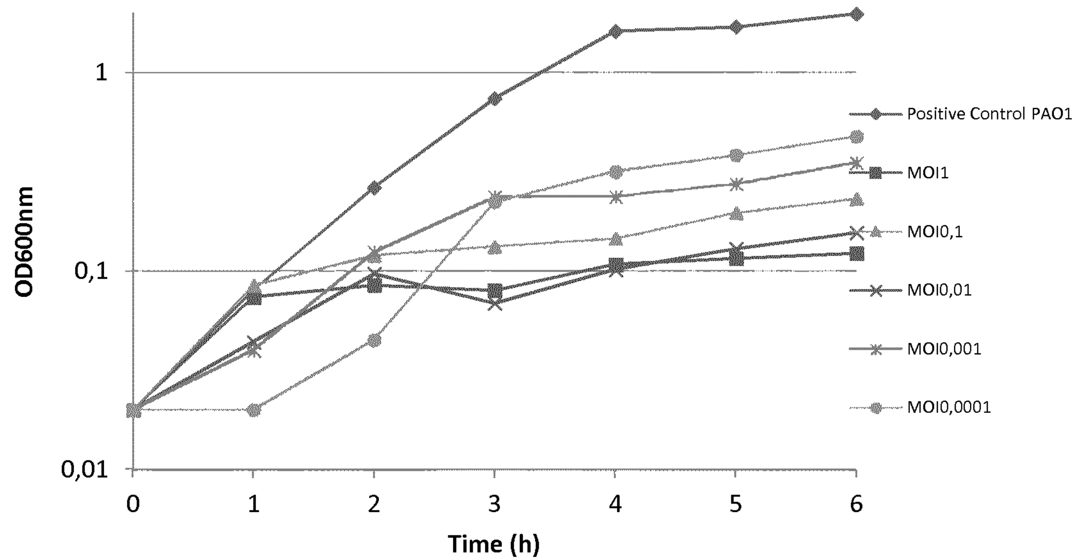
FIG. 2: Efficacy of bacteriophage 1777 on PAO1 strain.

FIG. 2 shows that bacteriophage 1777 is efficient at a MOI of 1.

Figure 3:
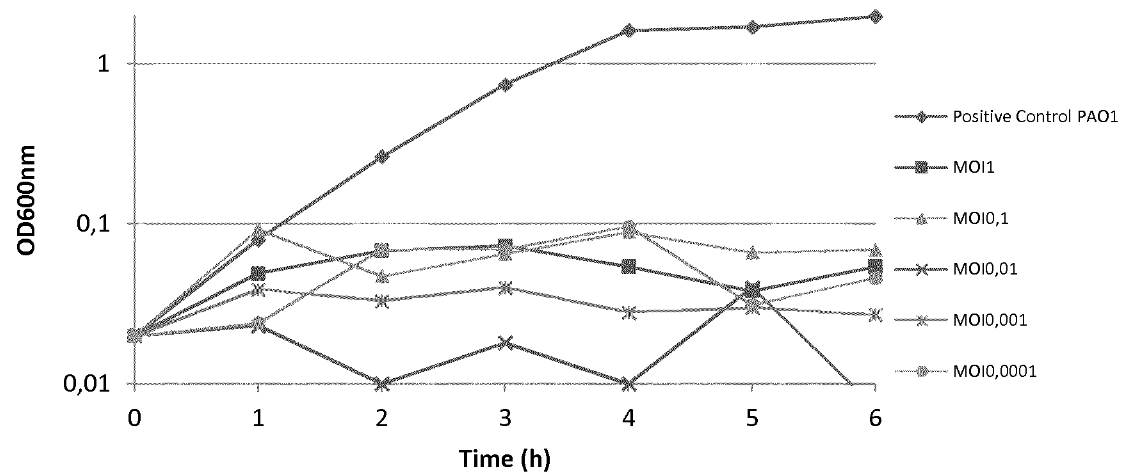
FIG. 3: Efficacy of bacteriophage 1792 on PAO1 strain.

FIG. 3 shows that Bacteriophage 1792 is active against PAO1 strain during at least 6 h even at a MOI $10^{e-4}$.

Figure 4:
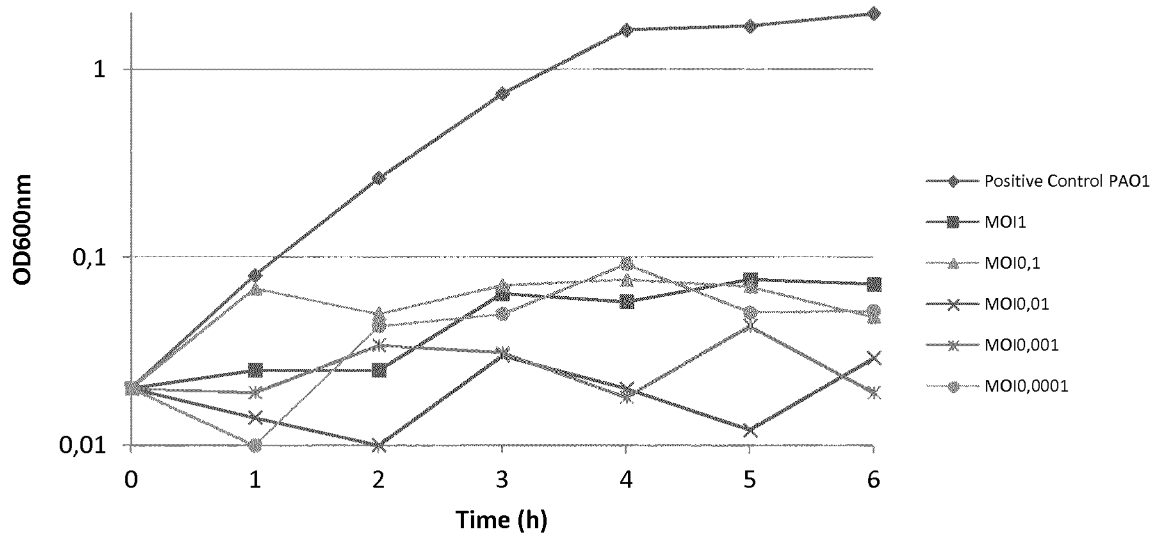
FIG. 4: Efficacy of bacteriophage 1797 on PAO1 strain.

FIG. 4 shows that bacteriophage 1797 is active against PAO1 strain during at least 6 h even at a MOI $10^{e-4}$.

Figure 5:
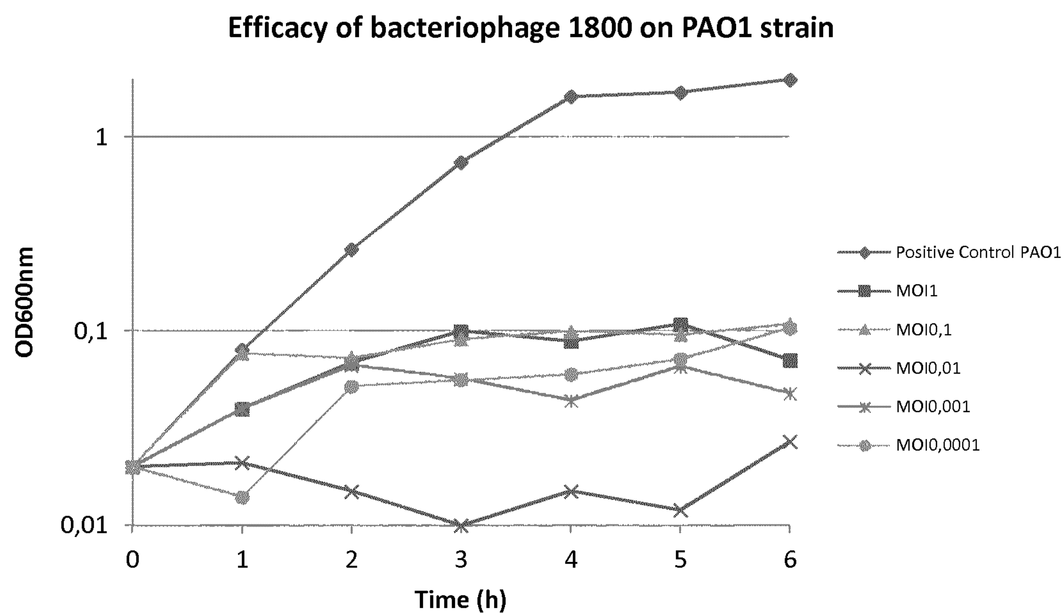
FIG. 5: Efficacy of bacteriophage 1800 on PAO1 strain.

FIG. 5 shows that bacteriophage 1800 is active against PAO1 strain during at least 6 h even at a MOI $10^{e-4}$.

Figure 6:
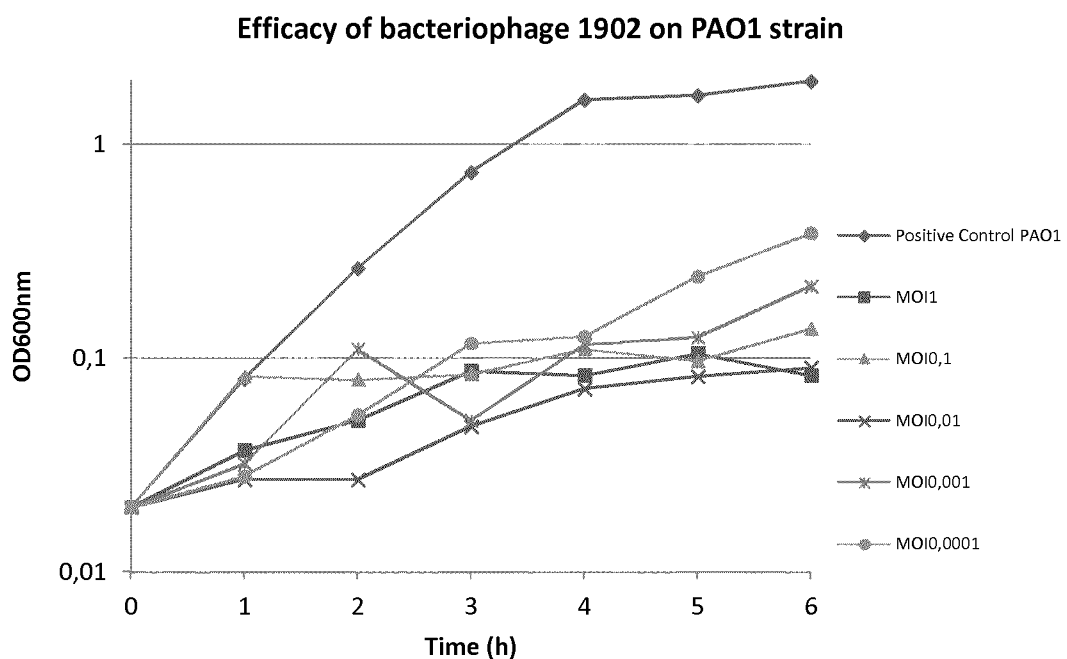
FIG. 6: Efficacy of bacteriophage 1902 on PAO1 strain.

FIG. 6 shows that, depending on the MOI, bacteriophage 1800 is active against PAO1 strain during at least 6 h.

Figure 7:
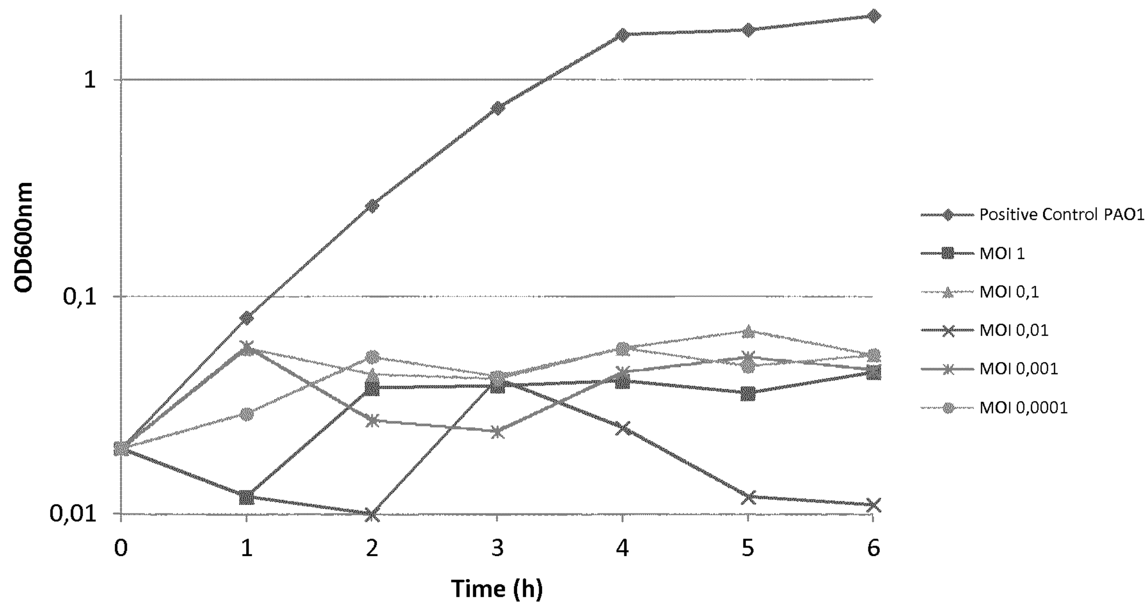
FIG. 7: Efficacy of bacteriophage cocktail on PAO1 strain.

FIG. 7 shows the efficacy of bacteriophage cocktail VI on PAO1 strain. The cocktail is highly active against PAO1 strain during at least 6 h even at a MOI $10^{e-4}$ and is more efficient than the phages individually.

Example 7: Efficiency of a Bacteriophage Cocktail of the Invention on Cystic Fibrosis Antibiotic Resistant *P. aeruginosa* Strains Several strains were chosen to represent *P. aeruginosa* that causes respiratory problems. They were grown individually and the bacteriophage cocktail VI was added at a MOI of 1 to $10^{e-4}$, i.e. at a dilution ratio (bacteria/phage) of 1 to 10 000.

TABLE 8 information about the bacterial strains

| Bacterium | Country | Year | Source | Resistance to antibiotics |
|---|---|---|---|---|
| CF1 | Canada | 2010 | Hospital | Aztreonam 16<br>Tobramycin 8 |
| CF2 | United State | 2010 | Analysis laboratory | Aztreonam 0.5<br>Tobramycin 8 |
| CF3 | France | 2014 | Patient expectoration | Multiresistant |

Figure 8:
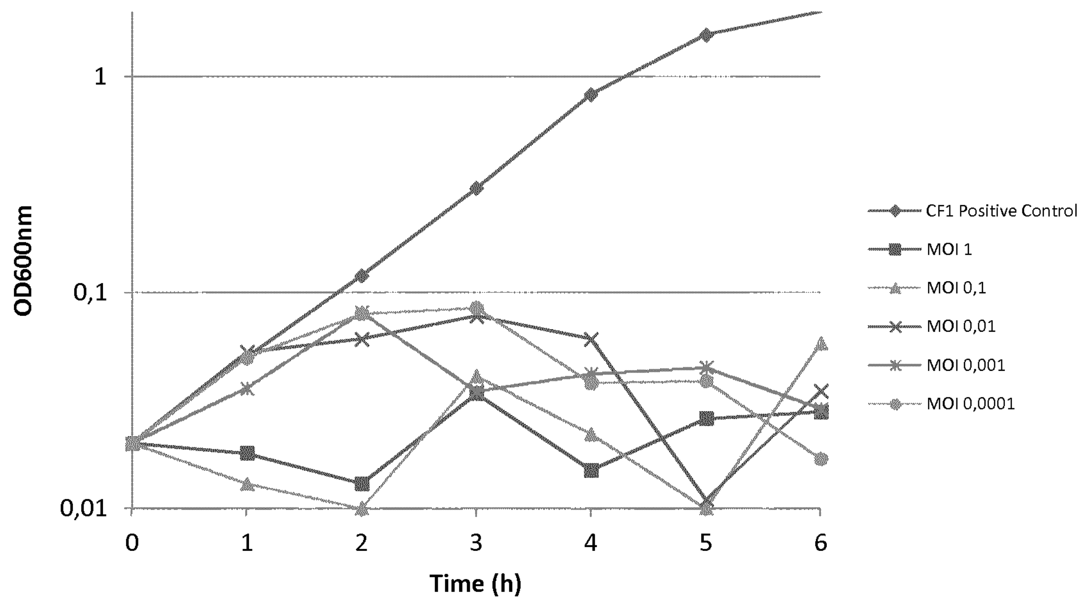
FIG. 8: Efficacy of bacteriophage cocktail on CF1 strain.
Figure 9:
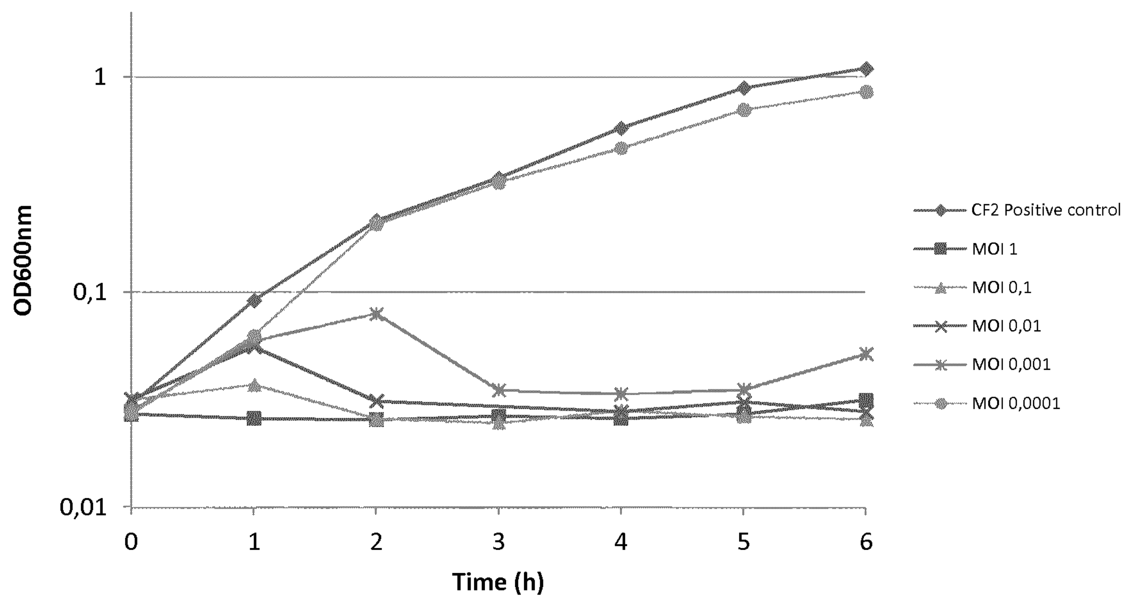
FIG. 9: Efficacy of bacteriophage cocktail on CF2 strain.
Figure 10:
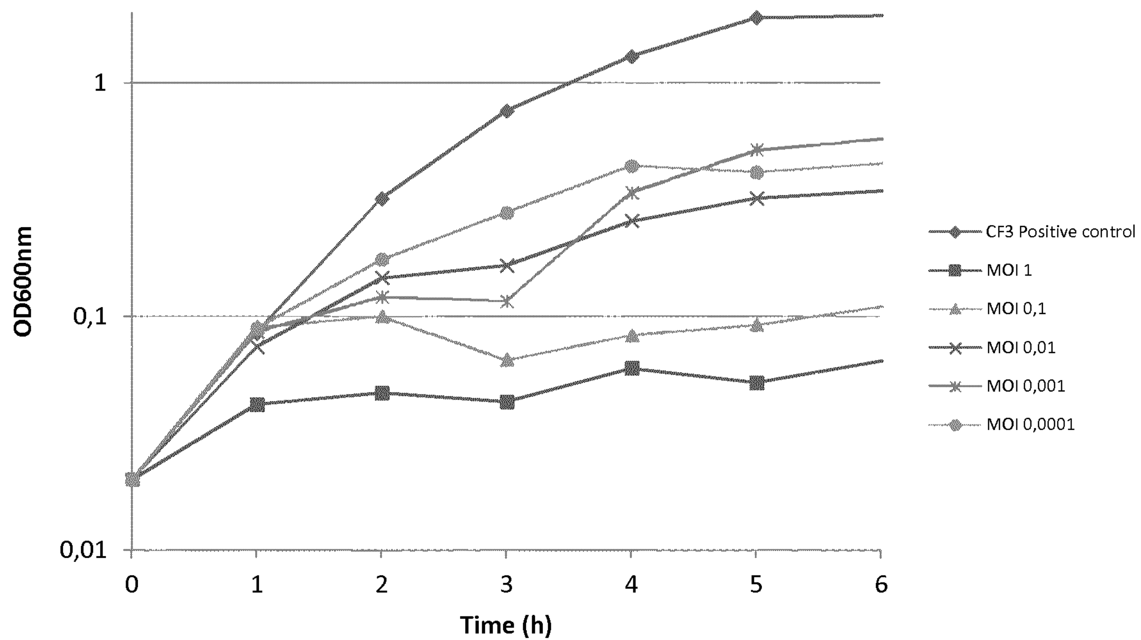
FIG. 10: Efficacy of bacteriophage cocktail on CF3 strain.

The results are presented in FIGS. 8, 9 and 10.

FIG. 8 shows that the cocktail is fully efficient on CF1 strain even after 6 h and with a very low MOI.

FIG. 9 shows that the cocktail is highly efficient on CF2 strain even after 6 h.

FIG. 10 shows that the cocktail is efficient on CF3 strain.

The results show that bacteriophage cocktail VI was very efficient on three nosocomial bacterial *P. aeruginosa* strains isolated from hospitalized patients, even after being diluted up to a ten thousand fold. These results thus demonstrate that compositions of the invention can be used to treat *P. aeruginosa* infection in vivo, and are active against multi-resistant bacterial strains.

REFERENCES

Clark W A, 1962, Appl Microbiol. Comparison of several methods for preserving bacteriophages. 1962 September; 10:466-71.

Drulis-Kawa Z, Majkowska-Skrobek G, Maciejewska B, Delattre A S, Lavigne R, 2012, Learning from bacteriophages—advantages and limitations of phage and phage-encoded protein applications.; 13(8):699-722.

Fordos J. 1859. Receuil des travaux de la Societé d'Emulation pour les Sciences Pharmaceutiques, vol 3 Societé d'Emulation pour les Sciences Pharmaceutiques, Paris, France.

Freeman L. 1916. Chronic general infection with the Bacillus pyocyaneus. Ann. Surg. 64:195-202.

Gang R K, Bang R L, Sanyal S C, Mokaddas E, Lari A R. 1999. *Pseudomonas aeruginosa* septicaemia in burns. Burns 25:611-616.

Jones A M, et al. 2010. Clinical outcome for cystic fibrosis patients infected with transmissible *Pseudomonas aeruginosa*: an 8-year prospective study. Chest 137:1405-1409.

Kang C I, et al. 2005. Bloodstream infections caused by antibiotic-resistant gram-negative bacilli: risk factors for mortality and impact of inappropriate initial antimicrobial therapy on outcome. Antimicrob. Agents Chemother. 49:760-766.

Micek S T, et al. 2005. *Pseudomonas aeruginosa* bloodstream infection: importance of appropriate initial antimicrobial treatment. Antimicrob. Agents Chemother. 49:1306-1311.

Strateva T. and Yordanov D. 2009. *Pseudomonas aeruginosa*—a phenomenon of bacterial resistance. Journal of Medical Microbiology 58, 1133-1148.

Weinbauer M G. Ecology of prokaryotic viruses. FEMS Microbiol Rev 2004; 28:127-81.

Williams E P, Cameron K. 1894. Infection by the Bacillus pyocyaneus a cause of infantile mortality. Public Health Pap. Rep. 20:355-360.

The invention claimed is:

1. An antibacterial composition comprising at least two bacteriophages having lytic activity against a *Pseudomonas aeruginosa* (*P. aeruginosa*) strain and a pharmaceutically acceptable excipient or carrier, said at least two bacteriophages being selected from the bacteriophages having a genome comprising a nucleotide sequence of any one of SEQ ID NOs: 1 to 7 or a sequence having at least 99% identity thereto; and said pharmaceutically acceptable excipient or carrier comprising a preservative in an amount effective to preserve the activity of the bacteriophages.

2. The composition of claim 1, comprising at least three distinct bacteriophages selected from the bacteriophages having a genome comprising a nucleotide sequence of any one of SEQ ID NOs: 1 to 7 or a sequence having at least 99% identity thereto.

3. The composition of claim 1, comprising at least a bacteriophage having a genome comprising a nucleotide sequence of SEQ ID NO: 3 or 4, or a sequence having at least 99% identity thereto.

4. The composition of claim 1, comprising:

a bacteriophage having a genome comprising a nucleotide sequence of SEQ ID NO: 4 or a sequence having at least 99% identity thereto; and a bacteriophage having a genome comprising a nucleotide sequence of SEQ ID NO: 6 or a sequence having at least 99% identity thereto.

5. The composition of claim 1, comprising any one of the cocktails of bacteriophages of Table 4.

6. The composition of claim 1, comprising:

a bacteriophage having a genome comprising a nucleotide sequence of SEQ ID NO: 1 or a sequence having at least 99% identity thereto;

a bacteriophage having a genome comprising a nucleotide sequence of SEQ ID NO: 2 or a sequence having at least 99% identity thereto;

a bacteriophage having a genome comprising a nucleotide sequence of SEQ ID NO: 3 or a sequence having at least 99% identity thereto;

a bacteriophage having a genome comprising a nucleotide sequence of SEQ ID NO: 4 or a sequence having at least 99% identity thereto;

a bacteriophage having a genome comprising a nucleotide sequence of SEQ ID NO: 5 or a sequence having at least 99% identity thereto;

a bacteriophage having a genome comprising a nucleotide sequence of SEQ ID NO: 6 or a sequence having at least 99% identity thereto; and a bacteriophage having a genome comprising a nucleotide sequence of SEQ ID NO: 7 or a sequence having at least 99% identity thereto.

7. The composition of claim 1, which is lytic against antibiotic-resistant *P. aeruginosa* strains.

8. The composition of claim 1, which is lytic against more than 90% of all bacterial strains of the LMG collection.

9. The composition of claim 1, in the form of a liquid, semi-liquid, solid or lyophilized formulation.

10. The composition of claim 9, which comprises between $10^{e4}$ and $10^{e12}$ PFU of each bacteriophage.

11. A method of treatment of an infection in a mammal in need thereof comprising contacting the mammal infected with a *Pseudomonas aeruginosa* (*P. aeruginosa*) strain with an antibacterial composition in an amount effective to treat said *P. aeruginosa* infection, wherein said composition comprises at least two bacteriophages having lytic activity against said *P. aeruginosa* strain, said at least two bacteriophages being selected from the bacteriophages having a genome comprising a nucleotide sequence of any one of SEQ ID NOs: 1 to 7 or a sequence having at least 99% identity thereto.

12. The method of claim 11, wherein the infection is an infection of the respiratory tract.

13. A method for improving the condition of a mammal by modifying the microbial flora in said mammal comprising contacting microbial flora of the mammal with an effective amount of an antibacterial composition, wherein said composition comprises at least two bacteriophages having lytic activity against a *Pseudomonas aeruginosa* (*P. aeruginosa*) strain, said at least two bacteriophages being selected from the bacteriophages having a genome comprising a nucleotide sequence of any one of SEQ ID NOs: 1 to 7 or a sequence having at least 99% identity thereto and said microbial flora comprises said *P. aeruginosa* strain.

14. A method for decontaminating a material, comprising exposing the material to an amount of an antibacterial composition effective to decontaminate said material, wherein said composition comprises at least two bacteriophages having lytic activity against a *Pseudomonas aeruginosa* (*P. aeruginosa*) strain, said at least two bacteriophages being selected from the bacteriophages having a genome comprising a nucleotide sequence of any one of SEQ ID NOs: 1 to 7 or a sequence having at least 99% identity thereto.

15. A method for preparing a composition comprising separately producing said at least two bacteriophages selected from the bacteriophages having a genome comprising a nucleotide sequence of any one of SEQ ID NOs: 1 to 7 or a sequence having at least 99% identity thereto, and combining said bacteriophages with a suitable carrier or excipient.

16. A method for treating an infection in a mammal, comprising exposing the mammal having a *Pseudomonas aeruginosa* infection to an effective amount of:

a) a bacteriophage having lytic activity to a *Pseudomonas aeruginosa* (*P. aeruginosa*) strain and having a genome comprising a nucleotide sequence selected from any one of SEQ ID NOs: 2 to 7 or a sequence having at least 99% identity thereto; or b) isolated nucleic acid comprising a nucleotide sequence selected from any one of SEQ ID NOs: 2 to 7 or a sequence having at least 99% identity thereto; or c) isolated polypeptide encoded by a bacteriophage having lytic activity to a *Pseudomonas aeruginosa* (*P. aeruginosa*) strain and having a genome comprising a nucleotide sequence selected from any one of SEQ ID NOs: 2 to 7 or a sequence having at least 99% identity thereto or a polypeptide encoded by an isolated nucleic acid comprising a nucleotide sequence selected from any one of SEQ ID NOs: 2 to 7 or a sequence having at least 99% identity thereto.

17. The composition of claim 1, wherein the pharmaceutically acceptable excipient or carrier comprises buffered physiological saline.

* * * * *

UNITED STATES PATENT AND TRADEMARK OFFICE

CERTIFICATE OF CORRECTION

PATENT NO. : 10,898,530 B2
APPLICATION NO. : 15/524271
DATED : January 26, 2021
INVENTOR(S) : Flavie Pouillot and Hélène Blois It is certified that error appears in the above-identified patent and that said Letters Patent is hereby corrected as shown below:

In the Specification

Column 2,
Line 52, "bio films" should read --biofilms--.
Line 54, "bio films" should read --biofilms--.
Line 56, "bio films." should read --biofilms.--.
Line 61, "bio films" should read --biofilms--.
Line 67, "bio films" should read --biofilms--.

Column 3,
Line 63, "bio film" should read --biofilm--.

Column 6,
Line 31, "bio film-associated" should read --biofilm-associated--.
Line 34, "bio films)." should read --biofilms).--.

Column 12,
Line 30, "USA an and 120 000" should read --USA and 120 000--.
Line 63, "$10e^{4}$" should read --$10^{e4}$--.

Column 14,
Line 4, "VAT" should read --V/V--.

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*